(12) United States Patent
Nagata et al.

(10) Patent No.: US 7,220,773 B2
(45) Date of Patent: May 22, 2007

(54) PYRROLE DERIVATIVE

(75) Inventors: Ryu Nagata, Osaka (JP); Katsunori Maruta, Osaka (JP); Kiyotaka Iwai, Osaka (JP); Makoto Kitoh, Osaka (JP); Kantaro Ushiroda, Osaka (JP); Kozo Yoshida, Osaka (JP)

(73) Assignee: Dainippon Sumitomo Pharma Co., Ltd., Osaka-Fu (JP)

( * ) Notice: Subject to any disclaimer, the term of this patent is extended or adjusted under 35 U.S.C. 154(b) by 514 days.

(21) Appl. No.: 10/474,943

(22) PCT Filed: Apr. 17, 2002

(86) PCT No.: PCT/JP02/03790

§ 371 (c)(1),
(2), (4) Date: Oct. 16, 2003

(87) PCT Pub. No.: WO02/085851

PCT Pub. Date: Oct. 31, 2002

(65) Prior Publication Data

US 2004/0162331 A1 Aug. 19, 2004

(30) Foreign Application Priority Data

Apr. 19, 2001 (JP) .............................. 2001-120887

(51) Int. Cl.
*C07D 207/46* (2006.01)
*A61K 31/40* (2006.01)

(52) U.S. Cl. ..................................... 514/408; 548/571

(58) Field of Classification Search ................ 548/571; 514/408
See application file for complete search history.

(56) References Cited

U.S. PATENT DOCUMENTS 6,310,217 B1 * 10/2001 Lehr .......................... 548/492

FOREIGN PATENT DOCUMENTS

| WO | 98/05637 | 2/1998 |
| WO | 99/46244 | 9/1999 |
| WO | 01/53257 A2 | 7/2001 |
| WO | 01/90067 | 11/2001 |

OTHER PUBLICATIONS

Lehr, M., "Synthesis, Biological Evaluation, and Structure-Activity Relationships of 3-Acylindole-2-carboxylic Acids as Inhibitors of the Cytosolic Phospholipase $A_2$", *J. Med. Chem.*, vol. 40, pp. 2694 to 2705 (1997).

* cited by examiner

*Primary Examiner*—Kamal A. Saeed
(74) *Attorney, Agent, or Firm*—Wenderoth, Lind & Ponack, L.L.P.

(57) ABSTRACT

A novel pyrrole derivative represented by the following formula (1) and a salt thereof:

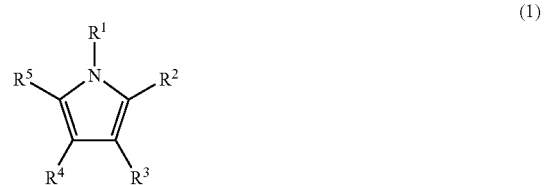

(1)

wherein $R^1$ means substituted alkenyl, etc.; $R^2$ means substituted benzoyl, etc.; and $R^3$ to $R^5$ each means hydrogen, alkyl, halogeno, etc. The derivative and salt have antidiabetic activity.

64 Claims, No Drawings

PYRROLE DERIVATIVE

TECHNICAL FIELD

The present invention relates to novel pyrrole derivatives and salts thereof. In detail the present invention relates to novel pyrrole derivatives and salts thereof which have antidiabetic activity. In more detail the present invention relates to novel pyrrole derivatives and salts thereof which have antidiabetic activity improving insulin resistance and safely controlling blood sugar level.

BACKGROUND ART

Recently due to westernization of eating-habit and increase of social stress, the number of patients with diabetes mellitus has been significantly increasing. Diabetes mellitus is a disease as main cause of chronically hyperglycemia and presents the symptom of said disease by lack of insulin or an excess of inhibitory factor for activity of insulin. Namely, diabetes mellitus is characterized as absolute or relative lack of insulin activity. Diabetes mellitus is clinically classified into insulin-dependent diabetes mellitus (IDDM) and non-insulin-independent diabetes mellitus (NIDDM).

Therapeutic exercise or dietetic therapy is first tried for treatment of diabetes mellitus. In case that decrease of blood sugar is insufficient even by these therapies, therapy by medicine is then tried. As an oral antidiabetic agent, sulfonyl urea (SU agent) is often used. The activity of this agent is based on promotion of insulin secretion in pancreas and therefore hypoglycemia occurs as side effect. Further, it is known that secondary inactivity occurs due to exhaustion of pancreas by plenty uses of a SU agent. On the other hand, thiazolidinedione derivatives for an antidiabetic agent, which were recently found (Diabetes 2 Nihon Rinsho, 725:125–145 (1997)), was paid attention by the reason as an agent which can control blood sugar by new mechanism showing improvement effect of peripheral insulin resistance. However, liver disturbance as significant side effect was reported on these derivatives and said derivatives have a big trouble in safety.

DISCLOSURE OF INVENTION

The problem to be solved is to provide an antidiabetic agent which improves insulin resistance and is higher in safety.

The present inventors have extensively studied to find that pyrrole derivatives improve hyperglycemia by improvement of insulin resistance and that it is superior in the safety and useful as an antidiabetic agent. Then the present invention was completed.

The present invention relates novel pyrrole derivatives and salts thereof.

Namely the present invention relates to (1) a pyrrole derivative of a generic formula (1):

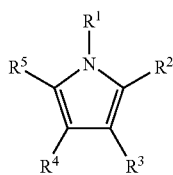

wherein
$R^1$ is a formula (2):

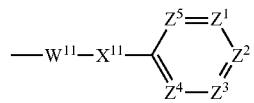

[wherein
$X^{11}$ is a single bond, an oxygen atom or a sulfur atom;
$W^{11}$ is $C_{2-5}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl, $C_{1-4}$ alkoxy, hydroxy, $C_{1-4}$ alkanoyloxy or a halogen; or
$C_{2-5}$ alkynylene optionally substituted by $C_{1-4}$ alkyl, $C_{1-4}$ alkoxy, hydroxy, $C_{1-4}$ alkanoyloxy or a halogen;
either of $Z^1$ and $Z^2$ is a carbon atom substituted by a formula:
—$X^1$—$Y^1$—$COR^6$ (wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
the other is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen); and $Z^3$, $Z^4$ and $Z^5$ are independently from each other, a carbon atom substituted by hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen];

a formula (3):

  (3)

[wherein $Ar^1$ is naphthyl substituted at least by a formula: $-X^2-Y^2-COR^7$ (wherein $X^2$ is a single bond, an oxygen atom or a sulfur atom;
$Y^2$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^7$ is hydroxy; $C_{1-4}$ alkoxy optionally substituted by $C_{1-4}$ alkyl; $C_{1-4}$ alkylsulfonylamio optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen), and optionally substituted by hydroxy;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{1-4}$ alkoxy optionally substituted by $C_{1-4}$ alkyl, $C_{1-4}$ alkoxy or a halogen;
a halogen;
cyano;
carbamoyl;
$C_{2-5}$ alkylaminocarbonyl; or
$C_{3-9}$ dialkylaminocarbonyl);
$X^{12}$ is a single bond, an oxygen atom or a sulfur atom; and
$W^{12}$ is $C_{1-4}$ alkylene optionally substituted by $C_{1-4}$ alkyl, $C_{1-4}$ alkoxy, hydroxy, $C_{1-4}$ alkanoyloxy or a halogen];

a formula (4):

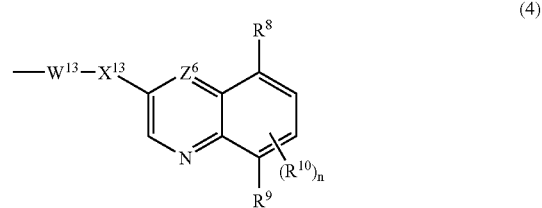

[wherein $X^{13}$ is a single bond, an oxygen atom or a sulfur atom;
$W^{13}$ is $C_{1-4}$ alkylene optionally substituted by $C_{1-4}$ alkyl, $C_{1-4}$ alkoxy, hydroxy, $C_{1-4}$ alkanoyloxy or a halogen;

either of $R^8$ and $R^9$ is

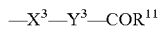

(wherein $X^3$ is a single bond, an oxygen atom or a sulfur atom;
$Y^3$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^{11}$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen);
and the other is
hydrogen;
hydroxy;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{1-4}$ alkoxy optionally substituted by $C_{1-4}$ alkyl, $C_{1-4}$ alkoxy or a halogen;
a halogen;

cyano;
carbamoyl;
$C_{2-5}$ alkylaminocarbonyl; or
$C_{3-9}$ dialkylaminocarbonyl);
$Z^6$ is a nitrogen atom, or a carbon atom substituted by
hydrogen;
hydroxy;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{1-4}$ alkoxy optionally substituted by $C_{1-4}$ alkyl, $C_{1-4}$ alkoxy or a halogen;
a halogen;
cyano;
carbamoyl;
$C_{2-5}$ alkylaminocarbonyl; or
$C_{3-9}$ dialkylaminocarbonyl;
$R^{10}$ is hydroxy;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{1-4}$ alkoxy optionally substituted by $C_{1-4}$ alkyl, $C_{1-4}$ alkoxy or a halogen;
a halogen;
cyano;
carbamoyl;
$C_{2-5}$ alkylaminocarbonyl; or
$C_{3-9}$ dialkylaminocarbonyl; and
n is an integer of 1 or 2]; or
a formula (5):

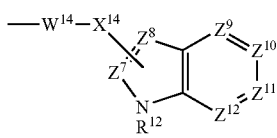

(5)

[wherein either of $Z^7$ and $Z^8$ is a carbon atom bound with $-W^{14}-X^{14}$ and the other is a carbon atom substituted by a hydrogen atom;
$X^{14}$ is a single bond, an oxygen atom or a sulfur atom;
$W^{14}$ is $C_{1-4}$ alkylene optionally substituted by $C_{1-4}$ alkyl, $C_{1-4}$ alkoxy, hydroxy, $C_{1-4}$ alkanoyloxy or a halogen;
any one of $Z^9$, $Z^{10}$, $Z^{11}$ and $Z^{12}$ is a carbon atom substituted by $-X^4-Y^4-COR^{13}$ (wherein $X^4$ is a single bond, an oxygen or a sulfur atom; $Y^4$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^{13}$ is hydroxy; $C_{1-4}$ alkoxy optionally substituted by $C_{1-4}$ alkyl; $C_{1-4}$ alkylsulfonylamio optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
the other is a carbon atom substituted by
hydrogen;
hydroxy;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{1-4}$ alkoxy optionally substituted by $C_{1-4}$ alkyl, $C_{1-4}$ alkoxy or a halogen;
a halogen;
cyano;
carbamoyl;
$C_{2-5}$ alkylaminocarbonyl; or
$C_{3-9}$ dialkylaminocarbonyl, and
$R^{12}$ is hydrogen, or $C_{1-4}$ alkyl optionally substituted by $C_{1-4}$ alkyl or a halogen];
either of $R^2$ and $R^3$ is a formula: $-W^{21}-A^{21}$
(wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl;
—CONH—; or —CONHCH$_2$—; and
$A^{21}$ is unsubstituted $C_{6-12}$ aryl; $C_{6-12}$ aryl substituted by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by $C_{7-8}$ aralkyl optionally substituted by $C_{1-4}$ alkoxy, $C_{1-4}$ alkyl, halogeno $C_{1-4}$ alkyl or a halogen,
by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by phenoxy optionally substituted by $C_{1-4}$ alkoxy, $C_{1-4}$ alkyl, halogeno $C_{1-4}$ alkyl or a halogen, or
by $C_{3-4}$ alkenyloxy, hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl
$C_{2-5}$ alkenyl,
$C_{1-4}$ alkylsulfonyloxy,
$C_{1-4}$ alkylsulfonyl,
$C_{1-4}$ alkylthio or
cyano;
unsaturated mono- or di-heterocycic ring containing 1–3, the same or different, heteroatoms selected from the group consisting of a nitrogen atom, an oxygen atom and a sulfur atom;
unsaturated mono- or di-heterocycic ring containing 1–3, the same or different, heteroatoms selected from the group consisting of a nitrogen atom, an oxygen atom and a sulfur atom substituted
by $C_{1-4}$ alkyl optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$
dialkylsulfamoyl or cyano, or
by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl or
cyano; and
the other is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen;
$R^4$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen; and
$R^5$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen;
or a halogen,
or its salt.

(2) The pyrrole derivative or its salt in the above (1) represented by the formula (1), wherein $R^1$ is a formula (2):

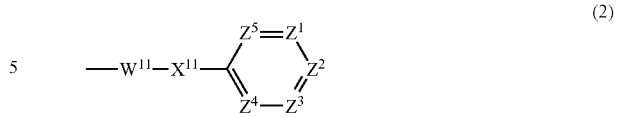

[wherein
$X^{11}$ is a single bond, an oxygen atom or a sulfur atom;
$W^{11}$ is $C_{2-5}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl, $C_{1-4}$ alkoxy, hydroxy, $C_{1-4}$ alkanoyloxy or a halogen; or
$C_{2-5}$ alkynylene optionally substituted by $C_{1-4}$ alkyl, $C_{1-4}$ alkoxy, hydroxy, $C_{1-4}$ alkanoyloxy or a halogen;
either of $Z^1$ and $Z^2$ is a carbon atom substituted by a formula:
—$X^1$—$Y^1$—$COR^6$
(wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
the other is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen); and
$Z^3$, $Z^4$ and $Z^5$ are independently from each other, a carbon atom substituted by
hydrogen;

hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen].

(3) The pyrrole derivative or its salt in the above (2) wherein $Z^1$ is a carbon atom substituted by a formula:
—$X^1$—$Y^1$—$COR^6$
(wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
$Z^2$ is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen.

(4) The pyrrole derivative or its salt in the above (2) wherein $Z^2$ is a carbon atom substituted by a formula:
—$X^1$—$Y^1$—$COR^6$
(wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
$Z^1$ is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen.

(5) The pyrrole derivative or its salt in the above (3) wherein $R^2$ is a formula: -$W^{21}$-$A^{21}$
(wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl;
—CONH—; or —CONHCH$_2$—; and
$A^{21}$ is unsubstituted $C_{6-12}$ aryl; $C_{6-12}$ aryl substituted
by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by $C_{7-8}$ aralkyl optionally substituted by $C_{1-4}$ alkoxy, $C_{1-4}$ alkyl, halogeno $C_{1-4}$ alkyl or a halogen,
by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by phenoxy optionally substituted by $C_{1-4}$ alkoxy, $C_{1-4}$ alkyl, halogeno $C_{1-4}$ alkyl or a halogen, or by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl
$C_{2-5}$ alkenyl,
$C_{1-4}$ alkylsulfonyloxy,
$C_{1-4}$ alkylsulfonyl,
$C_{1-4}$ alkylthio or
cyano;

unsaturated mono- or di-heterocycic ring containing 1–3, the same or different, heteroatoms selected from the group consisting of a nitrogen atom, an oxygen atom and a sulfur atom; or unsaturated mono- or di-heterocycic ring containing 1–3, the same or different, heteroatoms selected from the group consisting of a nitrogen atom, an oxygen atom and a sulfur atom substituted by $C_{1-4}$ alkyl optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, or $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl or
cyano; and $R^3$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen.

(6) The pyrrole derivative or its salt in the above (3) wherein $R^3$ is a formula: -$W^{21}$-$A^{21}$ wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen; $C_{2-5}$ alkenylene optionally substituted by $C_{1-4}$ alkyl; —CONH—; or —CONHCH$_2$—; and $A^{21}$ is unsubstituted $C_{6-12}$ aryl; $C_{6-12}$ aryl substituted by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by $C_{7-8}$ aralkyl optionally substituted by $C_{1-4}$ alkoxy, $C_{1-4}$ alkyl, halogeno $C_{1-4}$ alkyl or a halogen, by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by phenoxy optionally substituted by $C_{1-4}$ alkoxy, $C_{1-4}$ alkyl, halogeno $C_{1-4}$ alkyl or a halogen, or by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl,
$C_{2-5}$ alkenyl,
$C_{1-4}$ alkylsulfonyloxy,
$C_{1-4}$ alkylsulfonyl,
$C_{1-4}$ alkylthio or
cyano;

unsaturated mono- or di-heterocycic ring containing 1–3, the same or different, heteroatoms selected from the group consisting of a nitrogen atom, an oxygen atom and a sulfur atom; or unsaturated mono- or di-heterocycic ring containing 1–3, the same or different, heteroatoms selected from the group consisting of a nitrogen atom, an oxygen atom and a sulfur atom substituted by $C_{1-4}$ alkyl optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, or $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl or
cyano) and $R^2$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen;

or a halogen.

(7) The pyrrole derivative or its salt in the above (4) wherein $R^2$ is a formula: $-W^{21}-A^{21}$ (wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen; $C_{2-5}$ alkenylene optionally substituted by $C_{1-4}$ alkyl; —CONH—; or —CONHCH$_2$—; and $A^{21}$ is unsubstituted $C_{6-12}$ aryl; $C_{6-12}$ aryl substituted
by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by $C_{7-8}$ aralkyl optionally substituted by $C_{1-4}$ alkoxy, $C_{1-4}$ alkyl, halogeno $C_{1-4}$ alkyl or a halogen,
by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by phenoxy optionally substituted by $C_{1-4}$ alkoxy, $C_{1-4}$ alkyl, halogeno $C_{1-4}$ alkyl or a halogen, or
by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl
$C_{2-5}$ alkenyl,
$C_{1-4}$ alkylsulfonyloxy,
$C_{1-4}$ alkylsulfonyl,
$C_{1-4}$ alkylthio or
cyano;
unsaturated mono- or di-heterocycic ring containing 1–3, the same or different, heteroatoms selected from the group consisting of a nitrogen atom, an oxygen atom and a sulfur atom;
unsaturated mono- or di-heterocycic ring containing 1–3, the same or different, heteroatoms selected from the group consisting of a nitrogen atom, an oxygen atom and a sulfur atom substituted
by $C_{1-4}$ alkyl optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, or
by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl or
cyano); and
$R^3$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen;
or a halogen.

The present invention also relates to (8) a pyrrole derivative of a generic formula (1a) and a salt thereof:

(1a)

wherein
$R^{4'}$ is hydrogen, $C_{1-4}$ alkyl optionally substituted by $C_{1-4}$ alkyl or a halogen, or a halogen;
$R^{5'}$ is hydrogen, $C_{1-4}$ alkyl optionally substituted by $C_{1-4}$ alkyl or a halogen, or a halogen;
$R^{14'}$ is a carboxyl or a group which is convertible to a carboxyl by hydrolysis in vivo;
$X^{1'}$ is a single bond, an oxygen atom or a sulfur atom;
$Y^{1'}$ is $C_{1-4}$ alkylene optionally substituted by $C_{1-4}$ alkyl, $C_{1-4}$ alkoxy, hydroxy or a halogen;
$C_{2-5}$ alkenylene optionally substituted by $C_{1-4}$ alkyl, $C_{1-4}$ alkoxy, hydroxy or a halogen; or
$C_{2-5}$ alkynylene optionally substituted by $C_{1-4}$ alkyl, $C_{1-4}$ alkoxy, hydroxy or a halogen;
$W^{11'}$ is $C_{2-5}$ alkylene optionally substituted by $C_{1-4}$ alkyl or a halogen;
$C_{2-5}$ alkenylene optionally substituted by $C_{1-4}$ alkyl or a halogen; or
$C_{2-5}$ alkynylene optionally substituted by $C_{1-4}$ alkyl or a halogen;
$W^{21'}$ is $C_{1-4}$ alkylene in which methylene may form carbonyl, and said alkylene is optionally substituted by $C_{1-4}$ alkyl;
$C_{2-5}$ alkenylene in which methylene may form carbonyl, and said alkenylene is optionally substituted by $C_{1-4}$ alkyl; —CONH—; or —CONHCH$_2$—; and
$A^{21'}$ is unsubstituted $C_{6-12}$ aryl; $C_{6-12}$ aryl substituted
by $C_{1-4}$ alkyl optionally substituted by hydroxy, a halogen, $C_{1-4}$ alkoxy or $C_{2-8}$ dialkylamino,
by $C_{1-4}$ alkoxy optionally substituted by a halogen, $C_{1-4}$ alkoxy or $C_{2-8}$ dialkylamino,
by a halogen or $C_{2-12}$ dialkylamino;
unsaturated mono- or di-heterocycic ring containing 1–3, the same or different, heteroatoms selected from the group consisting of a nitrogen atom, an oxygen atom and a sulfur atom;
unsaturated mono- or di-heterocycic ring containing 1–3, the same or different, heteroatoms selected from the group consisting of a nitrogen atom, an oxygen atom and a sulfur atom substituted
by $C_{1-4}$ alkyl optionally substituted by hydroxy, a halogen, $C_{1-4}$ alkoxy or $C_{2-8}$ dialkylamino, by $C_{1-4}$ alkoxy optionally substituted,
by $C_{2-8}$ dialkylamino,
by a halogen, or
by $C_{2-12}$ dialkylamino;

(9) the pyrrole derivative or its salt in the above (8) wherein $R^{4'}$ is hydrogen or $C_{1-4}$ alkyl, and $R^{5'}$ is hydrogen;

(10) the pyrrole derivative or its salt in the above (8) wherein $R^{4'}$ and $R^{5'}$ are hydrogen;

(11) the pyrrole derivative or its salt in the above (8) wherein $R^{14'}$ is carboxyl;

(12) the pyrrole derivative or its salt in the above (8) wherein $X^{1'}$ is a single bond;

(13) the pyrrole derivative or its salt in the above (8) wherein $X^{1'}$ is an oxygen atom;

(14) the pyrrole derivative or its salt in the above (8) wherein $X^{1'}$ is a sulfur atom;

(15) the pyrrole derivative or its salt in the above (8) wherein $Y^{1'}$ is $C_{1-4}$ alkylene optionally substituted by $C_{1-4}$ alkyl, $C_{1-4}$ alkoxy, hydroxy or a halogen;

(16) the pyrrole derivative or its salt in the above (8) wherein $Y^{1'}$ is methylene optionally substituted by $C_{1-4}$ alkyl;

(17) the pyrrole derivative or its salt in the above (8) wherein $W^{11'}$ is unsubstituted $C_{2-5}$ alkylene, unsubstituted $C_{2-5}$ alkenylene or unsubstituted $C_{2-5}$ alkynylene;

(18) the pyrrole derivative or its salt in the above (8) wherein $W^{11'}$ is propenylene;

(19) the pyrrole derivative or its salt in the above (8) wherein $W^{11'}$ is propenylene and $X^{1'}$ is an oxygen atom;

(20) the pyrrole derivative or its salt in the above (8) wherein $W^{21'}$ is carbonyl, —CONH—, —CONHCH$_2$— or —C(=O)CH$_2$—;

(21) the pyrrole derivative or its salt in the above (8) wherein $W^{21'}$ is carbonyl;

(22) the pyrrole derivative or its salt in the above (8) wherein $W^{21'}$ is carbonyl and $X^{1'}$ is an oxygen atom;

(23) the pyrrole derivative or its salt in the above (8) wherein $A^{21'}$ is unsubstituted phenyl or phenyl substituted by $C_{1-4}$ alkyl optionally substituted by a halogen, $C_{1-4}$ alkoxy or $C_{2-8}$ dialkylamino, by $C_{1-4}$ alkoxy optionally substituted by a halogen, $C_{1-4}$ alkoxy or $C_{2-8}$ dialkylamino, or by a halogen or $C_{2-12}$ dialkylamino;

(24) the pyrrole derivative or its salt in the above (8) wherein $A^{21'}$ is unsubstituted phenyl or phenyl substituted by $C_{1-4}$ alkyl optionally substituted by a halogen, or by $C_{1-4}$ alkoxy optionally substituted by a halogen;

(25) the pyrrole derivative or its salt in the above (8) wherein $A^{21'}$ is unsubstituted phenyl or phenyl substituted by $C_{1-4}$ alkyl;

(26) the pyrrole derivative or its salt in the above (8) wherein $X^{1'}$ is an oxygen atom, and $A^{21'}$ is unsubstituted phenyl or phenyl substituted by $C_{1-4}$ alkyl;

(27) the pyrrole derivative or its salt in the above (8) wherein $R^{4'}$ and $R^{5'}$ are hydrogen, and $R^{14'}$ is carboxyl;

(28) the pyrrole derivative or its salt in the above (8) wherein $R^{4'}$ and $R^{5'}$ are hydrogen, $R^{14'}$ is carboxyl, and $Y^{1'}$ is $C_{1-4}$ alkylene optionally substituted by $C_{1-4}$ alkyl, $C_{1-4}$ alkoxy, hydroxy or a halogen;

(29) the pyrrole derivative or its salt in the above (8) wherein $R^{4'}$ and $R^{5'}$ are hydrogen, $R^{14'}$ is carboxyl, $X^{1'}$ is an oxygen atom, and $Y^{1'}$ is $C_{1-4}$ alkylene optionally substituted by $C_{1-4}$ alkyl, $C_{1-4}$ alkoxy, hydroxy or a halogen.

(30) the pyrrole derivative or its salt in the above (8) wherein $R^{4'}$ and $R^{5'}$ are hydrogen, $R^{14'}$ is carboxyl, and $W^{11'}$ is unsubstituted $C_{2-5}$ alkylene, unsubstituted $C_{2-5}$ alkenylene or unsubstituted $C_{2-5}$ alkynylene;

(31) the pyrrole derivative or its salt in the above (8) wherein $R^{4'}$ and $R^{5'}$ are hydrogen, $R^{14'}$ is carboxyl, $X^{1'}$ is an oxygen and $W^{11'}$ is unsubstituted $C_{2-5}$ alkylene, unsubstituted $C_{2-5}$ alkenylene or unsubstituted $C_{2-5}$ alkynylene;

(32) the pyrrole derivative or its salt in the above (8) wherein $R^{4'}$ and $R^{5'}$ are hydrogen, $R^{14'}$ is carboxyl, and $W^{11'}$ is propenylene;

(33) the pyrrole derivative or its salt in the above (8) wherein $R^{4'}$ and $R^{5'}$ are hydrogen, $R^{14'}$ is carboxyl, $W^{11'}$ is propenylene, and $X^{1'}$ is an oxygen;

(34) the pyrrole derivative or its salt in the above (8) wherein $R^{4'}$ and $R^{5'}$ are hydrogen, $R^{14'}$ is carboxyl, and $W^{21'}$ is carbonyl, —CONH—, —CONHCH$_2$— or —C(=O)CH$_2$—;

(35) the pyrrole derivative or its salt in the above (8) wherein $R^{4'}$ and $R^{5'}$ are hydrogen, $R^{14'}$ is carboxyl, $X^{1'}$ is an oxygen, and $W^{21'}$ is carbonyl, —CONH—, —CONHCH$_2$— or —C(=O)CH$_2$—;

(36) the pyrrole derivative or its salt in the above (8) wherein $R^{4'}$ and $R^{5'}$ are hydrogen, $R^{14'}$ is carboxyl, and $W^{21'}$ is carbonyl;

(37) the pyrrole derivative or its salt in the above (8) wherein $R^{4'}$ and $R^{5'}$ are hydrogen, $R^{14'}$ is carboxyl, $W^{21'}$ is carbonyl, and $X^{1'}$ is an oxygen;

(38) the pyrrole derivative or its salt in the above (8) wherein $R^{4'}$ and $R^{5'}$ are hydrogen, $R^{14'}$ is carboxyl, and $A^{21'}$ is unsubstituted phenyl or phenyl substituted by $C_{1-4}$ alkyl optionally substituted by a halogen, or by $C_{1-4}$ alkoxy optionally substituted by a halogen;

(39) the pyrrole derivative or its salt in the above (8) wherein $R^{4'}$ and $R^{5'}$ are hydrogen, $R^{14'}$ is carboxyl, $X^{1'}$ is an oxygen, and $A^{21'}$ is unsubstituted phenyl or phenyl substituted by $C_{1-4}$ alkyl optionally substituted by a halogen, or by $C_{1-4}$ alkoxy optionally substituted by a halogen;

(40) the pyrrole derivative or its salt in the above (8) wherein $R^{4'}$ and $R^{5'}$ are hydrogen, $R^{14'}$ is carboxyl, $W^{11'}$ is propenylene, and $Y^{1'}$ is $C_{1-4}$ alkylene optionally substituted by $C_{1-4}$ alkyl, $C_{1-4}$ alkoxy, hydroxy or a halogen;

(41) the pyrrole derivative or its salt in the above (8) wherein $R^{4'}$ and $R^{5'}$ are hydrogen, $R^{14'}$ is carboxyl, $W^{11'}$ is propenylene, $X^{1'}$ is an oxygen, and $Y^{1'}$ is $C_{1-4}$ alkylene optionally substituted by $C_{1-4}$ alkyl, $C_{1-4}$ alkoxy, hydroxy or a halogen;

(42) the pyrrole derivative or its salt in the above (8) wherein $R^{4'}$ and $R^{5'}$ are hydrogen, $R^{14'}$ is carboxyl, and $W^{21'}$ is carbonyl, —CONH—, —CONHCH$_2$— or —C(=O)CH$_2$—, and $Y^{1'}$ is $C_{1-4}$ alkylene optionally substituted by $C_{1-4}$ alkyl, $C_{1-4}$ alkoxy, hydroxy or a halogen.

(43) the pyrrole derivative or its salt in the above (8) wherein $R^{4'}$ and $R^{5'}$ are hydrogen, $R^{14'}$ is carboxyl, $X^{1'}$ is an oxygen, $W^{21'}$ is carbonyl, —CONH—, —CONHCH$_2$— or —C(=O)CH$_2$—, and $Y^{1'}$ is $C_{1-4}$ alkylene optionally substituted by $C_{1-4}$ alkyl, $C_{1-4}$ alkoxy, hydroxy or a halogen;

(44) the pyrrole derivative or its salt in the above (8) wherein $R^{4'}$ and $R^{5'}$ are hydrogen, $R^{14'}$ is carboxyl, $W^{21'}$ is carbonyl, and $Y^{1'}$ is methylene optionally substituted by $C_{1-4}$ alkyl;

(45) the pyrrole derivative or its salt in the above (8) wherein $R^{4'}$ and $R^{5'}$ are hydrogen, $R^{14'}$ is carboxyl, $W^{21'}$ is carbonyl, $X^{1'}$ is an oxygen, and $Y^{1'}$ is methylene optionally substituted by $C_{1-4}$ alkyl;

(46) the pyrrole derivative or its salt in the above (8) wherein $R^{4'}$ and $R^{5'}$ are hydrogen, $R^{14'}$ is carboxyl, $A^{21'}$ is unsubstituted phenyl or phenyl substituted by $C_{1-4}$ alkyl, and $Y^{1'}$ is $C_{1-4}$ alkylene optionally substituted by $C_{1-4}$ alkyl, $C_{1-4}$ alkoxy, hydroxy or a halogen;

(47) the pyrrole derivative or its salt in the above (8) wherein $R^{4'}$ and $R^{5'}$ are hydrogen, $R^{14'}$ is carboxyl, $A^{21'}$ is unsubstituted phenyl or phenyl substituted by $C_{1-4}$ alkyl, $X^{1'}$ is an oxygen, and $Y^{1'}$ is $C_{1-4}$ alkylene optionally substituted by $C_{1-4}$ alkyl, $C_{1-4}$ alkoxy, hydroxy or a halogen;

(48) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, —CONH—, —CONHCH$_2$— or —C(=O)CH$_2$—, and $Y^{1'}$ is $C_{1-4}$ alkylene optionally substituted by $C_{1-4}$ alkyl, $C_{1-4}$ alkoxy, hydroxy or a halogen;

(49) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, —CONH—, —CONHCH$_2$— or —C(=O)CH$_2$—, $X^{1'}$ is an oxygen, and $Y^{1'}$ is $C_{1-4}$ alkylene optionally substituted by $C_{1-4}$ alkyl, $C_{1-4}$ alkoxy, hydroxy or a halogen;

(50) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, and $Y^{1'}$ is methylene optionally substituted by $C_{1-4}$ alkyl;

(51) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, $X^{1'}$ is an oxygen, and $Y^{1'}$ is methylene optionally substituted by $C_{1-4}$ alkyl;

(52) the pyrrole derivative or its salt in the above (8) wherein $R^{4'}$ and $R^{5'}$ are hydrogen, $R^{14'}$ is carboxyl, $W^{11'}$ is propenylene, $Y^{1'}$ is methylene optionally substituted by $C_{1-4}$ alkyl, and $A^{21'}$ is unsubstituted phenyl or phenyl substituted by $C_{1-4}$ alkyl;

(53) the pyrrole derivative or its salt in the above (8) wherein $R^{4'}$ and $R^{5'}$ are hydrogen, $R^{14'}$ is carboxyl, $W^{11'}$ is propenylene, $X^{1'}$ is an oxygen, $Y^{1'}$ is methylene optionally substituted by $C_{1-4}$ alkyl, and $A^{21'}$ is unsubstituted phenyl or phenyl substituted by $C_{1-4}$ alkyl;

(54) the pyrrole derivative or its salt in the above (8) wherein $R^{4'}$ and $R^{5'}$ are hydrogen, $R^{14'}$ is carboxyl, $W^{21'}$ is carbonyl, $Y^{1'}$ is methylene optionally substituted by $C_{1-4}$ alkyl, and $A^{21'}$ is unsubstituted phenyl or phenyl substituted by $C_{1-4}$ alkyl;

(55) the pyrrole derivative or its salt in the above (8) wherein $R^{4'}$ and $R^{5'}$ are hydrogen, $R^{14'}$ is carboxyl, $W^{21'}$ is carbonyl, $X^{1'}$ is an oxygen, $Y^{1'}$ is methylene optionally substituted by $C_{1-4}$ alkyl, and $A^{21'}$ is unsubstituted phenyl or phenyl substituted by $C_{1-4}$ alkyl;

(56) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, and $A^{21'}$ is unsubstituted phenyl or phenyl substituted by $C_{1-4}$ alkyl;

(57) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, $X^{1'}$ is an oxygen, and $A^{21'}$ is unsubstituted phenyl or phenyl substituted by $C_{1-4}$ alkyl;

(58) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, $Y^{1'}$ is methylene optionally substituted by $C_{1-4}$ alkyl, and $A^{21'}$ is unsubstituted phenyl or phenyl substituted by $C_{1-4}$ alkyl; and

(59) the pyrrole derivative or its salt in the above (8) wherein $R^{4'}$ and $R^{5'}$ are hydrogen, $R^{14'}$ is carboxyl, $W^{11'}$ is propenylene, $W^{21'}$ is carbonyl, $X^{1'}$ is an oxygen atom, $Y^{1'}$ is methylene optionally substituted by $C_{1-4}$ alkyl, and $A^{21'}$ is unsubstituted phenyl or phenyl substituted by $C_{1-4}$ alkyl.

Furthermore, the present invention relates to (60) a medicament containing the pyrrole derivative or its salt in any one of the above (1) to (59);

(61) an antidiabetic agent or an arrest for diabetes mellitus containing the pyrrole derivative or its salt in any one of the above (1) to (59);

(62) a type II antidiabetic agent or an arrest for diabetes mellitus containing the pyrrole derivative or its salt in any one of the above (1) to (59); and

(63) a blood sugar controlling agent containing the pyrrole derivative or its salt in any one of the above (1) to (59).

THE BEST MODE FOR CARRYING OUT PRESENT INVENTION

The definition in the formula of pyrrole derivatives represented by the formula (1) is illustratively explained as follows.

Alkylene moiety of $C_{2-5}$ alkylene group optionally substituted in $W^{11}$ includes, for example, ethylene, trimethylene, tetramethylene, pentamethylene, etc.

$C_{1-4}$ Alkyl which is a substituent on said alkylene group includes, for example, methyl, ethyl, propyl, butyl, etc.

$C_{1-4}$ Alkoxy which is a substituent on said alkylene group includes, for example, methoxy, ethoxy, propoxy, butoxy, etc.

$C_{1-4}$ Alkanoyloxy which is a substituent on said alkylene group includes, for example, formyloxy, acetyloxy, propanoyloxy, butanoyloxy, etc.

A halogen which is a substituent on said alkylene group includes, for example, fluorine, chlorine, bromine, etc.

Methylene moiety in said alkylene group may form a carbonyl. The methylene moiety, except the methylene bound to pyrrole ring, preferably forms a carbonyl.

The number of substituents on said alkylene group may be one or more, preferably 1 to 2. When the substituents are plural, said substituents may be the same or different.

Alkenylene moiety of $C_{2-5}$ alkenylene group optionally substituted in $W^{11}$ includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

$C_{1-4}$ Alkyl which is a substituent on said alkenylene group includes, for example, methyl, ethyl, propyl, butyl, etc.

$C_{1-4}$ Alkoxy which is a substituent on said alkenylene group includes, for example, methoxy, ethoxy, propoxy, butoxy, etc.

$C_{1-4}$ Alkanoyloxy which is a substituent on said alkenylene group includes, for example, formyloxy, acetyloxy, propanoyloxy, butanoyloxy, etc.

A halogen which is a substituent on said alkenylene group includes, for example, fluorine, chlorine, bromine, etc.

Methylene moiety in said alkenylene group may form a carbonyl. The methylene moiety, except the methylene bound to pyrrole ring, preferably forms a carbonyl.

The number of substituents on said alkenylene group may be one or more, preferably 1 to 2. When the substituents are plural, said substituents may be the same or different.

Alkynylene moiety of $C_{2-5}$ alkynylene group optionally substituted in $W^{11}$ includes, for example, ethynylene, 1-propynylene, 2-propynylene, 1-butynylene, 2-butynylene, 3-butynylene, 1-pentynylene, 2-pentynylene, 3-pentynylene, 4-pentynylene, etc.

$C_{1-4}$ Alkyl which is a substituent on said alkynylene group includes, for example, methyl, ethyl, propyl, butyl, etc.

$C_{1-4}$ Alkoxy which is a substituent on said alkynylene group includes, for example, methoxy, ethoxy, propoxy, butoxy, etc.

$C_{1-4}$ Alkanoyloxy which is a substituent on said alkynylene group includes, for example, formyloxy, acetyloxy, propanoyloxy, butanoyloxy, etc.

A halogen which is a substituent on said alkylene group includes, for example, fluorine, chlorine, bromine, etc.

Methylene moiety in said alkynylene group may form a carbonyl. The methylene moiety, except the methylene bound to pyrrole ring, preferably forms a carbonyl.

The number of substituents on said alkynylene group may be one or more, preferably 1 to 2. When the substituents are plural, said substituents may be the same or different.

Alkylene moiety of $C_{1-4}$ alkylene group optionally substituted in $Y^1$, $Y^2$, $Y^3$ and $Y^4$ includes methylene, ethylene, trimethylene, tetramethylene, etc.

Alkyl moiety of $C_{1-4}$ alkyl group optically substituted which is the substituent on said alkylene group includes, for example, methyl, ethyl, propyl, butyl, etc.

A halogen which is a substituent on said alkyl group includes, for example, fluorine, chlorine, bromine, etc.

Said substituted alkyl moiety includes, for example, fluoromethyl, trifluoromethyl, chloromethyl, 2-fluoroethyl, 3-fluoropropyl, 4-fluorobutyl, etc.

Alkoxy moiety of $C_{1-4}$ alkoxy optionally substituted which is an substituent on said alkylene group includes for example, methoxy, ethoxy, propoxy, butoxy, etc.

A halogen which is a substituent on said alkoxy group includes, for example, fluorine, chlorine, bromine, etc.

Said substituted alkoxy moiety includes, for example, fluoromethoxy, trifluoromethoxy, chloromethoxy, 2-fluoroethoxy, 3-fluoropropyloxy, 4-fluorobutoxy, etc.

$C_{1-4}$ alkanoyloxy which is a substituent on said alkylene group includes, for example, formyloxy, acetyloxy, propanoyloxy, butanoyloxy, etc.

A halogen which is a substituent on said alkylene group includes, for example, fluorine, chlorine, bromine, etc. And methylene moiety in said alkylene group may form a carbonyl. The number of substituents on said alkylene group may be one or more, preferably 1 to 2. When the substituents are plural, said substituents may be the same or different.

Alkenylene moiety of $C_{2-5}$ alkeylene group in $Y^1$, $Y^2$, $Y^3$ and $Y^4$ includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

Alkyl moiety of $C_{1-4}$ alkyl optionally substituted which is a substituent on said alkenylene group includes, for example, methyl, ethyl, propyl, butyl, etc. A halogen which is a substituent on said alkyl group includes, for example, fluorine, chlorine, bromine, etc. Said substituted alkyl moiety includes, for example, fluoromethyl, trifluoromethyl, chloromethyl, 2-fluoroethyl, 3-fluoropropyl, 4-fluorobutyl, etc.

Alkoxy moiety of $C_{1-4}$ alkoxy optionally substituted which is a substituent on said alkenylene group includes, for example, methoxy, ethoxy, propyloxy, butyloxy, etc. A halogen which is a substituent on said alkoxy group includes, for example, fluorine, chlorine, bromine, etc. Said substituted alkoxy moiety includes, for example, fluoromethoxy, trifluoromethoxy, chloromethoxy, 2-fluoroethoxy, 3-fluoropropyloxy, 4-fluorobuoxy, etc.

$C_{1-4}$ alkanoyloxy which is a substituent on said alkenylene group includes, for example, formyloxy, acetyloxy, propanoyloxy, butanoyloxy, etc. A halogen which is a substituent on said alkenylene group includes, for example, fluorine, chlorine, bromine, etc.

Methylene moiety in said alkenylene group may form a carbonyl.

The number of substituents on said alkenylene group may be one or more, preferably 1 to 2. When the substituents are plural, said substituents may be the same or different.

Alkynylene moiety of $C_{2-5}$ alkynylene group in $Y^1$, $Y^2$, $Y^3$ and $Y^4$ includes, for example, ethynylene, 1-propynylene, 2-propynylene, 1-butynylene, 2-butynylene, 3-butynylene, 1-pentynylene, 2-pentynylene, 3-pentynylene, 4-pentynylene, etc.

Alkyl moiety of $C_{1-4}$ alkyl optionally substituted which is a substituent on said alkynylene group includes, for example, methyl, ethyl, propyl, butyl, etc. A halogen which is a substituent on said alkyl group includes, for example, fluorine, chlorine, bromine, etc. Said substituted alkyl moiety includes, for example, fluoromethyl, trifluoromethyl, chloromethyl, 2-fluoroethyl, 3-fluoropropyl, 4-fluorobutyl, etc.

Alkoxy moiety of $C_{1-4}$ alkoxy optionally substituted which is a substituent on said alkynylene group includes, for example, methoxy, ethoxy, propyloxy, butyloxy, etc. A halogen which is a substituent on said alkoxy group includes, for example, fluorine, chlorine, bromine, etc.

Said substituted alkoxy moiety includes, for example, fluoromethoxy, trifluoromethoxy, chloromethoxy, 2-fluoroethoxy, 3-fluoropropyloxy, 4-fluorobuoxy, etc.

$C_{1-4}$ Alkanoyloxy which is a substituent on said alkynylene group includes, for example, formyloxy, acetyloxy, propanoyloxy, butanoyloxy, etc.

A halogen which is a substituent on said alkynylene group includes, for example, fluorine, chlorine, bromine, etc. And methylene moiety in said alkynylene group may be substituted by two hydroxys to form a carbonyl. The number of substituents on said alkynylene group may be one or more, preferably 1 to 2. When the substituents are plural, said substituents may be the same or different.

Alkoxy moiety of $C_{1-4}$ alkoxy group optionally substituted in $R^6$, $R^7$, $R^{11}$ and $R^{13}$ includes, for example, methoxy, ethoxy, propoxy, butoxy, etc. The substiuent on said alkoxy group includes $C_{1-4}$ alkyl, for example, methyl, ethyl, propyl, butyl, etc. The number of substituents may be one or more, preferably 1 to 2. When the substituents are plural, said substituents may be the same or different.

Alkylsulfonyl moiety of $C_{1-4}$ alkylsulfonylamino group in $R^6$, $R^7$, $R^{11}$ and $R^{13}$ includes, for example, methylsulfonyl, ethylsulfonyl, propylsulfonyl, butylsulfonyl, etc. The substituent on said alkylsulfonyl includes $C_{1-4}$ alkyl, such as methyl, ethyl, propyl, butyl, etc., a halogen, such as fluorine, chlorine, bromine, etc. The number of substituents may be one or more, preferably 1 to 2. When the substituents are plural, said substituents may be the same or different.

The substituent on phenylsulfonylamino group in $R^6$, $R^7$, $R^{11}$ and $R^{13}$ includes unsubstituted $C_{1-4}$ alkyl (e.g., methyl, ethyl, propyl, butyl, etc.), $C_{1-4}$ alkyl (e.g., methyl, ethyl, propyl, butyl, etc.) substituted by $C_{1-4}$ alkyl (e.g., methyl, ethyl, propyl, butyl, etc.), and $C_{1-4}$ alkyl (e.g., methyl, ethyl, propyl, butyl, etc.) substituted by halogen atom (e.g., fluorine, chlorine, bromine, etc.), such as fluoromethyl, trifluoromethyl, chloromethyl, 2-fluoroethyl, 3-fluoropropyl, 4-fluorobutyl, etc., unsubstituted alkoxy (e.g., methoxy, ethoxy, propoxy, butoxy, etc.), $C_{1-4}$ alkoxy (e.g., methoxy, ethoxy, propoxy, butoxy, etc. as said alkoxy moiety) substituted by $C_{1-4}$ alkyl (e.g., methyl, ethyl, propyl, butyl, etc.) or a halogen, such as fluorine, chlorine, bromine, etc., and a halogen (e.g., fluorine, chlorine, bromine, etc.). The number of substituents may be one or more, preferably 1 to 2. When the substituents are plural, said substituents may be the same or different.

Alkyl moiety of $C_{1-4}$ alkyl optionally substituted, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, methyl, ethyl, propyl, 2-propyl, butyl, etc.

Examples of the substituent on said alkyl are illustrated as follows:

$C_{1-4}$ alkyl including, for example, methyl, ethyl, propyl, butyl, etc.;

$C_{1-4}$ Alkoxy including, for example, methoxy, ethoxy, propyloxy, butyloxy, etc.;

$C_{2-5}$ Alkoxycarbonyl including, for example, methoxycarbonyl, ethoxycarbonyl, propyloxycarbonyl, butyloxycarbonyl, etc.;

$C_{2-5}$ Alkylcarbonyl including, for example, methylcarbonyl, ethylcarbonyl, propylcarbonyl, butylcarbonyl, etc.;

$C_{1-4}$ Acyloxy group including, for example, formyloxy, acetyloxy, propanoyloxy, butanoyloxy, etc.;

A halogen including, for example, fluorine, chlorine, bromine, etc.;

$C_{1-4}$ Alkylamino including, for example, methylamino, ethylamino, propylamino, 2-propylamino, butylamino, etc.;

$C_{2-8}$ Dialkylamino including an amino group substituted by the same or different alkyls, such as dimethylamino, diethylamino, ethylmethylamino, dipropylamino, methylpropylamino, di-2-propylamino, dibutylamino, etc. And said dialkyls in said dialkylamino may be combined together or combined together via an oxygen atom to form a 5–6 membered saturated heterocyclic ring. Said saturated heterocyclic ring includes 1-pyrrrolidinyl, 1-piperidinyl, 4-morpholinyl, etc.

The number of substituents may be one or more, preferably 1 to 3. When the substituents are plural, said substituents may be the same or different.

Alkenyl moiety of $C_{2-5}$ alkenyl, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, allyl, 2-butenyl, 3-butenyl, 2-pentenyl, 3-pentenyl, etc.

Examples of the substituent on said alkenyl are illustrated as follows:

$C_{1-4}$ Alkyl including, for example, methyl, ethyl, propyl, butyl, etc.;

$C_{1-4}$ Alkoxy including, for example, methoxy, ethoxy, propyloxy, butyloxy, etc.

$C_{2-5}$ Alkoxycarbonyl including, for example, methoxycarbonyl, ethoxycarbonyl, propyloxycarbonyl, butyloxycarbonyl, etc.;

$C_{2-5}$ Alkylcarbonyl including, for example, methylcarbonyl, ethylcarbonyl, propylcarbonyl, butylcarbonyl, etc.;

$C_{1-4}$ Acyloxy including, for example, formyloxy, acetyloxy, propanoyloxy, butanoyloxy, etc.;

A halogen including, for example, fluorine, chlorine, bromine, etc.;

$C_{1-4}$ Alkylamino including, for example, methylamino, ethylamino, propylamino, 2-propylamino, butylamino, etc.;

$C_{2-8}$ Dialkylamino including an amino substituted by the same or different alkyls, such as dimethylamino, diethylamino, ethylmethylamino, dipropylamino, methylpropylamino, di-2-propylamino, dibutylamino, etc. And dialkyls in said dialkylamino may be combined together or combined together via an oxygen atom to form a 5–6 membered saturated heterocyclic ring. Said saturated heterocyclic ring includes 1-pyrrolidinyl, 1-piperidinyl, 4-morpholinyl, etc.

The number of substituents may be one or more, preferably 1 to 3. When the substituents are plural, said substituents may be the same or different.

Alkynyl moiety of $C_{2-5}$ alkynyl, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, ethynyl, 2-propyny, 2-butynyl, 3-butynyl, 2-pentynyl, 3-pentynyl, 4-pentynyl, etc.

Examples of the substituent on said alkynyl are illustrated as follows:

$C_{1-4}$ alkyl including, for example, methyl, ethyl, propyl, butyl, etc.;

$C_{1-4}$ Alkoxy group including, for example, methoxy, ethoxy, propyloxy, butyloxy, etc.;

$C_{2-5}$ Alkoxycarbonyl including, for example, methoxycarbonyl, ethoxycarbonyl, propyloxycarbonyl, butyloxycarbonyl, etc.;

$C_{1-4}$ Acyloxy including, for example, formyloxy, acetyloxy, propanoyloxy, butanoyloxy, etc.;

$C_{2-5}$ Alkylcarbonyl including, for example, methylcarbonyl, ethylcarbonyl, propylcarbonyl, butylcarbonyl, etc.;

A halogen including, for example, fluorine, chlorine, bromine, etc.;

$C_{1-4}$ Alkylamino including, for example, methylamino, ethylamino, propylamino, 2-propylamino, butylamino, etc.;

$C_{2-8}$ Dialkylamino including an amino group substituted by the same or different alkyls, such as dimethylamino, diethylamino, ethylmethylamino, dipropylamino, methylpropylamino, di-2-propylamino, dibutylamino, etc. And dialkyls in said dialkylamino may be combined together or combined together via an oxygen atom to form a 5–6 membered saturated heterocyclic ring. Said saturated heterocyclic ring includes 1-pyrrolidinyl, 1-piperidinyl, 4-morpholinyl, etc.

The number of substituents may be one or more, preferably 1 to 3. When the substituents are plural, said substituents may be the same or different.

Alkoxyl moiety of $C_{1-4}$ alkoxyl, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, methoxy, ethoxy, propyloxy, butoxy, etc.

$C_{1-4}$ Alkyl which is a substituent on said alkoxy includes, for example, methyl, ethyl, propyl, butyl, etc. $C_{1-4}$ Alkoxy which is a substituent on said alkoxy group includes, for example, methoxy, ethoxy, propyloxy, butyloxy, etc. A halogen which is a substituent on said alkoxy includes for example, fluorine, chlorine, bromine, etc.

The number of substituents may be one or more, preferably 1 to 3. When the substituents are plural, said substituents may be the same or different.

A halogen, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, fluorine, chlorine, bromine, etc.

$C_{2-5}$ Alkylaminocarbonyl, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, methylaminocarbonyl, ethylaminocarbonyl, propylaminocarbonyl, 2-propylaminocarbonyl, butylaminocarbonyl, etc.

$C_{3-9}$ Dialkylaminocarbonyl, which is the substituent on carbon atom optionally substituted in $Z^1$, $Z^2$, $Z^3$, $Z^4$ and $Z^5$, the substituent on substituted naphthyl ring in $Ar^1$, the substituent on carbon atom optionally substituted in $Z^6$, or the substituent on carbon atom optionally substituted in $R^8$, $R^9$ and $R^{10}$, and $Z^9$, $Z^{10}$, $Z^{11}$ and $Z^{12}$ includes, for example, an aminocarbonyl group substituted by the same or different $C_{1-4}$ alkyls, such as dimethylaminocarbonyl, diethylaminocarbonyl, ethylmethylaminocarbonyl, dipropylaminocarbonyl, methylpropylaminocarbonyl, di-2-propylaminocarbonyl, dibutylaminocarbonyl, etc. And dialkyls in said dialkyaminocarbonyl may be combined together or combined together via an oxygen atom to form a 5–6 membered saturated heterocyclic ring. Said saturated heterocyclic ring includes 1-pyrrolidinyl, 1-piperidinyl, 4-morpholinyl, etc. Such a dialkylaminocarbonyl group includes 1-pyrrrolidinylcarbonyl, 1-piperidinylcarbonyl, 4-morpholinylcarbonyl, etc.

Alkylene moiety of $C_{1-4}$ alkylene group in $W^{12}$, $W^{13}$ and $W^{14}$ includes, for example, methylene, ethylene, trimethylene, tetramethylene, etc.

Examples of the substituent on said alkylene group are illustrated as follows:

$C_{1-4}$ Alkyl including, for example, methyl, ethyl, propyl, butyl, etc.;

$C_{1-4}$ Alkoxy including, for example, methoxy, ethoxy, propyloxy, butyloxy, etc.;

$C_{1-4}$ Alkanoyloxy group including, for example, formyloxy, acetyloxy, propanoyloxy, butanoyloxy, etc.;

A halogen including, for example, fluorine, chlorine, bromine, etc.

Two hydrogen atoms on methylene moiety in said alkylene group may be substituted with an oxygen atom to form a carbonyl. Methylene moiety, except the methylene bound to pyrrole ring preferably forms a carbonyl.

The number of substituents may be one or more, preferably 1 to 2. When the substituents are plural, said substituents may be the same or different.

Alkylene moiety of $C_{1-6}$ alkylene group in $W^{21}$ includes, for example, methylene, ethylene, trimethylene, tetramethylene, pentamethylene, hexamethylene, etc.

Examples of the substituents on said alkylene group are illustrated as follows:

$C_{1-4}$ alkyl including, for example, methyl, ethyl, propyl, butyl, etc.;

$C_{1-4}$ Alkoxy including, for example, methoxy, ethoxy, propyloxy, butyloxy, etc.;

$C_{1-4}$ Alkanoyloxy including, for example, formyloxy, acetyloxy, propanoyloxy, butanoyloxy, etc.;

A halogen including, for example, fluorine, chlorine, bromine, etc.

Methylene moiety in said alkylene group may form a carbonyl.

The number of substituents may be one or more, preferably 1 to 2. When the substituents are plural, said substituents may be the same or different.

Alkenylene moiety of $C_{2-5}$ alkenylene group optionally substituted in $W^{21}$ includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

$C_{1-4}$ Alkyl which is a substituent on said alkenylene group includes, for example, methyl, ethyl, propyl, butyl, etc.

Methylene moiety in said alkenylene group may form a carbonyl.

The number of substituents may be one or more, preferably 1 to 2. When the substituents are plural, said substituents may be the same or different.

Aryl moiety of $C_{6-12}$ aryl group optionally substituted in $A^{21}$ includes, for example, phenyl, naphthyl, etc., and includes biphenyl, too.

Examples of the substituents on said aryl group are illustrated as follows:

$C_{1-6}$ Alkyl including, for example, methyl, ethyl, propyl, butyl, cyclopentyl, cyclohexyl, etc.;

$C_{1-4}$ Alkyl optionally substituted by a halogen including, for example, methyl, ethyl, propyl, butyl, chloromethyl, trifluoromethyl, etc.;

$C_{7-8}$ Aralkyl including, for example, benzyl, phenethyl, etc.;

$C_{1-4}$ Alkoxy including, for example, methoxy, ethoxy, propyloxy, butyloxy, etc.;

$C_{3-4}$ Alkenyloxy including, for example, allyloxy, 2-butenyloxy, 3-butenyloxy, etc.;

$C_{1-4}$ Alkanoyloxy including, for example., formyloxy, acetyloxy, propanoyloxy, butanoyloxy, etc.;

A halogen including, for example, fluorine, chlorine, bromine, etc.;

$C_{1-6}$ Alkylamino group including, for example, methylamino, ethylamino, propylamino, 2-propylamino, butylamino, pentylamino, hexylamino, etc.;

$C_{2-12}$ Dialkylamino group including an amino group substituted by the same or different $C_{1-6}$ alkyls, such as dimethylamino, diethylamino, ethylmethylamino, dipropylamino, methylpropylamino, di-2-propylamino, dibutylamino, dipentylamino, dihexylamino, etc. And dialkyls in said dialkylamino may be combined together or combined together via an oxygen atom to form a 5–6 membered saturated heterocyclic ring. Said saturated heterocyclic ring includes 1-pyrrolidinyl, 1-piperidinyl, 4-morpholinyl, etc.;

$C_{2-7}$ Alkylaminocarbonyl including, for example, aminocarbonyl substituted by $C_{1-6}$ alkyl, such as methylaminocarbonyl, ethylaminocarbonyl, propylaminocarbonyl, 2-propylaminocarbonyl, butylaminocarbonyl, pentylaminocarbonyl, hexylaminocarbonyl, etc.;

$C_{3-14}$ Dialkylaminocarbonyl including, for example, aminocarbonyl substituted by the same or different $C_{1-6}$ alkyls, such as dimethylaminocarbonyl, diethylaminocarbonyl, ethylmethylaminocarbonyl, dipropylaminocarbonyl, methylpropylaminocarbonyl, di-2-propylaminocarbonyl, dibutylaminocarbonyl, dipentylaminocarbonyl, dihexylaminocarbonyl, etc. And dialkyls in said dialkyaminocarbonyl may be combined together or combined together via an oxygen atom, amino, or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminocarbonyl group includes 1-pyrrolidinylcarbonyl, 1-piperidinylcarbonyl, 1-piperazinylcarbonyl, 1-(4-methylpiperazinyl)carbonyl, 4-morpholinylcarbonyl, etc.;

$C_{1-6}$ Alkylsulfamoyl including, for example, methylsulfamoyl, ethylsulfamoyl, propylsulfamoyl, 2-propylsulfamoyl, butylsulfamoyl, pentylsulfamoyl, hexylsulfamoyl, etc.;

$C_{2-12}$ Dialkylsulfamoyl including, for example, sulfamoyl group substituted by the same or different $C_{1-6}$ alkyl, such as dimethylsulfamoyl, diethylsulfamoyl, ethylmethylsulfamoyl, dipropylsulfamoyl, methylpropylsulfamoyl, di-2-propylsulfamoyl, dibutylsulfamoyl, dipentylsulfamoyl, dihexylsulfamoyl, etc. And dialkyls in said dialkylsulfamoyl may be combined together or combined together via an oxygen atom, amino, or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylsulfamoyl includes 1-pyrrolidinylsulfonyl, 1-piperidinylsulfonyl, 1-piperazinylsulfonyl, 1-(4-methylpiperazinyl)sulfonyl, 4-morpholinylsulfonyl, etc.;

$C_{2-5}$ Alkenyl including, for example, vinyl, propenyl, 2-propenyl, butenyl, 2-butenyl, etc.;

$C_{1-4}$ Alkylsulfonyloxy including, for example, methylsulfonyloxy, ethylsulfonyloxy, propylsulfonyloxy, butylsulfonyloxy, 2-propylsulfonyloxy, etc.;

$C_{1-4}$ Alkylsulfonyl including, for example, methylsulfonyl, ethylsulfonyl, propylsulfonyl, butylsulfonyl, 2-propylsulfonyl, etc.;

$C_{1-4}$ Alkylthio including, for example, methyltio, ethylthio, propylthio, butylthio, 2-propylthio, etc.;

$C_{1-4}$ Alkanoyloxy which is a substituent on substituted alkoxy or substituted alkyl including, for example, formyloxy, acetyloxy, propanoyloxy, butanoyloxy, etc.;

A halogen which is a substituent on substituted alkoxy or substituted alkyl including, for example, fluorine, chlorine, bromine, etc.;

$C_{1-4}$ Alkylamino which is a substituent on substituted alkoxy or substituted alkyl including, for example, methylamino, ethylamino, propylamino, 2-propylamino, butylamino, etc.;

$C_{2-8}$ Dialkylamino which is a substituent on substituted alkoxy or substituted alkyl including, for example, amino group which is substituted the same or different $C_{1-4}$ alkyl, e.g., dimethylamino, diethylamino, ethylmethyamino, dipropylamino, methylpropylamino, di-2-propylamino, dibutylamino, etc. And dialkyls in said dialkyamino may be combined together or -combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc.;

$C_{2-5}$ Alkylaminocarbonyl which is a substituent on substituted alkoxy group or substituted alkyl group including, for example, methylaminocarbonyl, ethylaminocarbonyl, propylaminocarbonyl, 2-propylaminocarbonyl, butylaminocarbonyl, etc.;

$C_{3-9}$ Dialkylaminocarbonyl which is a substituent on substituted alkoxy or substituted alkyl including, for example, aminobonyl substituted by the same or different $C_{1-4}$ alkyls, such as dimethylaminocarbonyl, diethylaminocarbonyl, ethylmethylaminocarbonyl, dipropylaminocarbonyl, methylpropylaminocarbonyl, di-2-propylaminocarbonyl, dibutylaminocarbonyl, etc. And dialkyls in said dialkyaminocarbonyl may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminocarbonyl includes 1-pyrrolidinylcarbonyl, 1-piperidinylcarbonyl, 1-piperazinylcarbonyl, 1-(4-methylpiperazinyl)carbonyl, 4-morpholinylcarbonyl, etc.;

$C_{1-4}$ Alkylsulfamoyl which is a substituent on substituted alkoxy group or substituted alkyl group including, for example, methylsulfamoyl, ethylsulfamoyl, propylsulfamoyl, 2-propylsulfamoyl, butylsulfamoyl, etc.;

$C_{2-8}$ Dialkylsulfamoyl which is a substituent on substituted alkoxy or substituted alkyl including, for example, sulfamoyl group substituted by the same or different $C_{1-4}$ alkyl, such as dimethylsulfamoyl, diethylsulfamoyl, ethylmethylsulfamoyl, dipropylsulfamoyl, methylpropylsulfamoyl, di-2-propylsulfamoyl, dibutylsulfamoyl, etc. And dialkyls in dialkyaminosulfamoyl may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminosulfonyl includes 1-pyrrolidinylsulfonyl, 1-piperidinylsulfonyl, 1-piperazinylsulfonyl, 1-(4-methylpiperazinyl)sulfonyl, 4-morpholinylsulfonyl, etc.

The number of substituents may be one or more, preferably 1 to 2. When the substituents are plural, said substituents may be the same or different.

When there are plural substituents selected from alkyl group and alkoxy group and they are adjacent each other, they may be combined to form a 5–7 membered cyclic ring. Said substituent includes, such as methylenedioxy (—OCH$_2$O—), ethylenedioxy (—O—CH$_2$—CH$_2$—O—), 2-methyl-methylenedioxy (—O—CHMe-O—), 2-methyl-ethylenedioxy (—O—CH$_2$—CHMe-O—), 1-oxy-2-ethylene (—O—CH$_2$—CH$_2$—), 1-oxy-2-propylene (—O—CH$_2$—CH$_2$—CH$_2$—), propylene (—CH$_2$—CH$_2$—CH$_2$—), butylene (—CH$_2$—CH$_2$—CH$_2$—CH$_2$—), etc.

Monocyclic or bicyclic unsaturated hetero ring containing 1 to 3, the same or different, hetero atoms selected from N, O and S atoms in $A^{21}$ includes, for example, a five membered unsaturated monocyclic hetero ring, e.g., thiophene, furan, pyrrole, imidazole, pyrazole, thiazole, oxazole, isothiazole, isoxazole, etc., a six membered unsaturated monocyclic hetero ring, e.g., pyridine, pyrimidine, pyrazine, pyridazine, triazine, etc., an unsaturated bicyclic hetero ring, e.g., indole, isoindole, indolizine, indazole, purine, 4-H-quinolizine, quinoline, isoquinoline, phtharazine, naphthyridine, quinoxaline, quinazoline, benzothiazole, benzoxazole, benzoisothiazole, benzoisoxazole, benzofuran, benzothiophen, etc.

Examples of the substituent on said unsaturated hetero ring are illustrated as follows:

$C_{1-4}$ Alkyl including, for example, methyl, ethyl, propyl, butyl, etc.;

$C_{1-4}$ Alkoxy including, for example, methoxy, ethoxy, propyloxy, butyloxy, etc.;

$C_{3-4}$ Alkenyloxy including, for example, allyloxy, 2-butenyloxy, 3-butenyloxy, etc.;

$C_{1-4}$ Alkanoyloxy group including, for example, formyloxy, acetyloxy, propanoyloxy, butanoyloxy, etc.;

A halogen including, for example, fluorine, chlorine, bromine, etc.;

$C_{1-6}$ Alkylamino including, for example, methylamino, ethylamino, propylamino, 2-propylamino, butylamino, pentylamino, hexylamino, etc.;

$C_{2-12}$ Dialkylamino including, for example, amino which is substituted by the same or different $C_{1-6}$ alkyl, such as dimethylamino, diethylamino, ethylmethyamino, dipropylamino, methylpropylamino, di-2-propylamino, dibutylamino, dipentylamino, dihexylamino, etc. And dialkyls in said dialkyamino may be combined together or combined together via an oxygen atom, to form a 5–6 membered saturated heterocyclic ring. Said saturated heterocyclic ring includes 1-pyrrolidinyl, 1-piperidinyl, 4-morpholinyl, etc.;

$C_{2-7}$ Alkylaminocarbonyl including, for example, aminocarbonyl substituted by $C_{1-6}$ alkyl, such as methylaminocarbonyl, ethylaminocarbonyl, propylaminocarbonyl, 2-propylaminocarbonyl, butylaminocarbonyl, pentylaminocarbonyl, hexylaminocarbonyl, etc.;

$C_{3-14}$ Dialkylaminocarbonyl including, for example, aminocarbonyl substituted by the same or different $C_{1-6}$ alkyls, such as dimethylaminocarbonyl, diethylaminocarbonyl, ethylmethylaminocarbonyl, dipropylaminocarbonyl, methylpropylaminocarbonyl, di-2-propylaminocarbonyl, dibutylaminocarbonyl, dipentylaminocarbonyl, dihexylaminocarbonyl, etc. And dialkyls in said dialkyaminocarbonyl may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminocarbonyl includes 1-pyrrolidinylcarbonyl, 1-piperidinylcarbonyl, 1-piperazinylcarbonyl, 1-(4-methylpiperazinyl)carbonyl, 4-morpholinylcarbonyl, etc.;

$C_{1-6}$ Alkylsulfamoyl including, for example, methylsulfamoyl, ethylsulfamoyl, propylsulfamoyl, 2-propylsulfamoyl, butylsulfamoyl, pentylsulfamoyl, hexylsulfamoyl, etc.;

$C_{2-12}$ Dialkylsulfamoyl including, for example, sulfamoyl substituted by the same or different $C_{1-6}$ alkyl, e.g., dimethylsulfamoyl, diethylsulfamoyl, ethylmethylsulfamoyl, dipropylsulfamoyl, methylpropylsulfamoyl, di-2-propylsulfamoyl, dibutylsulfamoyl, dipentylsulfamoyl, dihexylsulfamoyl, etc. And dialkyls in said dialkyaminosulfamoyl may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminosulfonyl includes 1-pyrrolidinylsulfonyl, 1-piperidinylsulfonyl, 1-piperazinylsulfonyl, 1-(4-methylpiperazinyl)sulfonyl, 4-morpholinylsulfonyl, etc.;

$C_{1-4}$ Alkanoyloxy which is a substituent on substituted alkoxy or substituted alkyl including, for example, formyloxy, acetyloxy, propanoyloxy, butanoyloxy, etc.;

A halogen which is a substituent on substituted alkoxy or substituted alkyl including, for example, fluorine, chlorine, bromine, etc.;

$C_{1-4}$ Alkylamino which is a substituent on substituted alkoxy or substituted alkyl including, for example, methylamino, ethylamino, propylamino, 2-propylamino, butylamino, etc.;

$C_{2-8}$ Dialkylamino which is a substituent on substituted alkoxy group or substituted alkyl group including, for example, amino group which is substituted by the same or different $C_{1-4}$ alkyl, such as dimethylamino, diethylamino, ethylmethyamino, dipropylamino, methylpropylamino, di-2-propylamino, dibutylamino, etc. And dialkyls in said dialkylamino may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc.;

$C_{2-5}$ Alkylaminocarbonyl which is a substituent on substituted alkoxy or substituted alkyl including, for example, methylaminocarbonyl, ethylaminocarbonyl, propylaminocarbonyl, 2-propylaminocarbonyl, butylaminocarbonyl, etc.;

$C_{3-9}$ Dialkylaminocarbonyl which is a substituent on substituted alkoxy or substituted alkyl including, for example, aminocarbonyl substituted by the same or different $C_{1-4}$ alkyls, such as dimethylaminocarbonyl, diethylaminocarbonyl, ethylmethylaminocarbonyl, dipropylaminocarbonyl, methylpropylaminocarbonyl, di-2-propylaminocarbonyl, dibutylaminocarbonyl, etc. And dialkyls in said dialkyaminocarbonyl group may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminocarbonyl group includes 1-pyrrolidinylcarbonyl, 1-piperidinylcarbonyl, 1-piperazinylcarbonyl, 1-(4-methylpiperazinyl)carbonyl, 4-morpholinylcarbonyl, etc.;

$C_{1-4}$ Alkylsulfamoyl which is a substituent on substituted alkoxy or substituted alkyl including, for example, methylsulfamoyl, ethylsulfamoyl, propylsulfamoyl, 2-propylsulfamoyl, butylsulfamoyl, etc.;

$C_{2-8}$ Dialkylsulfamoyl which is a substituent on substituted alkoxy or substituted alkyl including, for example, sulfamoyl group substituted by the same or different $C_{1-4}$ alkyl, e.g., dimethylsulfamoyl diethylsulfamoyl, ethylmethylsulfamoyl, dipropylsulfamoyl, methylpropylsulfamoyl, di-2-propylsulfamoyl, dibutylsulfamoyl, etc. And dialkyls in said dialkyaminosulfamoyl group may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc. Such a dialkylaminosulfonyl includes 1-pyrrolidinylsulfonyl, 1-piperidinylsulfonyl, 1-piperazinylsulfonyl, 1-(4-methylpiperazinyl)sulfonyl, 4-morpholinylsulfonyl, etc.

The number of substituents may be one or more, preferably 1 to 2. When the substituents are plural, said substituents may be the same or different.

$C_{1-4}$ Alkyl in $C_{1-4}$ alkyl optionally substituted in $R^2$, $R^3$, $R^4$ and $R^5$ includes, for example, methyl, ethyl, propyl, 2-propyl, butyl, etc.

$C_{1-4}$ Alkyl which is a substituent on $C_{1-4}$ alkyl optionally substituted in $R^2$, $R^3$, $R^4$ and $R^5$ includes, for example, methyl, ethyl, propyl, butyl, etc. $C_{1-4}$ Alkoxy which is said substituent includes, for example, methoxy, ethoxy, propyloxy, butyloxy, etc. $C_{1-4}$ Alkanoyloxy group which is said substituent includes, for example, formyloxy, acetyloxy, propanoyloxy, butanoyloxy, etc. A halogen which is said substituent includes for example, fluorine, chlorine, bromine, etc.

The number of said substituents may be one or more, preferably 1 to 3. When the substituents are plural, said substituents may be the same or different.

A halogen in $R^2$, $R^3$, $R^4$ and $R^5$ includes for example, fluorine, chlorine, bromine, etc.

The definition in pyrrole derivative represented by the formula (1a) is in detail explained as follows.

Alkylene moiety of $C_{2-5}$ alkylene group optionally substituted in $W^{11'}$ includes, for example, ethylene, trimethylene, tetramethylene, pentamethylene, etc.

$C_{1-4}$ Alkyl moiety which is a substituent on said alkylene group includes, for example, methyl, ethyl, propyl, butyl, etc.

A halogen which is a substituent on said alkylene group includes, for example, fluorine, chlorine, bromine, etc.

Alkenylene moiety of $C_{2-5}$ alkenylene group optionally substituted in $W^{11'}$ includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

$C_{1-4}$ Alkyl moiety which is a substituent on said alkenylene group includes, for example, methyl, ethyl, propyl, butyl, etc.

A halogen which is a substituent on said alkenylene group includes, for example, fluorine, chlorine, bromine, etc.

Alkynylene moiety of $C_{2-5}$ alkynylene group optionally substituted in $W^{11'}$ includes, for example, ethynylene, 1-propynylene, 2-propynylene, 1-butynylene, 2-butynylene, 3-butynylene, 1-pentynylene, 2-pentynylene, 3-pentynylene, 4-pentynylene, etc.

$C_{1-4}$ Alkyl moiety which is a substituent on said alkynylene group includes, for example, methyl, ethyl, propyl, butyl, etc. A halogen includes, for example, fluorine, chlorine, bromine, etc.

Alkylene moiety of $C_{1-4}$ alkylene group optionally substituted in $Y^{1'}$ includes, for example, methylene, ethylene, trimethylene, tetramethylene, etc.

$C_{1-4}$ Alkyl moiety which is a substituent on said alkylene group includes, for example, methyl, ethyl, propyl, butyl, etc.

$C_{1-4}$ Alkoxy group which is a substituent on said alkylene group includes, for example, methoxy, ethoxy, propyloxy, butyloxy, etc.

A halogen which is a substituent on said alkylene group includes, for example, fluorine, chlorine, bromine, etc.

Alkenylene moiety of $C_{2-5}$ alkenylene group optionally substituted in $Y^{1'}$ includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

$C_{1-4}$ Alkyl moiety which is a substituent on said alkenylene group includes, for example, methyl, ethyl, propyl, butyl, etc.

$C_{1-4}$ Alkoxy which is a substituent on said alkenylene group includes, for example, methoxy, ethoxy, propyloxy, butyloxy, etc.

A halogen which is a substituent on said alkenylene group includes, for example, fluorine, chlorine, bromine, etc.

Alkynylene moiety of $C_{2-5}$ alkynylene group optionally substituted in $Y^{1'}$ includes, for example, ethynylene, 1-propynylene, 2-propynylene, 1-butynylene, 2-butynylene, 3-butynylene, 1-pentynylene, 2-pentynylene, 3-pentynylene, 4-pentynylene, etc.

$C_{1-4}$ Alkyl moiety which is a substituent on said alkynylene group includes, for example, methyl, ethyl, propyl, butyl, etc. $C_{1-4}$ Alkoxy which is a substituent on said alkynylene group includes, for example, methoxy, ethoxy, propyloxy, butyloxy, etc.

A halogen which is a substituent on said alkynylene group includes, for example, fluorine, chlorine, bromine, etc.

Alkylene moiety of $C_{1-4}$ alkylene group optionally substituted in $W^{21'}$ includes, for example, methylene, ethylene, trimethylene, tetramethylene, etc.

$C_{1-4}$ Alkyl moiety which is a substituent on said alkylene group includes, for example, methyl, ethyl, propyl, butyl, etc.

Alkenylene moiety of $C_{2-5}$ alkenylene group optionally substituted in $W^{21'}$ includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

$C_{1-4}$ Alkyl moiety which is a substituent on said alkenylene group includes, for example, methyl, ethyl, propyl, butyl, etc.

Aryl moiety of $C_{6-12}$ aryl group optionally substituted in $A^{21'}$ includes, for example, phenyl, naphthyl, etc. and includes biphenyl, too.

Examples of the substituent on said aryl group are illustrated as follows:

$C_{1-4}$ Alkyl including, for example, methyl, ethyl, propyl, butyl, etc.;

$C_{1-4}$ Alkyl optionally substituted by halogen atom including, for example, methyl, ethyl, propyl, butyl, chloromethyl, trifluoromethyl, etc.;

$C_{1-4}$ Alkoxy group including, for example, methoxy, ethoxy, propyloxy, butyloxy, etc.;

A halogen including, for example, fluorine, chlorine, bromine, etc.;

$C_{2-12}$ Dialkylamino including, for example, amino group which is substituted the same or different $C_{1-6}$ alkyl, such as dimethylamino, diethylamino, ethylmethyamino, dipropylamino, methylpropylamino, di-2-propylamino, dibutylamino, dipentylamino, dihexylamino, etc. And dialkyls in said dialkyamino group may be combined together or combined together via an oxygen atom to form a 5–6 membered saturated heterocyclic ring. Said saturated heterocyclic ring includes 1-pyrrolidinyl, 1-piperidinyl, 4-morpholinyl, etc.;

$C_{2-8}$ Dialkylamino including, for example, amino group which is substituted by the same or different $C_{1-4}$ alkyl, such as dimethylamino, diethylamino, ethylmethyamino, dipropylamino, methylpropylamino, di-2-propylamino, dibutylamino, etc. And dialkyls in said dialkyamino may be combined together or combined together via an oxygen atom, amino or $C_{1-3}$ alkylamino to form a 5–6 membered saturated heterocyclic ring. Said saturated heterocyclic ring includes 1-pyrrolidinyl, 1-piperidinyl, 1-piperazinyl, 1-(4-methylpiperazinyl), 4-morpholinyl, etc.

Monocyclic or bicyclic unsaturated hetero ring containg 1 to 3, the same or different, hetero atoms selected from N, O and S atoms in $A^{21'}$ includes, for example, a five membered unsaturated monocyclic hetero ring, e.g., thiophene, furan, pyrrole, imidazole, pyrazole, thiazole, oxazole, isothiazole, isoxazole, a six membered unsaturated monocyclic hetero ring, e.g., pyridine, pyrimidine, pyrazine, pyridazine, triazine, etc., and, such as an unsaturated bicyclic hetero ring, e.g., indole, isoindole, indolizine, indazole, purine, 4-H-quinolizine, quinoline, isoquinoline, phtharazine, naphthyridine, quinoxaline, quinazoline, benzothiazole, benzoxazole, benzoisothiazole, benzoisoxazole, benzofuran, benzothiophen, etc.

When there are plural substituents selected from alkyl group and alkoxy group and the substituents are adjacent each other, they may be combined to form a 5–7 membered cyclic ring. Said combined substituent includes, such as methylenedioxy (—OCH$_2$O—), ethylenedioxy (—O—CH$_2$—CH$_2$—O—), 2-methyl-methylenedioxy (—O—CHMe-O—), 2-methyl-ethylenedioxy (—O—CH$_2$—CHMe-O—), 1-oxy-2-ethylene (—O—CH$_2$—CH$_2$—), 1-oxy-2-propylene (—O—CH$_2$—CH$_2$—CH$_2$—), propylene (—CH$_2$—CH$_2$—CH$_2$—), butylene (—CH$_2$—CH$_2$—CH$_2$—CH$_2$—), etc.

$C_{1-4}$ Alkyl, $C_{1-4}$ alkoxy, a halogen, $C_{2-8}$ dialkylamino, and $C_{2-12}$ dialkylamino, which are a substituent on monocyclic or bicyclic unsaturated hetero ring containing 1 to 3, the same or different, hetero atoms selected from N, O and S atoms include the same substituent as that on the above $C_{6-12}$ aryl.

$C_{1-4}$ Alkyl optionally substituted in $R^{4'}$ and $R^{5'}$ include for example, methyl, ethyl, propyl, 2-propyl, butyl, etc. $C_{1-4}$ Alkyl which is a substituent on said alkyl includes methyl, ethyl, propyl, butyl, etc. A halogen which is said substituent includes for example, fluorine, chlorine, bromine, etc.

A halogen on $R^{4'}$ or $R^{5'}$ includes for example, fluorine, chlorine, bromine, etc.

The group which is convertible into carboxyl group by hydrolysis in vivo in $R^{14'}$ is not limited as far as the carboxyl group is reproduced, and includes the group as used in case of introduction into compounds which is generally called prodrug.

The salts of pyrrole derivatives represented by formulae (1) and (1a) include preferably pharmaceutically acceptable salts, in case that said pyrrole derivatives have an acidic group, for example, alkali metal salts, such as sodium salt, potassium salt, etc., alkaline earth metal salts, such as calcium salt, magnesium salt, etc., inorganic metal salts such as zinc salt, etc., organic basic salts, such as triethylaminate, triethanolaminate, trihydroxymethylmethylaminate, etc., and in case of that said pyrrole derivatives have a basic group, for example, inorganic salts, such as hydrochloride, hydrobromide, sulfate, phosphate, nitrate, etc., and organic acid salts, such as acetate, propionate, succinate, lactate, maleate, tartarate, citrate, maleate, fumarate, methansulfonate, p-toluenesulfonate, benzenesulfonate, ascorbate, etc.

The present invention includes prodrugs of pyrrole derivatives represented by the formula (1) and (1a), and hydrate or solvates (e.g., ethanol solvate) of pyrrole derivatives of the formula (1) and (1a) or prodrugs thereof or pharmaceutically acceptable salts, etc. are included.

A pyrrole derivative of the formula (1) is prepared, for example, by the following methods.

Method 1

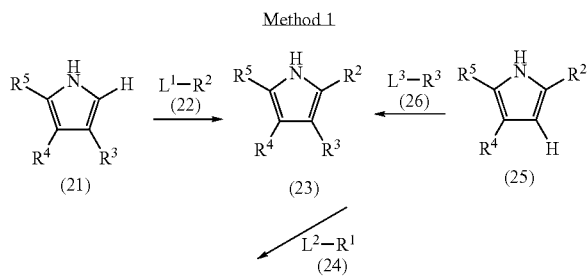

-continued

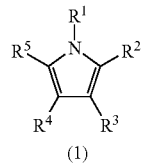

(1)

wherein $R^1$, $R^2$, $R^3$, $R^4$ and $R^5$ are the same as defined above, $L^1$, $L^2$ and $L^3$ are a leaving group, such as a halogen (e.g., Cl, Br, I), methanesulfonyloxy, trifluoromethanesulfonyloxy, etc.

Compound (23) is prepared by reacting compound (21) with compound (22) in an inert solvent in the presence of a base.

The base includes alkali metal hydrides, such as sodium hydride, potassium hydride, etc., alkali metal alkoxides such as potassium t-butoxide, etc., Grignard reagents such as ethylmagnesium bromide, etc., organic lithium reagents such as butyllithium, etc.

The inert solvent includes, for example, aprotic solvents such as dimethylformamide, etc., ethers, such as tetrahydrofuran (THF), dioxane, etc., or a mixture thereof.

The reaction is carried out at a temperature of about 0° C. to about 80° C.

The compound (23) can be prepared by reacting compound (21) with compound (22) in an inert solvent in the presence of a Lewis acid.

The inert solvent includes hologenohydrocarbons, such as dichloromethane, dichloroethane, etc.

Lewis acids include halogenated compounds, such as aluminum chloride, zinc chloride, trifluoroborane, etc, rare earth sulfonates, such as lanthanium trifluoromethanesulfonate, ytterbium trifluoromethanesulfonate, etc.

The reaction is carried out at a temperature of about 0° C. to the boiling point of the solvent.

Compound (23) is prepared by reacting compound (25) with compound (26) in an inert solvent in the presence of a base.

The base includes alkali metal hydrides, such as sodium hydride, potassium hydride, etc., alkali metal alkoxides such as potassium t-butoxide, etc., Grignard reagents such as ethylmagnesium bromide, etc., organic lithium reagents such as butyllithium, etc.

The inert solvent includes, for example, aprotic solvents such as dimethylformamide, ethers, such as tetrahydrofuran (THF), dioxane, etc., or a mixture thereof.

The reaction is carried out at a temperature of about 0° C. to about 80° C.

The compound (23) can be prepared by reacting compound (25) with compound (26) in an inert solvent in the presence of a Lewis acid.

The inert solvent includes hologenohydrocarbons, such as dichloromethane, dichloroethane, etc.

Lewis acids include halogenated compounds, such as aluminum chloride, zinc chloride, trifluoroborane, etc, rare earth sulfonates, such as lanthanium trifluoromethanesulfonate, ytterbium trifluoromethanesulfonate, etc.

The reaction carried out at a temperature of about 0 C to the boiling point of the solvent.

Compound (1) of the present invention is prepared by reacting compound (23) with compound (24) in an inert solvent in the presence of a base.

The base includes alkali metal hydrides, such as sodium hydride, potassium hydride, etc., alkali metal alkoxides such as potassium t-butoxide, etc., Grignard reagents such as ethylmagnesium bromide, etc., organic lithium reagents such as butyllithium, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

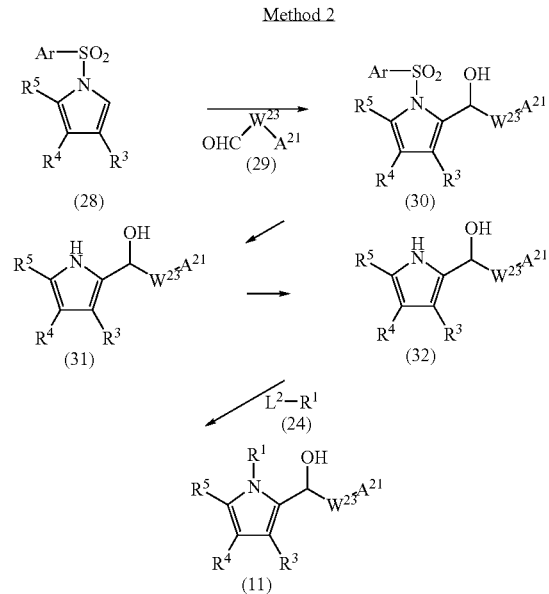

wherein $R^1$, $R^3$, $R^4$, $R^5$ and $L^2$ are the same as defined above, $W^{23}$ is a single bond, alkylene, substituted alkylene, alkenylene, or substituted alkenylen, and $A^{21}$ is substituted aryl, or unsaturated hetero ring optionally substituted.

Compound (30) is prepared by reaction compound (28) with aldehyde derivative (29) in an inert solvent in the presence of a lithiumamide reagent such as lithium-2,2,6,6-tetramethylpiperidine, etc.

The inert solvent includes ethers such as THF, etc., hydrocarbons such as toluene, etc.

The reaction is carried out at a temperature of about −100° C. to room temperature.

Compound (31) is prepared by hydrolyzing compound (30) in a solvent in the presence of a base.

The base includes alkali metal hydroxides, such as sodium hydroxide, potassium hydroxide, etc., bases such as tetrabutylammoniumfluoride, etc.

The inert solvent includes, for example, ethers, such as THF, dioxane, etc., alcohols, such as methanol, ethanol, etc., water, or a mixture thereof.

The reaction is carried out at a temperature of about room temperature to the boiling point of the solvent.

Compound (32) is prepared by reducing compound (31) in an inert solvent with a reducing agent.

The reducing agent includes reducing agents, such as sodium borohydride-isopropanol, triethylsilanetrifluoroacetic acid, etc.

The inert solvent includes ethers, such as THF, dioxane, etc., hologenohydrocarbons, such as dichloromethane, chlorobenzene, etc.

The reaction is carried out at a temperature of about −20° C. to the boiling point of the solvent.

Compound (11) of the present invention is prepared by reacting compound (32) with compound (24) in an inert solvent in the presence of a base.

The base includes alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

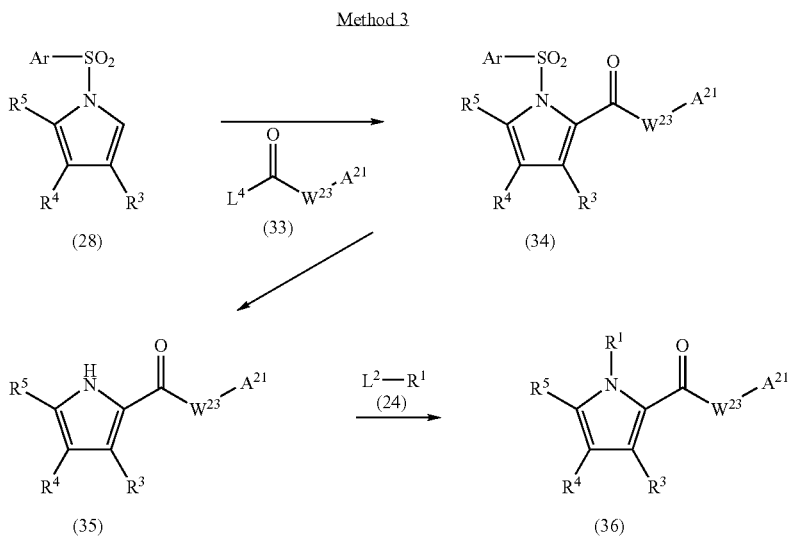

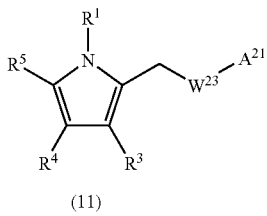

(11)

wherein $R^1$, $R^3$, $R^4$, $R^5$ and $L^2$ are the same as defined above, $W^{23}$ is a single bond, alkylene, substituted alkylene, alkenylene, or substituted alkenylen, and $A^{21}$ is substituted aryl, or unsaturated hetero ring optionally substituted, and $L^4$ is a leaving group, such as a halogen (e.g., Cl, Br, I), methanesulfonyloxy, trifluoromethanesulfonyloxy, etc.

Compound (34) can be prepared by reacting compound (28) with compound (33) in an inert solvent in the presence of a Lewis acid.

Lewis acids include, for example, trifluoroborane, zinc chloride, tin(IV) chloride, lanthanium trifluoromethanesulfonate, ytterbium trifluoromethanesulfonate, etc.

The inert solvent includes hologenohydrocarbons, such as dichloromethane, dichloroethane, etc.

The reaction is carried out at a temperature of room temperature to the boiling point of the solvent.

Compound (35) is prepared by hydrolyzing compound (34) in a solvent in the presence of a base.

The base includes alkali metal hydroxides, such as sodium hydroxide, potassium hydroxide, etc., bases such as tetrabutylammonium fluoride, etc.

The inert solvent includes, for example, ethers, such as THF, dioxane, etc., alcohols, such as methanol, ethanol, etc., water, or a mixture thereof.

The reaction is carried out at a temperature of about room temperature to the boiling point of the solvent.

Compound (36) is prepared by reacting compound (35) with compound (24) in an inert solvent in the presence of a base.

The base includes alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

The compound of the present invention represented by the formula (11) is prepared by reducing compound (36) in a inert solvent with a reducing agent.

The reducing agent includes reducing agents, such as sodium borohydride-isopropanol, hydrazine-base (potassium hydroxide, sodium hydroxide, etc.), zinc amalgamhydrochloric acid, etc.

The inert solvent includes ethers, such as THF, dioxane, etc.

The reaction is carried out at a temperature of about 0 C to the boiling point of the solvent.

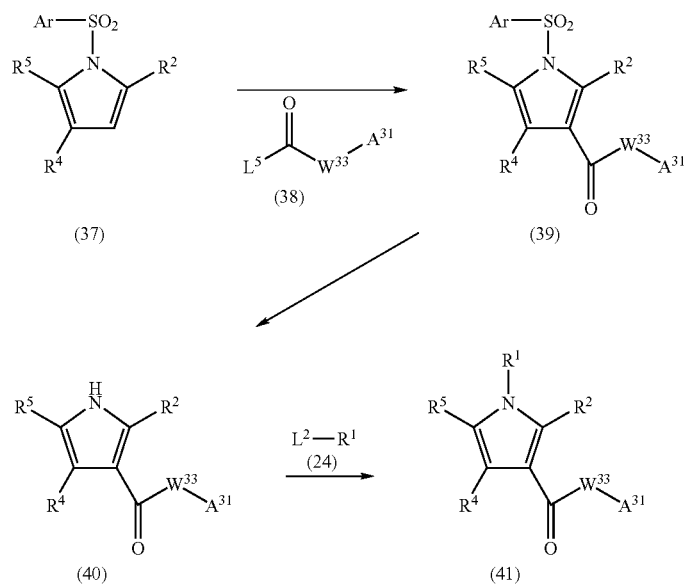

Method 4

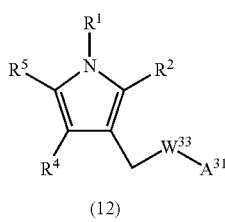

(12)

wherein $R^1$, $R^2$, $R^4$, $R^5$ and $L^2$ are the same as defined above, $W^{33}$ is a single bond, alkylene, substituted alkylene, alkenylene, or substituted alkenylen, $A^{31}$ is substituted aryl, or unsaturated hetero ring optionally substituted, and $L^5$ is a leaving group such as a halogen (e.g., Cl, Br, I), methanesulfonyloxy, trifluoromethanesulfonyloxy, etc.

Compound (39) can be prepared by reacting compound (37) with compound (38) in an inert solvent in the presence of a Lewis acid.

Lewis acids include, for example, aluminum chloride, iron chloride, etc.

The inert solvent includes hologenohydrocarbons, such as dichloromethane, dichloroethane, etc.

The reaction is carried out at a temperature of room temperature to the boiling point of the solvent.

Compound (40) is prepared by hydrolyzing compound (39) in a solvent in the presence of a base.

The base includes alkali metal hydroxides, such as sodium hydroxide, potassium hydroxide, etc., bases such as tetrabutylammonium fluoride, etc.

The inert solvent includes, for example, ethers, such as THF, dioxane, etc., alcohols, such as methanol, ethanol, etc., water, or a mixture thereof.

The reaction is carried out at a temperature of about room temperature to the boiling point of the solvent.

Compound (41) is prepared by reacting compound (40) with compound (24) in an inert solvent in the presence of a base.

The base includes alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

The compound of the present invention represented by the formula (12) is prepared by reducing compound (41) in a inert solvent with a reducing agent.

The reducing agent includes reducing agents, such as sodium borohydride-isopropanol, hydrazine-base (an alkali metal hydroxide, such as potassium hydroxide, sodium hydroxide, etc.), zinc amalgam-hydrochloric acid, etc.

The inert solvent includes, for example, ethers, such as THF, dioxane, etc.

The reaction is carried out at a temperature of about 0° C. to the boiling point of the solvent.

Method 5

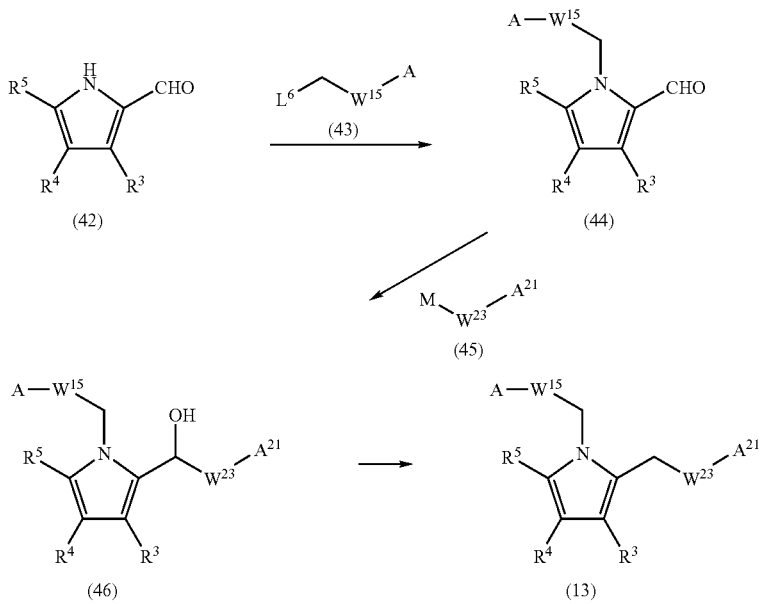

wherein $R^3$, $R^4$, $R^5$, $W^{23}$ and $A^{21}$ are the same as defined above, A is the other group except $W^{11}$ and $X^{11}$ of the above formula (2), $W^{12}$ and $X^{12}$ of the above formula (3), $W^{13}$ and $X^{13}$ of the above formula (4), and $W^{14}$ and $X^{14}$ of the above formula (5), $W^{15}$ is $C_{1-4}$ alkylene optionally substituted, $C_{2-4}$ alkenylene optionally substituted, and $L^6$ is a leaving group such as a halogen (e.g., Cl, Br, I), methanesulfonyloxy, trifluoromethanesulfonyloxy, etc., and M is an alkali metal such as lithium, etc., magnesium bromide, magnesium iodide, etc.

Compound (44) is prepared by reacting compound (42) with compound (43) in an inert solvent in the presence of a base.

The base includes alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

Compound (46) is prepared by reacting compound (44) in an inert solvent with organic metal compound (45).

The inert solvent includes, for example, ethers such as THF, etc., hydrocarbons, such as toluene, n-hexane, etc., or a mixture thereof.

The reaction is carried out at a temperature of about −100° C. to room temperature.

The compound of the present invention represented by the formula (13) is prepared by reducing compound (46) in a inert solvent with a reducing agent.

The reducing agent includes reducing agents, such as sodium borohydride-isopropanol, triethylsilanetrifluoroacetic acid, etc.

The inert solvent includes, for example, ethers such as THF, dioxane, etc., halogenohydrocarbons, such as dichloromethane, chlorobenzene, etc.

The reaction is carried out at a temperature of about −20° C. to the boiling point of the solvent.

wherein $R^3$, $R^4$, $R^5$, $W^{15}$, $W^{23}$, $A^{21}$ and A are the same as defined above, and $L^7$ is a leaving group such as a halogen (e.g., Cl, Br, I), methanesulfonyloxy, trifluoromethanesulfonyloxy, etc.

Compound (48) is prepared by reacting compound (47) in an inert solvent with a halogenating agent.

The halogenating agent includes, for example, thionyl chloride, oxalyl chloride, etc. Dimethylformamide may be added as catalyst.

The solvent includes, for example, halogeno hydrocarbons, such as dichloromethane, dichloroethane, etc., aromatic hydrocarbons, such as toluene, benzene, etc.

The reaction is carried out at a temperature of about 0 C to the boiling point of the solvent.

Compound (50) is prepared by reacting compound (48) in an inert solvent in the presence of tetrakis (triphenylphosphine) palladium and cesium carbonate with compound (49).

The solvent includes, for example, hydrocarbons, such as toluene, n-hexane, etc.

The reaction is carried out at a temperature of room temperature to the boiling point of the solvent.

Compound (50) can be obtained by reacting compound (48) in an inert solvent with $A^{21}$-$W^{23}$—MgBr.

The inert solvent includes, for example, ethers such as THF, diethyl ether, etc., hydrocarbons, such as toluene, n-hexane, etc.

The reaction is carried out at a temperature of about −100 C to room temperature.

The compound of the present invention represented by the formula (13) is prepared by reacting compound (50) with compound (51) in an inert solvent in the presence of a base.

The base includes, for example, alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

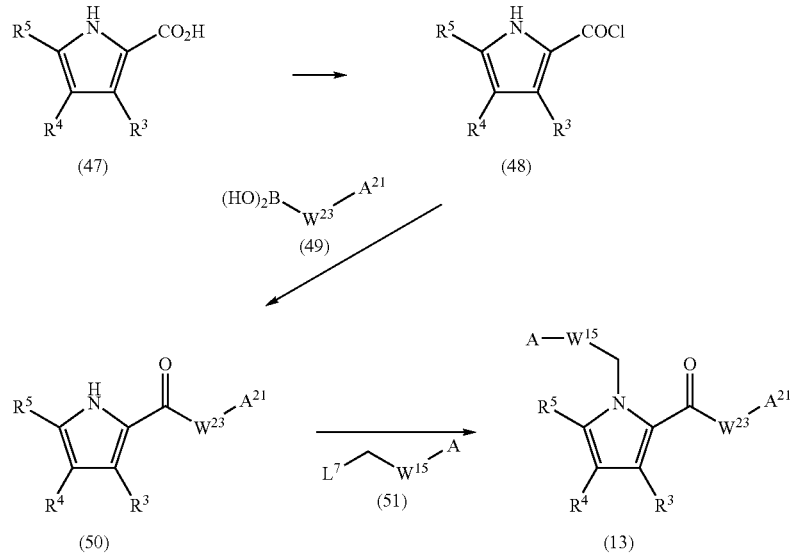

Method 6

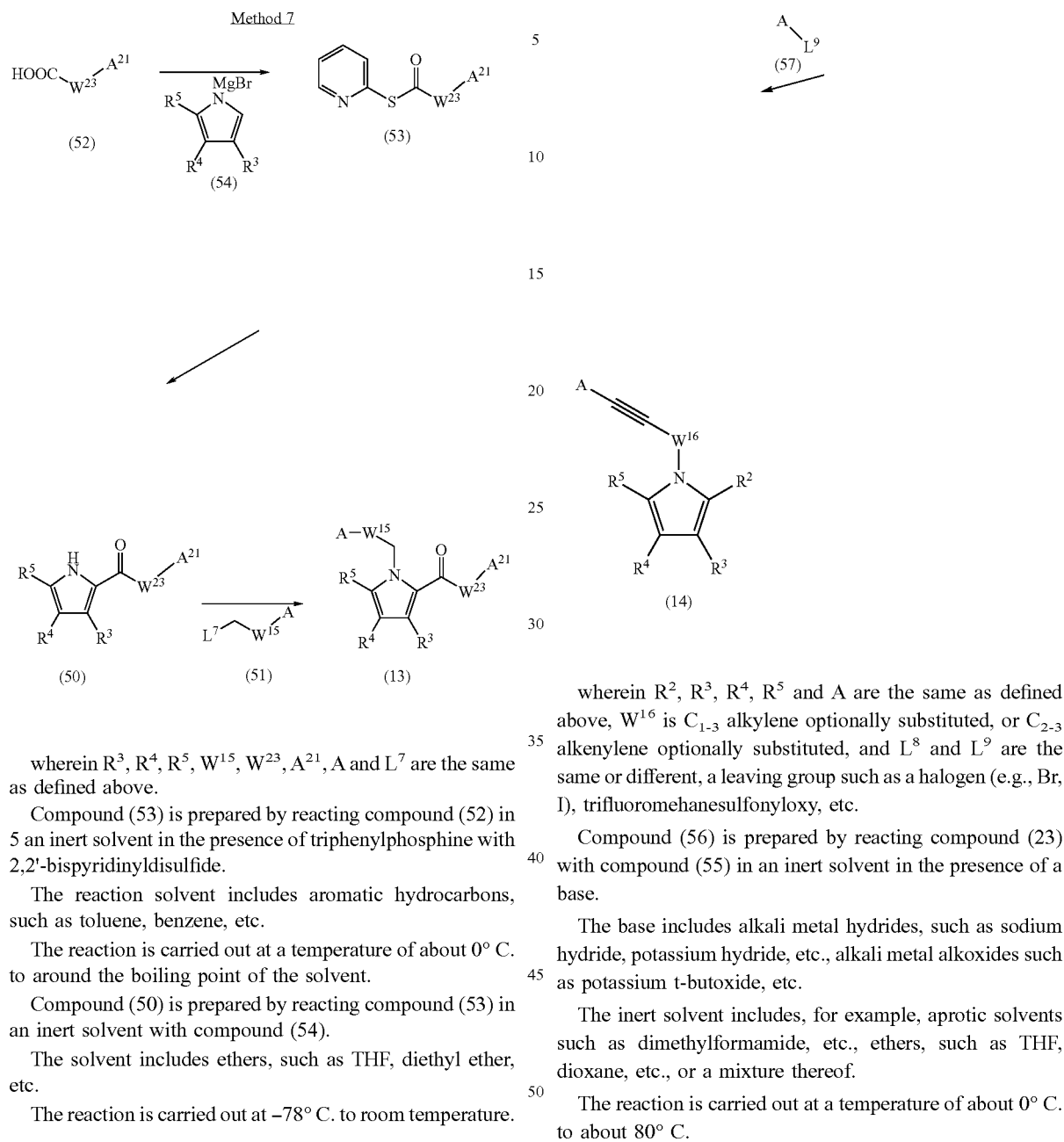

wherein $R^3$, $R^4$, $R^5$, $W^{15}$, $W^{23}$, $A^{21}$, A and $L^7$ are the same as defined above.

Compound (53) is prepared by reacting compound (52) in an inert solvent in the presence of triphenylphosphine with 2,2'-bispyridinyldisulfide.

The reaction solvent includes aromatic hydrocarbons, such as toluene, benzene, etc.

The reaction is carried out at a temperature of about 0° C. to around the boiling point of the solvent.

Compound (50) is prepared by reacting compound (53) in an inert solvent with compound (54).

The solvent includes ethers, such as THF, diethyl ether, etc.

The reaction is carried out at −78° C. to room temperature.

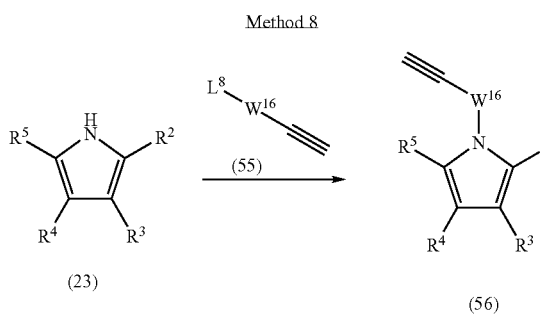

wherein $R^2$, $R^3$, $R^4$, $R^5$ and A are the same as defined above, $W^{16}$ is $C_{1-3}$ alkylene optionally substituted, or $C_{2-3}$ alkenylene optionally substituted, and $L^8$ and $L^9$ are the same or different, a leaving group such as a halogen (e.g., Br, I), trifluoromehanesulfonyloxy, etc.

Compound (56) is prepared by reacting compound (23) with compound (55) in an inert solvent in the presence of a base.

The base includes alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

The compound of the present invention represented by the formula (14) is prepared by reacting compound (56) in an inert solvent in the presence of copper bromide, dichlorobis(triphenylphosphine)palladium and a base with compound (57).

The base includes alkylamines, such as triethylamine, ethyldiisopropylamine, diethylamine, etc.

The inert solvent includes, for example, aprotic solvents such as dimethylformamide, etc., ethers, such as THF, dioxane, etc., or a mixture thereof.

The reaction is carried out at a temperature of about 0° C. to about 80° C.

Method 9

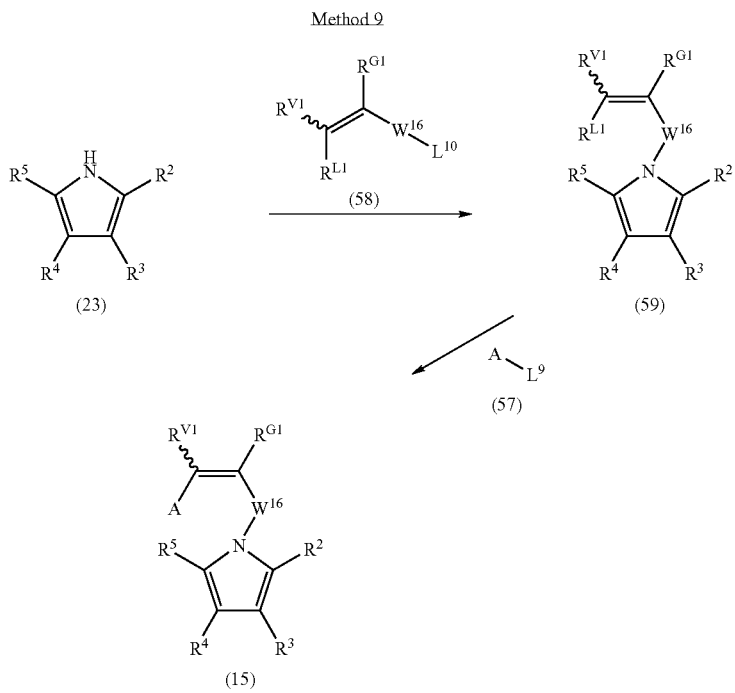

wherein $R^2$, $R^3$, $R^4$, $R^5$, A, $L^9$ and $W^{16}$ are the same as defined above, $R^{G1}$ and $R^{V1}$ are the same or different, hydrogen or alkyl, $R^{L1}$ is hydrogen, trialkyl Sn, substituted boron, etc., and $L^{10}$ is a leaving group such as a halogen (e.g., Cl, Br, I), methanesulfonyloxy, trifluoromethanesulfonyloxy, etc.

Compound (59) is prepared by reacting compound (23) with compound (58) in an inert solvent in the presence of a base.

The base includes, for example, alkali metal hydrides, such as sodium hydride, potassium hydride, etc., alkali metal alkoxides such as potassium t-butoxide, etc.

The inert solvent includes, for example, aprotic solvents such as dimethylformamide, etc., ethers, such as THF, dioxane, etc., or a mixture thereof.

The reaction is carried out at a temperature of about 0° C. to about 80 ° C.

The compound of the present invention represented by the formula (15) is prepared by reacting compound (59) in an inert solvent in the presence of transition metal catalyst and a base with compound (57).

The base includes alkylamines, such as triethylamine, ethyldiisopropylamine, etc., metal carbonate, such as potassium carbonate, silver carbonate, etc.

The transition metal catalyst includes zero vallent palladium catalyst, such as tetrakis(triphosphine)palladium, palladium dibenzylidene, etc., bivalent palladium catalyst, such as palladium acetate, dichlorobis(triphenylphosphine)palladium, etc., platinum catalyst, nickel catalyst, etc. In this reaction may be added a monovalent ligand, such as triphenylphosphine, tris(o-tolyl)phosphine, etc., or a divalent ligand, such as diphenylphosphynopropane, diphenylphosphynobutan.

The inert solvent includes, for example, aprotic solvents, such as acetonitrile, dimethylformamide, etc., ethers, such as THF, dioxane, etc., hydrocarbons, such as toluene, n-hexane, etc.

The reaction is carried out at a temperature of about 0° C. to about 80° C.

Examples of the substituents described in the above methods are as follows.

Alkylene moiety of $C_{1-4}$ alkylene group optionally substituted includes, for example, methylene, ethylene, trimethylene, tetramethylene, etc.

A substituent on substituted $C_{1-4}$ alkylene includes $C_{1-4}$ alkyl (e.g., methyl, ethyl, propyl, butyl, etc.), $C_{1-4}$ alkoxy (e.g., methoxy, ethoxy, propoxy, butoxy, etc.), hydroxy, $C_{1-4}$ alkanoyloxy (e.g., formyloxy, acetyloxy, propanoyloxy, butanoyloxy, etc.), a halogen (e.g., fluorine, chlorine, bromine, etc.), etc. And two hydrogen atoms on said alkylene group may be substituted with an oxygen atom to form a carbonyl.

Alkenylene moiety of $C_{2-4}$ alkenylene group optionally substituted includes, for example, cis or trans-vinylene, cis or trans-1-propenylene, cis or trans-2-propenylene, cis or trans-1-butenylene, cis or trans-2-butenylene, cis or trans-3-butenylene, etc.

A substituent on substituted $C_{2-4}$ alkenylene includes, $C_{1-4}$ alkyl (e.g., methyl, ethyl, propyl, butyl, etc.), etc. Methylene moiety in said alkenylene may form a carbonyl.

Alkynylene moiety of $C_{2-4}$ alkynylene group optionally substituted includes, for example, ethynylene, 1-propynylene, 2-propynylene, 1-butynylene, 2-butynylene, 3-butynylene, etc.

A substituent on substituted $C_{2-4}$ alkynylene includes, $C_{1-4}$ alkyl (e.g., methyl, ethyl, propyl, butyl, etc.), etc. Methylene moiety in said alkynylene may form a carbonyl.

Alkylene moiety of $C_{1-3}$ alkylene optionally substituted includes, for example, methylene, ethylene, trimethylene, etc.

A substituent on substituted $C_{1-3}$ alkylene includes $C_{1-4}$ alkyl (e.g., methyl, ethyl, propyl, butyl, etc.), $C_{1-4}$ alkoxy (e.g., methoxy, ethoxy, propoxy, butoxy, etc.), hydroxy, $C_{1-4}$ alkanoyloxy (e.g., formyloxy, acetyloxy, propanoyloxy, butanoyloxy, etc.), a halogen (e.g., fluorine, chlorine, bromine, etc.). And methylene moiety in said alkylene group may form a carbonyl.

Alkenylene moiety of $C_{2-3}$ alkenylene optionally substituted includes, for example, cis or trans-vinylene, cis or trans-1-propenylene, cis or trans-2-propenylene, etc.

A substituent on substituted $C_{2-3}$ alkenylene includes, $C_{1-4}$ alkyl (e.g., methyl, ethyl, propyl, butyl, etc.), etc. Methylene moiety in said alkenylene may form a carbonyl.

Alkylene moiety of alkylene optionally substituted includes, for example, $C_{1-5}$ alkylene, such as methylene, ethylene, trimethylene, tetramethylene, pentamethylene, etc.

A substituent on substituted alkylene includes $C_{1-4}$ alkyl (e.g., methyl, ethyl, propyl, butyl, etc.), $C_{1-4}$ alkoxy (e.g., methoxy, ethoxy, propoxy, butoxy, etc.), hydroxy, $C_{1-4}$ alkanoyloxy (e.g., formyloxy, acetyloxy, propanoyloxy, butanoyloxy, etc.), a halogen (e.g., fluorine, chlorine, bromine, etc.), etc. And methylene moiety in said alkylene may form a carbonyl.

Alkenylene moiety of alkenylene optionally substituted includes, for example, cis or trans-vinylene, cis or trans-1-propenylene, cis or trans-2-propenylene, cis or trans-1-butenylene, cis or trans-2-butenylene, cis or trans-3-butenylene, cis or trans-1-pentenylene, cis or trans-2-pentenylene, cis or trans-3-pentenylene, cis or trans-4-pentenylene, etc.

A substituent on substituted alkenylene includes, $C_{1-4}$ alkyl (e.g., methyl, ethyl, propyl, butyl, etc.), etc. Methylene moiety in said alkenylene may form a carbonyl.

Alkynylene moiety of alkynylene group optionally substituted includes $C_{2-5}$ alkynylene, such as ethynylene, 1-propynylene, 2-propynylene, 1-butynylene, 2-butynylene, 3-butynylene, 1-pentynylene, 2-pentynylene, 3-pentynylene, 4-pentynylene, etc.

A substituent on substituted alkynylene includes, $C_{1-4}$ alkyl (e.g., methyl, ethyl, propyl, butyl, etc.), etc. Methylene moiety in said alkynylene may form a carbonyl.

When the pyrrole derivatives or prodrugs thereof of the present invention exist in the form of an optical isomer, then the present invention also includes each isomer or a mixture thereof. In order to obtain an optical isomer of the present compound in pure form, there are for example, optical resolution methods.

One of the optical resolutions is to make the compound of the present invention or its intermediate form a salt, in an inert solvent (e.g., alcohols, such as methanol, ethanol, 2-propanol, ethers such as diethyl ether, esters such as ethyl acetate, aromatic hydrocarbons, such as toluene, acetonitrile, or a mixture thereof), with an optically active acid (e.g., a monocarboxylic acid, such as mandelic acid, N-benzyloxyalanine, lactic acid, a dicarboxylic acid, such as tartaric acid, o-diisopropilidene tartrate, malic acid, or a sulfonic acid, such as camphor sulfonic acid, bromocamphor sulfonic acid, etc.).

When the compound of the present invention, its prodrug or its intermediate has an acidic substituent such as carboxyl group, the compound can form a salt with an optically active amine (e.g., organic amine, α-phenethylamine, kinin, quinidine, cinchonidine, cinchonine, strychnine, etc.).

The reaction for a salt formation is carried out at a temperature of room temperature to the boiling point of the solvent. It is preferable to raise the temperature to around the boiling point of the solvent once to obtain the compound with optically high purity.

It may be possible to raise the yield by cooling the reaction mixture, if necessary, before collection the precipitated crystals.

The amount of an optically active acid or amine is about 0.5 to about 2.0 moles to the substrate, preferably about 1 mole. The resulting precipitate is, if necessary, recrystallized from an inert solvent (e.g., alcohols, such as methanol, ethanol, 2-propanol, ethers such as diethyl ether, esters such as ethyl acetate, aromatic hydrocarbons, such as toluene, acetonitrile, or a mixture thereof) to prepare a salt with its optically higher purity. The salt is further, if necessary converted into a free compound.

The pyrrole derivative of the present invention, or a prodrug thereof can be administered either orally or parenterally. The compound is orally administered in a usual manner. The compound is parenterally administered in the form of local administration, injection, dermal application, or nasal application. The pharmaceutical composition for oral administration or rectal administration includes, for example, capsules, tablets, pills, powders, cachets, suppositories, liquids, etc. The injections is in form of sterile solution or emulsion. The composition for local administration includes e.g., creams, ointments, lotions, preparations for dermal application (patches, matrixes, etc.).

These formulations are prepared by a conventional method with pharmaceutically acceptable excipients or additives. The pharmaceutically acceptable excipients and additives include carriers, binders, perfumes, buffering agents, viscosity-increasing agents, coloring agents, stabilizing agents, emulsifying agents, dispersing agents, suspending agents, preserving agents, etc.

The pharmaceutically acceptable carrier include magnesium carbonate, magnesium stearate, talc, sugar, lactose, pectin, dextrin, starch, gelatin, tragacanth, methyl cellulose, carboxymethylcellulose sodium, liquid wax, cacao butter, etc. Capsules are prepared by putting the compound of the present invention with pharmaceutically acceptable carriers into them. The compound of the present invention which is mixed with pharmaceutically acceptable excipients, or without excipients can be put in capsules. The cachets are prepare by the same manner as capsules.

The solution for injection includes solutions, suspensions or emulsions, such as aqueous solution or water-propylene glycol solution. The solution may contain water, and may be prepared in polyethylene glycol or/and propylene glycol solution. The solution suitable for oral administration is prepared by mixing the compound of the present invention with water, perfumes, coloring agents, stabilizing agents, sweetening agents, solubilizing agents, viscosity-increasing agents, if necessary. The solution suitable for oral administration is also prepared by adding the compound of the present invention with a dispersing agent to water to make it viscous.

The viscosity-increasing agent includes, for example, a pharmaceutically acceptable natural or synthetic gum, resin, methylcellulose, carboxymethylcellulose sodium, or a known suspending agent.

The preparation for local administration includes the above solutions, creams, aerosols, sprays, powders, lotions, and ointments. The preparation for local administration is prepared by mixing the compound of the present invention with conventional pharmaceutically acceptable diluents and carriers. The ointments or creams are prepared by adding viscosity-increasing agents and/or gel agents to an aqueous or oily base to prepare the preparation. The base includes water, liquid paraffin, plant-oil (peanut oil, castor oil), etc. The viscosity-increasing agent includes soft paraffin, aluminum stearate, cetostearyl alcohol, propylene glycol, polyethylene glycol, lanolin, hydrogenated lanolin, bees wax, etc.

The lotion is prepared by adding a stabilizing agent, a suspending agent, an emulsifying agent, a dispersing agent, a viscosity-increasing agent, a coloring agent, a perfume, etc., to a oily or aqueous base.

The powder is prepared with a base for a pharmaceutically acceptable. Said base includes talc, lactose, starch, etc. The drop is prepared with an oily or aqueous base and one or more pharmaceutically acceptable dispersing agent, suspending agent, soluvilizing agent, etc.

The preparation for local administration may contain, if necessary, a preservative agent, such as methyl hydroxybenzoate, propyl hydoxybenzoate, chlorocresol, benzalkonium chloride, a bacteria multiplication inhibitor, etc.

The pyrrole derivative or its salt can be administered to patients with diabetes mellitus, especially type II diabetes or noninsulin-dependent diabetes mellitus. The pyrrole derivative or its salt can control blood sugar of the patients. The dosage and the frequency of administration may vary according to the diseases, ages, weights of the patients and the administration form, etc., but the present compounds can usually be administered orally in a dose of about 1 to about 500 mg per day, preferably in a dose of about 5 to about 100 mg per day, in an adult, once a day, or divided into several dosage units. When the present compound is administered in an injection preparation, the dosage thereof is in the range of about 0.1 to about 300 mg per day, preferably in the range of about 1 to about 100 mg per day, in an adult, once a day, or divided into several dosage units.

The compounds of the present invention are illustrated as follows:

| Ex. No. | Structure |
|---|---|
| 1 | 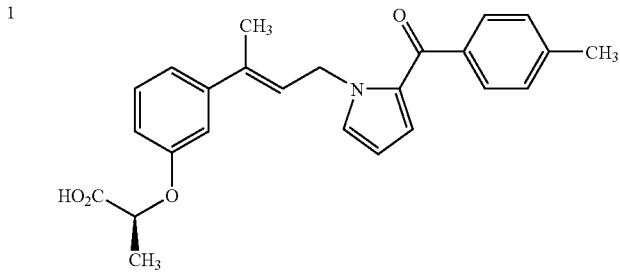 |
| 2 | 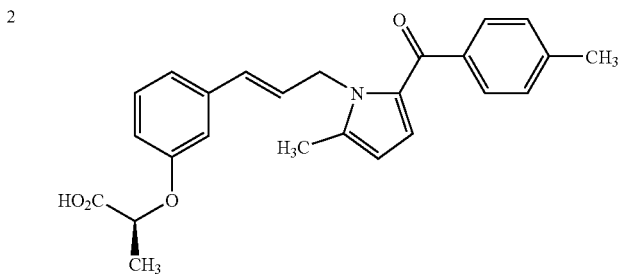 |
| 3 | 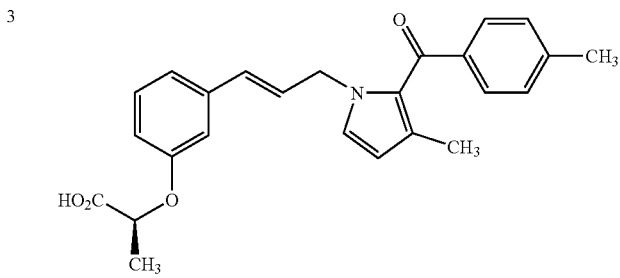 |

-continued
| Ex. No. | Structure |
|---|---|
| 4 | 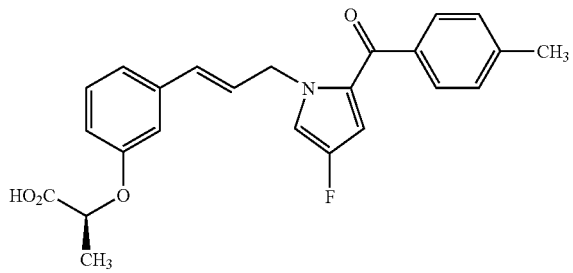 |
| 5 | 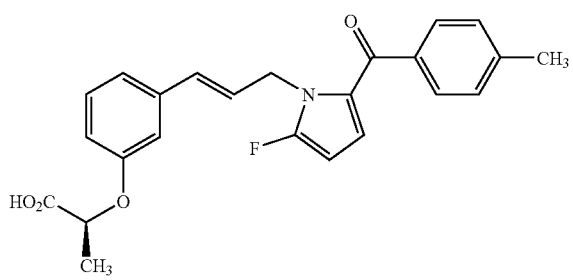 |
| 6 | 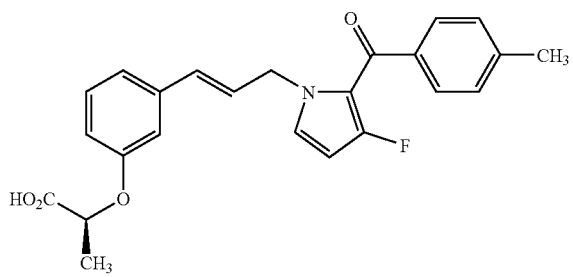 |
| 7 | 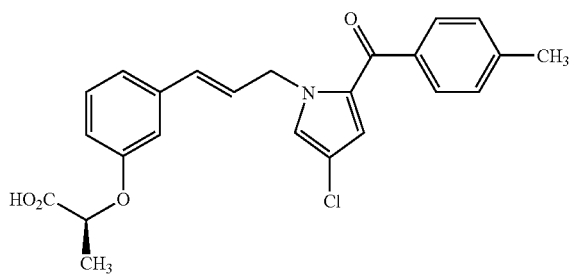 |
| 8 | 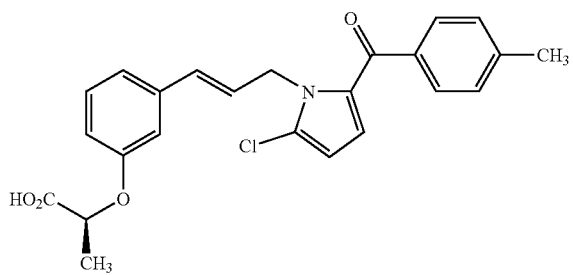 |

-continued
| Ex. No. | Structure |
|---|---|
| 9 | 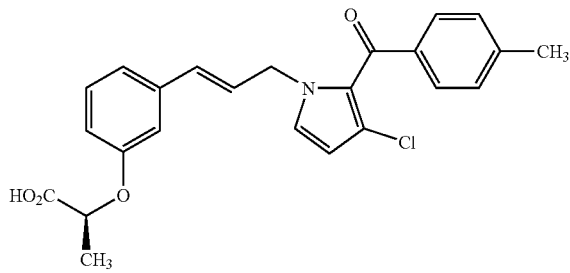 |
| 10 | 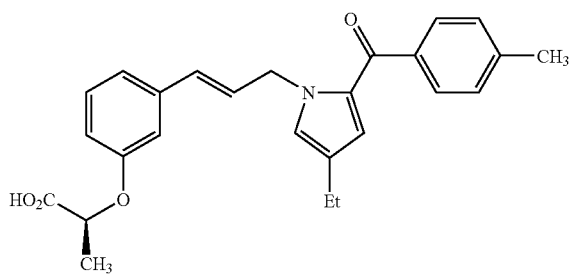 |
| 11 | 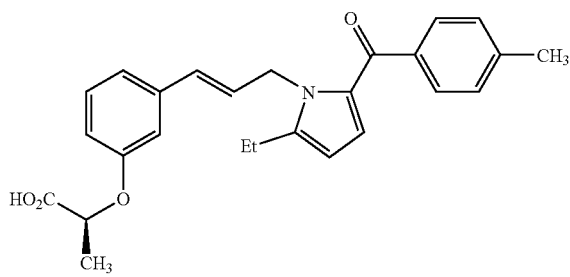 |
| 12 | 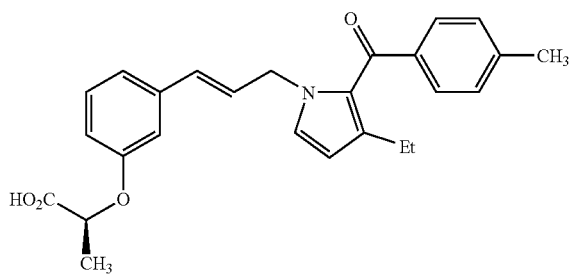 |
| 13 | 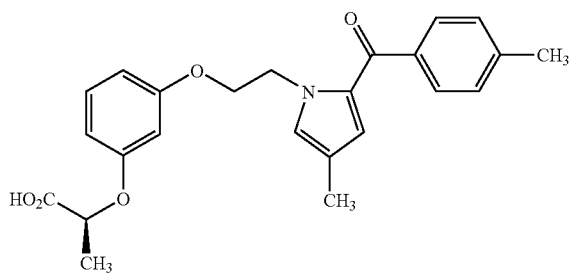 |

-continued
| Ex. No. | Structure |
|---|---|
| 14 | 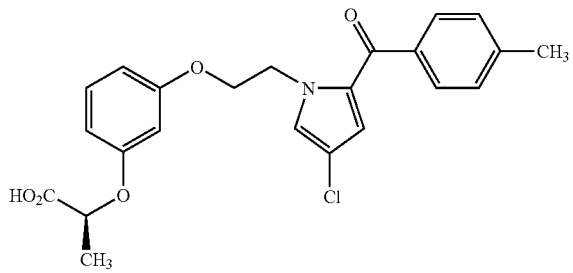 |
| 15 | 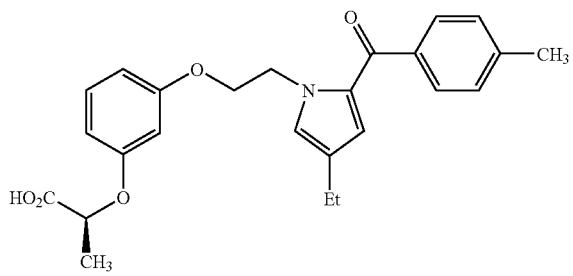 |
| 16 | 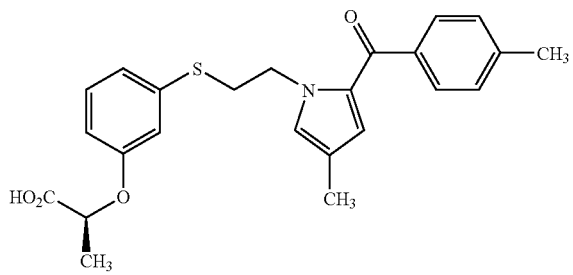 |
| 17 | 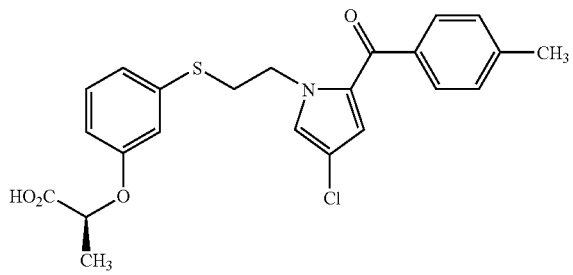 |
| 18 | 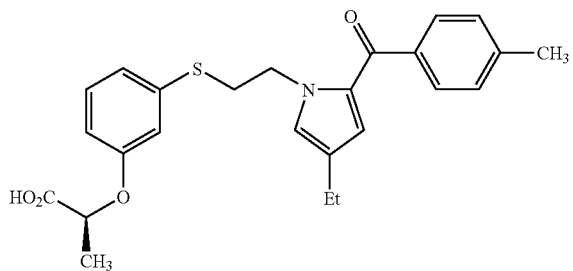 |

-continued
| Ex. No. | Structure |
|---|---|
| 19 | 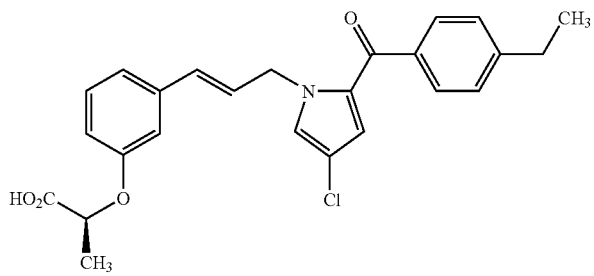 |
| 20 | 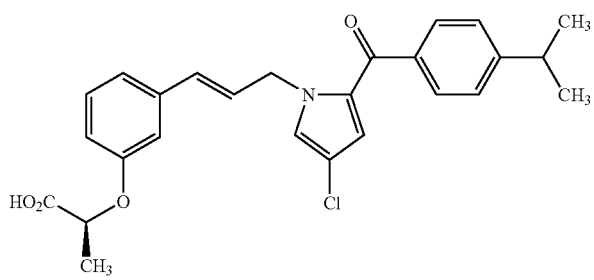 |
| 21 | 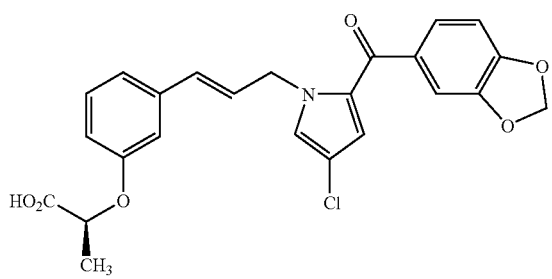 |
| 22 | 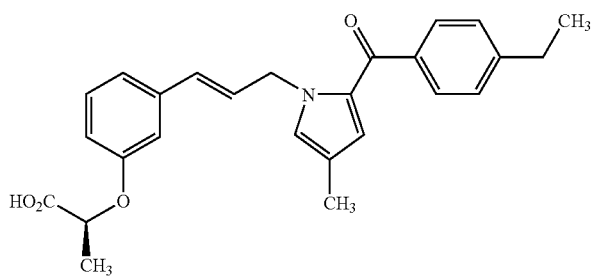 |
| 23 | 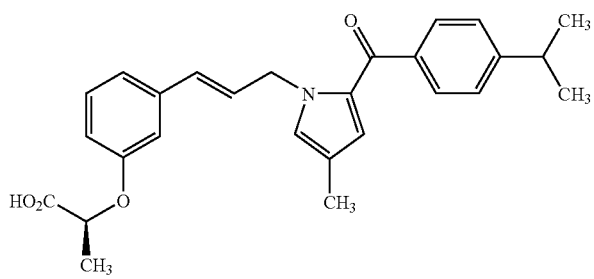 |

| Ex. No. | Structure |
|---|---|
| 24 | 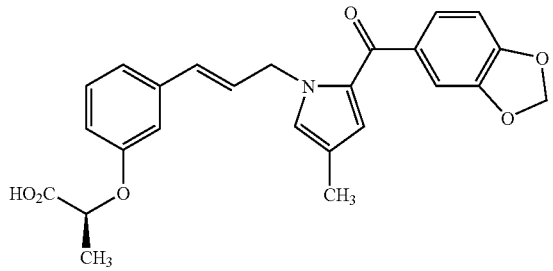 |
| 25 | 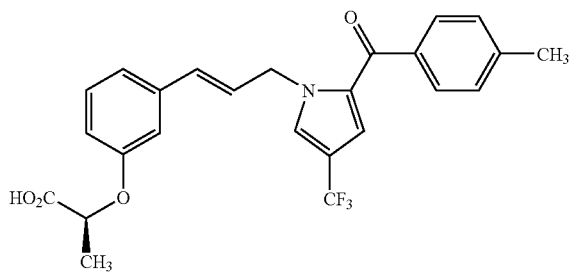 |
| 26 | 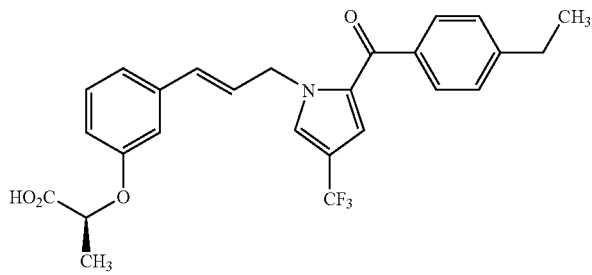 |
| 27 | 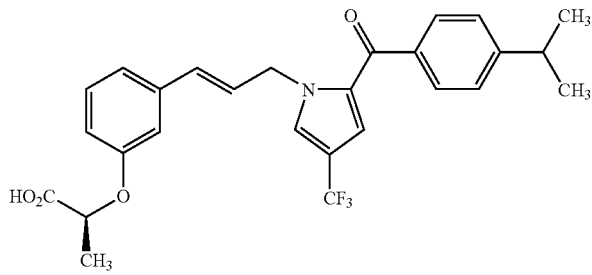 |
| 28 | 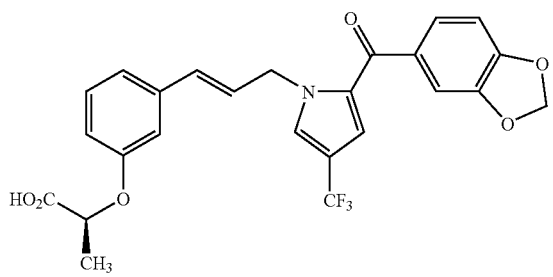 |

-continued
| Ex. No. | Structure |
|---|---|
| 29 | 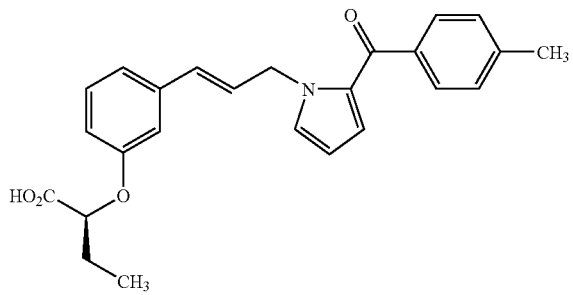 |
| 30 | 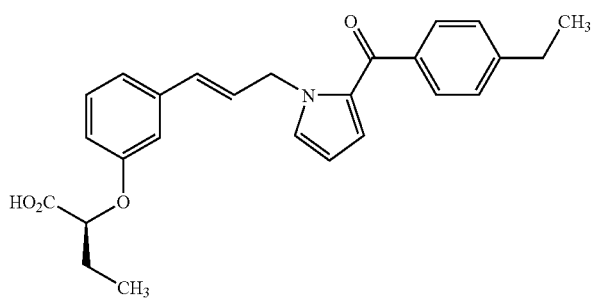 |
| 31 | 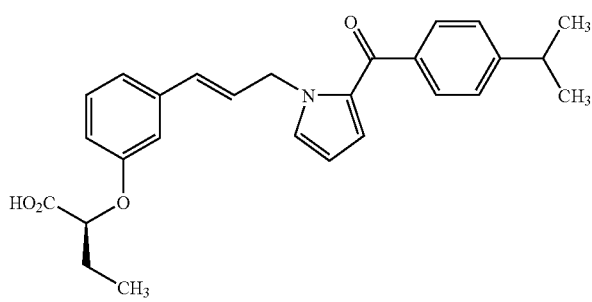 |
| 32 | 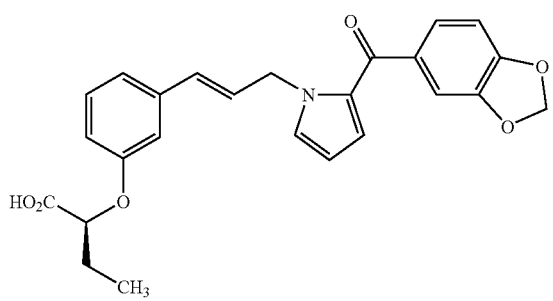 |
| 33 | 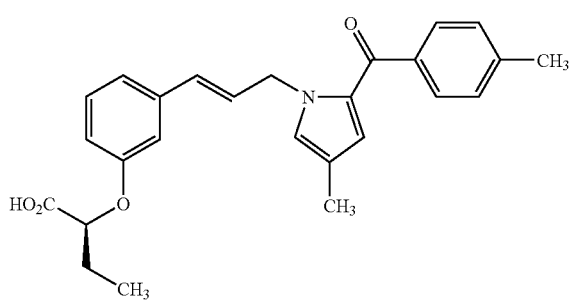 |

-continued
| Ex. No. | Structure |
|---|---|
| 34 | 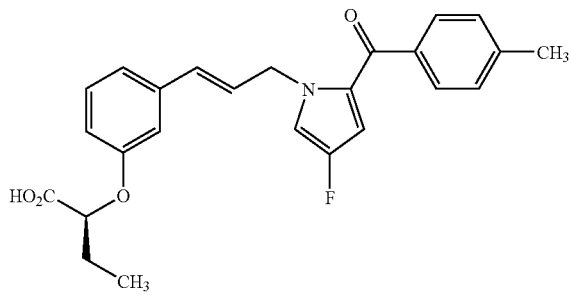 |
| 35 | 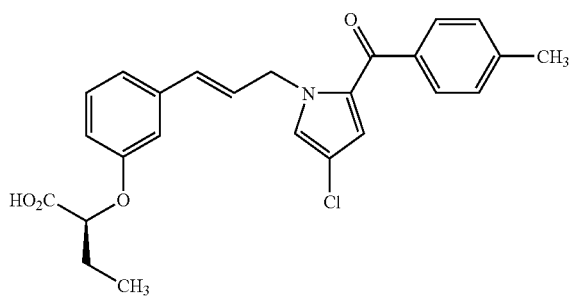 |
| 36 | 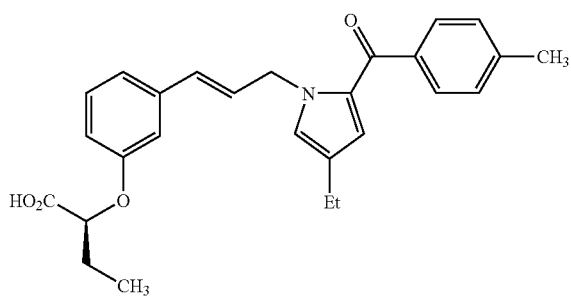 |
| 37 | 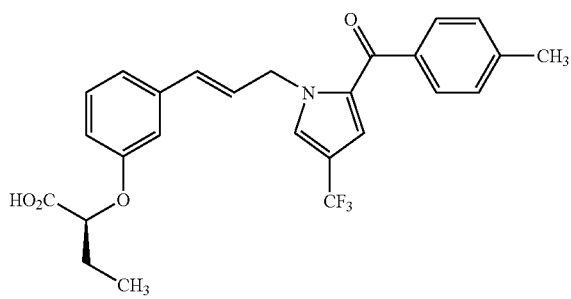 |
| 38 | 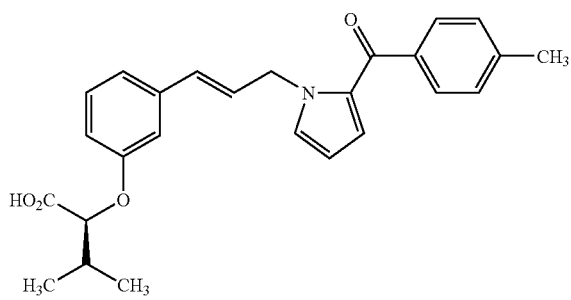 |

| Ex. No. | Structure |
|---|---|
| 39 | 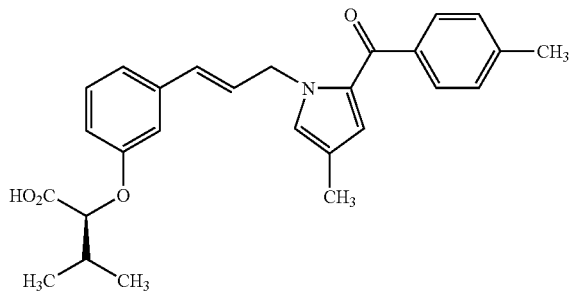 |
| 40 | 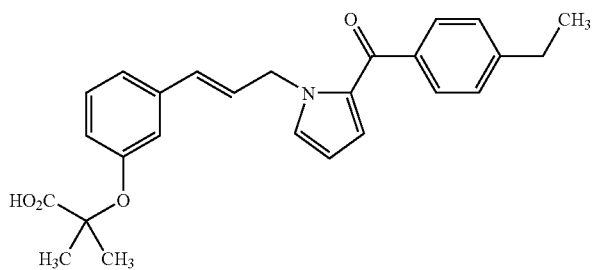 |
| 41 | 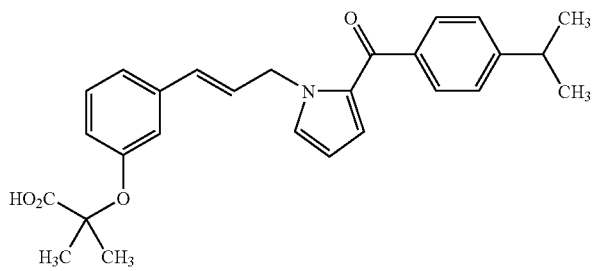 |
| 42 | 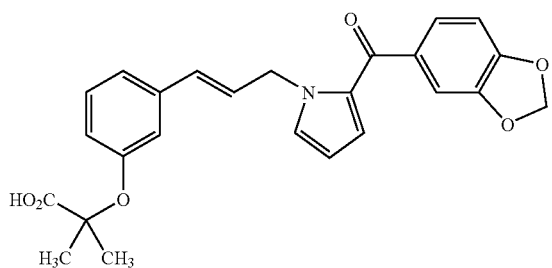 |
| 43 | 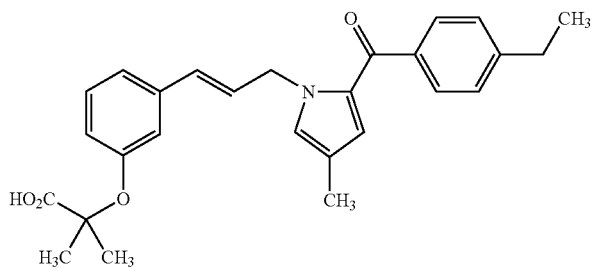 |

-continued
| Ex. No. | Structure |
|---|---|
| 44 | 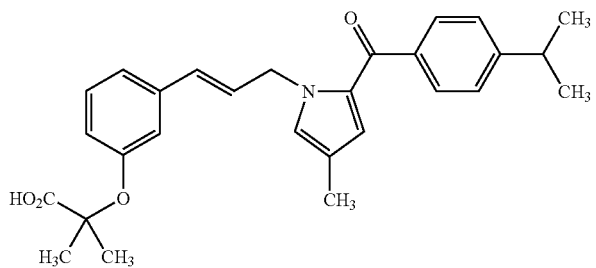 |
| 45 | 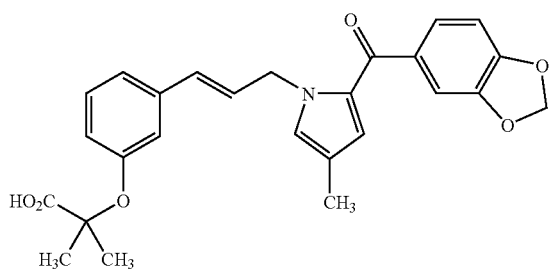 |
| 46 | 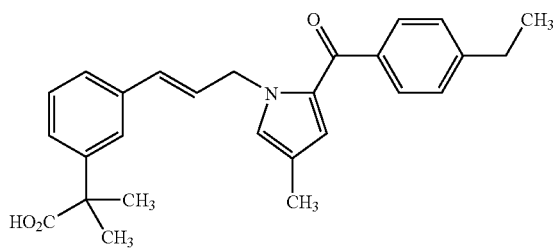 |
| 47 | 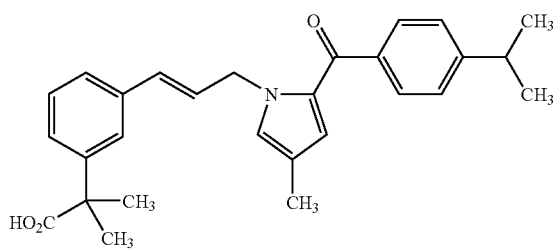 |
| 48 | 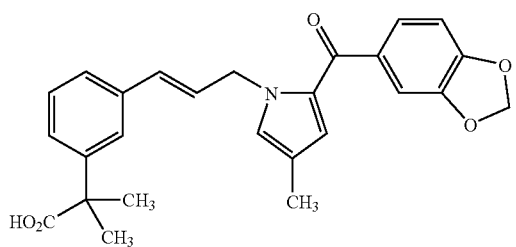 |

The present invention is explained by the following examples and reference examples.

EXAMPLE

Reference Example 1

Preparation for (1H-pyrrol-2-yl)(4-methylphenyl)ketone

Reference Example 1-1

Preparation for (1-benzenesulfonyl-1H-pyrrol-2-yl)(4-methylphenyl)ketone

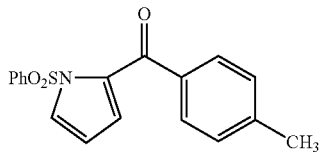

To a solution of 1-benzenesulfonyl-1H-pyrrole (284 g, 1.37 mol) in dichloromethane (1.0 L) were added p-toluoyl chloride (318 g, 2.06 mol) and boron trifluoride-diethyl ether (350 g, 2.47 mol) under an atmosphere of nitrogen. The mixture was allowed to stand at room temperature for 7 days. The reaction solution was washed with 1N hydrochloric acid (750 ml) twice, an aqueous 1N sodium hydroxide solution (750 ml) and a saturated aqueous sodium chloride solution (100 ml) in the order, dried and filtered. The filtrate was further concentrated to about 500 ml at atmospheric pressure, followed by addition of hexane (500 ml). Further the solution was concentrated to about 500 ml and cooled to 10° C. The precipitate was filtered, washed with hexane and toluene in the order, and dried to give the subject compound (315 g, 71%).

$^1$H NMR (CDCl$_3$, 300 MHz) δ 8.12 (d, 2 H, J=8.3 Hz), 7.75–7.78 (m, 1 H), 7.72 (brd, 2 H, J=7.9 Hz), 7.65 (brt, 1 H, J=7.9 Hz), 7.58 (brt, 2 H, J=7.9 Hz), 7.25 (d, 2 H, J=8.3 Hz), 6.69–6.72 (m, 1 H), 6.35 (dd, 1 H, J=3.1 and 0.5 Hz), 2.42 (s, 3 H).

Reference Example 1-2

Preparation for (1H-pyrrol-2-yl)(4-methylphenyl)ketone

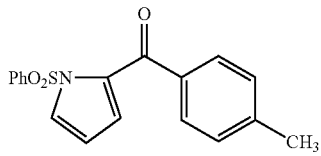

The compound (145 g, 446 mol) prepared by Reference example 1-1 was suspended in methanol (1.0 L) and thereto was added an aqueous 5N sodium hydroxide solution (1.1 kg). The mixture was refluxed under heating for 30 min. and then gradually cooled to 0° C. The precipitate was collected by filtration and dried to give the subject compound (80 g, 97%).

$^1$H NMR (CDCl$_3$, 300 MHz) δ 9.52 (brs, 1 H), 8.25 (d, 2 H, J=8.3 Hz), 7.29 (d, 2 H, J=8.3 Hz), 7.12 (brs, 1 H), 6.88–6.91 (m, 1 H), 6.32–6.36 (m, 1 H), 2.44 (s, 3 H).

Reference Example 2

Preparation for (1H-pyrrol-2-yl)[4-(methoxy)phenyl]ketone

Reference Example 2-1

Preparation for (1-benzenesulfonyl-1H-pyrrol-2-yl)[4-(methoxy)phenyl]ketone

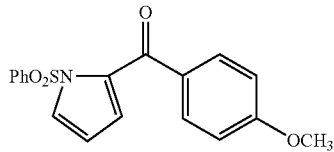

The subject compound was prepared starting from 4-methoxybenzoyl chloride in the same manner as Reference example 1-1.

$^1$H NMR (CDCl$_3$, 400 MHz) δ 8.12 (dt, 2 H, J=7.2 and 1.5 Hz), 7.84 (d, 2 H, J=8.9 Hz), 7.73 (dd, 1 H, J=1.7 and 3.2 Hz), 7.65 (tt, 1 H, J=1.5 and 7.2 Hz), 7.58 (tt, 2 H, J=1.5 and 7.2 Hz), 6.93 (d, 2 H, J=8.9 Hz), 6.68 (dd, 1 H, J=1.7 and 3.6 Hz), 6.34 (dd, 1 H, J=3.2 and 3.6 Hz), 3.87 (s, 3 H).

Reference Example 2-2

Preparation for (1H-pyrrol-2-yl)[4-(methoxy)phenyl]ketone

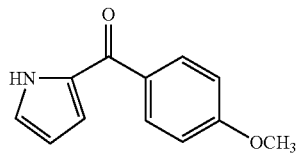

The subject compound was prepared starting from the compound of Reference example 2-1 in the same manner as Reference example 1-2.

$^1$H NMR (CDCl$_3$, 400 MHz) δ 9.54 (brs, 1 H), 7.94 (d, 2 H, J=8.9 Hz), 7.12 (dt, 1 H, J=1.3 and 2.7 Hz), 6.93 (d, 2 H, J=8.9 Hz), 6.89 (ddd, 1 H, J=3.8, 2.4 and 1.3 Hz), 6.34 (dt, 1 H, J=3.8 and 2.7 Hz), 3.89 (s, 3 H).

Reference Example 3

Preparation for (4-methyl-1H-pyrrol-2-yl)(4-methoxyphenyl)ketone

Reference Example 3-1

Preparation for (4-formyl-1H-pyrrol-2-yl)(4-methoxyphenyl)ketone

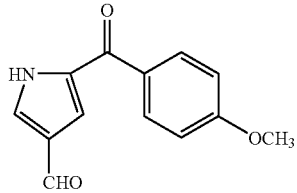

The compound (1.50 g, 7.45 mmol) of Reference example, 2-2 was dissolved in nitromethane (8.0 g) and ethylene dichloride (8.0 g). Thereto was added aluminum chloride (3.99 g, 29.8 mmol) under cooling at 10° C. To the mixture was dropped dichloromethyl methyl ether (1.88 g, 16.4 mmol) in ethylene dichloride(3.0 g) and the mixture was stirred for 1 hour. To the mixture was added hydrochloric acid and the solution was extracted with chloroform. The organic layer was treated with magnesium sulfate and charcoal, filtered and concentrated. The residue was washed with toluene to give the subject compound (1.2 g, 70%).

$^1$H NMR (CDCl$_3$, 400 MHz) δ 10.20 (brs, 1 H), 9.90 (s, 1 H), 7.98 (d, 2 H, J=8.9 Hz), 7.72 (dd, 1 H, J=3.3 and 1.4 Hz), 7.33 (dd, 1 H, J=2.3 and 1.4 Hz), 7.01 (d, 2 H, J=8.9 Hz), 3.91 (s, 3 H).

Reference Example 3-2

Preparation for (4-methyl-1H-pyrrol-2-yl)(4-methoxyphenyl)ketone

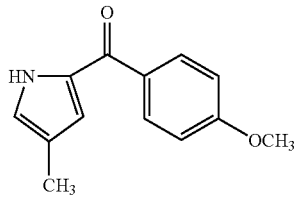

The compound (230 mg, 1.00 mmol) of Reference example 3-1 was stirred for 8 hours with 10% palladium-carbon (230 mg) in tetrahydrofuran (3.0 ml) under an atmosphere of hydrogen. The mixture was filtered and the filtrate was concentrated. The residue was purified with silica gel chromatography to give the subject compound (130 mg, 60%).

$^1$H NMR (CDCl$_3$, 400 MHz) δ 9.38 (brs, 1 H), 7.92 (d, 2 H, J=8.9 Hz), 6.97 (d, 2 H, J=8.9 Hz), 6.89–6.90 (m, 1 H), 6.70 (dd, 1 H, J=1.2, 2.0 Hz), 3.88 (s, 3 H), 2.15 (s, 3H).

Reference Example 4

Preparation for (1H-pyrrol-3-yl)(4-methylphenyl)ketone

Reference Example 4-1

Preparation for (1-benzenesulfonyl-1H-pyrrol-3-yl)(4-methylphenyl)ketone

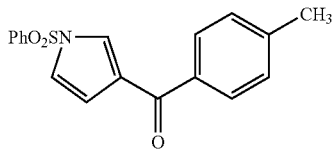

A solution of p-toluoyl chloride (4.91 g, 31.8 mmol) in ethylene dichloride (5 ml) was added to a suspension of aluminum chloride (4.62 g, 34.7 mmol) in ethylene dichloride (5 ml) in a 10 minutes period under an atmosphere of nitrogen. After 30 minutes thereto was added a solution of 1-benzenesulfonyl-1H-pyrrole (6.00 g, 28.9 mmol) in ethylene dichloride in a 10 minutes period and the mixture was stirred at room temperature for 2 hours. The reaction mixture was poured into ice-water and the aqueous layer was extracted with dicloromethane twice. The organic layers were combined, dried and filtered. The filtrate was concentrated and the residue was purified with silica gel chromatography to give the subject compound (9.9 g, 100%).

$^1$H NMR (CDCl$_3$, 300 MHz) δ 7.89 (brd, 2 H, J=7.9 Hz), 7.73 (d, 2 H, J=8.0 Hz), 7.65 (brt, 1 H, J=7.9 Hz), 7.65 (brs, 1 H), 7.34 (brt, 2 H, J=7.9 Hz), 7.29 (d, 2 H, J=8.0 Hz), 7.22 (dd, 1 H, J=2.2 and 2.8 Hz), 6.80 (dd, 1 H, J=1.5 and 2.8 Hz), 2.44 (s, 3 H).

Reference Example 4-2

Preparation for (1H-pyrrol-3-yl)(4-methylphenyl)ketone

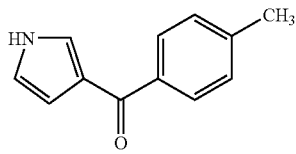

The compound (6.50 g, 20.0 mmol) of Reference example 4-1, an aqueous 5N sodium hydroxide solution (70 ml) and tetrahydrofuran (70 ml) were stirred for 6 hours at 45° C. The organic layer was separated, concentrated to 5 ml and allowed to stand at room temperature for 2 days. The resulting crystals were filtered and washed with cold tetrahydrofuran to give the subject compound (3.1 g, 84%).

$^1$H NMR (CDCl$_3$, 300 MHz) δ 7.76 (d, 2 H, J=8.1 Hz), 7.35 (brquint., 1 H, J=1.5 Hz), 7.26 (d, 2 H, J=8.1 Hz), 6.84 (brq, 1 H, J=1.5 Hz), 6.76 (brs, 1 H), 2.43 (s, 3 H).

Reference Example 5

Preparation for (1H-pyrrol-2-yl)(2-methylphenyl)ketone

Reference Example 5-1

Preparation for (1-benzenesulfonyl-1H-pyrrol-2-yl) (2-methylphenyl)ketone

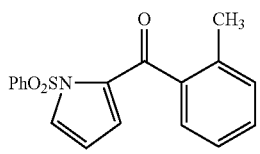

The subject compound was prepared starting from 2-methylbenzoyl chloride in the same manner as Reference example 1-1.

$^1$H NMR (CDCl$_3$, 400 MHz) δ 8.09–8.12 (m, 2 H), 7.84 (dd, 1 H, J=3.1, 1.8 Hz), 7.62–7.77 (m, 1 H), 7.54–7.59 (m,2 H), 7.27–7.36 (m, 2 H), 7.15–7.21 (m, 2 H), 6.56 (dd, 1 H, J=3.7 and 1.8 Hz), 6.31 (dd, 1 H, J=3.7 and 3.1 Hz), 2.19 (s, 3 H).

Reference Example 5-2

Preparation for the Following Compound:

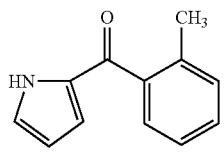

The above compound was prepared starting from the compound of Reference example 5-1 in the same manner as Reference example 1-2.

$^1$H NMR (CDCl$_3$, 400 MHz) δ 9.43 (brs, 1 H), 7.49 (dd, 1 H, J=7.5 and 1.3 Hz), 7.37 (dt, 1 H, J=7.5 and 1.4 Hz), 7.22–7.29 (m, 2 H), 7.13 (dt, 1 H, J=2.5 and 1.3 Hz), 6.62 (ddd, 1 H, J=3.8, 2.5 and 1.3 Hz), 6.30 (dt, 1 H, J=3.8 and 2.5 Hz), 2.41 (s, 3 H).

Reference Example 6

Preparation for methyl {3-[(1E)-3-bromo-1-propenyl]phenoxy}acetate

Referential Example 6-1

Preparation for methyl (3-iodophenoxy)acetate

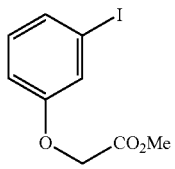

3-Iodophenol (4.00 g, 18.2 mmol), ethyl bromoacetate (2.98 g, 18.2 mmol) and potassium carbonate (2.51 g, 18.2 mmol) were refluxed in acetone (40 ml) for 2 hours. The reaction mixtute was poured into water and extracted with ethyl acetate. The organic layer was dried, and filtered. The filtrate was concentrated and the residue was purified with silica gel chromatography to give the subject compound (5.30 g, 99%).

$^1$H NMR (CDCl$_3$, 400 MHz) δ 7.34 (brd, 1 H, J=8.0 Hz), 7.25–7.28 (m, 1 H), 7.01 (t, 1 H, J=8.0 Hz), 6.88 (ddd, 1 H, J=8.0, 2.4 and 0.4 Hz), 4.61 (s, 2 H), 3.82 (s, 3 H).

Reference Example 6-2

Preparation for methyl {3-[(1E)-3-oxo-1-propenyl]phenoxy}acetate

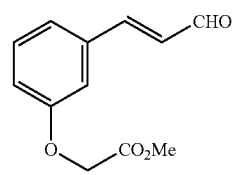

A mixture of the compound (4.80 g, 16.4 mmol) of Reference example 6-1, acrolein (1.84 g, 32.8 mmol), sodium hydrogencarbonate (2.76 g, 32.9 mmol), benzyltriethylammonium chloride (3.74, 16.4 mmol) and palladium acetate (70.0 mg, 0.320 mmol) in N,N-dimethylformamide (35 ml) was stirred for 8 hours at 50° C. The reaction mixture was diluted with water. After the insoluble materials were removed by filtration, the filtrate was extracted with toluene. The organic layer was washed with an aqueous 5% sodium thiosulfate solution, water and an aqueous saturated sodium chloride solution in the order and dried over magnesium sulfate. The solvent was removed under reduced pressure to give the subject compound (3.56 g, 98%).

$^1$H NMR (CDCl$_3$, 400 MHz) δ 9.71 (d, 1 H, J=7.7 Hz), 7.44 (d, 1 H, J=15.9 Hz), 7.37 (t, 1 H, J=8.0 Hz), 7.22 (brd, 1 H, J=8.0 Hz), 7.10 (t, 1 H, J=2.3 Hz), 6.99 (ddd, 1 H, J=8.0, 2.3 and 0.7 Hz), 6.69 (dd, 1 H, J=15.9 and 7.7 Hz), 4.68 (s, 2 H), 3.83 (s, 3 H).

Reference Example 6-3

Preparation for methyl {3-[(1E)-3-hydroxy-1-propenyl]phenoxy}acetate

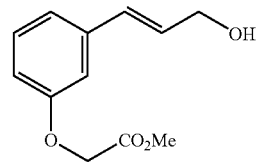

To a solution of the compound (3.94 g, 17.9 mmol) of Reference example 6-2 in tetrahydrofuran (20 ml) and methanol (20 ml) was added sodium borohydride (650 mg, 17.2 mmol) under ice cooling and the mixture was stirred for 1 hour at 0° C. Thereto was added diluted hydrochloric acid and the mixture was extracted with ethyl acetate. The organic layer was washed with water and an aqueous saturated sodium chloride solution in the order, and dried over magnesium sulfate. The solvent was removed under reduced pressure. The residue was separated and purified with silica gel chromatography (hexane:ethyl acetate=1:1→ethyl acetate) to give the subject compound (2.28 g, 57%).

¹H NMR (CDCl₃, 400 MHz) δ 7.25 (t, 1 H, J=8.0 Hz), 7.04 (brd, 1 H, J=8.0 Hz), 6.94 (t, 1 H, J=2.3 Hz), 6.79 (dd, 1 H, J=8.0 and 2.3 Hz), 6.58 (d, 1 H, J=15.9 Hz), 6.35 (dt, 1 H, J=15.9 and 5.6 Hz), 4.65 (s, 2 H), 4.33 (dt, 2 H, J=1.4 and 5.8 Hz), 3.82 (s, 3 H), 1.45 (t, 1 H, J=5.8 Hz).

Reference Example 6-4

Preparation for methyl {3-[(1E)-3-bromo-1-propenyl]phenoxy}acetate

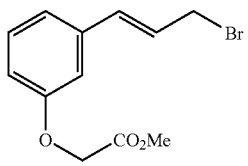

To a solution of the compound (330 mg, 1.45 mmol) of Reference example 6-3 and triphenylphosphine (440 mg, 1.68 mmol) in dichloromethane (5.0 ml) was added under ice cooling N-bromosuccinimide (310 mg, 1.74 mmol) and the solution was stirred for 30 minutes at 0° C. To the reaction solution were further added triphenylphosphine (80.0 mg, 0.310 mmol) and N-bromosuccinimide (60.0 mg, 0.34 mmol) and the mixture was stirred for additional 30 minutes at room temperature. The reaction mixture was concentrated under reduced pressure and the residue was purified with silica gel chromatography (hexane:ethyl acetate=6:1→2:1) to give the subject compound (370 mg, 90%).

¹H NMR (CDCl₃, 400 MHz) δ 7.25 (t, 1 H, J=8.0 Hz), 7.04 (d, 1 H, J=8.0 Hz), 6.94 (t, 1 H, J=2.3 Hz), 6.82 (dd, 1 H, J=8.0 and 2.3 Hz), 6.60 (d, 1 H, J=15.6 Hz), 6.38 (dt, 1 H, J=15.6 and 7.8 Hz), 4.65 (s, 2 H), 4.15 (dd, 2 H, J=7.8 and 0.7 Hz), 3.82 (s, 3 H).

Example 1

Preparation for (3-{(1E)-3-[2-(4-methylbenzoyl)-1H-pyrrol-1-yl]-1-propenyl}phenoxy)acetic acid Example 1-1

Preparation for methyl (3-{(1E)-3-[2-(4-methylbenzoyl)-1H-pyrrol-1-yl]-1-propenyl}phenoxy)acetate

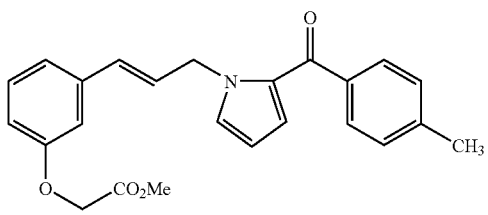

To a solution of potassium t-butoxide (160 mg, 1.43 mmol) in terahydrofuran (3.0 ml) was added the compound (240 mg, 1.30 mmol) of Reference example 1 in tetrahydrofuran (2.0 ml) and the mixture was stirred for 20 minutes at room temperature. Thereto was added a solution of the compound (370 mg, 1.30 mmol) of Reference example 6 in tetrahydrofuran (4.0 ml) under ice cooling and the solution was stirred for 1.5 hours at room temperature. To the solution was added an aqueous 5% potassium hydrogensulfate solution and the mixture was extracted with ethyl acetate. The organic layer was washed with an aqueous saturated sodium chloride solution and dried over magnesium sulfate. The solvent was removed under reduced pressure and the residue was purified with silica gel chromatography (hexane:ethyl acetate=4:1→chloroform:methanol=10:1) to give the subject compound (155 mg, 31%).

¹H NMR (CDCl₃, 400 MHz) δ 7.73 (d, 2 H, J=8.1 Hz), 7.25 (d, 2 H, J=8.1 Hz), 7.21 (t, 1 H, J=7.6 Hz), 7.04 (dd, 1 H, J=2.5 and 1.7 Hz), 7.00 (brd, 1 H, J=7.6 Hz), 6.90 (dd, 1 H, J=4.0 and 1.6 Hz), 6.76–6.79 (m, 1 H), 6.77 (dd, 1 H, J=4.0 and 1.7 Hz), 6.46 (d, 1 H, J=15.6 Hz), 6.41 (dt, 1 H, J=15.6 and 4.8 Hz), 6.20 (dd, 1 H, J=4.0 and 2.5 Hz), 5.19 (d, 2 H, J=4.8 Hz), 4.62 (s, 2 H), 3.80 (s, 3 H), 2.42 (s, 3 H).

Example 1-2

Preparation for (3-{(1E)-3-[2-(4-methylbenzoyl)-1H-pyrrol-1-yl]-1-propenyl}phenoxy)acetic acid

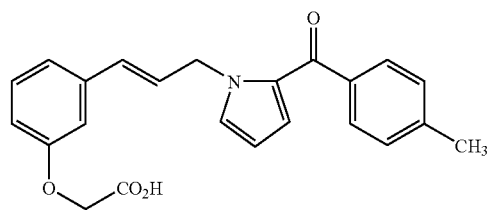

A solution of the compound (153 mg, 0.393 mmol) of Example 1-1 in an aqueous 1N lithium hydroxide solution (1.0 ml), terahydrofuran (1.0 ml) and methanol (1.0 ml) was stirred for 30 minutes at room temperature. Thereto was added diluted hydrochloric acid and the solution was extracted with ethyl acetate. The organic layer was washed with an aqueous saturated sodium chloride solution and dried over magnesium sulfate. The solvent was removed under reduced pressure to give the subject compound (148 mg, 100%).

¹H NMR (CDCl₃, 400 MHz) δ 7.72 (d, 2 H, J=8.1 Hz), 7.25 (d, 2 H, J=8.1 Hz), 7.21 (t, 1 H, J=8.0 Hz), 7.03 (dd, 1 H, J=2.5 and 1.7 Hz), 7.01 (brd, 1 H, J=8.0 Hz), 6.90–6.92 (m, 1 H), 6.76–6.81 (m, 1 H), 6.77 (dd, 1 H, J=4.0 and 1.7 Hz), 6.38–6.47 (m, 2 H), 6.20 (dd, 1 H, J=4.0 and 2.5 Hz), 5.17–5.20 (m, 2 H), 4.63 (s, 2 H), 2.42 (s, 3 H).

Example 2

Preparation for (3-{(1E)-3-[3-(4-methylbenzoyl)-1H-pyrrol-1-yl]-1-propenyl}phenoxy)acetic acid

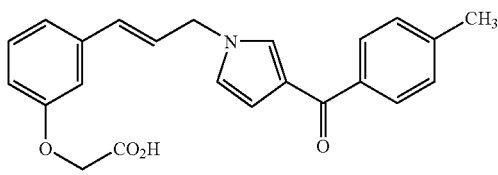

To a solution of potassium t-butoxide (90 mg, 0.80 mmol) in terahydrofuran (1.5 ml) was added the compound (133 mg, 0.718 mmol) of Reference example 4 in tetrahydrofuran (1.5 ml) and the mixture was stirred for 5 minutes at room temperature. Thereto was added the compound (200 mg, 0.700 mmol) of Reference example 6 under ice cooling and the mixture was stirred for 16 hours at room temperature. To the reaction mixture was added an aqueous 5% potassium hydrogensulfate solution and the mixture was extracted with ethyl acetate. The organic layer was washed with water and an aqueous saturated sodium chloride solution, and dried over magnesium sulfate. The solvent was removed under reduced pressure and the resulting methyl ester of the subject compound (309 mg) was dissolved in terahydrofuran (3.0 ml) and methanol (3.0 ml). Thereto was added an aqueous 1N lithium hydroxide solution (3.0 ml) and the mixture was stirred for 2 hours at room temperature. The reaction mixture was diluted with water and washed with diethyl ether. The aqueous layer was acidified with diluted hydrochloric acid and the mixture was extracted with diethyl ether. The organic layer was washed with an aqueous saturated sodium chloride solution and dried over magnesium sulfate. The solvent was removed under reduced pressure to give the subject compound (240 mg, 91%).

$^1$H NMR (CDCl$_3$, 400 MHz) δ 7.76 (d, 2 H, J=8.1 Hz), 7.28–7.31 (m, 1 H), 7.25–7.28 (m, 1 H), 7.25 (d, 2 H, J=8.1 Hz), 7.03 (bd, 1 H, J=7.8 Hz), 6.92–6.94 (m, 1 H), 6.84 (dd, 1 H, J=7.8 and 2.1 Hz), 6.71–6.74 (m, 2 H), 6.48 (d, 1 H, J=15.8 Hz), 6.30 (dt, 1 H, J=15.8 and 6.1 Hz), 4.68 (s, 2 H), 4.67–4.70 (m, 2 H), 2.42 (s, 3 H).

Example 3

Preparation for (3-{(1E)-3-[2-(4-methoxybenzoyl)-1H-pyrrol-1-yl]-1-propenyl}phenoxy)acetic acid

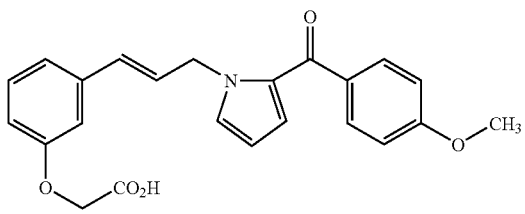

The subject compound was prepared starting from the compound of Reference example 6 and the compound of Reference example 2 in the same manner as Example 2.

$^1$H NMR (CDCl$_3$, 400 MHz) δ 7.84 (d, 2 H, J=8.8 Hz), 7.23 (t, 1 H, J=8.0 Hz), 7.01–7.05 (m, 2 H), 6.95 (d, 2 H, J=8.8 Hz), 6.91–6.93 (m, 1 H), 6.80 (dd, 1 H, J=8.0 and 2.3 Hz), 6.77 (dd, 1 H, J=4.0 and 1.7 Hz), 6.42–6.47 (m, 2 H), 6.22 (dd, 1 H, J=4.0 and 2.5 Hz), 5.17–5.20 (m, 2 H), 4.66 (s, 2 H), 3.88 (s, 3 H).

Example 4

Preparation for (3-{(1E)-3-[2-(4-methoxybenzoyl)-4-methyl-1H-pyrrol-1-yl]-1-propenyl}phenoxy)acetic acid

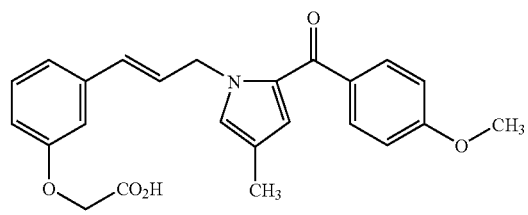

The subject compound was prepared starting from the compound of Reference example 6 and the compound of Reference example 3 in the same manner as Example 2.

$^1$H NMR (CDCl$_3$, 400 MHz) δ 7.83 (d, 2 H, J=8.8 Hz), 7.23 (t, 1 H, J=8.0 Hz), 7.04 (brd, 1 H, J=8.0 Hz), 6.95 (d, 2 H, J=8.8 Hz), 6.91–6.95 (m, 1 H), 6.82 (brs, 1 H), 6.80 (dd, 1 H, J=8.0 and 2.5 Hz), 6.57 (brs, 1 H), 6.38–6.48 (m, 2 H), 5.11–5.13 (m, 2 H), 4.66 (s, 2 H), 3.88 (s, 3 H), 2.09 (3 H, s).

Example 5

Preparation for (3-{(1E)-3-[2-(2-methylbenzoyl)-1H-pyrrol-1-yl]-1-propenyl}phenoxy)acetic acid

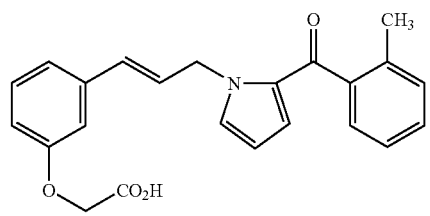

The subject compound was prepared starting from the compound of Reference example 6 and the compound of Reference example 5 in the same manner as Example 2.

$^1$H NMR (CDCl$_3$, 400 MHz) δ 7.36 (brd, 1 H, J=7.7 Hz), 7.32 (dd, 1 H, J=7.7 and 1.4 Hz), 7.23 (brd, 2 H, J=7.7 Hz), 7.21 (t, 1 H, J=7.8 Hz), 7.05 (t, 1 H, J=2.0 Hz), 7.03 (d, 1 H, J=7.8 Hz), 6.93 (dd, 1 H, J=2.5 and 1.7 Hz), 6.81 (dd, 1 H, J=7.8 and 2.0 Hz), 6.53 (dd, 1 H, J=4.0 and 1.7 Hz), 6.43–6.50 (m, 1 H), 6.43 (d, 1 H, J=15.9 Hz), 6.16 (dd, 1 H, J=4.0 and 2.5 Hz), 5.26–5.28 (m, 2 H), 4.67 (s, 2 H), 2.33 (s, 3 H).

Reference Example 7-1

Preparation for 1-iodo-3-(methoxymethoxy)benzene

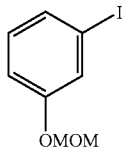

To a solution of m-iodophenol (3.00 g, 13.6 mmol) in acetone (30 ml) were added potassium carbonate (2.30 g, 16.6 mmol) and chloromethyl methyl ether (1.20 g, 14.9 mmol) under ice cooling and the mixture was stirred for 65 hours at room temperature. To the reaction mixture were further added potassium carbonate (0.600 g, 4.30 mmol) and chloromethyl methyl ether (0.300 g, 3.70 mmol), and the mixture was stirred for 2 hours at room temperature. To the reaction mixture was added water and the mixture was extracted with ethyl acetate. The organic layer was washed with an aqueous saturated sodium chloride solution, and dried over magnesium sulfate. The solvent was removed under reduced pressure to give the subject compound (3.68 g, 102%).

$^1$H NMR (CDCl$_3$, 400 MHz) δ 7.40–7.42 (m, 1 H), 7.34 (dt, 1 H, J=3.6 and 1.6 Hz), 6.99–7.02 (m, 2 H), 5.15 (s, 2 H), 3.47 (s, 3 H).

Reference Example 7-2

Preparation for (2E)-3-[3-(methoxymethoxy)phenyl]-2-propanal

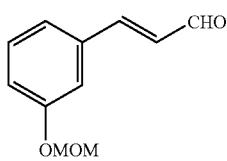

The subject compound was prepared starting from the compound of Reference example 7-1 in the same manner as Reference example 6-2.

$^1$H NMR (CDCl$_3$, 400 MHz) δ 9.70 (d, 1 H, J=7.7 Hz), 7.45 (d, 1 H, J=15.9 Hz), 7.35 (t, 1 H, J=7.9 Hz), 7.25 (brt, 1 H, J=2.4 Hz), 7.22 (brd, 1 H, J=7.9 Hz), 7.13 (ddd, 1 H, J=7.9, 2.4 and 0.8 Hz), 6.71 (dd, 1 H, J=15.9 and 7.7 Hz), 5.21 (s, 2 H), 3.49 (s, 3 H).

Reference Example 7-3

Preparation for (2E)-3-[3-(methoxymethoxy)phenyl]-2-propen-1-ol

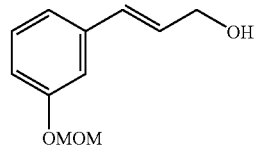

The subject compound was prepared starting from the compound of Reference example 7-2 in the same manner as Reference example 6-3.

$^1$H NMR (CDCl$_3$, 400 MHz) δ 7.24 (t, 1 H, J=8.0 Hz), 7.08 (t, 1 H, J=2.0 Hz), 7.04 (d, 1 H, J=8.0 Hz), 6.93 (ddd, 1 H, J=8.0, 2.0 and 0.7 Hz), 6.59 (d, 1 H, J=15.9 Hz), 6.37 (dt, 1 H, J=15.9 and 5.7 Hz), 5.18 (s, 2 H), 4.32 (dt, 2 H, J=5.7 and 1.4 Hz), 3.49 (s, 3 H), 1.46 (t, 1 H, J=5.7 Hz).

Reference Example 7-4

Preparation for 1-[(1E)-3-bromo-1-propenyl]-3-(methoxymethoxy)benzene

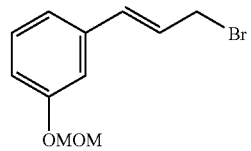

The subject compound was prepared starting from the compound of Reference example 7-3 in the same manner as Reference example 6-4.

$^1$H NMR (CDCl$_3$, 400 MHz) δ 7.24 (t, 1 H, J=7.9 Hz), 7.07 (t, 1 H, J=2.4 Hz), 7.03 (d, 1 H, J=7.9 Hz), 6.95 (ddd, 1 H, J=7.9, 2.4 and 0.8 Hz), 6.61 (d, 1 H, J=15.5 Hz), 6.39 (dt, 1 H, J=15.5 and 7.8 Hz), 5.18 (s, 2 H), 4.15 (dd, 2 H, J=7.8 and 0.8 Hz), 3.48 (s, 3 H).

Example 6

Example 6-1

Preparation for (1-{(2E)-3-[3-(methoxymethoxy)phenyl]-2-propenyl}-1H-pyrrol-2-yl)(4-methylphenyl)methanone

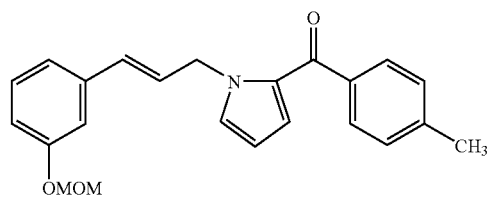

The subject compound was prepared starting from the compound of Reference example 7 and the compound of Reference example 1 in the same manner as Example 1-1.

¹H NMR (CDCl₃, 400 MHz) 7.73 (d, 2 H, J=8.1 Hz), 7.25 (d, 2 H, J=8.1 Hz), 7.20 (t, 1 H, J=8.0 Hz), 7.05 (dd, 1 H, J=2.5, 1.7 Hz), 6.99–7.04 (m, 2 H), 6.91 (ddd, 1 H, J=8.0, 2.4 and 0.8 Hz), 6.77 (dd, 1 H, J=4.0 and 1.7 Hz), 6.47 (d, 1 H, J=15.8 Hz), 6.42 (dt, 1 H, J=15.8 and 4.9 Hz), 6.21 (dd, 1 H, J=4.0 and 2.5 Hz), 5.20 (d, 2 H, J=4.9 Hz), 5.16 (s, 2 H), 3.47 (s, 3 H), 2.43 (s, 3 H).

Example 6-2

Preparation for {1-[(2E)-3-(3-hydroxyphenyl)-2-propenyl]-1H-pyrrol-2-yl}(4-methylphenyl)methanone

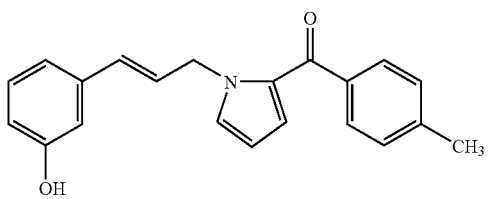

To a solution of the compound (4.53 g, 12.5 mmol) of Example 6-1 in methanol (15 ml) and dioxane (10 ml) was added 4N hydrochloric acid in dioxane (10 ml) and the mixture was stirred for 30 minutes at room temperature. To the reaction mixture was added water and the mixture was extracted with ethyl acetate. The organic layer was washed with an aqueous saturated sodium chloride solution, and dried over magnesium sulfate. The solvent was removed under reduced pressure and the residue was purified with silica gel chromatography (hexane:ethyl acetate=4:1) to give the subject compound (3.71 g, 93%).

¹H NMR (CDCl₃, 400 MHz) 7.73 (d, 2 H, J=8.1 Hz), 7.25 (d, 2 H, J=8.1 Hz), 7.15 (t, 1 H, J=7.9 Hz), 7.04 (dd, 1 H, J=2.4 and 1.7 Hz), 6.92 (brd, 1 H, J=7.9 Hz), 6.82–6.84 (m, 1 H), 6.77 (dd, 1 H, J=4.0 and 1.7 Hz), 6.70 (ddd, 1 H, J=7.9, 2.5 and 0.8 Hz), 6.44 (d, 1H. J=15.8 Hz), 6.39 (dt, 1 H, J=15.8 and 4.8 Hz), 6.20 (dd, 1 H, J=4.0 and 2.4 Hz), 5.19 (d, 2 H, J=4.8 Hz), 4.94 (s, 1 H), 2.42 (s, 3 H).

Example 6-3

Preparation for ethyl 4-(3-{(1E)-3-[2-(4-methylbenzoyl)-1H-pyrrol-1-yl]-1-propenyl}phenoxy)butyrate

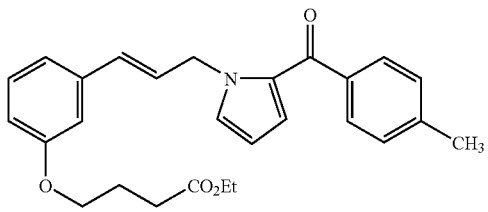

To a solution of the compound (180 mg, 0.567 mmol) of Example 6-2 in N,N-dimethylformamide (3.0 ml) was added potassium carbonate (100 mg, 0.724 mmol) and ethyl 4-bromo-n-bytyrate (105 mg, 0.538 mmol), and the mixture was stirred for 2 hours at 45° C. To the reaction mixture was further added ethyl 4-bromo-n-butyrate (20.0 mg, 0.100 mmol) and the mixture was stirred for additional 9 hours at 50° C. Thereto was added an aqueous sodium hydrogencarbonate solution and the mixture was extracted with ethyl acetate. The organic layer was washed with an aqueous saturated sodium chloride solution, and dried over magnesium sulfate. The solvent was removed under reduced pressure. The residue was purified with silica gel chromatography (hexane:ethyl acetate=4:1) to give the subject compound (199 mg, 81%).

¹H NMR (CDCl₃, 400 MHz) δ 7.73 (d, 2 H, J=8.1 Hz), 7.25 (d, 2 H, J=8.1 Hz), 7.19 (t, 1 H, J=7.9 Hz), 7.05 (dd, 1 H, J=2.4 and 1.7 Hz), 6.94 (brd, 1 H, J=7.9 Hz), 6.87–6.89 (m, 1 H), 6.76 (dd, 1 H, J=4.0 and 1.7 Hz), 6.74–6.77 (m, 1 H), 6.47 (d, 1 H, J=15.8 Hz), 6.41 (dt, 1 H, J=15.8 and 5.0 Hz), 6.20 (dd, 1 H, J=4.0 and 2.4 Hz), 5.20 (d, 2 H, J=5.0 Hz), 4.14 (q, 2 H, J=7.1 Hz), 3.99 (t, 2 H, J=6.1 Hz), 2.50 (t, 2 H, J=7.3 Hz), 2.43 (s, 3 H), 2.09 (tt, 2 H, J=7.3 and 6.1 Hz), 1.25 (t, 3 H, J=7.1 Hz).

Example 6-4

Preparation for 4-(3-{(1E)-3-[2-(4-methylbenzoyl)-1H-pyrrol-1-yl]-1-propenyl}phenoxy)butyric acid

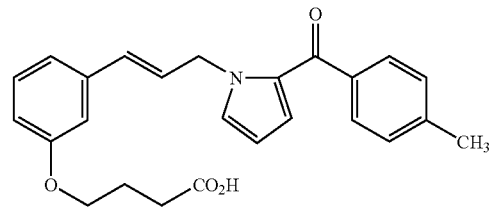

The subject compound was prepared starting from the compound of Example 6-3 in the same manner as Example 1-2.

¹H NMR (CDCl₃, 400 MHz) δ 7.74 (d, 2 H, J=8.1 Hz), 7.25 (d, 2 H, J=8.1 Hz), 7.19 (t, 1 H, J=8.1 Hz), 7.05 (dd, 1 H, J=2.5 and 1.6 Hz), 6.93 (brd, 1 H, J=8.1 Hz), 6.92–6.94 (m, 1 H), 6.77 (dd, 1 H, J=4.0 and 1.6 Hz), 6.74–6.77 (m, 1 H), 6.48 (d, 1 H, J=15.6 Hz), 6.44 (dt, 1 H, J=15.6 and 4.0 Hz), 6.20 (dd, 1 H, J=4.0 and 2.5 Hz), 5.17–5.19 (m, 2 H), 4.03 (t, 2 H, J=6.2 Hz), 2.57 (t, 2 H, J=7.1 Hz), 2.42 (s, 3 H), 2.07–2.14 (m, 2 H).

Reference Example 8-1

Preparation for {3-[(1E)-3-t-butoxy-3-oxo-1-propenyl]phenyl}acetic acid

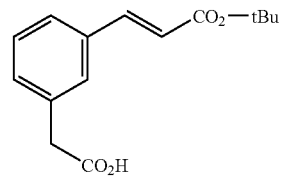

A mixture of m-bromophenylacetic acid (4.0 g, 18.6 mmol), t-butyl acrylate (4.85 g, 37.8 mmol), triethylamine (3.8 g, 37.6 mmol), tri-o-tolylphosphine (310 mg, 1.02 mmol) and palladium acetate (130 mg, 0.580 mmol) in N,N-dimethylformamide (50 ml) was stirred for 4 hours at 50° C. and then 10 hours at 90° C. The reaction mixture was diluted with an aqueous sodium hydrogencarbonate solution and washed with ethyl acetate. The aqueous layer was acidified (about pH 3) and extracted with ethyl acetate. The organic layer was washed with an aqueous sodium chloride solution and dried over magnesium sulfate. The solvent was removed under reduced pressure to give the crude subject compound (5.50 g).

$^1$H NMR (CDCl$_3$, 400 MHz) δ 7.56 (d, 1 H, J=16.0 Hz), 7.41–7.45 (m, 2 H), 7.35 (t, 1 H, J=7.9 Hz), 7.28–7.32 (m, 1 H), 6.37 (d, 1 H, J=16.0 Hz), 3.67 (s, 2 H), 1.53 (s, 9 H).

Reference Example 8-2

Preparation for (2E)-3-[3-(2-methoxy-2-oxoethyl)phenyl]-2-propenoic acid

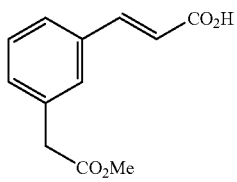

To a solution the crude compound (5.50 g) of Reference example 8-1 in acetone (60 ml) were added potassium carbonate (4.80 g, 34.7 mmol) and dimethylsulfate (3.00 g, 23.8 mmol), and the mixture was stirred for 1.5 hours at room temperature. To the reaction mixture was added water and the mixture was extracted with ethyl acetate. The organic layer was washed with an aqueous saturated sodium chloride solution and dried over magnesium sulfate. The solvent was removed under reduced pressure to give methyl ester of the compound of Reference example 8-1. The methyl ester was dissolved in dichloromethane (30 ml). Thereto was added trifluoroacetic acid (30 ml), and the mixture was stirred for 1.5 hours at room temperature. The reaction mixture was diluted with an aqueous sodium hydrogencarbonate solution and washed with diethyl ether. The aqueous layer was acidified (about pH 3) and extracted with diethyl ether. The organic layer was washed with an aqueous saturated sodium chloride solution and dried over magnesium sulfate. The solvent was removed under reduced pressure to give the subject compound (3.90 g, total yield of three steps: 95%).

NMR of Methyl Ester of the Compound of Reference Example 8-1:

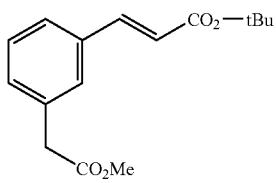

$^1$H NMR (CDCl$_3$, 400 MHz) δ 7.57 (d, 1 H, J=16.0 Hz), 7.40–7.44 (m, 2 H), 7.34 (t, 1 H, J=7.9 Hz), 7.28–7.31 (m, 1 H), 6.37 (d, 1 H, J=16.0 Hz), 3.70 (s, 3 H), 3.64 (s, 2 H), 1.53 (s, 9 H).

Reference Example 8-3

Preparation for methyl {3-[(1E)-3-hydroxy-1-propenyl]phenyl}acetate

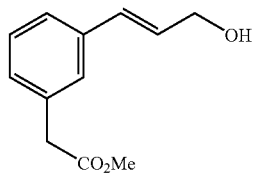

To a solution of the compound (3.90 g, 17.7 mmol) of Reference example 8-2 and triethylamine (2.35 g, 23.2 mmol) in tetrahydrofuran (50 ml) was added ethyl chloroformate (2.50 g, 23.0 mmol) at 0° C. under an atmosphere of nitrogen and the mixture was stirred for 1 hour at 0° C. To the reaction mixture was further added triethylamine (0.700 g, 6.92 mmol) and ethyl chloroformate (0.750 g, 6.91 mmol) and the mixture was stirred for additional 20 minutes at 0° C. To the reaction mixture was dropped sodium borohydride (3.65 g, 96.5 mmol) in water (30 ml) and the mixture was stirred at 0° C. for 20 minutes. The reaction mixture was acidified (pH 2–3) with 1N hydrochloric acid and extracted with ethyl acetate. The extract was washed with an aqueous sodium chloride solution and dried over magnesium sulfate. The solvent was removed under reduced pressure and the residue was purified with silica gel chromatography (hexane:ethyl acetate=3:1→1:1) to give the subject compound (3.00 g, 82%).

$^1$H NMR (CDCl$_3$, 400 MHz) δ 7.28–7.32 (m, 3 H), 7.15–7.18 (m, 1 H), 6.61 (dt, 1 H, J=15.9 and 1.4 Hz), 6.38 (dt, 1 H, J=15.9 and 5.8 Hz), 4.33 (dt, 2 H, J=5.8 and 1.4 Hz), 3.70 (s, 3 H), 3.62 (s, 2 H), 1.43 (t, 1 H, J=5.8 Hz).

Reference Example 8-4

Preparation for methyl {3-[(1E)-3-bromo-1-propenyl]phenyl}acetate

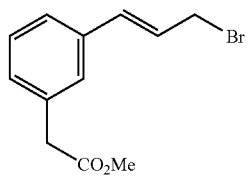

The subject compound was prepared starting from the compound of Reference example 8-3 in the same manner as Reference example 6-4.

$^1$H NMR (CDCl$_3$, 400 MHz) δ 7.29–7.32 (m, 3 H), 7.17–7.22 (m, 1 H), 6.63 (d, 1 H, J=15.6 Hz), 6.40 (dt, 1 H, J=15.6 and 7.8 Hz), 4.16 (dd, 2 H, J=7.8 and 0.7 Hz), 3.70 (s, 3 H), 3.62 (s, 2 H).

Example 7

Preparation for (3-{(1E)-3-[2-(4-methylbenzoyl)-1H-pyrrol-1-yl]-1-propenyl}phenyl)acetic acid

Example 7-1

Preparation for methyl (3-{(1E)-3-[2-(4-methylbenzoyl)-1H-pyrrol-1-yl]-1-propenyl}phenyl}acetate

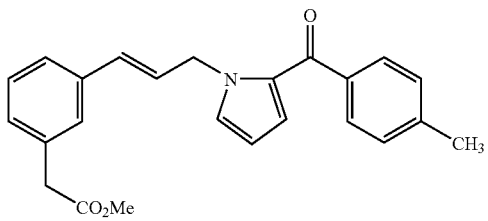

The subject compound was prepared starting from the compound of Reference example 8 and the compound of Reference example 1 in the same manner as Example 1-1.

$^1$H NMR (CDCl$_3$, 400 MHz) δ 7.74 (d, 2 H, J=8.1 Hz), 7.25 (d, 2 H, J=8.1 Hz), 7.23–7.29 (m, 3 H), 7.13–7.17 (m, 1 H), 7.04 (dd, 1 H, J=2.5 and 1.6 Hz), 6.77 (dd, 1 H, J=4.0 and 1.6 Hz), 6.48 (d, 1 H, J=15.8 Hz), 6.44 (dt, 1 H, J=15.8 and 4.9 Hz), 6.20 (dd, 1 H, J=4.0 and 2.5 Hz), 5.20 (d, 2 H, J=4.9 Hz), 3.68 (s, 3 H), 3.59 (s, 2 H), 2.43 (s, 3 H).

Example 7-2

Preparation for (3-{(1E)-3-[2-(4-methylbenzoyl)-1H-pyrrol-1-yl]-1-propenyl}phenyl}acetic acid

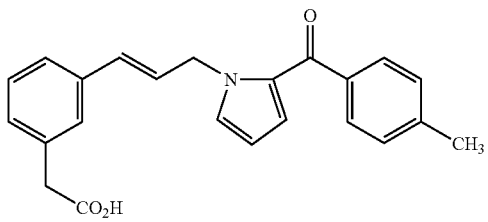

The subject compound was prepared starting from the compound of Example 7-1 in the same manner as Example 1-2.

$^1$H NMR (CDCl$_3$, 400 MHz) δ 7.73 (d, 2 H, J=8.1 Hz), 7.25–7.31 (m, 3 H), 7.25 (d, 2 H, J=8.1 Hz), 7.14–7.18 (m, 1 H), 7.04 (dd, 1 H, J=2.5 and 1.7 Hz), 6.77 (dd, 1 H, J=4.0 and 1.7 Hz), 6.49 (d, 1 H, J=15.6 Hz), 6.44 (dt, 1 H, J=15.6 and 4.8 Hz), 6.20 (dd, 1 H, J=4.0 and 2.5 Hz), 5.20 (d, 2 H, J=4.8 Hz), 3.63 (s, 2 H), 2.43 (s, 3 H).

Example 8

Preparation for (3-{(1E)-3-[2-(4-methoxybenzoyl)-4-methyl-1H-pyrrol-1-yl]-1-propenyl}phenyl}acetic acid

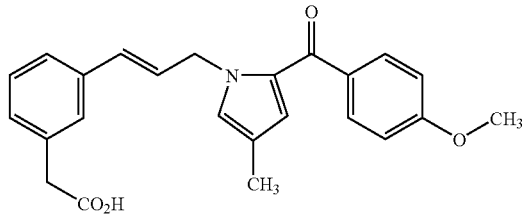

The subject compound was prepared starting from the compound of Reference example 8 and the compound of Reference example 3 in the same manner as Example 1-2.

$^1$H NMR (CDCl$_3$, 400 MHz) δ 7.83 (d, 2 H, J=8.8 Hz), 7.27–7.31 (m, 3 H), 7.14–7.18 (m, 1 H), 6.96 (d, 2 H, J=8.8 Hz), 6.81–6.84 (br, 1 H), 6.55–6.57 (br, 1 H), 6.48 (d, 1 H, J=15.9 Hz), 6.42 (dt, 1 H, J=15.9, 5.0 Hz), 5.12 (d, 2 H, J=5.0 Hz), 3.88 (s, 3 H), 3.63 (s, 2 H), 2.09 (s, 3 H).

Example 9

Preparation for methyl (2-methoxy-5-{(1E)-3-[2-(4-methylbenzoyl)-1H-pyrrol-1-yl]-1-propenyl}phenoxy)acetate

Example 9-1

Preparation for 4-methoxy-3-(methoxymethoxy)benzaldehyde

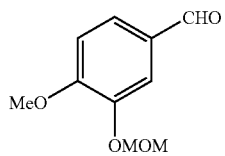

To a solution of isovanillin (5.00 g, 32.9 mmol) in N,N-dimethylformamide (300 ml) were added potassium carbonate (5.00 g, 36.1 mmol) and chloromethyl methyl ether (2.91 g, 36.1 mmol), and the mixture was stirred for 4 hours at 50° C. The mixture was allowed to cool to room temperature, followed by addition of water. The mixture was extracted with ethyl acetate-toluene (3:1). The organic layer was washed with water and an aqueous saturated sodium chloride solution in the order, and dried over anhydrous magnesium sulfate. The solvent was removed under reduced pressure and the residue was purified with silica gel chromatography (hexane:ethyl acetate=3:1) to give the subject compound (5.80 g, 89.9%).

$^1$H NMR (CDCl$_3$, 400 MHz) δ 9.86 (s, 1 H), 7.67 (d, 1 H, J=1.9 Hz), 7.55 (dd, 1 H, J=1.9 and 8.3 Hz), 7.01 (d, 1 H, J=8.3 Hz), 5.29 (s, 2 H), 3.97 (s, 3 H), 3.53 (s, 3 H).

Example 9-2

Preparation for ethyl (2E)-3-[4-methoxy-3-(methoxymethoxy)phenyl]-2-propenoate

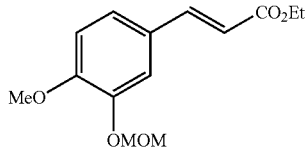

The compound (3.42 g, 17.4 mmol) of Example 9-1 was dissolved in N,N-dimethylformamide (30 ml) and tetrahydrofuran (30 ml) and then thereto were added ethyl diethylphosphonoacetate (3.91 g, 17.4 mmol) and sodium hydride (766 mg, 19.1 mmol). After stirring for 2 hours at 60° C., the mixture was allowed to cool to room temperature, and tetrahydrofuran was removed under reduced pressure. To the residue was added water, and the mixture was extracted with ethyl acetate-toluene (3:1). The organic layer was washed with water and an aqueous saturated sodium chloride solution in the order, dried over anhydrous magnesium sulfate. The solvent was removed under reduced pressure to give the subject compound (196 mg, 88.8%).

$^1$H NMR (CDCl$_3$, 400 MHz) δ 7.61 (d, 1 H, J=15.9 Hz), 7.37 (d, 1 H, J=2.0 Hz), 7.16 (dd, 1 H, J=2.0 and 8.4 Hz), 6.89 (d, 1 H, J=8.4 Hz), 6.31 (d, 1 H, J=15.9 Hz), 5.25 (s, 2 H), 4.25 (q, 2 H, J=7.1 Hz), 3.91 (s, 3 H), 3.53 (s, 3 H), 1.33 (t, 3 H, J=7.1 Hz).

Example 9-3

Preparation for (2E)-3-[4-methoxy-3-(methoxymethoxy)phenyl]-2-propene-1-ol

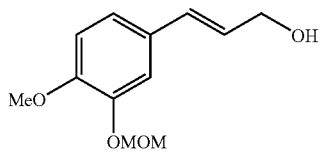

A solution of the compound (4.54 g, 17.0 mmol) of Example 9-2 in toluene (60 ml) was stirred at −78° C., and thereto was dropped diisobutylalminumhydride (1.0M in hexane: 35.8 ml, 35.8 mmol). The mixture was stirred for 1.5 hours at −78° C., followed by addition of an aqueous 2N sodium hydroxide solution. The precipitate was filtered off and the filtrate was extracted with ethyl acetate. The organic layer was washed with water and an aqueous sodium chloride solution in the order, and dried over anhydrous magnesium sulfate. The solvent was removed under reduced pressure to give the subject compound (3.65 g, 95.7%).

$^1$H NMR (CDCl$_3$, 400 MHz) δ 7.24 (d, 1 H, J=2.1 Hz), 7.00 (dd, 1 H, J=2.1 and 8.4 Hz), 6.85 (d, 1 H, J=8.4 Hz), 6.53 (d, 1 H, J=15.9 Hz), 6.26 (dt, 1 H, J=15.9 and 5.9 Hz), 5.24 (s, 2 H), 4.30 (d, 2 H, J=5.9 Hz), 3.88 (s, 3 H), 3.52 (s, 3 H).

Example 9-4

Preparation for {1-[(2E)-3-(3-hydroxy-4-methoxyphenyl)-2-propenyl]-1H-pyrrol-2-yl}(4-methylphenyl)methanone

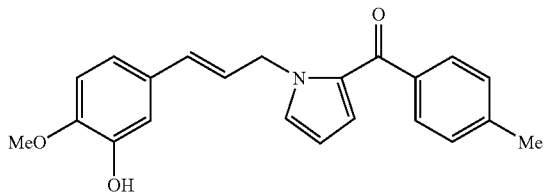

To a solution of the compound (400 mg, 1.78 mmol) of Example 9-3 in dichloromethane (3.0 ml) were added tetrabromomethane (590 mg, 1.78 mmol) and triphenylphosphine (467 mg, 1.78 mmol), and the mixture was stirred for 30 minutes at room temperature, followed by addition of ether. The precipitate was filtered off and the solvent was removed under reduced pressure from the filtrate. The residue was dissolved in tetrahydrofuran (4.0 ml). Thereto were added the compound (330 mg, 1.78 mmol) of Reference example 1 and potassium t-butoxide (300 mg, 2.67 mmol). The mixture was stirred for 2 hours, followed by addition of water and extracted with ethyl acetate. The organic layer was washed with water and an aqueous saturated sodium chloride solution in the order, and dried over anhydrous magnesium sulfate. The solvent was removed under reduced pressure and the residue was purified with silica gel chromatography (hexane:ethyl acetate=4:1). The purified product was further dissolved in methanol (2.0 ml). Thereto was added 4N hydrochloric acid-dioxane (2.0 ml) and the mixture was stirred for 1 hour at room temperature. The solvent was removed under reduced pressure and the residue was purified with silica gel chromatography (hexane:ethyl acetate=4:1), to give the subject compound (30.3 mg, 4.9%).

$^1$H NMR (CDCl$_3$, 400 MHz) δ 7.72 (d, 2 H, J=8.1 Hz), 7.23 (d, 2 H, J=8.1 Hz), 7.04 (dd, 1 H, J=1.7 and 2.5 Hz), 6.97 (d, 1 H, J=1.9 Hz), 6.82 (dd, 1 H, J=1.9 and 8.4 Hz), 6.75 (d, 1 H, J=8.4 Hz), 6.74 (dd, 1 H, J=1.7 and 4.0 Hz), 6.41 (brd, 1 H, J=15.9 Hz), 6.27 (dt, 1 H, J=15.9 and 6.2 Hz), 6.18 (dd, 1 H, J=2.5 and 4.0 Hz), 5.53 (s, 1 H), 5.16 (dd, 2 H, J=1.1 and 6.2 Hz), 3.86 (s, 3 H), 2.41 (s, 3 H).

Example 9-5

Preparation for methyl (2-methoxy-5-{(1E)-3-[2-(4-methylbenzoyl)-1H-pyrrol-1-yl]-1-propenyl}phenoxy)acetate

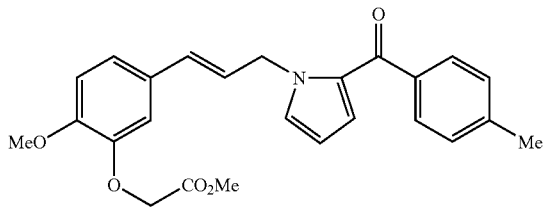

The subject compound was prepared starting from the compound of Example 9-4 in the same manner as Reference example 6-1.

¹H NMR (CDCl₃, 400 MHz) δ 7.73 (d, 2 H, J=8.1 Hz), 7.25 (d, 2 H, J=8.1 Hz), 7.05 (dd, 1 H, J=1.7 and 2.6 Hz), 6.98 (dd, 1 H, J=1.9 and 8.4 Hz), 6.86 (d, 1 H, J=1.9 Hz), 6.82 (d, 1 H, J=8.4 Hz), 6.76 (dd, 1 H, J=1.7 and 4.0 Hz), 6.42 (brd, 1 H, J=15.9 Hz), 6.26 (dt, 1 H, J=15.9 and 6.2 Hz), 6.20 (dd, 1 H, J=2.6 and 4.0 Hz), 5.17 (dd, 2 H, J=1.1 and 6.2 Hz), 4.68 (s, 2 H), 3.87 (s, 3 H), 3.79 (s, 3 H), 3.43 (s, 3 H).

Example 10

Preparation for sodium (2-methoxy-5-{(1E)-3-[2-(4-methylbenzoyl)-1H-pyrrol-1-yl]-1-propenyl}phenoxy)acetate

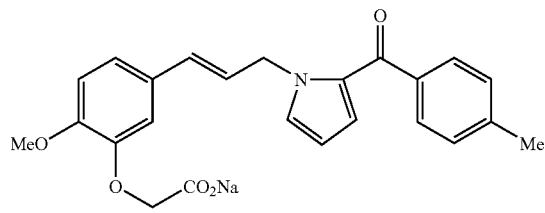

The compound (140 mg, 334 μmol) of Example 9 was dissolved in a mixture of tetrahydrofuran (1.0 ml) and methanol (1.0 ml), followed by addition of an aqueous 2N sodium hydroxide solution (2.0 ml), and the mixture was stirred for 30 minutes at room temperature. The mixture was neutralized with 1N hydrochloric acid and extracted with ethyl acetate. The organic layer was washed with water and an aqueous saturated sodium chloride solution, and dried over anhydrous magnesium sulfate. The solvent was removed under reduced pressure to give a free base of the subject compound (128 mg, 94.5%). To this compound was added equimolar of an aqueous sodium hydroxide solution to give the subject compound by dryness.

¹H NMR (CDCl₃, 400 MHz) δ 7.66 (d, 2 H, J=8.1 Hz), 7.35 (dd, 1 H, J=1.7 and 2.6 Hz), 7.31 (d, 2 H, J=8.1 Hz), 6.85–6.80 (m, 3 H), 6.67 (dd, 1 H, J=1.7 and 4.0 Hz), 6.33–6.26 (m, 2 H), 6.22 (dd, 1 H, J=2.6 and 4.0 Hz), 5.12 (d, 2 H, J=4.6 Hz), 4.09 (s, 2 H), 3.74 (s, 3 H), 2.39 (s, 3 H).

Reference Example 9

Preparation for 1-[(1E)-3-bromo-1-propenyl]-2-methoxy-3-(methoxymethoxy)benzene

Reference Example 9-1

Preparation for 3-hydroxy-2-methoxybenzaldehyde

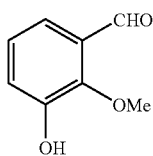

To a solution of 2,3-hydroxybenzaldehyde (200 mg, 1.45 mmol) in N,N-dimethylformamide (3.0 ml) was added sodium hydride (60.8 mg, 1.52 mmol) at room temperature, and the mixture was stirred for 1 hour at 50° C. The reaction mixture was cooled to room temperature and thereto was added methyl iodide (226 mg, 1.60 mmol). The mixture was stirred for 1 hour at 40° C. and allowed to cool to room temperature, followed by addition of water and extracted with ethyl acetate-toluene (3:1). The organic layer was washed with water and an aqueous saturated sodium chloride solution in the order, and dried over anhydrous magnesium sulfate. The solvent was removed under reduced pressure and the residue was recrystallized from hexane to give the subject compound (196 mg, 88.8%).

¹H NMR (CDCl₃, 400 MHz) δ 10.27 (s, 1 H), 7.37 (dd, 1 H, J=1.7 and 7.7 Hz), 7.23 (dd, 1 H, J=1.7 and 8.0 Hz), 7.15 (m, 1 H), 5.82 (s, 1 H), 3.98 (s, 3 H).

Reference Example 9-2

Preparation for 2-methoxy-3-(methoxymethoxy)benzaldehyde

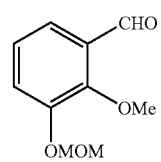

To a solution of the compound (5.98 g, 39.3 mmol) of Reference example 9-1 in tetrahydrofuran (200 ml) were added potassium carbonate (8.15 g, 59.0 mmol) and chloromethyl methyl ether (6.33 g, 78.6 mmol) and the mixture was stirred for 11 hours at 60° C. The precipitate was filtered off and the solvent was removed from the filtrate. To the residue was added water and the mixture was extracted with ethyl acetate. The organic layer was washed with water and an aqueous saturated sodium chloride solution in the order, and dried over anhydrous magnesium sulfate. The solvent was removed under reduced pressure and the residue was purified with silica gel chromatography (hexane:ethyl acetate=4:1) to give the subject compound (2.63 g, 34.1%).

¹H NMR (CDCl₃, 400 MHz) δ 10.42 (s, 1 H), 7.49 (d, 1 H, J=7.8 Hz), 7.40 (d, 1 H, J=8.1 Hz), 7.12 (m, 1 H)), 5.26 (s, 2 H), 4.01 (s, 3 H), 3.53 (s, 3 H).

Reference Example 9-3

Preparation for ethyl (2E)-3-[2-methoxy-3-(methoxymethoxy)phenyl]-2-propenoate

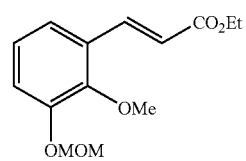

The subject compound was prepared starting from the compound of Reference example 9-2 in the same manner as Example 9-2.

¹H NMR (CDCl₃, 400 MHz) δ 7.98 (d, 1 H, J=16.2 Hz), 7.22 (dd, 1 H, J=1.4 and 8.0 Hz), 7.18 (dd, 1 H, J=1.4 and 8.0 Hz), 7.04 (dd, 1 H, J=8.0 and 8.0 Hz), 6.49 (d, 1 H, J=16.2 Hz), 5.23 (s, 2 H), 4.27 (q, 2 H, J=7.1 Hz), 3.88 (s, 3 H), 3.52 (s, 3 H), 1.34 (t, 3 H, J=7.1 Hz).

Reference Example 9-4

Preparation for (2E)-3-[2-methoxy-3-(methoxymethoxy)phenyl]-2-propen-1-ol

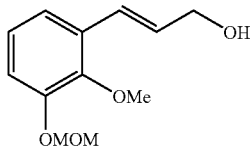

The subject compound was prepared starting from the compound of Reference example 9-3 in the same manner as Example 9-3.

¹H NMR (CDCl₃, 400 MHz) δ 7.16 (dd, 1 H, J=1.7 and 7.9 Hz), 7.06 (dd, 1 H, J=1.7 and 7.9 Hz), 7.00 (dd, 1 H, J=7.9 and 7.9 Hz), 6.92 (d, 1 H, J=16.1 Hz), 6.40 (dt, 1 H, J=16.1 and 5.8 Hz), 5.22 (s, 2 H), 4.35 (t, 2 H, J=5.8 Hz), 3.84 (s, 3 H), 3.52 (s, 3 H).

Reference Example 9-5

Preparation for 1-(1E)-3-bromo-1-propenyl]-2-methoxy-3-(methoxymethoxy)benzene

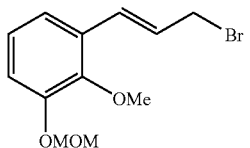

The subject compound was prepared starting from the compound of Reference example 9-4 in the same manner as Reference example 8-4.

¹H NMR (CDCl₃, 400 MHz) δ 7.14 (dd, 1 H, J=1.6 and 7.8 Hz), 7.08 (dd, 1 H, J=1.6 and 8.0 Hz), 7.00 (dd, 1 H, J=7.8 and 8.0 Hz), 6.95 (d, 1 H, J=15.8 Hz), 6.43 (dt, 1 H, J=15.8 and 7.8 Hz), 5.22 (s, 2 H), 4.19 (d, 2 H, J=7.8 Hz), 3.84 (s, 3 H), 3.52 (s, 3 H).

Example 11

Preparation for methyl (2-methoxy-3-{(1E)-3-[2-(4-methylbenzoyl)-1H-pyrrol-1-yl]-1-propenyl}phenoxy)acetate Example 11-1

Preparation for (1-{2E)-3-[2-methoxy-3-(methoxymethoxy)phenyl]-2-propenyl}-1H-pyrrol-2-yl)(4-methylphenyl)methanone

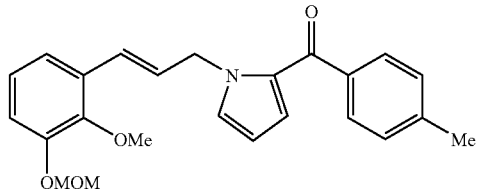

To a solution of the compound (160 mg, 557 μmol) of Reference example 9 and the compound (124 mg, 668 μmol) of Reference example 1 in tetrahydrofuran (3.0 ml) was added potassium t-butoxide (68.8 mg, 613 μmol), and the mixture was stirred for 2 hours. Thereto was added water and the mixture was extracted with ethyl acetate. The organic layer was washed with water and an aqueous saturated sodium chloride solution in the order, and dried over anhydrous magnesium sulfate. The solvent was removed under reduced pressure to give the subject compound (235 mg, quantitatively).

¹H NMR (CDCl₃, 400 MHz) δ 7.74 (d, 2 H, J=8.1 Hz), 7.25 (d, 2 H, J=8.1 Hz), 7.12 (dd, 1 H, J=1.2 and 8.0 Hz), 7.06 (dd, 1 H, J=1.7 and 2.5 Hz), 7.03 (dd, 1 H, J=1.2 and 8.0 Hz), 6.96 (dd, 1 H, J=8.0 and 8.0 Hz), 6.81 (brd, 1 H, J=16.0 Hz), 6.77 (dd, 1 H, J=1.7 and 4.0 Hz), 6.46 (dt, 1 H, J=16.0 and 6.2 Hz), 6.20 (dd, 1 H, J=2.5 and 4.0 Hz), 5.23 (dd, 2 H, J=1.3 and 6.2 Hz), 5.20 (s, 2 H), 3.76 (s, 3 H), 3.50 (s, 3 H), 2.42 (s, 3 H).

Example 11-2

Preparation for {1-[(2E)-3-(3-hydroxy-2-methoxyphenyl)-2-propenyl]-1H-pyrrol-2-yl}(4-methylphenyl)methanone

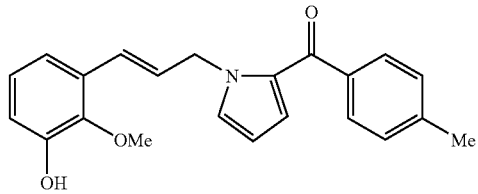

To a solution of the compound (229 mg, 0.585 mmol) of Example 11-1 in a mixture of dioxane (2.0 ml) and methanol (2.0 ml) was added 4N hydrochloric acid-dioxane (2.0 ml) and the mixture was stirred for 1 hour at room temperature. The solvent was removed under reduced pressure and the residue was purified with silica gel chromatography (hexane:ethyl acetate=9:1) to give the subject compound (172 mg, 84.6%).

¹H NMR (CDCl₃, 400 MHz) δ 7.73 (d, 2 H, J=8.1 Hz), 7.25 (d, 2 H, J=8.1 Hz), 7.05 (dd, 1 H, J=1.7 and 2.5 Hz), 6.97–6.91 (m, 2 H), 6.84 (dd, 1 H, J=1.2 and 8.0 Hz), 6.78 (dd, 1 H, J=1.7 and 4.0 Hz), 6.64 (brd, 1 H, J=16.0 Hz), 6.46

(dt, 1 H, J=16.0 and 6.0 Hz), 6.22 (dd, 1 H, J=2.5 and 4.0 Hz), 5.66 (s, 1 H), 5.24 (dd, 2 H, J=1.3 and 6.0 Hz), 3.69 (s, 3 H), 2.42 (s, 3 H).

Example 11-3

Preparation for methyl (2-methoxy-3-{(1E)-3-[2-(4-methylbenzoyl)-1H-pyrrol-1-yl]-1-propenyl}phenoxy)acetate

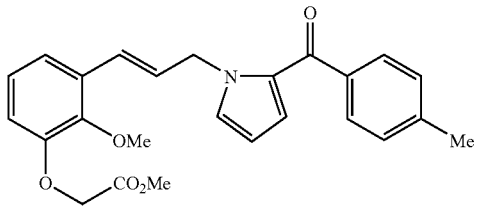

The subject compound was prepared starting from the compound of Example 11-2 in the same manner as Example 9-5.

$^1$H NMR (CDCl$_3$, 400 MHz) δ 7.74 (d, 2 H, J=8.1 Hz), 7.25 (d, 2 H, J=8.1 Hz), 7.12 (dd, 1 H, J=1.3 and 8.1 Hz), 7.06 (dd, 1 H, J=1.7 and 2.5 Hz), 6.95 (dd, 1 H, J=8.1 and 8.1 Hz), 6.81 (brd, 1 H, J=15.9 Hz), 6.77 (dd, 1 H, J=1.7 and 4.0 Hz), 6.72 (dd, 1 H, J=1.3 and 8.1 Hz), 6.46 (dt, 1 H, J=15.9 and 5.7 Hz), 6.20 (dd, 1 H, J=2.5 and 4.0 Hz), 5.22 (dd, 2 H, J=1.3 and 5.7 Hz), 4.68 (s, 2 H), 3.81 (s, 3 H), 3.78 (s, 3 H), 2.42 (s, 3 H).

Example 12

Preparation for (2-methoxy-3-{(1E)-3-[2-(4-methylbenzoyl)-1H-pyrrol-1-yl]-1-propenyl}phenoxy)acetic acid

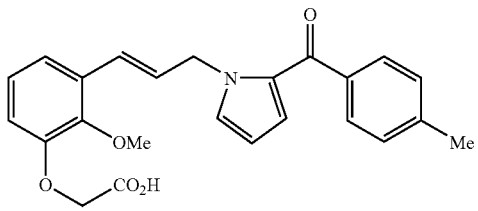

The subject compound was prepared starting from the compound of Example 11 in the same manner as Example 1-2.

$^1$H NMR (CDCl$_3$, 400 MHz) δ 7.73 (d, 2 H, J=8.1 Hz), 7.25 (d, 2 H, J=8.1 Hz), 7.18 (dd, 1 H, J=1.2 and 8.0 Hz), 7.05 (dd, 1 H, J=1.7 and 2.5 Hz), 7.01 (dd, 1 H, J=8.0 and 8.0 Hz), 6.83 (dd, 1 H, J=1.2 and 8.0 Hz), 6.78 (dd, 1 H, J=1.7 and 4.0 Hz), 6.73 (brd, 1 H, J=16.0 Hz), 6.49 (dt, 1 H, J=16.0 and 6.0 Hz), 6.22 (dd, 1 H, J=2.5 and 4.0 Hz), 5.23 (dd, 2 H, J=1.3 and 6.0 Hz), 4.68 (s, 2 H), 3.78 (s, 3 H), 2.42 (s, 3 H).

Example 13

Preparation for methyl (2-methoxy-3-{(1E)-3-[2-(4-methoxybenzoyl)-4-methyl-1H-pyrrol-1-yl]-1-propenyl}phenoxy)acetate

Example 13-1

Preparation for (1-{(2E)-3-[2-methoxy-3-(methoxymethoxy)phenyl]-2-propenyl}-4-methyl-1H-pyrrol-2-yl)(4-methoxyphenyl)methanone

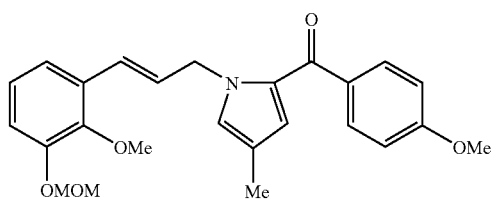

The subject compound was prepared starting from the compound of Reference example 3 and the compound of Reference example 9 in the same manner as Example 11-1.

$^1$H NMR (CDCl$_3$, 400 MHz) δ 7.83 (d, 2 H, J=7.8 Hz), 7.13 (dd, 1 H, J=1.3 and 8.0 Hz), 7.03 (dd, 1 H, J=1.3 and 8.0 Hz), 6.98–6.93 (m, 3 H), 6.84 (brd, 1 H), 6.80 (brd, 1 H, J=16.0 Hz), 6.56 (brd, 1 H), 6.44 (dt, 1 H, J=16.0 and 6.0 Hz), 5.20 (s, 2 H), 5.15 (dd, 2 H, J=1.3 and 6.0 Hz), 3.88 (s, 3 H), 3.77 (s, 3 H), 3.50 (s, 3 H), 2.05 (s, 3 H).

Example 13-2

Preparation for {1-[(2E)-3-(3-hydroxy-2-methoxyphenyl)-2-propenyl]-4-methyl-1H-pyrrol-2-yl}(4-methoxyphenyl)methanone

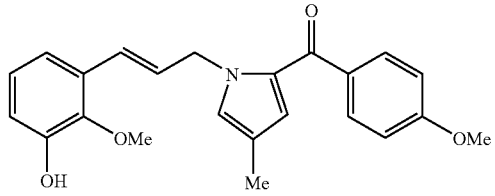

The subject compound was prepared starting from the compound of Example 13-1 in the same manner as Example 11-2.

$^1$H NMR (CDCl$_3$, 400 MHz) δ 7.82 (d, 2 H, J=8.8 Hz), 6.99–6.91 (m, 5 H), 6.84 (dd, 1 H, J.=1.9 and 8.4 Hz), 6.82 (brd, 1 H), 6.64 (brd, 1 H, J=15.9 Hz), 6.58 (brd, 1 H), 6.44 (dt, 1 H, J=15.9 and 6.0 Hz), 5.16 (dd, 2 H, J=1.3 and 6.0 Hz), 3.88 (s, 3 H), 3.69 (s, 3 H), 2.09 (s, 3 H).

Example 13-3

Preparation for methyl (2-methoxy-3-{(1E)-3-[2-(4-methoxybenzoyl)-4-methyl-1H-pyrrol-1-yl]-1-propenyl}phenoxy)acetate

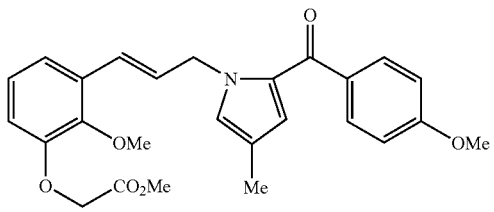

The subject compound was prepared starting from the compound of Example 13-2 in the same manner as Example 11-3.

$^1$H NMR (CDCl$_3$, 400 MHz) δ 7.83 (d, 2 H, J=8.8 Hz), 7.12 (dd, 1 H, J=1.3 and 8.1 Hz), 6.97–6.92 (m, 4 H), 6.84 (brd, 1 H), 6.80 (brd, 1 H, J=15.9 Hz), 6.72 (dd, 1 H, J=1.3 and 8.1 Hz), 6.56 (brd, 1 H), 6.44 (dt, 1 H, J=15.9 and 6.2 Hz), 5.14 (dd, 2 H, J=1.3 and 6.2 Hz), 4.68 (s, 2 H), 3.88 (s, 3 H), 3.81 (s, 3 H), 3.79 (s, 3 H), 2.08 (s, 3 H).

Example 14

Preparation for (2-methoxy-3-{(1E)-3-[2-(4-methoxybenzoyl)-4-methyl-1H-pyrrol-1-yl]-1-propenyl}phenoxy)acetic acid

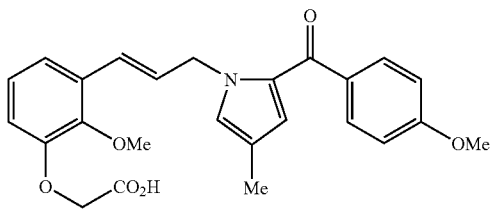

The subject compound was prepared starting from the compound of Example 13 in the same manner as Example 12.

$^1$H NMR (CDCl$_3$, 400 MHz) δ 7.83 (d, 2 H, J=8.8 Hz), 7.19 (dd, 1 H, J=1.3 and 8.0 Hz), 7.01 (dd, 1 H, J=8.0 and 8.0 Hz), 6.94 (d, 2 H, J=8.8 Hz), 6.84–6.82 (m, 2 H), 6.69 (brd, 1 H, J=16.0 Hz), 6.58 (d, 1 H, J=1.3 Hz), 6.47 (dt, 1 H, J=16.0 and 6.0 Hz), 5.15 (dd, 2 H, J=1.3 and 6.0 Hz), 4.68 (s, 2 H), 3.88 (s, 3 H), 3.79 (s, 3 H), 2.09 (s, 3 H).

Example 15

Preparation for sodium (4-methoxy-3-{(1E)-3-[2-(4-methoxybenzoyl)-4-methyl-1H-pyrrol-1-yl]-1-propenyl}phenoxy)acetate

Example 15-1

Preparation for 4-methylphenylmethylcarbonate

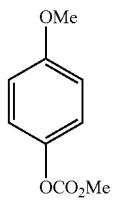

To a solution of 4-methoxyphenol (5.40 g, 43.5 mmol) in tetrahydrofuran (20 ml) was added pyridine (5.16 g, 65.3 mmol) Thereto was dropped methyl chloroformate (8.22 g, 87.0 mmol) under ice cooling and the mixture was stirred for 1 hour. To the mixture was added water and the mixture was extracted with ethyl acetate. The organic layer was washed with water and an aqueous saturated sodium chloride solution in the order, and dried over anhydrous magnesium sulfate. The solvent was removed under reduced pressure to give the subject compound (7.60 g, 95.9%).

$^1$H NMR (CDCl$_3$, 400 MHz) δ 7.09 (d, 2 H, J=9.1 Hz), 6.89 (d, 2 H, J=9.1 Hz), 3.89 (s, 3 H), 3.80 (s, 3 H).

Example 15-2

Preparation of 3-formyl-4-methoxyphenylmethylcarbonate

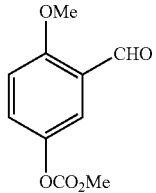

To a solution of the compound (7.50 g, 41.2 mmol) of Example 15-1 in dichloromethane (100 ml) was added at 0° C. under stirring a solution of titanium (IV) chloride (31.3 g, 164 mmol). Then thereto was dropped at 0° C. over a 30 minutes period a solution of dichloromethoxymethane (5.68 g, 49.4 mmol) in dicloromethane (40 ml). After dropping the mixture was warmed to room temperature, stirred for 30 minutes and poured into ice-water (10 g). Thereto were added concentrated hydrochloric acid (4 ml) and ether (10 ml) and the mixture was stirred for 1 hour at room temperature. The ether layer was separated, washed with water and an aqueous saturated sodium chloride solution in the order, and dried over anhydrous magnesium sulfate. The solvent was removed under reduced pressure to give the subject compound (8.62 g, quantitatively).

$^1$H NMR (CDCl$_3$, 400 MHz) δ 10.43 (s, 1 H), 7.62 (d, 1 H, J=3.1 Hz), 7.36 (dd, 1 H, J=3.1 and 9.0 Hz), 7.00 (d, 1 H, J=9.0 Hz), 3.94 (s, 3 H), 3.90 (s, 3 H).

Example 15-3

Preparation for ethyl (2E)-3-(5-hydroxy-2-methoxyphenyl)-2-propenoate

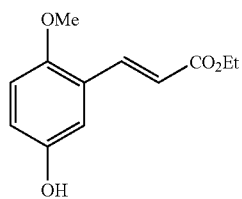

The subject compound was prepared starting from the compound of Example 15-2 in the same manner as Reference example 9-3.

$^1$H NMR (CDCl$_3$, 400 MHz) δ 7.87 (d, 1 H, J=16.1 Hz), 7.03 (d, 1 H, J=3.0 Hz), 6.86 (dd, 1 H, J=3.0 and 8.9 Hz), 6.79 (d, 1 H, J=8.9 Hz), 6.48 (d, 1 H, J=16.1 Hz), 4.26 (q, 2 H, J=7.1 Hz), 3.82 (s, 3 H), 1.33 (t, 3 H, J=7.1 Hz).

Example 15-4

Preparation for 3-[(1E)-3-hydroxy-1-propenyl]-4-methoxyphenol

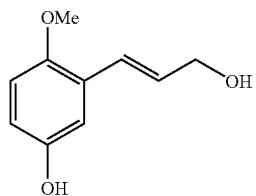

The subject compound was prepared starting from the compound of Example 15-3 in the same manner as Reference example 9-4.

$^1$H NMR (CDCl$_3$, 400 MHz) δ 8.90 (s, 1 H), 6.83 (d, 1 H, J=2.9 Hz), 6.79 (d, 1 H, J=8.8 Hz), 6.72 (d, 1 H, J=16.1 Hz), 6.60 (dd, 1 H, J=2.9 and 8.8 Hz), 6.20 (dt, 1 H, J=16.1 and 5.1 Hz), 4.81 (t, 1 H, J=5.5 Hz), 4.09 (dd, 2 H, J=5.1 and 5.5 Hz), 3.70 (s, 3 H).

Example 15-5

Preparation for methyl {3-[(1E)-3-hydroxy-1-propenyl]-4-methoxyphenoxy}acetate

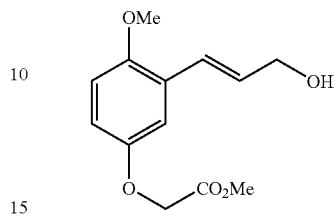

To a solution of the compound (740 mg, 4.11 mmol) of Example 15-4 in acetone (15 ml) were added potassium carbonate (1.14 g, 8.21 mmol) and methyl bromoacetate (629 mg, 4.11 mmol), and the mixture was stirred for 2 hours at 40° C. Thereto was added water and the mixture was extracted with ethyl acetate. The organic layer was washed with water and an aqueous saturated sodium chloride solution in the order, dried over anhydrous magnesium sulfate. The solvent was removed under reduced pressure to give the subject compound (842 mg, 81.1%).

$^1$H NMR (CDCl$_3$, 400 MHz) δ 7.04 (t, 1 H, J=1.5 Hz), 6.89 (d, 1 H, J=16.0 Hz), 6.79 (m, 2 H), 6.35 (dt, 1 H, J=5.8 and 16.0 Hz), 4.60 (s, 2 H), 4.32 (dd, 2 H, J=5.5 and 5.8 Hz), 3.81 (s, 3 H), 3.81 (s, 3 H), 1.47 (brt, 1 H).

Example 15-6

Preparation for sodium (4-methoxy-3-{(1E)-3-[2-methoxybenzoyl)-4-methyl-1H-pyrrol-1-yl]-1-propenyl}phenoxy)acetate

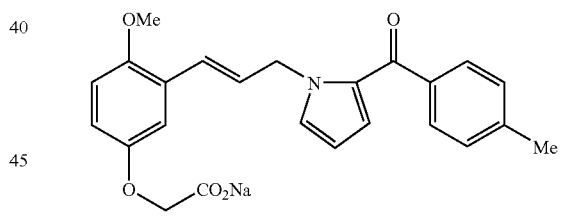

To a solution of the compound (317 mg, 1.26 mmol) of Example 15-5 in diclomethane (3.0 ml) were added at 0° C. under cooling triethylamine (180 μL, 1.30 mmol) and methanesulfonyl chloride (100 μL, 1.30 mmol and the mixture was stirred for 30 minutes. Thereto was added ethyl acetate (10 ml) and the precipitate was filtered off. The filtrate was concentrated, dissolved in tetrahydrofuran (3.0 ml) and stirred at 0° C. To the solution were added potassium t-butoxide (170 mg, 1.51 mmol) and the compound (233 mg, 1.26 mmol) of Reference example 1, and the mixture was stirred over a night at room temperature. To the reaction mixture was 1N hydrochloric acid and the mixture was extracted with ethyl acetate. The organic layer was washed with 1N hydrochloric acid and an aqueous saturated sodium chloride solution in the order, and dried over anhydrous magnesium sulfate. The solvent was removed under reduced pressure and the residue was purified with silica gel chromatography to give an oily product. The product was dissolved in terahydrofuran (1.0 ml)-methanol (1.0 ml) and thereto was added an aqueous 2N sodium hydroxide solution (2.0 ml). The mixture was stirred for 30 minutes at 0° C. and the white precipitate was filtered, washed with ether and dried to give the subject compound (110 mg, 21.5%).

$^1$H NMR (DMSO-$d_6$, 400 MHz) δ 7.66 (d, 2 H, J=8.1 Hz), 7.36 (dd, 1 H, J=1.6 and 2.6 Hz), 7.32 (d, 2 H, J=8.1 Hz), 6.88 (d, 1 H, J=3.0 Hz), 6.82 (d, 1 H, J=9.0 Hz), 6.68–6.66 (m, 2 H), 6.56 (d, 1 H, J=16.0 Hz), 6.37 (dt, 1 H, J=16.0 and 5.6 Hz), 6.22 (dd, 1 H, J=2.6 and 3.9 Hz), 5.16 (d, 2 H, J=5.6 Hz), 4.00 (s, 2 H), 3.66 (s, 3 H), 2.38 (s, 3 H).

Example 16

Preparation for methyl (3-methoxy-5-{(1E)-3-[2-(4-methylbenzoyl)-4-methyl-1H-pyrrol-1-yl]-1-propenyl}phenoxy)acetate Example 16-1

Preparation for 3-hydroxy-5-methoxybenzaldehyde

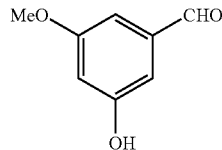

To a solution of 60% sodium hydride (2.77 g, 69.3 mmol) in N,N-dimethylformamide (50 ml) was gradually added at 0° C. ethanethiol (7 ml), and the solution was stirred at 0° C. for 30 minutes, followed by refluxing under heating for 1 hour. The mixture was cooled to room temperature, and thereto was added 3,5-dimethoxybenzaldehyde (3.84 g, 23.1 mmol) in N,N-dimethylformamide (90 ml) and the mixture was refluxed under heating for 1 hour. The mixture was cooled to room temperature, and thereto were added a saturated aqueous sodium chloride solution (700 ml), 26% aqueous formalin solution (70 ml) and acetic acid (130 ml) in the order. The mixture was stirred, extracted with ethyl acetate. The organic layer was washed with water and an aqueous saturated sodium chloride solution in the order, and dried over anhydrous magnesium sulfate. The solvent was removed under reduced pressure and the residue was purified with silica gel chromatography. (hexane:ethyl acetate=2:1) to give the subject compound (2.68 g, 17.6%).

$^1$H NMR (CDCl$_3$, 400 MHz) δ 9.88 (s, 1 H), 7.00 (m, 1 H), 6.96 (m, 1 H), 6.68 (t, 1 H, J=2.3 Hz), 3.84 (s, 3 H).

Example 16-2

Preparation for ethyl (2E)-3-(3-hydroxy-5-methoxyphenyl)-2-propenoate

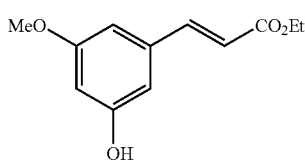

The subject compound was prepared starting from the compound of Example 16-1 in the same manner as Reference example 9-3.

$^1$H NMR (CDCl$_3$, 400 MHz) δ 7.58 (d, 1 H, J=16.0 Hz), 6.65–6.61 (m, 2 H), 6.45 (t, 1 H, J=2.2 Hz), 6.38 (d, 1 H, J=16.0 Hz), 4.27 (q, 2 H, J=7.1 Hz), 3.80 (s, 3 H), 1.34 (t, 3 H, J=7.1 Hz).

Example 16-3

Preparation for 3-[(1E)-3-hydroxy-1-propenyl]-5-methoxyphenol

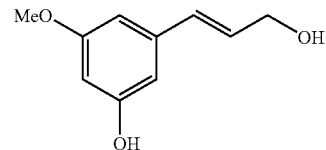

The subject compound was prepared starting from the compound of Example 16-2 in the same manner as Reference example 9-4.

$^1$H NMR (CDCl$_3$, 400 MHz) δ 6.54–6.47 (m, 3 H), 6.36–6.31 (m, 2 H), 4.92 (s, 1 H), 4.32 (d, 2 H, J=5.6 Hz), 3.79 (s, 3 H).

Example 16-4

Preparation for methyl {3-[(1E)-3-hydroxy-1-propenyl]-5-methoxyphenoxy}acetate

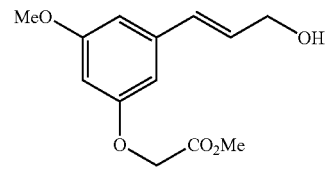

The subject compound was prepared starting from the compound of Example 16-3 in the same manner as Example 15-5.

$^1$H NMR (CDCl$_3$, 400 MHz) δ 6.59–6.52 (m, 3 H), 6.39 (dd, 1 H, J=2.3 and 2.3 Hz), 6.33 (dt, 1 H, J=15.9 and 5.6 Hz), 4.62 (s, 2 H), 4.32 (brs, 2 H), 3.81 (s, 3 H), 3.79 (s, 3 H), 1.49 (brt, 1 H).

Example 16-5

Preparation for methyl {3-[(1E)-3-bromo-1-propenyl]-5-methoxyphenoxy}acetate

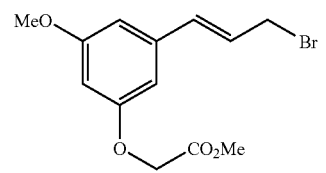

To a solution of the compound (150 mg, 0.594 mmol) of Example 16-4 in dicloromethane (2 ml) were added carbon tetrabromide (207 mg, 0.623 mmol) and triphenylphosphine (163 mg, 0.623 mmol), and the mixture was stirred for 30 minutes at room temperature. By adding ether to the reaction mixture, the resulting precipitate was filtered off. The filtrate was concentrated and the residue was purified with silica gel chromatography (hexane:ethyl acetate=2:1) to give the subject compound (141 mg, 75.3%).

$^1$H NMR (CDCl$_3$, 400 MHz) δ 6.58–6.52 (m, 3 H), 6.41 (dd, 1 H, J=2.2 and 2.2 Hz), 6.36 (dt, 1 H, J=7.8 and 15.9 Hz), 4.63 (s, 2 H), 4.14 (d, 2 H, J=7.8 Hz), 3.82 (s, 3 H), 3.79 (s, 3 H).

Example 16-6

Preparation for methyl (3-methoxy-5-{(1E)-3-[2-(4-methylbenzoyl)-4-methyl-1H-pyrrol-1-yl]-1-propenyl}phenoxy)acetate

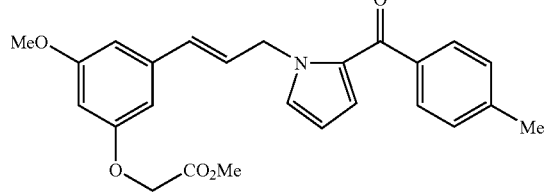

To a solution of the compound (130 mg, 0.412 mmol) of Example 16-5 in tetrahydrofuran (5.0 ml) were added at 0° C. the compound (80.1 mg, 0.433 mmol) of Reference example 1 and potassium t-butoxide (50.9 mg, 0.456 mmol), and the mixture was stirred for 3 hours at 40° C. Thereto was added ethyl acetate and the precipitate was filtered off. The filtrate was concentrated and the residue was purified with silica gel chromatography to give the subject compound (53.4 mg, 30.9%).

$^1$H NMR (CDCl$_3$, 400 MHz) δ 7.73 (d, 2 H, J=8.1 Hz), 7.25 (d, 2 H, J=8.1 Hz), 7.04 (dd, 1 H, J=1.6 and 2.6 Hz), 6.77 (dd, 1 H, J=1.6 and 4.0 Hz), 6.55 (t, 1 H, J=1.7 Hz), 6.49 (t, 1 H, J=1.7 Hz), 6.41–6.37 (m, 3 H), 6.21 (dd, 1 H, J=2.6 and 4.0 Hz), 5.19 (dd, 2 H, J=1.2, 2.7 Hz), 4.60 (s, 2 H), 3.80 (s, 3 H), 3.77 (s, 3 H), 2.43 (s, 3 H).

Example 17

Preparation for (3-methoxy-5-{(1E)-3-[2-(4-methylbenzoyl)-4-methyl-1H-pyrrol-1-yl]-1-propenyl}phenoxy)acetic acid

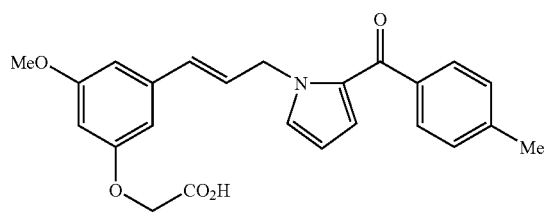

The subject compound was prepared starting from the compound of Example 16.

$^1$H NMR (CDCl$_3$, 400 MHz) δ 7.72 (d, 2 H, J=8.1 Hz), 7.25 (d, 2 H, J=8.1 Hz), 7.04 (dd, 1 H, J=1.6 and 2.5 Hz), 6.77 (dd, 1 H, J=1.6 and 4.0 Hz), 6.56 (dd, 1 H, J=1.7 and 1.7 Hz), 6.50 (dd, 1 H, J=1.7 and 1.7 Hz), 6.43–6.34 (m, 3 H), 6.21 (dd, 1 H, J=2.5 and 4.0 Hz), 5.18 (dd, 2 H, J=1.2 and 2.7 Hz), 4.62 (s, 2 H), 3.75 (s, 3 H), 2.42 (s, 3 H).

Reference Example 10

Preparation for methyl 3-(2-hydroxyethyl)phenoxyacetate

Example 10-1

Preparation for 2-(3-hydroxyphenyl)ethanol

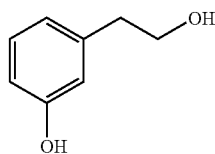

To a solution of 3-hydroxyphenylacetic acid (3.04 g, 20.0 mmol) in tetrahydrofuran (30 ml) was added at 0° C. borane-tetrahydrofuran complex (1M, 30.0 ml, 30.0 mmol) under an atmosphere of nitrogen. The mixture was stirred for 1 hour, followed by addition of water and the mixture was extracted with ethyl acetate. The organic layer was dried over magnesium sulfate, filtered and concentrated to give the subject compound (2.76 g, 100%).

$^1$H NMR (CDCl$_3$, 400 MHz) δ 7.19 (t, 1 H, J=7.4 Hz), 6.80 (d, 1 H, J=7.4 Hz), 6.72 (s, 1 H), 6.70 (d, 1 H, J=7.4 Hz), 3.86 (t, 2 H, J=6.5 Hz), 2.83 (t, 2 H, J=6.5 Hz).

Reference Example 10-2

Preparation for methyl 3-(2-hydroxyethyl)phenoxyacetate

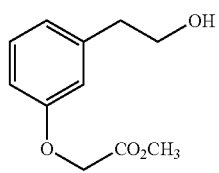

A solution of the compound (1.38 g, 10.0 mmol) of Reference example 10-1, methyl bromoacetate (1.68 g, 11.0 mmol) and potassium carbonate (2.07 g, 15.0 mmol) in acetone (20 ml) was refluxed for 1 hour. The reaction mixture was poured into water and extracted with ethyl acetate. The organic layer was dried over magnesium sulfate and filtered. The solvent was removed under reduced pressure and the residue was purified with silica gel chromatography (hexane:ethyl acetate=1:1) to give the subject compound (1.00 g, 66%).

¹H NMR (CDCl₃, 400 MHz) δ 7.24 (dd, 1 H, J=7.4 and 7.9 Hz), 6.87 (brd, 1 H, J=7.4 Hz), 6.81 (t, 1 H, J=2.0 Hz), 6.76 (dd, 1 H, J=7.9 and 2.0 Hz), 4.64 (s, 2 H), 3.86 (q, 2 H, J=6.4 Hz), 3.81 (s, 3 H), 2.85 (t, 2 H, J=6.4 Hz).

Example 18

Preparation for (3-{2-[2-(4-methylbenzoyl)-1H-pyrrol-1-yl]ethyl}phenoxy)acetic acid

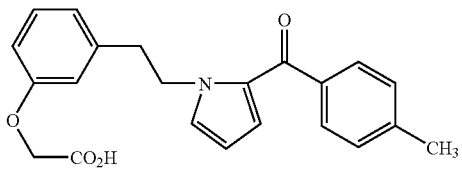

To a solution of the compound (456 mg, 2.17 mmol) of Reference example 10 in toluene (4.0 ml) was added triethylamine (455 mg, 4.50 mmol) and the mixture was cooled to 0° C. Thereto was dropped a solution of methanesulfonyl chloride (381 mg, 3.30 mmol) in toluene (1.0 ml) and the mixture was stirred for 10 minutes. The reaction was quenched by an aqueous 5% potassium hydrogensulfate solution and extracted with ethyl acetate. The organic layer was separated and concentrated. There was obtained a solution of a methanesulfonic acid derivative by adding tetrahydrofuran (4 ml) to the residue. To a solution of potassium t-butoxide (168 mg, 1.50 mmol) in tetrahydrofuran (2.0 ml) was added at 0° C. a solution of the compound (278 mg, 1.50 mmol) of Reference example 1 under an atmosphere of nitrogen. To this solution was added the solution of the methanesulfonyl derivative (2.0 ml) prepared previously, and the solution was stirred for 10 hours at room temperature. Thereto was added water and extracted with ethyl acetate. The organic layer was separated and the solvent was removed. The residue was purified with silica gel chromatography and the purified product was dissolved in a mixture of an aqueous 1N sodium hydroxide solution (2.0 ml), methanol (2.0 ml) and tetrahydrofuran (2.0 ml). The solution was stirred for 10 hours at room temperature and then concentrated to about 2 g. The concentrated mixture was washed with toluene 5 times and the aqueous layer was acidified with 1N hydrochloric acid and an aqueous 5% potassium hydrgensulfate solution. The mixture was extracted with ethyl acetate and the organic layer was concentrated to give the subject compound (11.4 mg, 2.9%).

¹H NMR (CDCl₃, 400 MHz) δ 7.68 (brd, 2 H, J=8.4 Hz), 7.27 (dd, 1 H, J=1.7 and 2.5 Hz), 7.26 (brd, 2 H, J=8.4 Hz), 7.19 (dd, 1 H, J=7.4 and 7.9 Hz), 6.82 (brd, 1 H, J=7.4 Hz), 6.76 (t, 1 H, J=2.0 Hz), 6.74 (dd, 1 H, J=1.7 and 4.0 Hz), 6.71 (dd, 1 H, J=7.9 and 2.0 Hz), 6.09 (dd, 1 H, J=2.5 and 4.0 Hz), 4.60 (s, 2 H), 4.59 (t, 2 H, J=7.2 Hz), 3.08 (t, 2 H, J=7.2 Hz) 2.42 (s, 3 H).

Example 19

Preparation for (3-{2-[2-(4-methoxybenzoyl)-4-methyl-1H-pyrrol-1-yl]ethyl}phenoxy)acetic acid

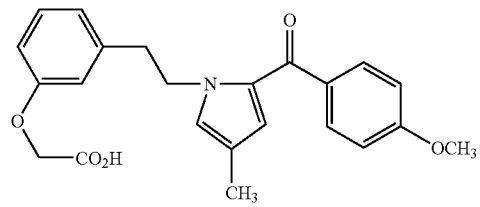

The subject compound was prepared starting from the compound of Reference example 10 and the compound of Reference example 3 in the same manner as Example 18.

¹H NMR (CDCl₃, 400 MHz) δ 7.78 (d, 2 H, J=8.7 Hz), 6.95 (dd, 1 H, J=7.4 and 7.9 Hz), 6.93 (d, 2 H, J=8.7 Hz), 6.85 (brd, 1 H, J=7.4 Hz), 6.76 (dd, 1 H, J=7.9 and 2.0 Hz), 6.74 (brs, 1 H), 6.60 (d, 1 H, J=1.1 Hz), 6.53 (d, 1 H, J=1.1 Hz), 4.62 (s, 2 H), 4.51 (t, 2 H, J=7.2 Hz), 3.87 (s, 3 H), 3.05 (t, 2 H, J=7.2 Hz), 2.04 (s, 3 H).

Example 20

Preparation for (2-chloro-5-{1E)-3-[2-(4-methylbenzoyl)-1H-pyrrol-1-yl]-1-propenyl}phenoxy)acetic acid

Example 20-1

2-Chloro-5-iodophenol

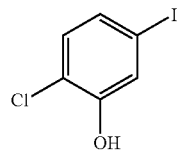

To a solution of 1-chloro-4-iodo-2-methoxybenzene (1.34 g, 5 mmol) in dichloromethane was dropped under ice cooling a solution of 0.91M boron tribromide in dichloromethane (6.6 ml, 6.00 mmol) and the mixture was reacted for 1 hour under ice cooling and then for 3 days at room temperature. To the mixture was added an aqueous sodium hydrogencarbonate solution and then the mixture was acidified with concentrated hydrochloric acid, followed by extraction with ethyl acetate. The organic layer was washed with an aqueous saturated sodium chloride solution, and dried over anhydrous magnesium sulfate. The solvent was removed and purified with silica gel chromatography (hexane:ethyl acetate, 10:1) to give the subject compound (1.11 g, 87%) as white crystals.

¹H NMR (CDCl₃, 400 MHz) δ 7.37 (d, 1 H, J=2.0 Hz), 7.19 (dd, 1 H, J=8.4 and 2.0 Hz), 7.02 (d 1 H, J=8.4 Hz), 5.52 (s, 1 H).

Example 20-2

Preparation for t-butyl (2-chloro-5-iodophenoxy)acetate

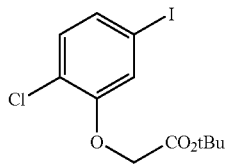

To a solution of 2-chloro-5-iodophenol (509 mg, 2.00 mmol) in dimethylformamide were added potassium carbonate (415 mg, 3.00 mmol) and t-butyl bromoacetate (0.440 ml, 3.00 mmol) and the mixture was stirred for 1 hour at room temperature. Thereto was added water and the mixture was extracted with ethyl acetate. The organic layer was washed with 10% aqueous citric acid solution, water, an aqueous saturated sodium hydrogencarbonate solution and an aqueous saturated sodium chloride solution in the order, and dried over magnesium sulfate. The solvent was removed and purified with silica gel chromatography (hexane:ethyl acetate, 20:1) to give t-butyl (2-chloro-5-iodophenoxy)acetate (851 mg, quantitatively) as a colorless oil.

$^1$H NMR (CDCl$_3$, 400 MHz) δ 7.25 (dd, 1 H, J=8.4 and 1.8 Hz), 7.08–7.11 (m, 2 H), 4.58 (s, 2 H), 1.49 (s, 9 H).

Example 20-3

Preparation for t-butyl {2-chloro-5-[(1E)-3-oxo-1-propenyl]phenoxy}acetate

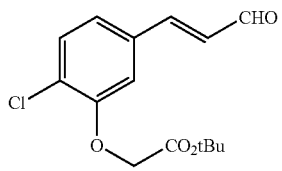

t-Butyl (2-chloro-5-iodophenoxy)acetate (851 mg, 2.00 mmol) was dissolved in dimethylformamide under an atmosphere of nitrogen, and thereto were acrolein (0.400 ml, 6.00 mmol), sodium carbonate (0.510 g, 6.00 mmol), benzyltriethylammonium chloride (683 mg, 3.00 mmol) and palladium acetate (14.0 mg, 60.0 μmol). The mixture was stirred for 3 hours at 60° C. The reaction mixture was cooled and thereto was added sodium thiosulfate. The mixture was extracted with ethyl acetate and the organic layer was washed with sodium thiosulfate, 10% aqueous citric acid solution, water, an aqueous saturated sodium hydrogencarbonate solution and an aqueous saturated sodium chloride solution in the order, and dried over magnesium sulfate. The solvent was removed to give the subject compound as yellow crystals (631 mg, quantitatively).

$^1$H NMR (CDCl$_3$, 400 MHz) δ 9.70 (d, 1 H, J=7.6 Hz), 7.45 (d, 1 H, J=8.2 Hz), 7.39 (d, 1 H, J=15.9 Hz), 7.15 (dd, 1 H, J=8.2 and 1.9 Hz), 6.98 (d, 1 H, J=1.8 Hz), 6.64 (dd, 1 H, J=15.9 and 7.6 Hz), 4.65 (s, 2 H), 1.49 (s, 9 H).

Example 20-4

Preparation for t-butyl {2-chloro-5-[(1E)-3-hydroxy-1-propenyl]phenoxy}acetate

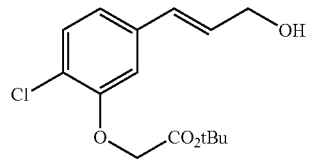

A solution of the compound (631 mg, 2.00 mmol) of Example 20-3 in tetrahydrofuran (4.0 ml) and methanol (2.0 ml) was stirred at ice cooling. Thereto was dropped an aqueous solution (0.20 ml) of sodium borohydride (38.0 mg, 1.00 mmol) under ice cooling and the mixture was stirred for 3 hour at the same temperature. Thereto was added 10% aqueous citric acid solution and the solution was extracted with ethyl acetate. The organic layer was washed with water, an aqueous saturated sodium hydrogencarbonate, solution and an aqueous saturated sodium chloride solution in the order, and dried over sodium sulfate. The solvent was removed to give the subject compound as a colorless oil (651 mg, quantitatively).

$^1$H NMR (CDCl$_3$, 400 MHz) δ 7.31 (d, 1 H, J=8.2 Hz), 6.95 (dd, 1 H, J=8.2 and 1.8 Hz), 6.83 (d, 1 H, J=1.8 Hz), 6.54 (d, 1 H, J=15.9 Hz), 6.30 (dt, 1 H, J=15.9 and 5.5 Hz), 4.61 (s, 2 H), 4.32 (br, 2 H), 1.51 (br, 1 H), 1.46 (s, 9 H).

Example 20-5

Preparation for (2-chloro-5-{(1E)-3-[2-(4-methylbenzoyl)-1H-pyrrol-1-yl]-1-propenyl}phenoxy)acetic acid

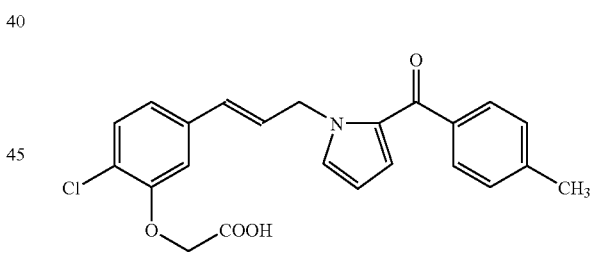

To a solution of the compound (299 mg, 1.00 mmol) of Example 20-4 in tetrahydrofuran (4.0 ml) were added under ice cooling triethylamine (0.210 ml, 1.50 mmol) and methanesulfonyl chloride (0.085 ml, 1.10 mmol) in the order. The mixture was stirred for 1 hour under ice cooling. To the reaction mixture were added cold 10% aqueous citric acid solution and the mixture was extracted with ethyl acetate. The organic layer was washed with cold 10% aqueous citric acid solution and cold aqueous saturated sodium hydrogencarbonate solution in the order and dried over sodium sulfate. The solvent was removed and the residue was dissolve in tetrahydrofuran (2.0 ml). Thereto was added lithium bromide (174 mg, 2.00 mmol) and the mixture was stirred for 3 hours. To the reaction mixture was added water and the mixture was extracted with ethyl acetate. The organic layer was washed with water and an aqueous saturated sodium chloride solution and dried over sodium sulfate. The solvent was removed and the residue was dissolved in tetrahydrofuran (2 ml). The solution was dropped into a solution of the compound (185 mg, 1.00 mmol) of Reference example 1 and potassium t-butoxide (112 mg, 1.00 mmol) in tetrahydrofuran (2 ml) under ice cooling. The mixture was stirred for 5 hours under ice cooling. Thereto were added methanol (2.0 ml) and an aqueous 1N sodium hydroxide solution (2.0 ml) and the mixture was stirred for 2 hours. The reaction mixture was washed with hexane and ether and acidified with potassium hydrogensulfate, and extracted with chloroform. The organic layer was washed with an aqueous saturated sodium chloride solution and dried over sodium sulfate. The solvent was removed to give the subject compound as brown crystals (281 mg, 60%).

$^1$H NMR (CDCl$_3$, 400 MHz) δ 7.72 (d, 2 H, J=8.1 Hz), 7.29 (d, 1 H, J=8.2 Hz), 7.25 (d, 2 H, J=8.1 Hz), 7.04 (dd, 1 H, J=1.6 and 2.5 Hz), 6.97 (dd, 1 H, J=8.2 and 1.8 Hz), 6.86 (d, 1 H, J=1.8 Hz), 6.78 (dd, 1 H, J=4.0 and 1.6 Hz), 6.35–6.45 (m, 2 H), 6.22 (dd, 1 H, J=4.0 and 2.5 Hz), 5.18 (d, 2 H, J=4.5 Hz), 4.75 (s, 2 H), 3.89 (br, 1 H), 2.42 (s, 3 H).

Example 21

Preparation for (4-chloro-3-{(1E)-3-[2-(4-methylbenzoyl)-1H-pyrrol-1-yl]-1-propenyl}phenoxy)acetic acid

Example 21-1

Preparation for 4-chloro-3-iodophenol

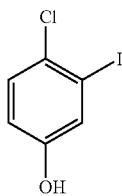

To a solution of 1-chloro-2-iodo-4-methoxybenzene (2.68 g, 10.0 mmol) in dichloromethane (20 ml) was dropped under ice cooling 0.91M boron tribromide in dichloromethane (13.0 ml, 12.0 mmol). The mixture was stirred for 1 hour under ice cooling and for a day at room temperature. To the reaction mixture was added an aqueous saturated sodium hydrogencarbonate solution. The mixture was acidified with concentrated hydrochloric acid and extracted with ethyl acetate. The organic layer was washed with an aqueous saturated sodium chloride solution and dried over sodium sulfate. The solvent was removed to give the subject compound as pale brown crystals (2.61 g, quantitatively).

$^1$H NMR (CDCl$_3$, 400 MHz) δ 7.35 (d, 1 H, J=2.9 Hz), 7.27 (d, 1 H, J=8.7 Hz), 6.78 (dd, 1 H, J=8.7 and 2.9 Hz), 5.30 (br, 1 H).

Example 21-2

Preparation for t-butyl (4-chloro-3-iodophenoxy)acetate

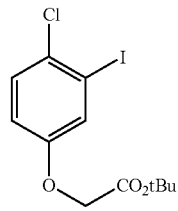

To a solution of the compound (509 mg, 2.00 mmol) of Example 20-1 in dimethylformamide (4.0 ml) were added potassium carbonate (415 mg, 3.00 mmol) and t-butyl bromoacetate (0.440 ml, 3.00 mmol), and the mixture was stirred at room temperature for 1 hour. Thereto was added water and the mixture was extracted with ethyl acetate. The organic layer was washed with 10% aqueous citric acid solution, water, an aqueous saturated sodium hydrogencarbonate solution and an aqueous saturated sodium chloride solution, and dried over magnesium sulfate. The solvent was removed and purified with silica gel chromatography (hexane:ethyl acetate, 10:1) to give the subject compound as a colorless oil (448 mg, 61%).

$^1$H NMR (CDCl$_3$, 400 MHz) δ 7.36 (d, 1 H, J=2.9 Hz), 7.32 (d, 1 H, J=8.8 Hz), 6.85 (dd, 2 H, J=8.8 and 2.9 Hz), 4.47 (s, 2 H), 1.49 (s, 9 H).

Example 21-3

Preparation for t-butyl {4-chloro-3-[(1E)-3-oxo-1-propenyl]phenoxy}acetate

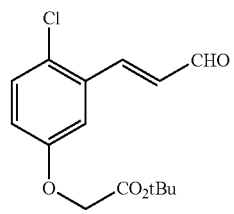

The compound (448 mg, 1.22 mmol) of Example 20-2 was dissolved in dimethylformamide (2.0 ml) under an atmosphere of nitrogen, and thereto were acrolein (0.170 ml, 2.50 mmol), sodium hydrogencarbonate (210 mg, 2.50 mmol), benzyltriethylammonium chloride (342 mg, 1.50 mmol) and palladium acetate (5.00 mg, 20.0 μmol). The mixture was stirred for 2 hours at 60° C. The reaction mixture was cooled and thereto was added sodium thiosulfate. The mixture was extracted with ethyl acetate and the organic layer was washed with sodium thiosulfate, 10% aqueous citric acid solution, water, an aqueous saturated sodium hydrogencarbonate solution and an aqueous saturated sodium chloride solution in the order, and dried over magnesium sulfate. The solvent was removed to give the subject compound as yellow crystals (399 mg, quantitatively).

$^1$H NMR (CDCl$_3$, 400 MHz) δ 9.77 (d, 1 H, J=7.7 Hz), 7.88 (d, 1 H, J=15.9 Hz), 7.37 (d, 1 H, J=8.8 Hz), 7.15 (d,

1 H, J=3.0 Hz), 6.93 (dd, 1 H, J=8.8 and 3.0 Hz), 6.64 (dd, 1 H, J=15.9 and 7.7 Hz), 4.54 (s, 2 H), 1.49 (s, 9 H).

Example 21-4

Preparation for t-butyl {4-chloro-3-[(1E)-3-hydroxy-1-propenyl]phenoxy}acetate

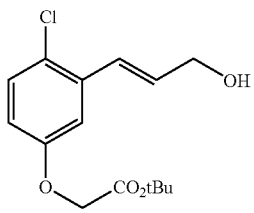

A solution of the compound (399 mg, 1.22 mmol) of Example 20-3 in tetrahydrofuran (3.0 ml) and methanol (1.5 ml) was stirred at ice cooling. Thereto was gradually dropped an aqueous solution (200 μl) of sodium borohydride (27.0 mg, 0.700 mmol) under ice cooling and the mixture was stirred for 1 hour at the same temperature. Thereto was added 10% aqueous citric acid solution and the solution was extracted with ethyl acetate. The organic layer was washed with water, an aqueous saturated sodium hydrogencarbonate solution and an aqueous saturated sodium chloride solution in the order, and dried over sodium sulfate. The solvent was removed to give the subject compound as a colorless oil (384 mg, quantitatively).

$^1$H NMR (CDCl$_3$, 400 MHz) δ 7.25 (d, 1 H, J=8.8 Hz), 7.06 (d, 1 H, J=3.0 Hz), 6.95 (dt, 1 H, J=15.9 and 1.6 Hz), 6.74 (dd, 1 H, J=8.8 and 3.0 Hz), 6.30 (dt, 1 H, J=15.9 and 5.5 Hz), 4.51 (s, 2 H), 4.36 (d, 2 H, J=5.5 Hz), 1.59 (br, 1 H), 1.49 (s, 9 H).

Example 21-5

Preparation for (4-chloro-3-{(1E)-3-[2-(4-methylbenzoyl)-1H-pyrrol-1-yl]-1-propenyl}phenoxy)acetic acid

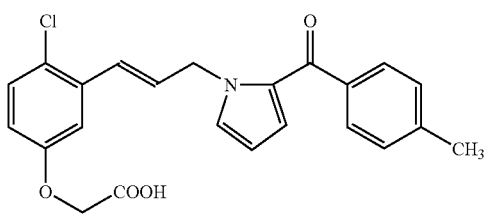

To a solution of the compound of Example 20-4 in tetrahydrofuran (5.0 ml) were added under ice cooling triethylamine (0.270 ml, 1.94 mmol) and methanesulfonyl chloride (0.110 ml, 1.42 mmol) in the order. The mixture was stirred for 1 hour under ice cooling. To the reaction mixture were added cold 10% aqueous citric acid solution and the mixture was extracted with ethyl acetate. The organic layer was washed with cold 10% aqueous citric acid solution and a cold aqueous saturated sodium hydrogencarbonate solution in the order and dried over sodium sulfate. The solvent was removed and the residue was dissolve in tetrahydrofuran (2.0 ml). Thereto was added lithium bromide (2.61 mg, 3.00 mmol) and the mixture was stirred for 3 hours. To the reaction mixture was added water and extracted with ethyl acetate. The organic layer was washed with water and an aqueous saturated sodium chloride solution and dried over sodium sulfate. The solvent was removed and the residue was dissolved in tetrahydrofuran (2 ml). The solution was dropped into a solution of the compound (185 mg, 1.00 mmol) of Reference example 1 and potassium t-butoxide (112 mg, 1.00 mmol) in tetrahydrofuran (2 ml) under ice cooling. The mixture was stirred for 5 hours under ice cooling. Thereto were added methanol (2.0 ml) and an aqueous 1N sodium hydroxide solution (2.0 ml) and the mixture was stirred for 2 hours at room temperature. The reaction mixture was washed with hexane and ether and acidified with potassium hydrogensulfate. The mixture was extracted with chloroform and the organic layer was washed with an aqueous saturated sodium chloride solution and dried over sodium sulfate. The solvent was removed and purified with silica gel chromatography (chloroform:methanol, 10:1) to give the subject compound (177 mg, 29%).

$^1$H NMR (DMSO-d$_6$, 400 MHz) δ 7.66 (d, 2 H, J=7.9 Hz), 7.28–7.38 (m, 3 H), 7.23 (m, 1 H), 7.09 (d, 1 H, J=8.8 Hz), 6.76 (dd, 1 H, J=8.8 and 2.6 Hz), 6.71 (brd, 1 H, J=3.4 Hz), 6.44–6.58 (m, 2 H), 6.23–6.25 (m, 1 H), 5.23 (d, 2 H, J=4.3 Hz), 4.43 (s, 2 H), 2.39 (s, 3 H).

Example 22

Preparation for sodium (3-{3-[2-(4-methylbenzoyl)-1H-pyrrol-1-yl]-1-propynyl}phenoxy)acetate Example 22-1

Preparation for t-butyl (3-iodophenoxy)acetate

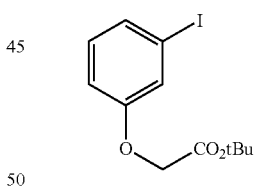

To a solution of 3-iodophenol (2.20 g, 10.0 mmol) in dimethylformamide (20 ml) were added potassium carbonate (2.07 g, 15.0 mmol) and t-butyl bromoacetate (1.62 ml, 11.0 mmol), and the mixture was stirred for 1 hour at room temperature. Thereto was added water and the mixture was extracted with ethyl acetate. The organic layer was washed with 10% aqueous citric acid solution, water, an aqueous saturated sodium hydrogencarbonate solution and an aqueous saturated sodium chloride solution in the order, and dried over magnesium sulfate. The solvent was removed to give the subject compound as a colorless oil (3.28 g, 98%).

$^1$H NMR (CDCl$_3$, 400 MHz) δ 7.31 (ddd, 1 H, J=8.0, 1.6 and 0.8 Hz), 7.23 (dd, 1 H, J=2.4 and 1.6 Hz), 7.00 (t, 1 H, J=8.0 Hz), 6.85 (ddd, 1 H, J=8.0, 2.4 and 0.8 Hz), 4.49 (s, 2 H), 1.49 (s, 9 H).

Example 22-2

Preparation for t-butyl [3-(3-hydroxy-1-propynyl)phenoxy]acetate

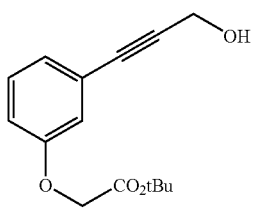

The compound (1.00 g, 3.00 mmol) of Example 22-1 was dissolved in triethylamine (30 ml) under an atmosphere of nitrogen. Thereto were added propargyl alcohol (0.35 ml, 6.00 mmol), copper(I) iodide (6.00 mg, 30.0 μmol) and dichlorobis(triphenylphosphine)palladium (II) (42.0 mg, 60.0 μmol) and the mixture was stirred for 1 hour at 70° C. The mixture was cooled and thereto was added ethyl acetate. The mixture was washed with 10% aqueous citric acid solution, water, an aqueous saturated sodium hydrogencarbonate solution and an aqueous saturated sodium chloride solution in the order and dried over sodium sulfate. The solvent was removed and purified with silica gel chromatography (hexane:ethyl acetate, 3:1–2:1) to give the subject compound as a yellow oil(537 mg, 68%).

$^1$H NMR (CDCl$_3$, 400 MHz) δ 7.23 (t, 1 H, J=8.0 Hz), 7.06 (ddd, 1 H,. J=8.0, 2.5 and 1.4 Hz), 6.95 (dd, 1 H, J=2.6 and 1.4 Hz), 6.89 (dt, 1 H, J=8.0 and 2.5 Hz), 4.50 (s, 2 H), 1.68 (br, 1 H), 1.49 (s, 9 H).

Example 22-3

Preparation for (3-{3-[2-(4-methylbenzoyl)-1H-pyrrol-1-yl]-1-propynyl}phenoxy)acetic acid

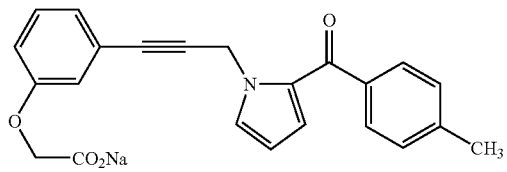

To a solution of the compound (537 mg, 2.05 mmol) of Example 22-2 in tetrahydrofuran (8.0 ml) were added under ice cooling triethylamine (0.420 ml, 3.00 mmol) and methanesulfonyl chloride (0.170 ml, 2.20 mmol) in the order. The mixture was stirred for 1 hour under ice cooling. To the reaction mixture were added cold 10% aqueous citric acid solution and the mixture was extracted with ethyl acetate. The organic layer was washed with cold 10% aqueous citric acid solution and a cold aqueous saturated sodium hydrogencarbonate solution in the order and dried over sodium sulfate. The solvent was removed and the residue was dissolve in tetrahydrofuran (4.0 ml). Thereto was added lithium bromide (500 mg, 5.80 mmol) and the mixture was stirred for 1 hour. To the reaction mixture was added water and the mixture was extracted with ethyl acetate. The organic layer was washed with water and an aqueous saturated sodium chloride solution and dried over sodium sulfate. The solvent was removed and the residue was dissolved in tetrahydrofuran (2 ml). The solution was dropped into a solution of the compound (259 mg, 1.40 mmol) of Reference example 1 and potassium t-butoxide (157 mg, 1.40 mmol) in tetrahydrofuran (4 ml) under ice cooling. The mixture was stirred for 7 hours under ice cooling. Thereto were added methanol (2.0 ml) and an aqueous 4N sodium hydroxide solution (2.0 ml) and the mixture was stirred for 2 hours at room temperature. The reaction mixture was washed with hexane and the precipitate was taken by filtration. The precipitate was washed with a mixture of hexane and ether (1:1) and dried under reduced pressure to give the subject compound (529 mg, 95%) as white crystals.

$^1$H NMR (CDCl$_3$, 400 MHz) δ 7.68 (d, 2 H, J=8.1 Hz), 7.49 (t, 1 H, J=2.0 Hz), 7.32 (d, 2 H, J=7.9 Hz), 7.18 (t, 1 H, J=7.9 Hz), 6.78–6.88 (m, 3 H), 6.71 (dd, 1 H, J=4.0 and 1.6 Hz), 6.25 (dd, 1 H, J=4.0 and 2.6 Hz), 5.49 (s, 2 H), 4.12 (s, 2 H), 2.40 (s, 3 H).

Reference Example 11

Preparation for t-butyl {4-[(1E)-3-hydroxy-1-propenyl]phenoxy}acetate

Reference Example 11-1

Preparation for t-butyl (4-iodophenoxy)acetate

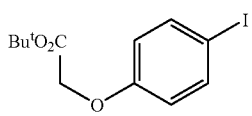

The subject compound was prepared starting from 4-iodophenol and t-butyl bromoacetate in the same manner as Reference example 6-1.

$^1$H NMR (CDCl$_3$, 400 MHz) δ 7.56 (d, 2 H, J=6.8 Hz), 6.67 (d, 2 H, J=6.8 Hz), 4.48 (s, 2 H), 1.48 (s, 9 H).

Reference Example 11-2

Preparation for t-butyl {4-[(1E)-3-oxo-1-propenyl]phenoxy}acetate

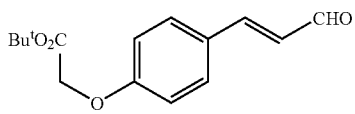

The subject compound was prepared starting from Reference example 11-1 in the same manner as Reference example 6-2.

$^1$H NMR (CDCl$_3$, 400 MHz) δ 9.66 (d, 1 H, J=7.7 Hz), 7.53 (d, 2 H, J=8.8 Hz), 7.42 (brd, 1 H, J=15.9 Hz), 6.94 (d, 2 H, J=8.8 Hz), 6.62 (dd, 1 H, J=7.7 and 15.9 Hz), 4.57 (s, 2 H), 1.49 (s, 9 H).

Reference Example 11-3

Preparation for t-butyl {4-[(1E)-3-hydroxy-1-propenyl]phenoxy}acetate

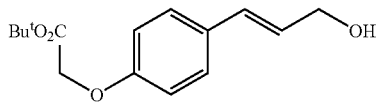

The subject compound was prepared starting from Reference example 11-2 in the same manner as Reference example 6-3.

$^1$H NMR (CDCl$_3$, 400 MHz) δ 7.33 (d, 2 H, J=8.8 Hz), 6.85 (d, 2 H, J=8.8 Hz), 6.55 (brd, 1 H, J=15.9 Hz), 6.25 (dt, 1 H, J=15.9 and 5.9 Hz), 4.51 (s, 2 H), 4.30 (t, 2 H, J=5.9 Hz), 1.49 (s, 9 H).

Example 23

Preparation for (4-{(1E)-3-[2-(4-methylbenzoyl)-1H-pyrrol-1-yl]-1-propenyl}phenoxy)acetic acid

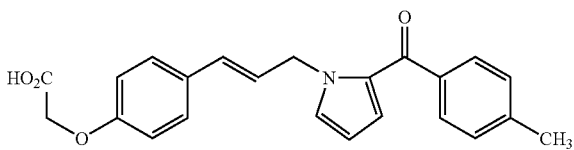

The subject compound was prepared starting from the compound of Reference example 1 and the compound of Reference example 11 in the same manner as Example 22-3.

$^1$H NMR (CDCl$_3$, 400 MHz) δ 7.73 (d, 2 H, J=8.1 Hz), 7.30 (d, 2 H, J=8.7 Hz), 7.24 (d, 2 H, J=8.1 Hz), 7.04 (dd, 1 H, J=1.6 and 2.5 Hz), 6.83 (d, 2 H, J=8.7 Hz), 6.76 (dd, 1 H, J=1.6 and 4.0 Hz), 6.45 (brd, 1 H, J=15.8 Hz), 6.31 (dt, 1 H, J=15.8 and 5.7 Hz), 6.19 (dd, 1 H, J=2.5 and 4.0 Hz), 5.17 (d, 2 H, J=5.7 Hz), 4.63 (s, 2 H), 2.42 (s, 3 H).

Example 24

Preparation for (4-{(1E)-3-[2-(4-methoxybenzoyl)-4-methyl-1H-pyrrol-1-yl]-1-propenyl}phenoxy)acetic acid

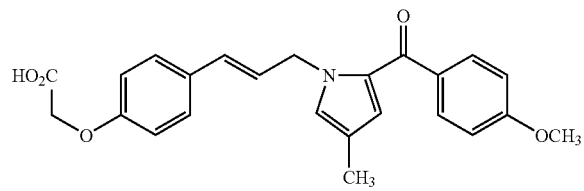

The subject compound was prepared starting from the compound of Reference example 3 and the compound of Reference example 11 in the same manner as Example 22-3.

$^1$H NMR (CDCl$_3$, 400 MHz) δ 7.82 (d, 2 H, J=8.8 Hz), 7.31 (d, 2 H, J=8.7 Hz), 6.94 (d, 2 H, J=8.8 Hz), 6.85 (d, 2 H, J=8.7 Hz), 6.83 (brd, 1 H, J=1.3 Hz), 6.56 (d, 1 H, J=1.3 Hz), 6.45 (d, 1 H, J=15.8 Hz), 6.30 (dt, 1 H, J=15.8 and 6.0 Hz), 5.09 (d, 2 H, J=6.0 Hz), 4.65 (s, 2 H), 3.88 (s, 3 H), 2.08 (s, 3 H).

Reference Example 12

Preparation for (1-allyl-1H-pyrrol-2-yl)(4-methylphenyl)methanone

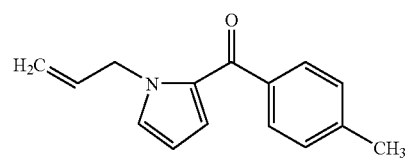

To a solution of potassium t-butoxide (1.05 g, 9.36 mmol) in tetrahydrofuran (10 ml) was added the compound (1.65 g, 8.91 mmol) of Reference example 1 and the mixture was stirred for 30 minutes at room temperature. Thereto was added allylbromide (1.62 g, 13.4 mmol) and the mixture was stirred for 2 hours. Thereto was added water and the mixture was extracted with ethyl acetate. The organic layer was concentrated and purified with silica gel chromatography to give the subject compound (1.61 g, 80%).

$^1$H NMR (CDCl$_3$, 400 MHz) δ 7.71 (d, 2 H, J=8.1 Hz), 7.25 (d, 2 H, J=8.1 Hz), 6.98 (dd, 1 H, J=1.6 and 2.5 Hz), 6.74 (dd, 1 H, J=1.6 and 4.0 Hz), 6.19 (dd, 1 H, J=2.5 and 4.0 Hz), 6.07 (ddt, 1 H, J=10.3, 16.7 and 5.6 Hz), 5.16 (dq, 1 H, J=10.3 and 1.3 Hz), 5.07 (dq, 1 H, J=16.7 and 1.3 Hz), 5.05 (dt, 2 H, J=5.6 and 1.3 Hz), 2.42 (brs, 3 H).

Reference Example 13

Preparation for (1-(3-butenyl)-1H-pyrrol-2-yl)(4-methylphenyl)methanone

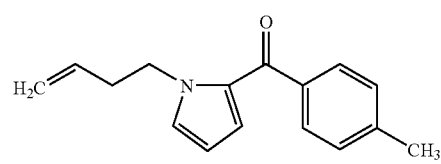

To a solution of the compound (0.95 g, 5.13 mmol) of Reference example 1 in tetrahydrofuran (10 ml) was added 60% sodium hydride (240 mg, 6.00 mmol), and the mixture was stirred for 10 minutes at room temperature. To the reaction mixture was added 4-bromo-1-butene (1.00 g, 7.41 mmol) and the mixture was stirred for 8 hours at 50° C. Thereto were further added 4-bromo-1-butene (200 mg, 1.48 mmol), 60% sodium hydride (100 mg, 2.50 mmol) and N,N-dimethylformamide (10 ml), and the mixture was stirred for 8 hours at 80° C. Thereto was added water and the mixture was extracted with ethyl acetate/toluene (1/1). The organic layer was washed with an aqueous saturated sodium chloride solution and dried over magnesium sulfate. The solvent was removed under reduced pressure and the residue was purified with silica gel chromatography (hexane:ethyl acetate=5:1 to give the subject compound (0.98 g, 80%).

$^1$H NMR (CDCl$_3$, 400 MHz) δ 7.71 (d, 2 H, J=8.1 Hz), 7.25 (d, 2 H, J=8.1 Hz), 6.95 (dd, 1 H, J=2.4 and 1.7 Hz), 6.72 (dd, 1 H, J=4.0 and 1.7 Hz), 6.14 (dd, 1 H, J=4.0 and 2.4 Hz), 5.79 (ddt, 1 H, J=17.1, 10.2 and 6.9 Hz), 5.00–5.09 (m, 2 H), 4.46 (t, 2 H, J=7.1 Hz), 2.57 (brq, 2 H, J=7.1 Hz), 2.43 (s, 3 H).

Example 25

Preparation for t-butyl [(4-{(1E)-3-[2-(4-methylbenzoyl)-1H-pyrrol-1-yl]-1-propenyl}phenyl)sulfanyl]acetate

Example 25-1

Preparation for t-butyl [(4-bromophenyl)sulfanyl]acetate

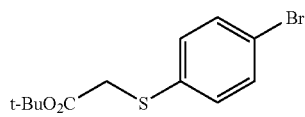

The subject compound was prepared starting from 4-bromobenzenethiol and t-butyl bromoacetate in the same manner as Reference example 6-1.

$^1$H NMR (CDCl$_3$, 400 MHz) δ 7.41 (d, 2 H, J=8.5 Hz), 7.27 (d, 2 H, J=8.5 Hz), 3.53 (s, 2 H), 1.41 (s, 9 H).

Example 25-2

Preparation for t-butyl [(4-{(1E)-3-[2-(4-methylbenzoyl)-1H-pyrrol-1-yl]-1-propenyl}phenyl)sulfanyl]acetate

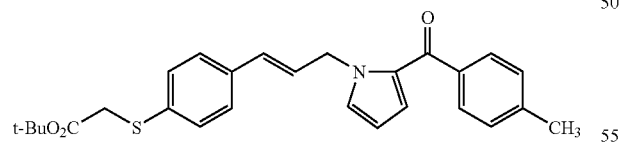

The subject compound was prepared starting from the compound of Example 25-1 and the compound of Reference example 12 in the same manner as Reference example 6-2.

$^1$H NMR (CDCl$_3$, 400 MHz) δ 7.73 (d, 2 H, J=8.1 Hz), 7.33–7.27 (m, 4 H), 7.24 (d, 2 H, J=8.1 Hz), 7.04 (dd, 1 H, J=1.7 and 2.5 Hz), 6.76 (dd, 1 H, J=1.7 and 4.0 Hz), 6.45–6.38 (m, 2 H), 6.20 (dd, 1 H, J=2.5 and 4.0 Hz), 5.19 (d, 2 H, J=4.7 Hz), 3.53 (s, 2 H), 2.43 (s, 3 H), 1.40 (s, 9 H).

Example 26

Preparation for [(4-{(1E)-3-[2-(4-methylbenzoyl)-1H-pyrrol-1-yl]-1-propenyl}phenyl)sulfanyl]acetic acid

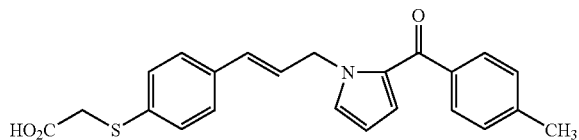

The subject compound was prepared starting from the compound of Example 25 in the same manner as Example 1-2.

$^1$H NMR (CDCl$_3$, 400 MHz) δ 7.72 (d, 2 H, J=8.1 Hz), 7.34–7.27 (m, 4 H), 7.25 (d, 2 H, J=8.1 Hz), 7.04 (dd, 1 H, J=1.7 and 2.5 Hz), 6.76 (dd, 1 H, J=1.7 and 4.0 Hz), 6.45–6.38 (m, 2 H), 6.20 (dd, 1 H, J=2.5 and 4.0 Hz), 5.19 (d, 2 H, J=4.7 Hz), 3.65 (s, 2 H), 2.42 (s, 3 H).

Example 27

Preparation for t-butyl (4-{(1E)-3-[2-(4-methylbenzoyl)-1H-pyrrol-1-yl]-1-butenyl}phenoxy)acetate

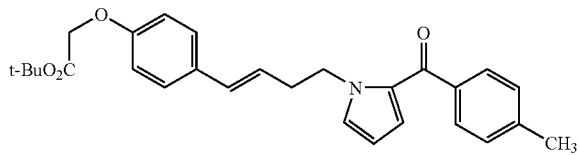

The subject compound was prepared starting from the compound of Reference example 11-1 and the compound Reference example 13 in the same manner as Reference example 6-2.

$^1$H NMR (CDCl$_3$, 400 MHz) δ 7.68 (d, 2 H, J=8.1 Hz), 7.24–7.19 (m, 4 H), 6.96 (dd, 1 H, J=1.7 and 2.5 Hz), 6.80 (d, 2 H, J=8.8 Hz), 6.72 (dd, 1 H, J=1.7 and 4.0 Hz), 6.32 (brd, 1 H, J=15.7 Hz), 6.15 (dd, 1 H, J=2.5 and 4.0 Hz), 6.03 (dt, 1 H, J=15.7 and 7.2 Hz), 4.52 (t, 2 H,. J=7.1 Hz), 4.49 (s, 2 H), 2.69 (dt, 2 H, J=7.2 and 7.1 Hz), 2.42 (s, 3 H), 1.49 (s, 9 H).

Example 28

Preparation for (4-{(1E)-4-[2-(4-methylbenzoyl)-1H-pyrrol-1-yl]-1-butenyl}phenyl)phenoxy)acetic acid

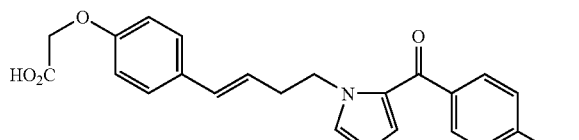

The subject compound was prepared starting from Example 27 in the same manner as Example 1-2.

¹H NMR (CDCl₃, 400 MHz) δ 7.69 (d, 2 H, J=8.1 Hz), 7.25–7.21 (m, 4 H), 6.96 (dd, 1 H, J=1.7 and 2.5 Hz), 6.82 (d, 2 H, J=8.8 Hz), 6.72 (dd, 1 H, J=1.7 and 4.0 Hz), 6.32 (brd, 1 H, J=15.7 Hz), 6.14 (dd, 1 H, J=2.5 and 4.0 Hz), 6.06 (dt, 1 H, J=15.7 and 7.2 Hz), 4.66 (s, 2 H), 4.52 (t, 2 H, J=7.1 Hz), 2.69 (dt, 2 H, J=7.2 and 7.1 Hz), 2.42 (s, 3 H).

Example 29

Preparation for methyl (4-{(1E)-3-[2-(4-methylbenzoyl)-1H-pyrrol-1-yl]-1-propenyl}phenyl)acetate

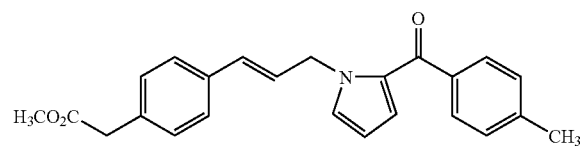

The subject compound was prepared starting from methyl (4-buromophenyl)acetate and the compound of Reference example 12 in the same condition as Reference example 6-2.

¹H NMR (CDCl₃, 400 MHz) δ 7.73 (d, 2 H, J=8.1 Hz), 7.32 (d, 2 H, J=8.2 Hz), 7.25 (d, 2 H, J=8.1 Hz), 7.20 (d, 2 H, J=8.2 Hz), 7.04 (dd, 1 H, J=1.7 and 2.5 Hz), 6.76 (dd, 1 H, J=1.7 and 4.0 Hz), 6.48 (brd, 1 H, J=15.7 Hz), 6.42 (dt, 1 H, J=15.7 and 5.5 Hz), 6.20 (dd, 1 H, J=2.5 and 4.0 Hz), 5.19 (d, 2 H, J=5.5 Hz), 3.68 (s, 3 H), 3.60 (s, 2 H), 2.43 (s, 3 H).

Example 30

Preparation for (4-{(1E)-3-[2-(4-methylbenzoyl)-1H-pyrrol-1-yl]-1-propenyl}phenyl)acetic acid

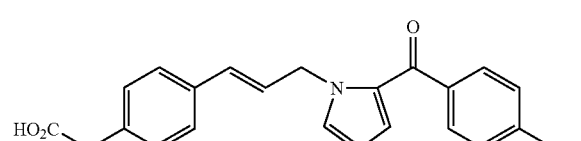

The subject compound was prepared starting from Example 29 in the same manner as Example 1-2.

¹H NMR (CDCl₃, 400 MHz) δ 7.72 (d, 2 H, J=8.1 Hz), 7.32 (d, 2 H, J=8.2 Hz), 7.26 (d, 2 H, J=8.1 Hz), 7.20 (d, 2 H, J=8.2 Hz), 7.04 (dd, 1 H, J=1.7 and 2.5 Hz), 6.76 (dd, 1 H, J=1.7 and 4.0 Hz), 6.48 (brd, 1 H, J=15.7 Hz), 6.42 (dt, 1 H, J=15.7 and 5.5 Hz), 6.20 (dd, 1 H, J=2.5 and 4.0 Hz), 5.20 (d, 2 H, J=5.5 Hz), 3.62 (s, 2 H), 2.42 (s, 3 H).

Example 31

Preparation for t-butyl (3-{(1E)-4-[2-(4-methylbenzoyl)-1H-pyrrol-1-yl]-1-butenyl}phenoxy)acetate Example 31-1

Preparation for t-butyl (3-iodophenoxy)acetate

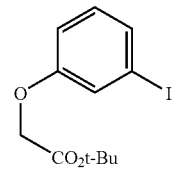

To a solution of m-iodophenol (1.22 g, 5.55 mmol) in N,N-dimethylformamide (15 ml) were added potassium carbonate (1.40 g, 10.1 mmol) and t-butyl bromoacetate (1.22 ml, 6.25 mmol), and the mixture was stirred for 3 hours at 50° C. Thereto was added an aqueous 5% potassium hydrogensulfate solution and the mixture was extracted with ethyl acetate. The organic layer was washed with an aqueous saturated sodium chloride solution, and dried over magnesium sulfate. The solvent was removed under reduced pressure and the residue was purified with silica gel chromatography (hexane:ethyl acetate=4:1) to give the subject compound (1.85 g, 100%).

¹H NMR (CDCl₃, 400 MHz) δ 7.32 (ddd, 1 H, J=7.8, 1.5 and 0.9 Hz), 7.24 (dd, 1 H, J=2.5 and 1.5 Hz), 7.00 (dd, 1 H, J=8.3 and 7.8 Hz), 6.87 (ddd, 1 H, J=8.3, 2.5 and 0.9 Hz), 4.49 (s, 2 H), 1.49 (s, 9 H).

Example 31-2

Preparation for t-butyl (3-{(1E)-4-[2-(4-methylbenzoyl)-1H-pyrrol-1-yl]-1-butenyl}phenoxy)acetate

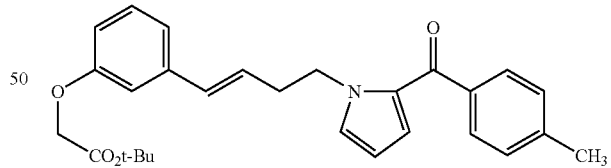

The subject compound was prepared starting from the compound of Example 31-1 and the compound of Reference example 13 in the same condition as Reference example 6-2.

¹H NMR (CDCl₃, 400 MHz) δ 7.69 (d, 2 H, J=8.0 Hz), 7.23 (d, 2 H, J=8.0 Hz), 7.18 (t, 1 H, J=7.9 Hz), 6.96 (dd, 1 H, J=2.5 and 1.7 Hz), 6.91 (brd, 1 H, J=7.9 Hz), 6.82 (brt, 1 H, J=2.0 Hz), 6.72–6.76 (m, 1 H), 6.72 (dd, 1 H, J=4.0 and 1.7 Hz), 6.32 (d, 1 H, J=15.8 Hz), 6.15 (dt, 1 H, J=15.8 and 7.2 Hz), 6.14 (dd, 1 H, J=4.0 and 2.5 Hz), 4.51 (t, 2 H, J=7.0 Hz), 4.47 (s, 2 H), 2.68–2.73 (m, 2 H), 2.42 (s, 3 H), 1.49 (s, 9 H).

Example 32

Preparation for (3-{(1E)-4-[2-(4-methylbenzoyl)-1H-pyrrol-1-yl]-1-butenyl}phenoxy)acetic acid

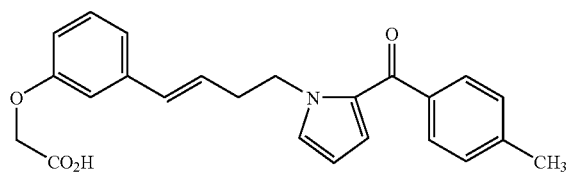

The subject compound was prepared starting from the compound of Example 31 in the same manner as Example 1-2.

¹H NMR (CDCl₃, 400 MHz) δ 7.68 (d, 2 H, J=8.0 Hz), 7.22 (d, 2 H, J=8.0 Hz), 7.21 (t, 1 H, J=8.1 Hz), 6.97 (dd, 1 H, J=2.5 and 1.6 Hz), 6.95 (brd, 1 H, J=8.1 Hz), 6.84 (brt, 1 H, J=2.2 Hz), 6.77 (dd, 1 H, J=8.1 and 2.2 Hz), 6.72 (dd, 1 H, J=4.0 and 1.6 Hz), 6.33 (d, 1 H, J=15.8 Hz), 6.17 (dt, 1 H, J=15.8 and 7.1 Hz), 6.15 (dd, 1 H, J=4.0 and 2.5 Hz), 4.62 (s, 2 H), 4.55 (t, 2 H,J=7.0 Hz),2.68–2.74 (m, 2 H), 2.42 (s, 3 H).

Example 33

Preparation for methyl (3-{(1E)-4-[2-(4-methylbenzoyl)-1H-pyrrol-1-yl]-1-butenyl}phenyl)acetate

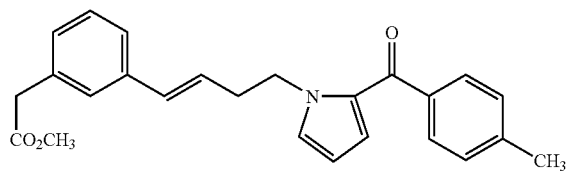

Crude (3-{(1E)-4-[2-(4-methylbenzoyl)-1H-pyrrol-1-yl]-1-butenyl}phenyl)acetic acid was prepared starting from 3-bromophenylacetic acid and the compound of Reference example 13 in the same manner as Reference example 6-2. The crude product was esterified with methanol and thionyl chloride to give the subject compound.

¹H NMR (CDCl₃, 400 MHz) δ 7.69 (d, 2 H, J=8.1 Hz), 7.23 (d, 2 H, J=8.1 Hz), 7.18–7.25 (m, 3 H), 7.12 (brd, 1 H, J=7.1 Hz), 6.97 (dd, 1 H, J=2.5 and 1.7 Hz), 6.73 (dd, 1 H, J=4.0 and 1.7 Hz), 6.37 (d, 1 H, J=15.8 Hz), 6.18 (dt, 1 H, J=15.8 and 7.2 Hz), 6.15 (dd, 1 H, J=4.0 and 2.5 Hz), 4.53 (t, 2 H, J=7.1 Hz), 3.69 (s, 3 H), 3.58 (s, 2 H), 2.71 (brq, 2 H, J=7.0 Hz), 2.42 (s, 3 H).

Example 34

Preparation for (3-{(1E)-4-[2-(4-methylbenzoyl)-1H-pyrrol-1-yl]-1-butenyl}phenyl)acetic acid

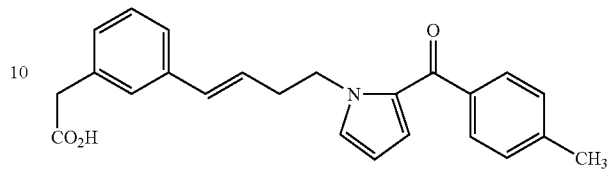

The subject compound was prepared starting from the compound of Example 33 in the same manner as Example 1-2.

¹H NMR (CDCl₃, 400 MHz) δ 7.68 (d, 2 H, J=8.1 Hz), 7.22 (d, 2 H, J=8.1 Hz), 7.19–7.25 (m, 3 H), 7.13 (brd, 1 H, J=7.0 Hz), 6.96 (dd, 1 H, J=2.5 and 1.7 Hz), 6.72 (dd, 1 H, J=4.0 and 1.7 Hz), 6.36 (d, 1 H, J=15.9 Hz), 6.18 (dt, 1 H, J=15.9 and 7.1 Hz), 6.14 (dd, 1 H, J=4.0 and 2.5 Hz), 4.53 (t, 2 H, J=7.0 Hz), 3.61 (s, 2 H), 2.71 (brq, 2 H, J=7.0 Hz), 2.42 (s, 3 H).

Example 35

Preparation for calcium (2S)-2-(3-{(1E)-3-[2-(4-methylbenzoyl)-1H-pyrrol-1-yl]prop-1-enyl}phenoxy)propionate.hydrate

Example 35-1

Preparation for (1R)-1-methyl-2-morpholin-4-yl-2-oxoethyl 4-methylbenzenesulfonate To a mixture of D-(+)-methyl lactate (20.8 g, 200 mmol) and morpholine (19.1 ml, 220 mmol) (800 mg, 20.0 mmol) was gradually added sodium hydride (60% in paraffin liquid) under stirrings ice cooling and an atmosphere of nitrogen, and the mixture was stirred at 50° C. for 3 hours under heating. After being cooled to room temperature, the mixture was azeotoropied with toluene to remove excess morpholine. The residue was dried under reduced pressure to give (2R)-1-morpholin-4-yl-1-oxopropane-2-ol (32.1 g).

To a suspension of sodium hydride (60% in paraffin liquid) (8.41 g, 210 mmol) in tetrahydrofuran (120 ml was dropped (2R)-1-morpholin-4-yl-1-oxopropane-2-ol (32.1 g) in tetrahydrofuran (150 ml) under stirring, ice cooling and an atmosphere of nitrogen. The mixture was then stirred for 30 minutes at 50° C. After being ice-cooled, thereto was dropped a solution of p-toluenesulfonyl chloride (45.8 g, 234 mmol) in tetrahydrofuran (180 ml), and the mixture was stirred for 4 hours at room temperature. Thereto was added 1N hydrochloric acid and the mixture was extracted with ethyl acetate. The organic layer was washed with water and an aqueous saturated sodium chloride solution and dried over magnesium sulfate. The solvent was removed under reduced pressure to give the oily residue. Thereto was added diethyl ether and the resulting precipitate was taken by filtration, washed with diethyl ether and dried under reduced pressure to give the subject compound as a white solid (36.1 g, 115 mmol, 58%).

$^1$H NMR (CDCl$_3$, 400 MHz) δ 7.81 (d, 2 H, J=8.0 Hz), 7.35 (d, 2 H, J=8.0 Hz), 5.27 (q, 1 H, J=6.8 Hz), 3.64–3.46 (m, 8H), 2.46 (s, 3 H), 1.47 (d, 3 H, J=6.8 Hz).

Example 35-2

Preparation for 4-[(2S)-2-(3-ibdophenoxy)propanoyl]morpholine

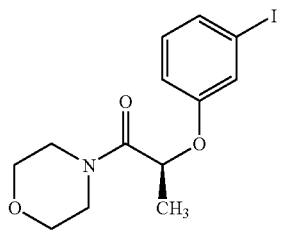

To a solution of m-iodophenol (11.0 g, 50.0 mmol) in dimethylformamide (100 ml) was added potassium carbonate (10.0 g, 72.4 mmol) and then thereto was added (1R)-1-methyl-2-morpholin-4-yl-2-oxoethyl 4-methylbenzenesulfonate (16.45 g, 52.5 mmol), and the mixture was stirred for 3 hours at 50° C. After the mixture was allowed to cool to room temperature, thereto was added an aqueous 5% potassium hydrogensulfate solution and the mixture was twice extracted with ethyl acetate. The organic layer was washed with water and an aqueous saturated sodium chloride solution, and dried over magnesium sulfate. The solvent was removed under reduced pressure and the residue was recrystallized from ethyl acetate to give the subject compound as a white solid (15.40 g, 42.6 mmol, 85%).

$^1$H NMR (CDCl$_3$, 400 MHz) δ 7.32 (dd, 1 H, J=1.7 and 7.8 Hz), 7.25 (dd, 1 H, J=1.7 and 2.4 Hz), 7.00 (dd, 1 H, J=7.8 and 8.1 Hz), 6.87 (dd, 1 H, J=2.4 and 8.1 Hz), 4.92 (q, 1 H, J=6.8 Hz), 3.67–3.46 (m, 8H), 1.60 (d, 3 H, J=6.8 Hz).

Example 35-3

Preparation for (2S)-2-(3-{(1E)-3-[2-(4-methylbenzoyl)-1H-pyrrol-1-yl]prop-1-enyl}phenoxy)propionic acid (1S)-1-phenylethylamine salt

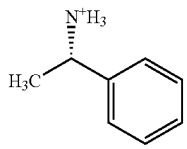

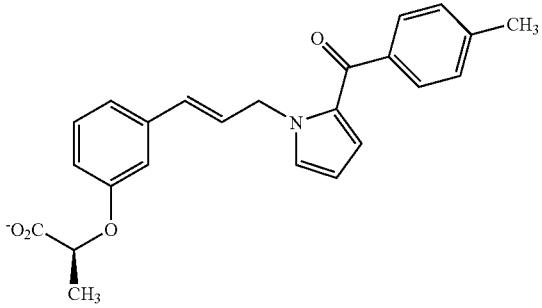

To a solution of (4-methylphenyl)(1-allyl-1H-pyrrol-1-yl)methanone (47.31 g, 210 mmol) in dimethylformamide (650 ml) were added 4-[(2S)-2-(3-iodophenoxy)propanoyl]morpholine (72.24 g, 200 mmol), sodium hydrogencarbonate (33.60 g, 400 mmol), benzyltriethylammonium chloride (45.56 g, 200 mmol) and palladium acetate (2.245 g, 10.0 mmol), and the mixture was stirred for 6 hours at 50–55° C. After the mixture was allowed to cool to room temperature, thereto was added water (1 L) and the mixture was extracted with toluene/ethyl acetate (1/2) twice (1 L and 0.5 L). The organic layer was washed with an aqueous 10% potassium hydrogensulfate solution three times and then water and an aqueous saturated sodium chloride solution. The organic layer was dried over magnesium sulfate. After addition of charcoal, the organic layer was filtered with Celite. The solvent was removed under reduced pressure to give {1-[(2E)-3-(3-{[(1S)-1-methyl-2-morpholin-4-yl-2-oxoethyl]oxy}phenyl)prop-2-enyl]-1H-pyrrol-2-yl}(4-methylphenyl)methanone (about 10 g). To a solution of {1-[(2E)-3-(3-{[(1S)-1-methyl-2-morpholin-4-yl-2-oxoethyl]oxy}phenyl)prop-2-enyl]-1H-pyrrol-2-yl}(4-methylphenyl)methanone (about 100 g) in tetrahydrofuran (350 ml) and methanol (350 ml) was added an aqueous 2N lithium hydroxide solution (500 ml) and the mixture was stirred for 5 hours at 70° C. The reaction mixture was concentrated, followed by addition of water. The mixture was acidified (pH 2–3) with 1N hydrochloric acid. The solution was extracted with toluene/ethyl acetate (1/2)(1 L×2) and dried over anhydrous magnesium sulfate. The solvent was removed and the residue was dried to give (2S)-2-(3-{(1E)-3-[2-(4-methylbenzoyl)-1H-pyrrol-1-yl]prop-1-enyl}phenoxy)propionic acid (about 90 g).

To a solution of (2S)-2-(3-{(1E)-3-[2-(4-methylbenzoyl)-1H-pyrrol-1-yl]prop-1-enyl}phenoxy)propionic acid (about 90 g) in isopropanol (500 ml) was dropped (L)-(–)-1-phenylethylamine (9.90 g) in isopropanol (100 ml) at room temperature under stirring. After completion of dropping, thereto were seeded crystals of (2S)-2-(3-{(1E)-3-[2-(4-methylbenzoyl)-1H-pyrrol-1-yl]prop-1-enyl}phenoxy)propionic acid (1S)-1-phenylethylamine salt and the mixture was stirred at room temperature. The resulting crystals were collected by filtration, washed with isopropanol and dried under reduced pressure to give the subject compound (55.71 g, 109 mmol, 54.5%). Further the filtrate was concentrated and the residue was recrystallized to give the subject compound (15.12 g, 29.6 mmol, 14.8%).

$^1$H NMR (CDCl$_3$, 400 MHz) δ 7.68 (d, 2 H, J=8.1 Hz), 7.26–7.20 (m, 7 H), 7.09 (dd, 1 H, J=7.8 and 8.0 Hz), 6.99 (dd, 1 H, J=1.7 and 2.5 Hz), 6.88 (d, 1 H, J=7.8 Hz), 6.82 (d, 1 H, J=1.3 Hz), 6.74 (dd, 1 H, J=1.6 and 4.0 Hz), 6.65

(dd, 1 H, J=1.3 and 8.0 Hz), 6.47–6.37 (m, 2 H), 6.17 (dd, 1 H, J=2.5 and 4.0 Hz), 5.10 (d, 2 H, J=3.0 Hz), 4.44 (q, 1 H, J=6.8 Hz), 3.98 (q, 1 H, J=6.8 Hz), 2.40 (s, 3 H), 1.40 (d, 3 H, J=6.8 Hz), 1.35 (d, 3 H, J=6.8 Hz).

Example 35-4

Preparation for calcium (2S)-2-(37-{(1E)-3-[2-(4-methylbenzoyl)-1H-pyrrol-1-yl]prop-1-enyl}phenoxy)propionate hydrate

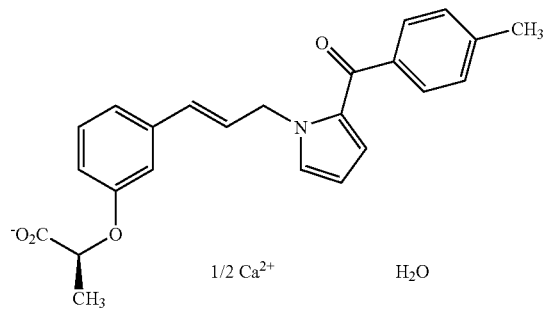

To a solution of (2S)-2-(3-{(1E)-3-[2-(4-methylbenzoyl)-1H-pyrrol-1-yl]prop-1-enyl}phenoxy)propionic acid (1S)-1-phenylethylamine salt (5.11 g, 10.0 mmol) in methanol (75 ml) and water (45 ml) was dropped a solution of calcium chloride dihydrate (809 mg, 5.50 mml) in water (30 ml) at 80° C. under stirring. After completion of dropping, the mixture was stirred for 30 minute at 90–100° C. After being allowed to cool, thereto were seeded the crystals at 7.0–80° C. and the mixture was stirred for 3 hours under heating at 70–80° C. When white crystals occurred, the mixture was allowed to cool under stirring. After being allowed to cool, the precipitate was collected by filtration, washed with water and dried to give the subject compound (3.67 g, 8.61 mmol, 86%).

$^{1}$H NMR (DMSO-d$_{6}$, 400 MHz) δ 7.65 (d, 2 H, J=8.1 Hz), 7.34 (dd, 1 H, J=1.6 and 2.4 Hz), 7.31 (d, 2 H, J=8.1 Hz), 7.10 (dd, 1 H, J=7.8 and 8.0 Hz), 6.83 (d, 1 H, J=7.8 Hz), 6.79 (s, 1 H), 6.69–6.67 (m, 2 H), 6.40 (dt, 1 H, J=16.0 and 5.4 Hz), 6.35 (brd, 1 H, J=16.0 Hz), 6.22 (dd, 1 H, J=2.5 and 4.0 Hz), 5.14 (d, 2 H, J=5.4 Hz), 4.31 (q, 1 H, J=6.7 Hz), 2.39 (s, 3 H), 1.38 (d, 3 H, J=6.7 Hz).

Example 36

Preparation for (3-{(1E)-3-[2-({[4-trifluoromethyl)benzyl]amino}carbonyl)-1H-pyrrol-1-yl]prop-1-enyl}phenoxy)acetic acid Example 36-1

Preparation for methyl 1H-pyrrole-2-carboxlate

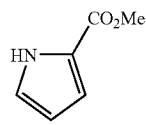

A suspension of 1H-pyrrole-2-carboxylic acid (5.5 g, 49.5 mmol), WSCI.HCl (12.2 g, 63.6 mmol), HOBt (8.4 g, 62.2 mmol), methanol (7.0 g, 218 mmol) and 4-dimethylaminopyridine (3.0 g, 24.5 mmol) in dimethylformamide (60 ml) was stirred for 70 hours at room temperature and for 2 hours at 60° C. To the reaction mixture was added an aqueous 5% potassium hydrogensulfate solution and the mixture was extracted with ethyl acetate/toluene (1/1). The organic layer was washed with an aqueous saturated sodium hydrogencarbonate solution, and an aqueous saturated sodium chloride solution, and dried over magnesium sulfate. The solvent was removed and the residue was purified with silica gel chromatography (hexane:ethyl acetate=5:1→3:1) to give the subject compound (4.88 g, 79%).

$^{1}$H NMR (CDCl$_{3}$, 400 MHz) δ 9.08 (brs, 1 H), 6.90–6.98 (m, 2 H), 6.25–6.29 (m, 1 H), 3.86 (s, 3 H).

Example 36-2

Preparation for methyl 1-allyl-1H-pyrrole-2-caboxylate

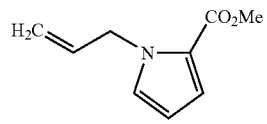

To a solution of methyl 1H-pyrrole -2-caboxylate (4.48 g, 35.8 mmol) in tetrahydrofuran (100 ml) were added potassium t-butoxide (4.2 g, 37.4 mmol) and dimethylformamide (20 ml), and the mixture was stirred for 10 minutes at room temperature. To the mixture was added allyl bromide (5.4 g, 44.6 mmol), and the mixture was stirred for 4 hours at room temperature. Thereto was added an aqueous 5% potassium hydrogensulfate solution and the mixture was extracted with ethyl acetate. The organic layer was washed with an aqueous saturated sodium chloride solution, and dried over magnesium sulfate. The solvent was removed and the residue was purified with silica gel chromatography (hexane:ethyl acetate=5:1→3:1) to give the subject compound (5.46 g, 92%).

$^{1}$H NMR (CDCl$_{3}$, 400 MHz) δ 6.97 (dd, 1 H, J=3.9, 1.8 Hz), 6.86 (dd, 1 H, J=2.6, 1.8 Hz), 6.16 (dd, 1 H, J=3.9, 2.6 Hz), 5.96–6.06 (m, 1 H), 5.12–5.17 (m, 1 H), 4.94–5.01 (m, 3 H), 3.80 (s, 3 H).

Example 36-3

Preparation for 1-allyl-1H-pyrrole-2-carboxlic acid

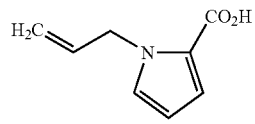

A mixture of methyl 1-allyl-1H-pyrrole-2-carboxlate (4.52 g, 27.4 mmol), tetrahydrofuran (30 ml), methanol (30 ml) and an aqueous 1N lithium hydroxide solution was stirred for 3 hours at room temperature, and for 5 hours at 60° C. Thereto was added additional lithium hydroxide (0.5 g) and the mixture was stirred for 5 hours at 60° C. Methanol and tetrahydrofuran were removed under reduced pressure and the residue was acidified with concentrated hydrochloric acid. The mixture was extracted with ethyl acetate and the organic layer was washed with water and an aqueous saturated sodium chloride solution and dried over magnesium sulfate. The solvent was removed to give the subject compound (4.24 g, 100%).

$^1$H NMR (CDCl$_3$, 400 MHz) δ 7.11 (dd, 1 H, J=4.0, 1.8 Hz), 6.91 (dd, 1 H, J=2.6, 1.8 Hz), 6.19 (dd, 1 H, J=4.0, 2.6 Hz), 6.00 (ddt, 1 H, J=17.0, 10.3, 5.2 Hz), 5.16 (ddd, 1 H, J=10.3, 2.6, 1.3 Hz), 4.93–5.03 (m, 3 H).

Example 36-4

Preparation for 1-{(2E)-3-[3-(2-t-butoxy-2-oxoethoxy)phenyl]prop-2-enyl}-1H-pyrrole-2-carboxylic acid

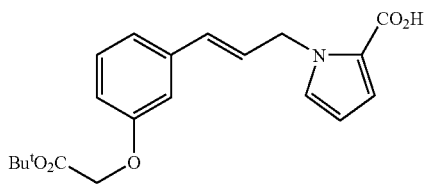

A mixture of t-butyl (3-iodophenoxy) acetate (2.4 g, 7.18 mmol), 1-allyl-1H-pyrrole-2-caboxylic acid (1.0 g, 6.62 mmol), palladium acetate (75 mg, 0.33 mmol), sodium hydrogencarbonate (1.5 g, 17.9 mmol) and benzyltriethylammonium chloride (1.6 g, 7.02 mmol) in dimethylformamide (30 ml) was stirred for 2 hours at 60° C. Thereto was added an aqueous sodium hydrogencarbonate solution and the mixture was washed with diethyl ether. The aqueous layer was acidified with an aqueous 5% sodium hydrogensulfate solution and extracted with ethyl acetate. The organic layer was washed with water and an aqueous saturated sodium chloride solution. The organic layer was dried over magnesium sulfate. The solvent was removed to give the subject compound (2.1 g, 89%).

$^1$H NMR (CDCl$_3$, 400 MHz) δ 7.18 (t, 1 H, J=8.0 Hz), 7.12 (dd, 1 H, J=4.0, 1.7 Hz), 6.95–6.99 (m, 2 H), 6.86–6.89 (m, 1 H), 6.78 (brdd, 1 H, J=8.0, 2.1 Hz), 6.37 (d, 1 H, J=15.9 Hz), 6.32 (dt, 1 H, J=15.9, 4.8 Hz), 6.21 (dd, 1 H, J=4.0, 2.3 Hz), 5.11 (brd, 2 H, J=4.8 Hz), 4.50 (s, 2 H), 1.47 (s, 9 H).

Example 36-5

Preparation for (3-{(1E)-3-[2-({[4-trifluoromethyl)benzyl]amino}carbonyl)-1H-pyrrol-1-yl]prop-1-enyl}phenoxy)acetic acid

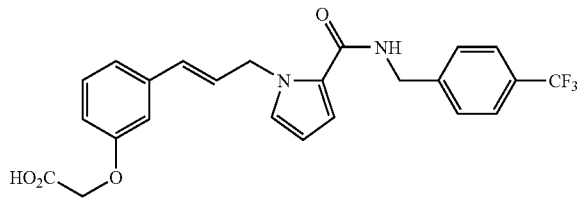

A suspension of 1-{(2E)-3-[3-(2-t-butoxy-2-oxoethoxy)phenyl]prop-2-enyl}-1H-pyrrole-2-carboxylic acid (315 mg, 0.88 mmol), 4-(trifluoromethyl)benzylamine (260 mg, 1.48 mmol), WSCI•HCl (190 mg, 0.99 mmol) and HOBt (130 mg, 0.99 mmol) in dimethylformamide (5 ml) was stirred for 65 hours at room temperature. To the reaction mixture was added an aqueous 5% potassium hydrogensulfate solution and the mixture was extracted with ethyl acetate. The organic layer was washed with water, an aqueous saturated sodium hydrogencarbonate solution and an aqueous saturated sodium chloride solution, and dried over magnesium sulfate. The solvent was removed and the residue was purified with silica gel chromatography (hexane:ethyl acetate=4:1→3:2) to give t-butyl (3-{(1E)-3-[2-({[4-trifluoromethyl)benzyl]amino}carbonyl)-1H-pyrrol-1-yl]prop-1-enyl}phenoxy)acetate (137 mg, 30%).

A mixture of thus obtained t-butyl (3-{(1E)-3-[2-({[4-trifluoromethyl)benzyl]amino}carbonyl)-1H-pyrrol-1-yl]prop-1-enyl}phenoxy)acetate (137 mg, 30%), tetrahydrofuran (2 ml), methanol (2 ml) and an aqueous 1N sodium hydroxide solution (2 ml) was stirred for 4 hours at room temperature. Thereto was added diluted hydrochloric acid and the mixture was extracted with ethyl acetate. The organic layer was washed with water, an aqueous saturated sodium chloride solution, and dried over magnesium sulfate. The solvent was removed to give the subject compound (120 mg, yield 100%).

$^1$H NMR (CDCl$_3$, 400 MHz) δ 7.47 (d, 2 H, J=8.1 Hz), 7.39 (d, 2 H, J=8.1 Hz), 7.25 (t, 1 H, J=8.0 Hz), 7.01 (brd, 1 H, J=8.0 Hz), 6.90–6.93 (m, 1 H), 6.87–6.89 (m, 1 H), 6.81 (brdd, 1 H, J=8.0, 2.5 Hz), 6.62 (dd, 1 H, J=3.9, 1.6 Hz), 6.39 (dt, 1 H, J=16.0, 4.6 Hz), 6.35 (d, 1 H, J=16.0 Hz), 6.25 (brs, 1 H), 6.16 (dd, 1 H, J=3.9, 2.6 Hz), 5.17 (brd, 2 H, J=4.6 Hz), 4.65 (s, 2 H), 4.62 (brd, 2 H, J=5.8 Hz).

Example 37

Preparation for (2S)-2-{3-[(1E)-3-(2-{[3-ethylphenyl)amino]carbonyl)-1H-pyrrol-1-yl]prop-1-enyl}phenoxy}propanoic acid The subject compound was prepared in the same manner as Example 36.

Example 37-1

Preparation for 1-allyl-N-(3-ethylphenyl)-1H-pyrrole-2-caboxamide

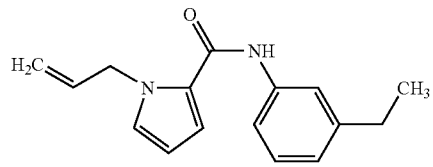

A mixture of 1-allyl-1H-pyrrole-2-caboxylic acid (270 mg, 1.79 mmol), m-ethylaniline (0.43 g, 2.48 mmol), BOP-Cl (500 mg, 1.96 mmol) and triethylamine (210 mg, 2.08 mmol) in dichloromethane (3 ml) was stirred for 2 hours at room temperature. To the reaction mixture was added an aqueous 5% potassium hydrogensulfate solution and the mixture was extracted with ethyl acetate. The organic layer was washed with water, an aqueous saturated sodium hydrogencarbonate solution and an aqueous saturated sodium chloride solution, and dried over magnesium sulfate. The solvent was removed and the residue was purified with silica gel chromatography (hexane:ethyl acetate=5:1→3:1) to give the subject compound (229 mg, 50%).

$^1$H NMR (CDCl$_3$, 400 MHz) δ 7.56 (brs, 1 H), 7.42 (brs, 1 H), 7.35 (brd, 1 H, J=7.7 Hz), 7.25 (t, 1 H, J=7.7 Hz), 6.96 (brd, 1 H, J=7.7 Hz), 6.85 (dd, 1 H, J=2.6, 1.6 Hz), 6.70 (dd, 1 H, J=3.9, 1.6 Hz), 6.18 (dd, 1 H, J=3.9, 2.6 Hz), 6.01–6.11 (m, 1 H), 5.13–5.18 (m, 1 H), 4.99–5.05 (m, 3 H), 2.65 (q, 2 H, J=7.6 Hz), 1.25 (t, 3 H, J=7.6 Hz).

Example 37-2

Preparation for (2S)-2-{3-[(1E)-3-(2-{[(3-ethylphenyl)amino]carbonyl}-1H-pyrrol-1-yl)prop-1-enyl]phenoxy}propanoic acid

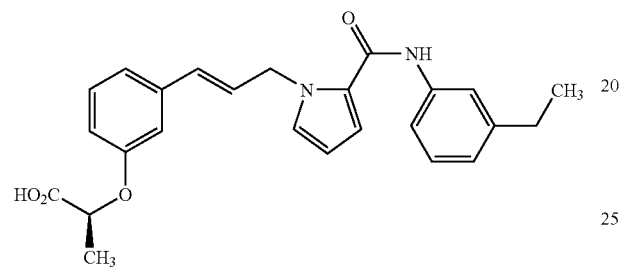

A mixture of (1R)-1-methyl-2-morpholin-4-yl-2-oxoethyl 4-methylbenzenesulfonate (310 mg, 0.858 mmol), 1-allyl-N-(3-ethylphenyl)-1H-pyrrole-2-carboxamide (210 mg, 0.826 mmol), palladium acetate (10 mg, 0.045 mmol), sodium hydrogencarbonate (140 mg, 1.66 mmol) and benzyltriethylammonium chloride (190 mg, 0.834 mmol) in dimethylformamide (5 ml) was stirred for 3 hours at 50° C. Thereto was added an aqueous 5% potassium hydrogensulfate solution and the mixture was extracted with ethyl acetate/toluene(2/1). The organic layer was washed with water, an aqueous sodium thiosulfate solution and an aqueous saturated sodium chloride solution, and dried over magnesium sulfate. The solvent was removed and the residue was purified with silica gel chromatography (hexane:ethyl acetate=5:1→3:1) to give N-(3-ethylphenyl)-1-[(2E)-3-(3-{[(1S)-1-methyl-2-morpholin-4-yl-2-oxoethyl]oxy}phenyl)prop-2-enyl]-1H-pyrrole-2-carboxamide (349 mg, 83%).

A mixture of N-(3-ethylphenyl)-1-[(2E)-3-(3-{[(1S)-1-methyl-2-morpholin-4-yl-2-oxoethyl]oxy}phenyl)prop-2-enyl]-1H-pyrrole-2-carboxamide (348 mg, 0.714 mmol) in tetrahydrofuran (4 ml), methanol (4 ml) and an aqueous 1N lithium hydroxide (6 ml) was stirred for 6 hours at 50° C. The reaction mixture was diluted with water, washed with diethyl ether. The aqueous layer was acidified with diluted hydrochloric acid and extracted with ethyl acetate. The organic layer was washed with water and an aqueous saturated sodium chloride solution and dried over magnesium sulfate. The solvent was removed to give the subject compound (264 mg, 88%).

$^1$H NMR (CDCl$_3$, 400 MHz) δ 7.60 (brs, 1 H), 7.41 (brs, 1 H), 7.35 (brd, 1 H, J=7.6 Hz), 7.25 (brt, 1 H, J=7.6 Hz), 7.20 (brt, 1 H, J=7.9 Hz), 6.99 (brd, 1 H, J=7.9 Hz), 6.96 (brd, 1 H, J=7.6 Hz), 6.89–6.91 (m, 2 H), 6.77 (brdd, 1 H, J=7.9, 2.1 Hz), 6.72 (dd, 1 H, J=3.9, 1.6 Hz), 6.41 (dt, 1 H, J=16.0, 4.4 Hz), 6.38 (d, 1 H, J=16.0 Hz), 6.19 (dd, 1 H, J=3.9, 2.6 Hz), 5.12–5.20 (m, 2 H), 4.78 (q, 1 H, J=6.8 Hz), 2.65 (q, 2 H, J=7.6 Hz), 1.63 (d, 3 H, J=6.8 Hz), 1.24 (t, 3 H, J=7.6 Hz).

Example 38

Preparation for (3-{2-[2-(4-methylbenzoyl)-1H-pyrrol-1-yl]ethoxy}phenoxy)acetic acid Example 38-1

Preparation for t-butyl [3-(2-hydroxyethoxy)phenoxy]acetate

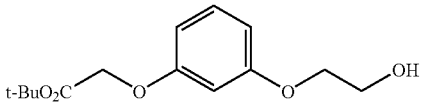

To a solution of 3-acetoxyphenol (3.04 g, 20 ml) in dimethylformamide were added calcium carbonate (2.76 g, 20 mmol) and ethyl bromoacetate (2.2 ml, 20 mmol), and the mixture was stirred for 2 hours at room temperature. The reaction was quenched by water and the mixture was extracted with ethyl acetate. The organic layer was washed with water, 10% aqueous citric acid solution, an aqueous saturated sodium hydrogencarbonate solution and an aqueous saturated sodium chloride solution, and dried over sodium sulfate. The solvent was removed under reduced pressure and the residue was purified with silica gel chromatography (hexane:ethyl acetate=10:1) to give ethyl [3-(acetyloxy)phenoxy]acetate (3.30 g, 69%).

To a solution of lithium aluminum hydride (455 mg, 12 mmol) in tetrahydrofuren was dropped ethyl [3-(acetyloxy)phenoxy]acetate (1.19 g, 5 mmol) in tetrahydrofuran (20 ml) at room temperature, and the mixture was stirred for 2 hours at room temperature. The reaction was quenched by 10% hydrochloric acid and the mixture was extracted with ethyl acetate. The organic layer was washed with water, 10% hydrochloric acid, an aqueous saturated sodium hydrogencarbonate solution and an aqueous saturated sodium chloride solution. The organic layer was dried over sodium sulfate. The solvent was removed under reduced pressure to give 3-(2-hydroxyethoxy)phenol (864 mg, quantitatively).

To a solution of 3-(2-hydroxyethoxy)phenol (864 mg, 5 mmol) in tetrahydrofuran (20 ml) were added potassium carbonate (967 mg, 7 mmol) and t-butyl bromoacetate (0.89 ml, 6 mmol), and the mixture was stirred for 2 hours at room temperature. The reaction was quenched by 10% aqueous citric acid solution and the mixture was extracted with ethyl acetate. The organic layer was washed with water, 10% aqueous citric acid solution, an aqueous saturated sodium hydrogencarbonate solution and an aqueous saturated sodium chloride solution. The organic layer was dried over sodium sulfate. The solvent was removed under reduced pressure and the residue was purified with silica gel chromatography (hexane:ethyl acetate=3:1) to give the subject compound (3.30 g, 69%).

$^1$H NMR (CDCl$_3$, 400 MHz) δ 7.18 (t, 1 H, J=8.1 Hz), 6.56 (dd, 1 H, J=8.1 Hz, 1.7 Hz), 6.46–6.52 (m, 2 H), 4.49 (s, 2 H), 4.06 (t, 2 H, J=4.5 Hz), 3.92–3.97 (m, 2 H), 2.04 (t, 2 H, J=6.2 Hz), 1.49 (s, 9 H).

Example 38-2

Preparation for (3-{2-[2-[(4-methylbenzoyl)-1H-pyrrol-1-yl]ethoxy}phenoxy)acetic acid

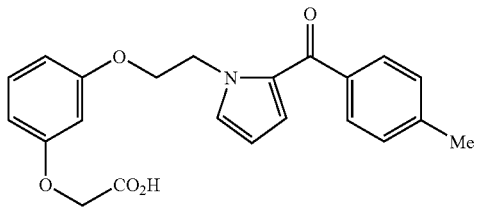

To a solution of t-butyl [3-(2-hydroxyethoxy)phenoxy]acetate (268 mg, 1 mmol) and triethylamine (0.21 ml, 1.5 mmol) in tetrahydrofuran (4 ml) was dropped at 0° C. methanesulfonyl chloride (0.093 ml, 1.2 mmol). The mixture was stirred for 1 hour at 0° C. The reaction was quenched by 10% aqueous citric acid solution and the mixture was extracted with ethyl acetate. The organic layer was washed with 10% aqueous citric acid solution and aqueous saturated sodium hydrogencarbonate solution and dried over sodium sulfate to give a mixture of mesylated compounds.

To a solution of the compound (222 mg, 1.2 mmol) of Reference example 1-2 in tetrahydrofuran (2 ml) was added potassium t-butoxide (135 mg, 1.2 mmol) at 0° C. The mixture was stirred for 10 minutes. Thereto was added the mixture of mesylated compounds prepared above in terahydrofuran (1 ml) and the reaction mixture was stirred for 5 hours at 0° C. The reaction was quenched by 10% aqueous citric acid solution and the mixture was extracted with ethyl acetate. The organic layer was washed with 10% aqueous citric acid solution, an aqueous saturated sodium hydrogencarbonate solution and an aqueous saturated sodium chloride solution, and dried over sodium sulfate. The solvent was removed under reduced pressure and the residue was purified with silica gel chromatography (hexane:ethyl acetate=4:1) to give a coupling compound.

The coupling compound was dissolved in an aqueous 10% sodium hydroxide solution (1 ml) and methanol(4 ml) and the solution was stirred for 1 hour at room temperature. The mixture was washed with hexane and the aqueous layer was acidified with an aqueous potassium hydrogensulfate solution. The mixture was extracted with chloroform. The organic layer was washed with an aqueous saturated sodium chloride solution. The organic layer was dried over sodium sulfate. The solvent was removed under reduced pressure. The residue was dried under reduced pressure to give the subject compound (56 mg, 15%).

$^1$H NMR (CDCl$_3$, 400 MHz) δ 7.70 (d, 2 H, J=8.1 Hz), 7.25 (d, 2 H, J=8.1 Hz), 7.16 (t, 1 H, J=8.3 Hz), 7.10 (dd, 1 H, J=2.4 Hz, 1.9 Hz), 6.77 (dd, 1 H, J=4.0 Hz, 1.7 Hz), 6.48–6.56 (m, 3 H), 6.17 (dd, 1 H, J=4.0 Hz, 2.5 Hz), 4.76 (t, 2 H, J=5.0 Hz), 4.63 (s, 2 H), 4.34 (t, 2 H, J=5.0 Hz), 2.42 (s, 3 H).

Reference Example 14

Preparation for methyl 3-(3-iodophenyl)propionate

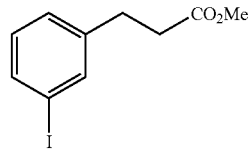

m-Nitrocinnamic acid (10.5 g, 54.4 mmol) was stirred for 2 hours in the presence of 10% palladium-carbon (6.0 g) in methanol under an atmosphere of hydrogen. The mixture was filtered and the filtrate was concentrated to give a mixture of 3-(3-aminophenyl)propionic acid (9.8 g).

Sodium nitrite (4.0 g, 58.0 mmol) was gradually dissolved in concentrated sulfuric acid under ice cooling. To the solution was added a suspension of the mixture of 3-(3-aminophenyl)propionic acid (9.8 g) in acetic acid (30 ml)-concentrated sulfuric acid (10 ml) under ice cooling. The reaction mixture was stirred for 1.5 hours at 0° C. The reaction mixture was dropped to a solution of potassium iodide (12.0 g, 72.3 mmol) in water (100 ml) and the mixture was stirred for 1 hour at 40° C. The reaction mixture was diluted with water and extracted with toluene:ethyl acetate (2:1). The organic layer was washed with an aqueous sodium thiosulfate solution, water and an aqueous saturated sodium chloride solution. The organic layer was dried over magnesium sulfate. The solvent was removed under reduced pressure to give a mixture of 3-(3-iodophenyl)propionic acid (12.0 g).

To a solution of the mixture of 3-(3-iodophenyl)propionic acid (12.0 g) in methanol (200 ml) was added thionyl chloride (11.0 g, 92.5 mmol), and the mixture was stirred for 30 minutes at 40° C. To the mixture was added an aqueous saturated sodium hydrogencarbonate solution and the mixture was extracted with toluene:ethyl acetate (1:1). The organic layer was washed with water and an aqueous saturated sodium chloride solution, and dried over sodium sulfate. The solvent was removed under reduced pressure and the residue was separated and purified with silica gel chromatography (hexane:ethyl acetate=5:1→4:1) to give the subject compound (9.66 g, 61%:total of 3 steps).

$^1$H NMR (CDCl$_3$, 400 MHz) δ 7.53–7.58 (m, 2 H), 7.18 (brd, 1 H, J=7.7 Hz), 7.02 (t, 1 H, J=7.7 Hz), 3.68 (s, 3 H), 2.89 (t, 2 H, J=7.8 Hz), 2.61 (t, 2 H, J=7.8 Hz).

Reference Example 15

Preparation for methyl 2-(3-iodobenzyl)butyrate

Reference Example 15-1

Preparation for dimethyl (3-iodobetzyl)malonate

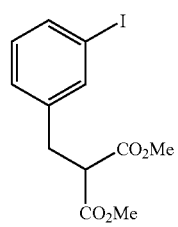

To a solution of m-iodobenzylalcohol (5.0 g, 21.4 mmol) in toluene (60 ml) was added thionyl chloride (5.5 g, 46.2 mmol), and the mixture was stirred for 2 hours at 60° C. Additional thionyl chloride (3.5 g, 29.4 mmol) was added thereto and the mixture was further stirred for 2 hours at 90° C. The reaction mixture was concentrated under reduced pressure to give a mixture of m-iodobenzyl chloride.

To a solution of dimethyl malonate (2.3 g, 17.4 mmol) in methanol (20 ml) was added sodium methoxide/methanol (28%, 3.3 g, 17.4 mmol), and the mixture was stirred for 2 hours at 60° C. Thereto was added the mixture of m-iodobenzyl chloride in tetrahydrofuran (50 ml) at 60° C. and the mixture was stirred for 2 hours at 60° C. and for 90 hours at room temperature. The solvent was removed and the residue was diluted with diluted hydrochloric acid and extracted with ethyl acetate. The organic layer was washed with water and an aqueous saturated sodium chloride solution, and dried over magnesium sulfate. The solvent was removed and the residue was purified with silica gel chromatography (hexane:ethyl acetate=8:1→2:1) to give the subject compound (0.98 g, 16%).

$^1$H NMR (CDCl$_3$, 400 MHz) δ 7.54–7.58 (m, 2 H), 7.17 (brd, 1 H, J=7.9 Hz), 7.02 (brt, 1 H, J=7.9 Hz), 3.71 (s, 6 H), 3.63 (t, 1 H, J=7.8 Hz), 3.15 (d, 2 H, J=7.8 Hz).

Reference Example 15-2

Preparation for dimethyl ethyl(3-iodobenzyl)malonate

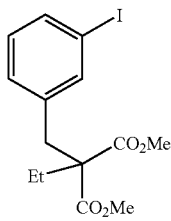

To a solution of diisopropylamine (0.42 g, 4.15 mmol) in tetrahydrofuran (7 ml) was added n-butyl lithium in hexane (1.56M, 2.2 ml, 3.43 mmol) under ice cooling, and the mixture was stirred for 15 minutes at 0° C. Thereto was added dimethyl (3-iodobenzyl)malonate (0.98 g, 2.82 mmol) in tetrahydrofuran (8 ml) under ice cooling, and the mixture was stirred for 10 minutes at 0° C. Thereto was added ethyl iodide (0.70 g, 4.49 mmol) and the mixture was stirred for 1 hour at 60° C. Additional ethyl iodide (0.60 g, 3.85 mmol) was added thereto and the mixture was stirred for 3 hours at 60° C. The reaction was quenched by an aqueous 5% potassium hydrogensulfate solution and extracted with ethyl acetate. The organic layer was washed with an aqueous saturated sodium chloride solution, and dried over magnesium sulfate. The solvent was removed and the residue was purified with silica gel chromatography (hexane:ethyl acetate=4:1→3:1) to give the subject compound (0.78 g, 73%).

$^1$H NMR (CDCl$_3$, 400 MHz) δ 7.56 (dt, 1 H, J=7.7, 1.4 Hz), 7.43 (t, 1 H, J=1.4 Hz), 7.04 (dt, 1 H, J=7.7, 1.4 Hz), 6.99 (t, 1 H, J=7.7 Hz), 3.72 (s, 6 H), 3.16 (s, 2 H), 1.83 (q, 2 H, J=7.6 Hz), 0.91 (t, 3 H, J=7.6 Hz).

Reference Example 15-3

Preparation for methyl 2-(3-iodobenzyl)butyrate

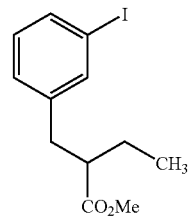

A solution of dimethyl ethyl (3-iodobenzyl)malonate (0.77 g, 2.05 mmol), sodium chloride (0.33 g, 5.65 mmol) and water (40 mg, 2.22 mmol) in dimethyl sulfoxide (10 ml) was stirred for 6 hours at 170° C. The mixture was diluted with water and extracted with ethyl acetate/toluene (2/1). The organic layer was washed with an aqueous saturated sodium chloride solution and dried over magnesium sulfate. The solvent was removed and the residue was purified with silica gel chromatography (hexane:ethyl acetate=6:1→3:1) to give the subject compound (0.47 g, 74%).

$^1$H NMR (CDCl$_3$, 400 MHz) δ 7.51–7.55 (m, 2 H), 7.12 (brd, 1 H, J=7.7 Hz), 7.00 (t, 1 H, J=7.7 Hz), 3.62 (s, 3 H), 2.87 (dd, 1 H, J=13.6, 6.5 Hz), 2.68 (dd, 1 H, J=13.6, 8.5 Hz), 2.52–2.61 (m, 1 H), 1.60–1.71 (m, 1 H), 1.50–1.60 (m, 1 H), 0.91 (t, 3 H, J=7.4 Hz).

Reference Example 16

Preparation for methyl 3-(3-iodophenyl)-2-methylpropionate

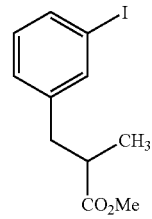

The subject compound was prepared in the same manner as Reference example 16.

$^1$H NMR (CDCl$_3$, 400 MHz) δ 7.52–7.56 (m, 2 H), 7.12 (brd, 1 H, J=7.7 Hz), 7.01 (t, 1 H, J=7.7 Hz), 3.65 (s, 3 H), 2.96 (dd, 1 H, J=13.4, 7.0 Hz), 2.65–2.77 (m, 1 H), 2.68 (dd, 1 H, J=13.4, 7.6 Hz), 1.15 (d, 3 H, J=6.9 Hz).

The following compounds of Examples 39–201 were prepared according to the methods of the examples mentioned above.

| Ex. No. | Structure | NMR |
|---|---|---|
| 39 | 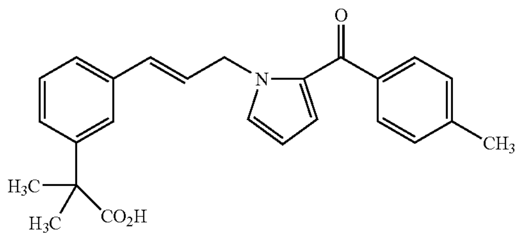 | $^1$H NMR (CDCl$_3$, 400 MHz) δ 7.73 (d, 2H, J=6.6 Hz), 7.35 (d, 1H, J=1.2 Hz), 7.23–7.29 (m, 5H), 7.05 (dd, 1H, J=4.0, 1.7 Hz), 6.42–6.50 (m, 2H), 6.21 (dd, 1H, J=4.0, 2.5 Hz), 5.20 (d, 2H, J=5.4 Hz), 2.42 (s, 3H), 1.58 (s, 6H). |
| 40 | 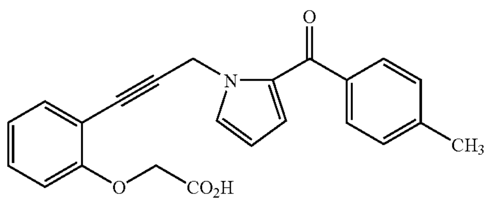 | $^1$H NMR (CDCl$_3$, 400 MHz) δ 7.73 (d, 2H, J=8.1 Hz), 7.42 (dd, 1H, J=7.6, 1.7 Hz), 7.38 (dd, 1H, J=2.4, 1.8 Hz), 7.27–7.24 (m, 3H), 7.00–6.96 (m, 1H), 6.83–6.79 (m, 2H), 6.22 (dd, 1H, J=4.0, 2.6 Hz), 5.49 (s, 2H), 4.64 (s, 2H), 2.42 (s, 3H). |
| 41 | 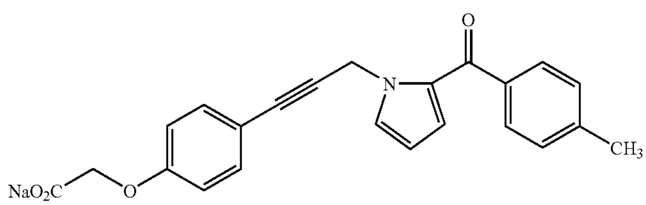 | $^1$H NMR (DMSO-d$_6$, 400 MHz) δ 7.67 (d, 2H, J=8.1 Hz), 7.48 (t, 1H, J=2.1 Hz), 7.32 (d, 2H, J=8.1 Hz), 7.25 (d, 2H, J=8.8 Hz), 6.77 (d, 2H, J=8.8 Hz), 6.70 (dd, 1H, J=4.0, 1.6 Hz), 6.24 (dd, 1H, J=4.0, 2.6 Hz), 5.46 (s, 2H), 4.18 (s, 2H), 2.40 (s, 3H). |
| 42 | 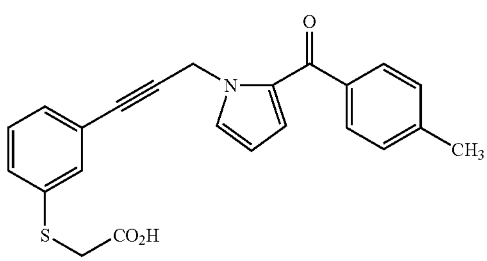 | $^1$H NMR (CDCl$_3$, 400 MHz) δ 7.74 (d, 2H, J=8.1 Hz), 7.48 (t, 1H, J=1.6 Hz), 7.38–7.24 (m, 6H), 6.79 (dd, 1H, J=4.0, 1.7 Hz), 6.24 (dd, 1H, J=4.0, 2.6 Hz), 5.51 (s, 2H), 3.67 (s, 2H), 3.20–2.70 (br, 1H), 2.43 (s, 3H). |
| 43 | 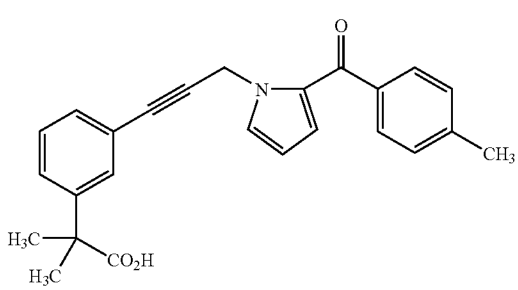 | $^1$H NMR (CDCl$_3$, 400 MHz) δ 7.74 (d, 2H, J=8.2 Hz), 7.47 (d, 1H, J=1.6 Hz), 7.43–7.17 (m, 6H), 6.80–6.78 (m, 1H), 6.25–6.22 (m, 1H), 5.52 (s, 2H), 2.43 (s, 3H), 1.58 (s, 6H). |
| 44 | 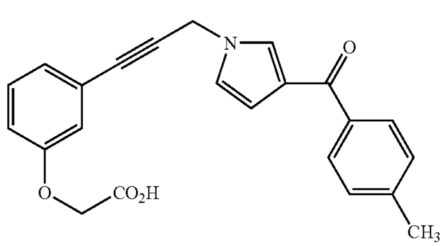 | $^1$H NMR (CDCl$_3$, 400 MHz) δ 7.76 (d, 2H, J=8.1 Hz), 7.43 (t, 1H, J=1.9 Hz), 7.22–7.28 (m, 3H), 7.10 (d, 1H, J=7.6 Hz), 6.90–6.99 (m, 2H), 6.84–6.86 (m, 1H), 6.72 (dd, 1H, J=2.9 Hz, 1.7 Hz), 4.93 (s, 2H), 4.67 (s, 2H), 2.42 (s, 3H). |

| Ex. No. | Structure | NMR |
|---|---|---|
| 45 | 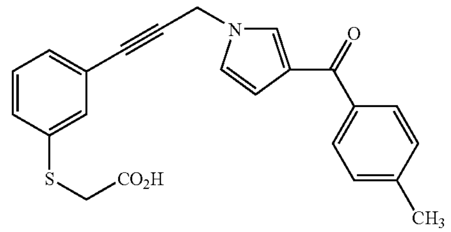 | ¹H NMR (CDCl₃, 400 MHz) δ 7.78 (d, 2H, J=8.1 Hz), 7.55–7.56 (m, 2H), 7.26–7.52 (m, 4H), 7.10–7.16 (m, 1H), 6.79–6.83 (m, 1H), 6.68 (dd, 1H, J=2.8, 1.7 Hz), 4.93 (s, 2H), 3.66 (s, 2H), 2.45 (s, 3H). |
| 46 | 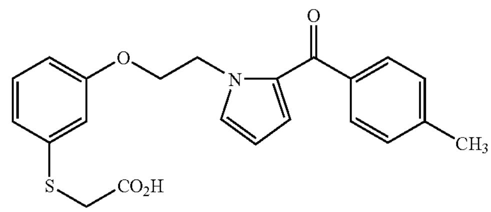 | ¹H NMR (CDCl₃, 400 MHz) δ 7.70 (d, 2H, J=8.1 Hz), 7.25 (d, 2H, J=8.1 Hz), 7.18 (t, 1H, J=7.7 Hz), 7.12 (t, 1H, J=2.1 Hz), 6.99–6.95 (m, 2H), 6.80–6.72 (m, 2H), 6.20–6.16 (m, 1H), 4.75 (t, 2H, J=5.2 Hz), 4.37 (t, 2H, J=5.2 Hz), 3.65 (s, 2H), 2.43 (s, 3H). |
| 47 | 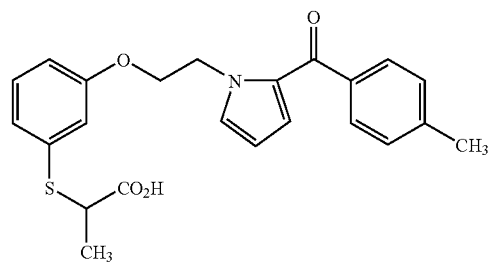 | ¹H NMR (CDCl₃, 400 MHz) δ 7.71 (d, 2H, J=8.1 Hz), 7.25 (d, 2H, J=8.1 Hz), 7.18 (t, 1H, J=8.1 Hz), 7.12 (t, 1H, J=2.0 Hz), 7.06–7.00 (m, 2H), 6.79–6.77 (m, 2H), 6.18 (dd, 1H, J=4.0, 2.6 Hz), 4.76 (t, 2H, J=5.1 Hz), 4.36 (t, 2H, J=5.0 Hz), 3.79 (q, 1H, J=7.1 Hz), 2.43 (s, 3H), 1.49 (d, 3H, J=7.1 Hz). |
| 48 | 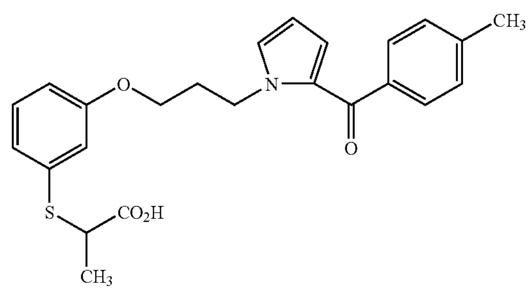 | ¹H NMR (CDCl₃, 400 MHz) δ 7.68 (d, 2H, J=8.1 Hz), 7.27–7.15 (m, 3H), 7.06–7.01 (m, 2H), 6.96 (t, 1H, J=2.1 Hz), 6.82–6.79 (m, 1H), 6.75 (dd, 1H, J=4.0, 1.6 Hz), 6.14 (dd, 1H, J=4.0, 2.5 Hz), 4.57 (t, 2H, J=6.8 Hz), 3.96 (t, 2H, J=6.0 Hz), 3.79 (q, 1H, J=7.1 Hz), 2.42 (s, 3H), 2.34–2.27 (m, 2H), 1.49 (d, 3H, J=7.2 Hz). |
| 49 | 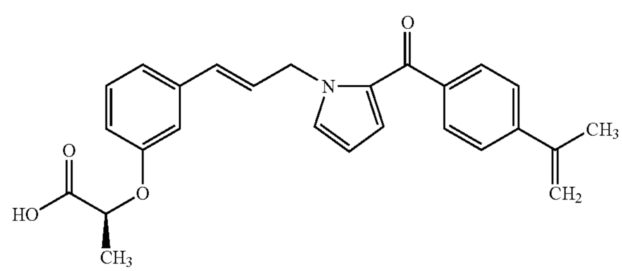 | ¹H NMR (CDCl₃, 400 MHz) δ 7.78 (d, 2H, J=8.4 Hz), 7.53 (d, 2H, J=8.4 Hz), 7.19 (t, 1H, J=8.0 Hz), 7.06–7.04 (m, 1H), 7.00 (d, 1H, J=7.9 Hz), 6.92 (t, 1H, J=2.2 Hz), 6.81–6.75 (m, 2H), 6.45–6.42 (m, 2H), 6.20 (dd, 1H, J=4.0, 2.5 Hz), 5.48 (s, 1H), 5.20–5.17 (m, 3H), 4.80 (q, 1H, J=6.8 Hz), 2.19 (s, 3H), 1.64 (d, 3H, J=6.8 Hz). |
| 50 | 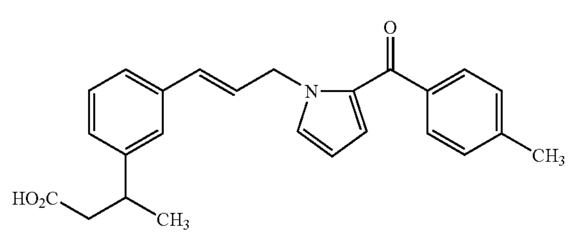 | ¹H NMR (CDCl₃, 400 MHz) δ 8.71 (br, 1H), 7.73 (d, 2H, J=8.1 Hz), 7.35–7.18 (m, 5H), 7.09–7.04 (m, 2H), 6.77 (dd, 1H, J=4.0, 1.8 Hz), 6.52–6.40 (m, 2H), 6.20 (dd, 1H, J=4.0, 2.5 Hz), 5.19 (d, 2H, J=5.3 Hz), 3.27–3.19 (m, 1H), 2.64 (dd, 1H, J=15.6, 6.6 Hz), 2.54 (dd, 1H, J=15.6, 8.3 Hz), 2.42 (s, 3H), 1.28 (d, 3H, J=7.0 Hz). |

-continued

| Ex. No. | Structure | NMR |
|---|---|---|
| 51 | 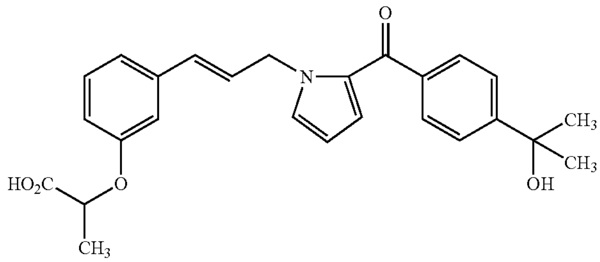 | ¹H NMR (CDCl₃, 400 MHz) δ 7.78 (d, 2H, J=8.4 Hz), 7.55 (d, 2H, J=8.4 Hz), 7.20 (t, 1H, J=8.0 Hz), 7.05 (t, 1H, J=2.0 Hz), 7.01–6.98 (m, 1H), 6.89–6.85 (m, 2H), 6.79–6.76 (m, 2H), 6.42–6.40 (m, 2H), 6.21 (dd, 1H, J=4.0, 2.5 Hz), 5.18 (d, 2H, J=3.9 Hz), 4.78 (q, 1H, J=6.8 Hz), 1.63–1.58 (m, 9 H). |
| 52 | 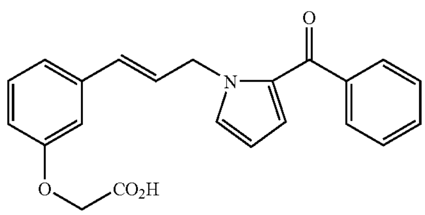 | ¹H NMR (CDCl₃, 400 MHz) δ 7.80 (d, 2H, J=7.9 Hz), 7.53 (dd, 1H, J=7.4, 7.4 Hz), 7.45 (dd, 2H, J=7.9, 7.4 Hz), 7.22 (dd, 1H, J=8.1, 7.7 Hz), 7.07–7.06 (m, 1H), 7.02 (d, 1H, J=7.7 Hz), 6.92 (s, 1H), 6.78 (d, 1H, J=8.1 Hz), 6.77–6.76 (m, 1H), 6.47 (d, 1H, J=15.8 Hz), 6.43 (dt, 1H, J=15.8, 4.4 Hz), 6.23–6.21 (m, 1H), 5.21 (d, 2H, J=4.4 Hz), 4.65 (s, 2H). |
| 53 | 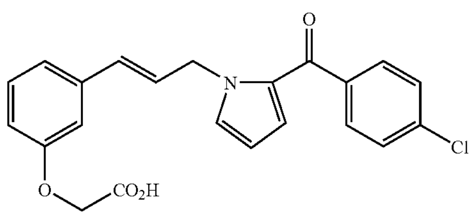 | ¹H NMR (CDCl₃, 400 MHz) δ 7.75 (d, 2H, J=8.5 Hz), 7.42 (d, 2H, J=8.5 Hz), 7.22 (dd, 1H, J=8.1, 7.8 Hz), 7.08–7.07 (m, 1H), 7.01 (d, 1H, J=7.8 Hz), 6.92 (s, 1H), 6.79 (d, 1H, J=8.1 Hz), 6.76–6.74 (m, 1H), 6.45 (d, 1H, J=15.7 Hz), 6.39 (dt, 1H, J=15.7, 4.6 Hz), 6.23–6.22 (m, 1H), 5.19 (d, 2H, J=4.6 Hz), 4.65 (s, 2H). |
| 54 | 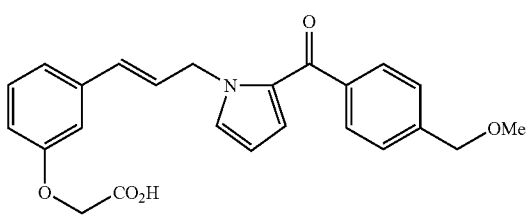 | ¹H NMR (CDCl₃, 400 MHz) δ 7.80 (d, 2H, J=8.2 Hz), 7.42 (d, 2H, J=8.2 Hz), 7.21 (dd, 1H, J=8.1, 7.8 Hz), 7.06–7.05 (m, 1H), 7.01 (d, 1H, J=7.8 Hz), 6.89 (s, 1H), 6.78 (d, 1H, J=8.1 Hz), 6.77–6.76 (m, 1H), 6.45 (d, 1H, J=15.9 Hz), 6.43 (dt, 1H, J=15.9, 4.4 Hz), 6.22–6.21 (m, 1H), 5.19 (d, 2H, J=4.4 Hz), 4.65 (s, 2H), 4.54 (s, 2H), 3.43 (s, 3H). |
| 55 | 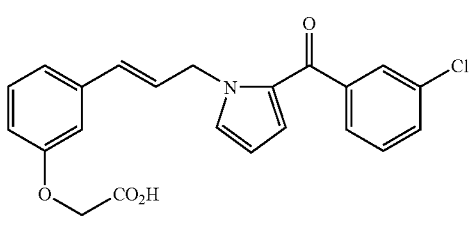 | ¹H NMR (CDCl₃, 400 MHz) δ 7.77 (dd, 1H, J=1.8, 1.8 Hz), 7.67 (ddd, 1H, J=7.7, 1.8, 1.3 Hz), 7.50 (ddd, 1H, J=7.9, 1.8, 1.3 Hz), 7.38 (dd, 1H, J=7.9, 7.7 Hz), 7.23 (dd, 1H, J=8.1, 7.8 Hz), 7.09–7.08 (m, 1H), 7.02 (d, 1H, J=7.8 Hz), 6.92 (s, 1H), 6.80 (d, 1H, J=8.1 Hz), 6.78–6.76 (m, 1H), 6.46 (d, 1H, J=15.9 Hz), 6.41 (dt, 1H, J=15.9, 4.7 Hz), 6.24–6.22 (m, 1H), 5.19 (d, 2H, J=4.7 Hz), 4.66 (s, 2H). |
| 56 | 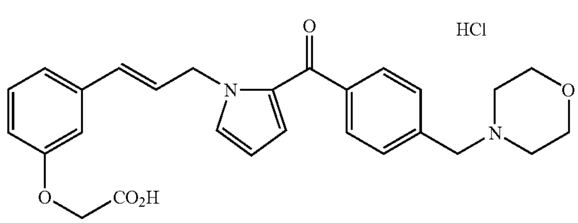 | ¹H NMR (CD₃OD, 400 MHz) δ 7.91 (d, 2H, J=8.2 Hz), 7.71 (d, 2H, J=8.2 Hz), 7.35–7.34 (m, 1H), 7.24 (dd, 1H, J=7.8, 7.8 Hz), 7.02 (d, 1H, J=7.8 Hz), 6.96 (s, 1H), 6.83–6.82 (m, 1H), 6.82 (d, 1H, J=7.8 Hz), 6.49 (dt, 1H, J=16.0, 4.6 Hz), 6.44 (d, 1H, J=16.0 Hz), 6.32–6.31 (m, 1H), 5.26 (d, 2H, J=4.6 Hz), 4.73 (s, 2H), 4.20–4.09 (m, 2H), 3.84–3.80 (m, 4H), 3.45–3.43 (m, 2H), 3.34–3.30 (m, 2H). |

-continued

| Ex. No. | Structure | NMR |
|---|---|---|
| 57 | 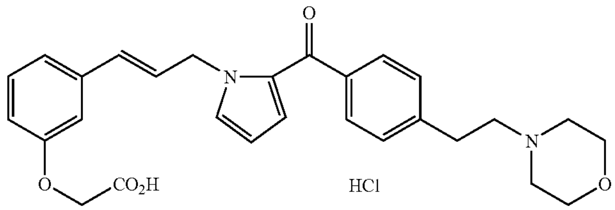 | ¹H NMR (CD₃OD, 400 MHz) δ 7.80 (d, 2H, J=8.2 Hz), 7.48 (d, 2H, J=8.2 Hz), 7.30–7.29 (m, 1H), 7.23 (dd, 1H, J=8.0, 7.7 Hz), 7.00 (d, 1H, J=7.7 Hz), 6.95 (s, 1H), 6.81 (d, 1H, J=8.0 Hz), 6.80–6.78 (m, 1H), 6.47 (dt, 1H, J=15.9, 4.7 Hz), 6.42 (d, 1H, J=15.9 Hz), 6.30–6.29 (m, 1H), 5.23 (d, 2H, J=4.7 Hz), 4.72 (s, 2H), 4.20–4.10 (m, 2H), 3.90–3.80 (m, 4H), 3.69–3.52 (m, 2H), 3.51–3.47 (m, 2H), 3.25–3.23 (m, 2H). |
| 58 | 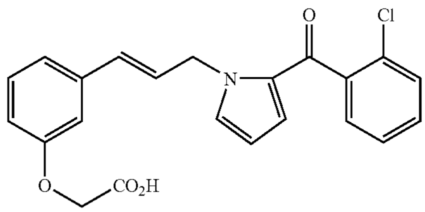 | ¹H NMR (CDCl₃, 400 MHz) δ 7.34 (m, 4H), 7.14 (dd, 1H, J=8.2, 7.8 Hz), 6.99–6.98 (m, 1H), 6.93 (d, 1H, J=7.8 Hz), 6.84 (s, 1H), 6.70 (d, 1H, J=8.2 Hz), 6.45–6.44 (m, 1H), 6.37 (d, 1H, J=15.9 Hz), 6.32 (dt, 1H, J=15.9, 3.9 Hz), 6.10–6.08 (m, 1H), 5.17 (d, 2H, J=3.9 Hz), 4.56 (s, 2H). |
| 59 | 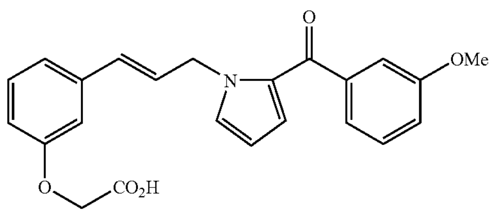 | ¹H NMR (CDCl₃, 400 MHz) δ 7.39 (ddd, 1H, J=7.6, 1.6, 1.4 Hz), 7.35 (dd, 1H, J=7.8, 7.6 Hz), 7.33 (dd, 1H, J=1.6, 1.6 Hz), 7.20 (dd, 1H, J=8.2, 7.7 Hz), 7.08 (ddd, 1H, J=7.8, 1.6, 1.4 Hz), 7.07–7.06 (m, 1H), 7.00 (d, 1H, J=7.7 Hz), 6.92 (s, 1H), 6.82–6.81 (m, 1H), 6.78 (d, 1H, J=8.2 Hz), 6.46 (d, 1H, J=15.9 Hz), 6.41 (dt, 1H, J=15.9, 4.3 Hz), 5.19 (d, 2H, J=4.3 Hz), 4.63 (s, 2H), 3.84 (s, 3H). |
| 60 | 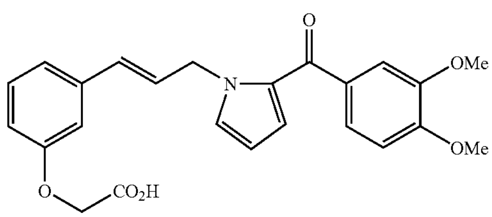 | ¹H NMR (CDCl₃, 400 MHz) δ 7.48 (dd, 1H, J=8.3, 1.9 Hz), 7.42 (d, 1H, J=1.9 Hz), 7.18 (dd, 1H, J=8.1, 7.7 Hz), 7.04–7.03 (m, 1H), 6.98 (d, 1H, J=7.7 Hz), 6.91 (s, 1H), 6.88 (d, 1H, J=8.3 Hz), 6.80–6.79 (m, 1H), 6.76 (d, 1H, J=8.1 Hz), 6.44 (d, 1H, J=15.8 Hz), 6.40 (dt, 1H, J=15.8, 5.4 Hz), 6.22–6.20 (m, 1H), 5.14 (d, 2H, J=5.4 Hz), 4.61 (s, 2H), 3.93 (s, 3H), 3.91 (s, 3H). |
| 61 | 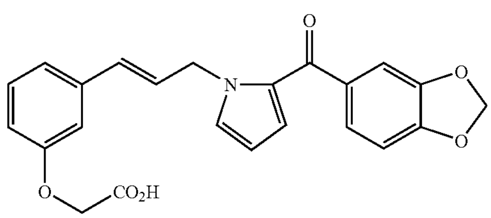 | ¹H NMR (CDCl₃, 400 MHz) δ 7.43 (dd, 1H, J=8.1, 1.6 Hz), 7.33 (d, 1H, J=1.6 Hz), 7.19 (dd, 1H, J=8.2, 7.7 Hz), 7.03–7.02 (m, 1H), 6.99 (d, 1H, J=7.7 Hz), 6.90 (s, 1H), 6.84 (d, 1H, J=8.1 Hz), 6.77 (d, 1H, J=8.2 Hz), 6.76–6.75 (m, 1H), 6.43 (d, 1H, J=15.9 Hz), 6.38 (dt, 1H, J=15.9, 4.2 Hz), 6.21–6.19 (m, 1H), 6.03 (s, 2H), 5.14 (d, 2H, J=4.2 Hz), 4.62 (s, 2H). |
| 62 | 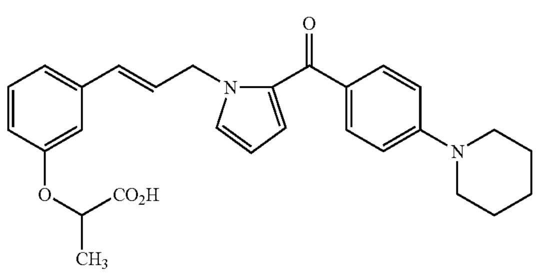 | ¹H NMR (CDCl₃, 400 MHz) δ 7.81 (d, 2H, J=9.0 Hz), 7.19 (dd, 1H, J=8.0, 7.9 Hz), 6.99 (d, 1H, J=7.9 Hz), 6.99–6.98 (m, 1H), 6.90 (d, 2H, J=9.0 Hz), 6.87 (s, 1H), 6.77 (d, 1H, J=8.0 Hz), 6.77–6.75 (m, 1H), 6.44 (d, 1H, J=15.9 Hz), 6.40 (dt, 1H, J=15.9, 4.2 Hz), 6.20–6.19 (m, 1H), 5.13 (d, 2H, J=4.2 Hz), 4.78 (q, 1H, J=6.8 Hz), 3.36–3.33 (m, 4H), 1.70–1.65 (m, 6H), 1.63 (d, 3H, J=6.8 Hz). |

| Ex. No. | Structure | NMR |
|---|---|---|
| 63 | 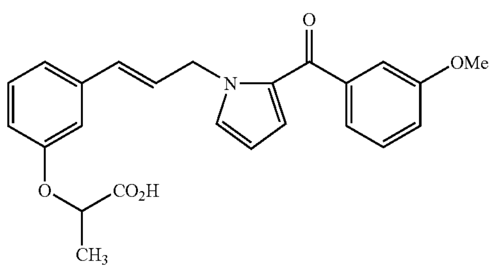 | $^1$H NMR (CDCl$_3$, 400 MHz) δ 7.39 (ddd, 1H, J=7.6, 1.6, 1.4 Hz), 7.35 (dd, 1H, J=7.8, 7.6 Hz), 7.33 (dd, 1H, J=1.6, 1.6 Hz), 7.22 (dd, 1H, J=8.0, 7.8 Hz), 7.08 (ddd, 1H, J=7.8, 1.6, 1.4 Hz), 7.06–7.05 (m, 1H), 7.01 (d, 1H, J=7.8 Hz), 6.91 (s, 1H), 6.81–6.79 (m, 1H), 6.78 (d, 1H, J=8.0 Hz), 6.45 (d, 1H, J=15.8 Hz), 6.40 (dt, 1H, J=15.8, 4.6 Hz), 6.22–6.20 (m, 1H), 5.19 (d, 2H, J=4.6 Hz), 4.80 (q, 1H, J=6.8 Hz), 3.86 (s, 3H), 1.62 (d, 3H, J=6.8 Hz). |
| 64 | 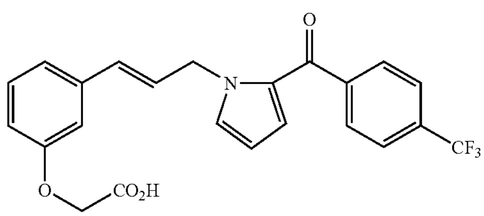 | $^1$H NMR (CDCl$_3$, 400 MHz) δ 7.88 (d, 2H, J=8.0 Hz), 7.71 (d, 2H, J=8.0 Hz), 7.23 (d, 2H, J=7.8, 8.0 Hz), 7.11–7.10 (m, 1H), 7.02 (d, 1H, J=7.8 Hz), 6.93 (s, 1H), 6.80 (d, 1H, J=8.0 Hz), 6.75–6.74 (m, 1H), 6.47 (d, 1H, J=15.9 Hz), 6.41 (dt, 1H, J=15.9, 4.7 Hz), 6.25–6.23 (m, 1H), 5.21 (d, 2H, J=4.7 Hz), 4.66 (s, 2H). |
| 65 | 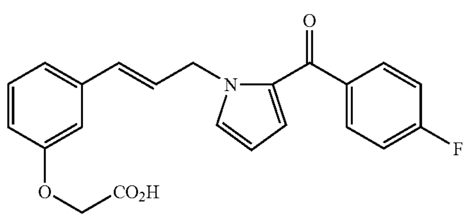 | $^1$H NMR (CDCl$_3$, 400 MHz) δ 7.83 (dd, 2H, J=8.8, 5.5 Hz), 7.20 (dd, 1H, J=8.2, 7.7 Hz), 7.12 (dd, 2H, J=8.8, 8.7 Hz), 7.07–7.06 (m, 1H), 6.99 (d, 1H, J=7.7 Hz), 6.91 (s, 1H), 6.77 (d, 1H, J=8.2 Hz), 6.76–6.74 (m, 1H), 6.44 (d, 1H, J=15.9 Hz), 6.39 (dt, 1H, J=15.9, 4.5 Hz), 6.23–6.21 (m, 1H), 5.17 (d, 2H, J=4.5 Hz), 4.63 (s, 2H). |
| 66 | 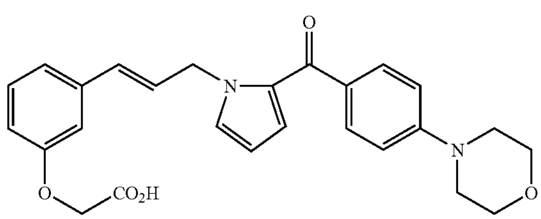 | $^1$H NMR (CDCl$_3$, 400 MHz) δ 7.83 (d, 2H, J=8.9 Hz), 7.22 (dd, 1H, J=7.9, 7.7 Hz), 7.01 (d, 1H, J=7.9 Hz), 7.01–7.00 (m, 1H), 6.91 (d, 2H, J=8.9 Hz), 6.89 (s, 1H), 6.79 (d, 1H, J=7.7 Hz), 6.77–6.76 (m, 1H), 6.45 (d, 1H, J=15.9 Hz), 6.41 (dt, 1H, J=15.9, 4.7 Hz), 5.22–5.20 (m, 1H), 5.16 (d, 2H, J=4.7 Hz), 4.64 (s, 2H), 3.87 (t, 4H, J=4.8 Hz), 3.30 (t, 4H, J=4.8 Hz). |
| 67 | 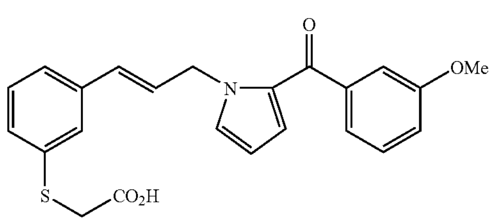 | $^1$H NMR (CDCl$_3$, 400 MHz) δ 7.41 (s, 1H), 7.39 (d, 1H, J=7.6 Hz), 7.35 (dd, 1H, J=7.8, 7.6 Hz), 7.34 (d, 1H, J=7.3 Hz), 7.26 (dd, 1H, J=7.8, 7.3 Hz), 7.23 (s, 1H), 7.22 (d, 1H, J=7.8 Hz), 7.08 (d, 1H, J=7.8 Hz), 7.07–7.05 (m, 1H), 6.82–6.80 (m, 1H), 6.46 (dt, 1H, J=15.9, 4.6 Hz), 6.42 (d, 1H, J=15.9 Hz), 6.22–6.21 (m, 1H), 5.19 (d, 2H, J=4.6 Hz), 3.85 (s, 3H), 3.65 (s, 2H). |
| 68 | 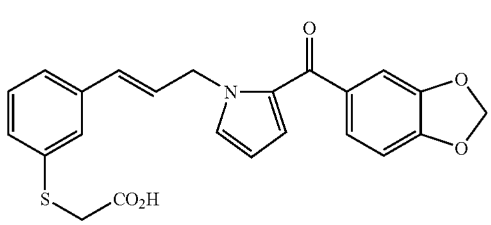 | $^1$H NMR (CDCl$_3$, 400 MHz) δ 7.41 (dd, 1H, J=8.1, 1.7 Hz), 7.38 (s, 1H), 7.31 (d, 1H, J=1.7 Hz), 7.26–7.18 (m, 3H), 7.02–7.00 (m, 1H), 6.83 (d, 1H, J=8.1 Hz), 6.76–6.74 (m, 1H), 6.44 (dt, 1H, J=15.9, 4.4 Hz), 6.36 (d, 1H, J=15.9 Hz), 6.20–6.18 (m, 1H), 6.02 (s, 2H), 5.13 (d, 2H, J=4.4 Hz), 3.63 (s, 2H). |

-continued

| Ex. No. | Structure | NMR |
|---|---|---|
| 69 | 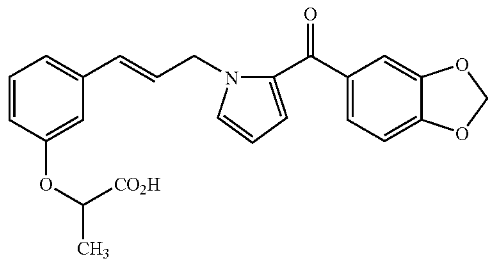 | ¹H NMR (CDCl₃, 400 MHz) δ 7.43 (dd, 1H, J=8.1, 1.7 Hz), 7.33 (d, 1H, J=1.7 Hz), 7.19 (dd, 1H, J=8.2, 7.8 Hz), 7.03–7.02 (m, 1H), 6.98 (d, 1H, J=7.7 Hz), 6.90 (s, 1H), 6.84 (d, 1H, J=8.1 Hz), 6.77 (d, 1H, J=8.2 Hz), 6.76–6.74 (m, 1H), 6.42 (d, 1H, J=15.9 Hz), 6.38 (dt, 1H, J=15.9, 4.6 Hz), 6.21–6.20 (m, 1H), 6.03 (s, 2H), 5.15 (d, 2H, J=4.6 Hz), 4.77 (q, 1H, J=6.9 Hz), 1.64 (d, 3H, J=6.9 Hz). |
| 70 | 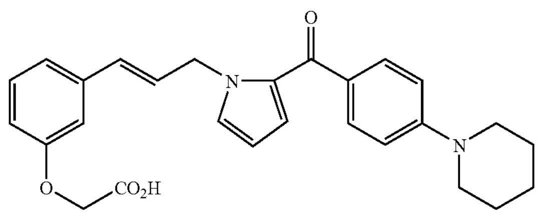 | ¹H NMR (CDCl₃, 400 MHz) δ 7.81 (d, 2H, J=9.0 Hz), 7.20 (dd, 1H, J=8.0, 7.9 Hz), 6.99 (d, 1H, J=7.9 Hz), 6.99–6.98 (m, 1H), 6.92 (d, 2H, J=9.0 Hz), 6.87 (s, 1H), 6.79 (d, 1H, J=8.0 Hz), 6.78–6.76 (m, 1H), 6.44 (d, 1H, J=15.9 Hz), 6.40 (dt, 1H, J=15.9, 4.1 Hz), 6.21–6.19 (m, 1H), 5.14 (d, 2H, J=4.1 Hz), 4.63 (s, 2H), 3.36–3.33 (m, 4H), 1.70–1.64 (m, 6H). |
| 71 | 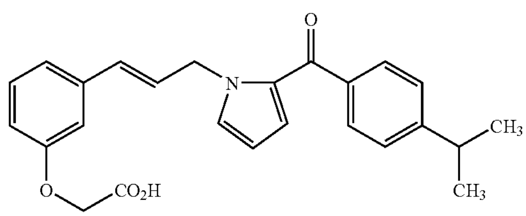 | ¹H NMR (CDCl₃, 400 MHz) δ 7.76 (d, 2H, J=8.2 Hz), 7.30 (d, 2H, J=8.2 Hz), 7.20 (dd, 1H, J=7.8, 7.8 Hz), 7.06–7.04 (m, 1H), 7.00 (d, 1H, J=7.8 Hz), 6.92 (s, 1H), 6.81–6.79 (m, 1H), 6.75 (d, 1H, J=7.8 Hz) 6.45 (d, 1H, J=16.0 Hz), 6.41 (dt, 1H, J=16.0, 4.7 Hz), 6.22–6.20 (m, 1H), 5.18 (d, 2H, J=4.7 Hz), 4.65 (s, 2H), 2.97 (sept, 1H, J=6.9 Hz), 1.28 (d, 6H, J=6.9 Hz). |
| 72 | 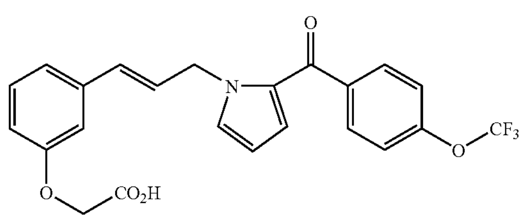 | ¹H NMR (CDCl₃, 400 MHz) δ 7.85 (d, 2H, J=8.8 Hz), 7.28 (d, 2H, J=8.8 Hz), 7.21 (dd, 1H, J=8.0, 7.8 Hz), 7.09–7.08 (m, 1H), 7.01 (d, 1H, J=7.8 Hz), 6.92 (s, 1H), 6.78 (d, 1H, J=8.0 Hz), 6.78–6.76 (m, 1H), 6.46 (d, 1H, J=15.8 Hz), 6.40 (dt, 1H, J=15.8, 4.6 Hz), 6.24–6.22 (m, 1H), 5.19 (d, 2H, J=4.6 Hz), 4.65 (s, 2H). |
| 73 | 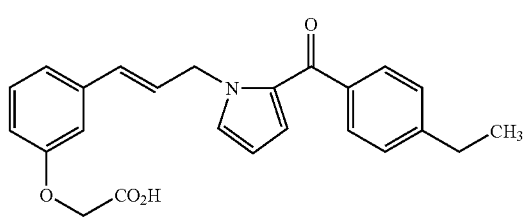 | ¹H NMR (CDCl₃, 400 MHz) δ 7.75 (d, 2H, J=8.2 Hz), 7.27 (d, 2H, J=8.2 Hz), 7.22 (dd, 1H, J=7.9, 7.9 Hz), 7.05–7.04 (m, 1H), 7.01 (d, 1H, J=7.9 Hz), 6.92 (s, 1H), 6.79 (d, 1H, J=7.9 Hz), 6.78–6.77 (m, 1H), 6.46 (d, 1H, J=15.9 Hz), 6.42 (dt, 1H, J=15.9, 4.6 Hz), 6.22–6.20 (m, 1H), 5.19 (d, 2H, J=4.6 Hz), 4.65 (s, 2H), 2.72 (q, 2H, J=7.6 Hz), 1.27 (t, 3H, J=7.6 Hz). |
| 74 | 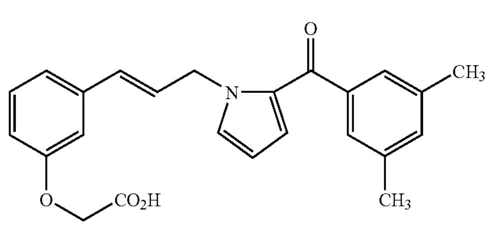 | ¹H NMR (CDCl₃, 400 MHz) δ 7.41 (s, 2H), 7.22 (dd, 1H, J=8.0, 7.8 Hz), 7.17 (s, 1H), 7.05–7.04 (m, 1H), 7.02 (d, 1H, J=7.8 Hz), 6.93 (s, 1H), 6.79 (d, 1H, J=8.0 Hz), 6.78–6.77 (m, 1H), 6.47 (d, 1H, J=15.9 Hz), 6.41 (dt, 1H, J=15.9, 4.7 Hz), 6.22–6.22 (m, 1H), 5.19 (d, 2H, J=4.7 Hz), 4.66 (s, 2H), 2.37 (s, 6H). |

| Ex. No. | Structure | NMR |
|---|---|---|
| 75 | 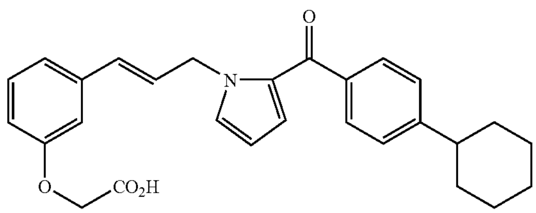 | $^1$H NMR (CDCl$_3$, 400 MHz) δ 7.75 (d, 2H, J=8.3 Hz), 7.28 (d, 2H, J=8.3 Hz), 7.22 (dd, 1H, J=7.8, 7.8 Hz), 7.05–7.03 (m, 1H), 7.02 (d, 1H, J=7.8 Hz), 6.92 (s, 1H), 6.81–6.80 (m, 1H), 6.79 (d, 1H, J=7.8 Hz), 6.45 (d, 1H, J=15.8 Hz), 6.42 (dt, 1H, J=15.8, 4.6 Hz), 6.22–6.20 (m, 1H), 5.19 (d, 2H, J=4.6 Hz), 4.66 (s, 2H), 2.57–2.56 (m, 1H), 1.91–1.75 (m, 4H), 1.47–1.25 (m, 6H). |
| 76 | 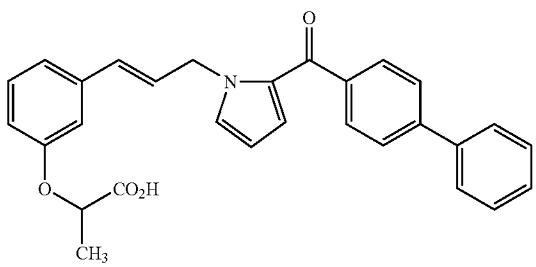 | $^1$H NMR (CDCl$_3$, 400 MHz) δ 7.90 (d, 2H, J=8.3 Hz), 7.68 (d, 2H, J=8.3 Hz), 7.64 (d, 2H, J=7.2 Hz), 7.48 (dd, 2H, J=7.3, 7.2 Hz), 7.39 (t, 1H, J=7.3 Hz), 7.21 (dd, 1H, J=8.1, 7.8 Hz), 7.07–7.06 (m, 1H), 7.02 (d, 1H, J=7.8 Hz), 6.92 (s, 1H), 6.85–6.83 (m, 1H), 6.77 (d, 1H, J=8.1 Hz), 6.47 (d, 1H, J=15.7 Hz), 6.42 (dt, 1H, J=15.7, 4.5 Hz), 4.80 (q, 1H, J=6.9 Hz), 1.65 (d, 3H, J=6.9 Hz). |
| 77 | 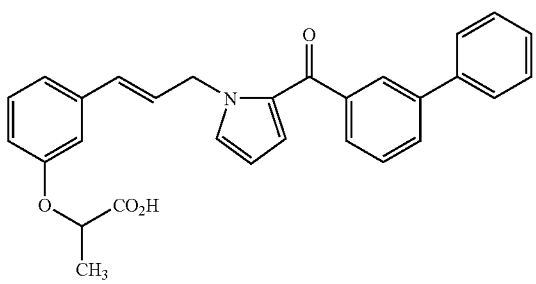 | $^1$H NMR (CDCl$_3$, 400 MHz) δ 8.03 (dd, 1H, J=1.5, 1.5 Hz), 7.78 (ddd, 1H, J=7.7, 1.5, 1.1 Hz), 7.76 (ddd, 1H, J=7.7, 1.5, 1.1 Hz), 7.62 (d, 2H, J=7.1 Hz), 7.52 (dd, 1H, J=7.7, 7.7 Hz), 7.45 (dd, 2H, J=7.3, 7.1 Hz), 7.37 (d, 1H, J=7.3 Hz), 7.21 (dd, 1H, J=8.1, 7.8 Hz), 7.07–7.06 (m, 1H), 7.02 (d, 1H, J=7.8 Hz), 6.93 (s, 1H), 6.83–6.82 (m, 1H), 6.77 (d, 1H, J=8.1 Hz), 6.48 (d, 1H, J=15.9 Hz), 6.42 (dt, 1H, J=15.9, 4.6 Hz), 6.23–6.22 (m, 1H), 5.22 (d, 2H, J=4.6 Hz), 4.80 (q, 1H, J=6.8 Hz), 1.63 (d, 3H, J=6.8 Hz). |
| 78 | 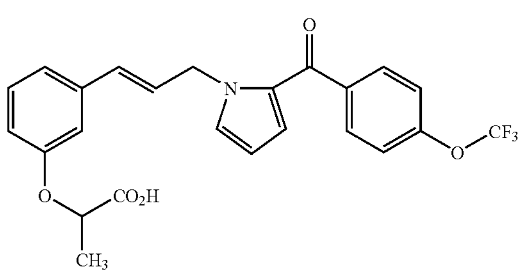 | $^1$H NMR (CDCl$_3$, 400 MHz) δ 7.85 (d, 2H, J=8.8 Hz), 7.28 (d, 2H, J=8.8 Hz), 7.21 (dd, 1H, J=7.9, 7.8 Hz), 7.08–7.07 (m, 1H), 7.01 (d, 1H, J=7.8 Hz), 6.92 (s, 1H), 6.77 (d, 1H, J=7.9 Hz), 6.45 (d, 1H, J=15.8 Hz), 6.40 (dt, 1H, J=15.8, 4.7 Hz), 6.23–6.22 (m, 1H), 5.19 (d, 2H, J=4.7 Hz), 4.80 (q, 1H, J=6.9 Hz), 1.66 (d, 3H, J=6.9 Hz). |
| 79 | 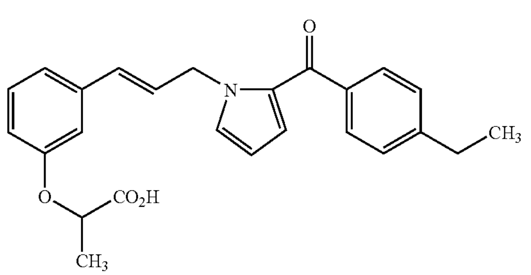 | $^1$H NMR (CDCl$_3$, 400 MHz) δ 7.75 (d, 2H, J=8.2 Hz), 7.27 (d, 2H, J=8.2 Hz), 7.21 (dd, 1H, J=8.0, 7.8 Hz), 7.04–7.03 (m, 1H), 7.01 (d, 1H, J=7.8 Hz), 6.91 (s, 1H), 6.79–6.77 (m, 1H), 6.77 (d, 1H, J=8.0 Hz), 6.45 (d, 1H, J=16.0 Hz), 6.40 (dt, 1H, J=16.0, 4.3 Hz), 6.22–6.20 (m, 1H), 5.19 (d, 2H, J=4.3 Hz), 4.80 (q, 1H, J=6.8 Hz), 2.72 (q, 2H, J=7.6 Hz), 1.64 (d, 3H, J=6.8 Hz), 1.28 (t, 3H, J=7.6 Hz). |

| Ex. No. | Structure | NMR |
|---|---|---|
| 80 | 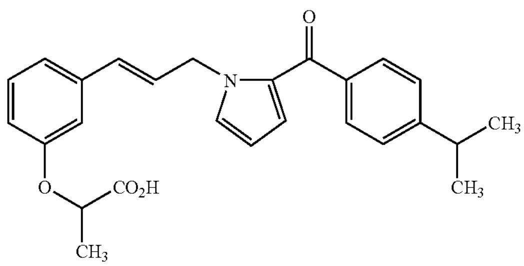 | $^1$H NMR (CDCl$_3$, 400 MHz) δ 7.75 (d, 2H, J=8.3 Hz), 7.30 (d, 2H, J=8.3 Hz), 7.21 (dd, 1H, J=8.0, 7.4 Hz), 7.05–7.03 (m, 1H), 7.00 (d, 1H, J=7.4 Hz), 6.91 (s, 1H), 6.80–6.78 (m, 1H), 6.77 (d, 1H, J=8.0 Hz), 6.45 (d, 1H, J=16.1 Hz), 6.40 (dt, 1H, J=16.1, 4.3 Hz), 6.21–6.20 (m, 1H), 5.19 (d, 2H, J=4.3 Hz), 4.80 (q, 1H, J=6.8 Hz), 2.97 (sept, 1H, J=6.9 Hz), 1.65 (d, 3H, J=6.8 Hz), 1.28 (d, 6H, J=6.9 Hz). |
| 81 | 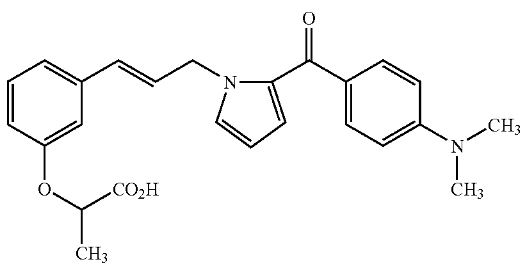 | $^1$H NMR (CDCl$_3$, 400 MHz) δ 7.84 (d, 2H, J=9.0 Hz), 7.21 (dd, 1H, J=7.9, 7.9 Hz), 6.99 (d, 1H, J=7.9 Hz), 6.99–6.98 (m, 1H), 6.89 (s, 1H), 6.76 (d, 1H, J=7.9 Hz), 6.76–6.75 (m, 1H), 6.68 (d, 2H, J=9.0 Hz), 6.45 (d, 1H, J=15.9 Hz), 6.40 (dt, 1H, J=15.9, 4.2 Hz), 6.20–6.18 (m, 1H), 5.14 (d, 2H, J=4.2 Hz), 4.79 (q, 1H, J=6.8 Hz), 3.05 (s, 6H), 1.63 (d, 3H, J=6.8 Hz). |
| 82 | 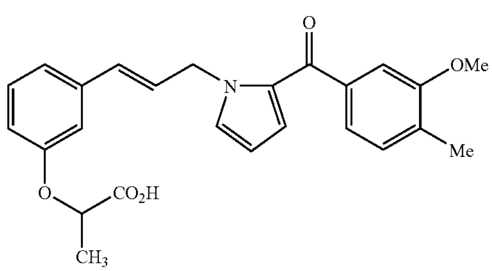 | $^1$H NMR (CDCl$_3$, 400 MHz) δ 7.33 (dd, 1H, J=7.5, 1.5 Hz), 7.30 (d, 1H, J=1.5 Hz), 7.20 (dd, 1H, J=7.8, 7.8 Hz), 7.18 (d, 1H, J=7.8 Hz), 7.05–7.04 (m, 1H), 6.99 (d, 1H, J=7.8 Hz), 6.91 (s, 1H), 6.81–6.80 (m, 1H), 6.75 (d, 1H, J=7.8 Hz), 6.45 (d, 1H, J=15.9 Hz), 6.43 (dt, 1H, J=15.9, 5.4 Hz), 6.22–6.20 (m, 1H), 5.17 (d, 2H, J=5.4 Hz), 4.79 (q, 1H, J=6.8 Hz), 3.87 (s, 3H), 2.28 (s, 3H), 1.63 (d, 3H, J=6.8 Hz). |
| 83 | 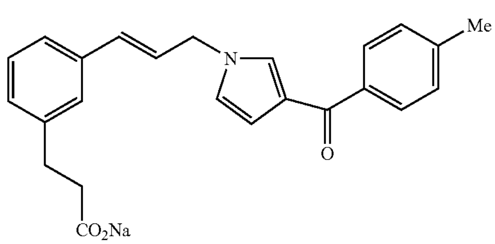 | $^1$H NMR (CDCl$_3$, 400 MHz) δ 7.76 (d, 2H, J=8.1 Hz), 7.30 (brt, 1H, J=1.8 Hz), 7.21–7.28 (m, 5H), 7.13 (brd, 1H, J=7.0 Hz), 6.70–6.75 (m, 2H), 6.51 (d, 1H, J=15.8 Hz), 6.31 (dt, 1H, J=15.8, 6.2 Hz), 4.68 (brd, 2H, J=6.2 Hz), 2.95 (brt, 2H, J=7.7 Hz), 2.68 (brt, 2H, J=7.7 Hz), 2.42 (s, 3H). |
| 84 | 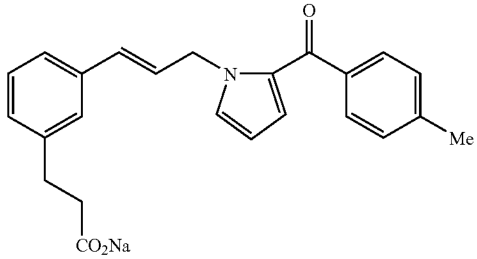 | $^1$H NMR (CDCl$_3$, 400 MHz) δ 7.73 (d, 2H, J=8.1 Hz), 7.25 (d, 2H, J=8.1 Hz), 7.20–7.23 (m, 3H), 7.06–7.10 (m, 1H), 7.05 (dd, 1H, J=2.5, 1.7 Hz), 6.77 (dd, 1H, J=4.0, 1.7 Hz), 6.48 (d, 1H, J=15.8 Hz), 6.43 (dt, 1H, J=15.8, 5.0 Hz), 6.20 (dd, 1H, J=4.0, 2.5 Hz), 5.20 (d, 2H, J=5.0 Hz), 2.93 (t, 2H, J=7.8 Hz), 2.66 (t, 2H, J=7.8 Hz), 2.42 (s, 3H). |

| Ex. No. | Structure | NMR |
|---|---|---|
| 85 | 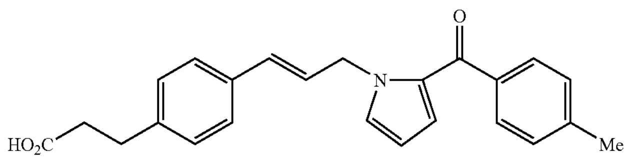 | $^1$H NMR (CDCl$_3$, 400 MHz) δ 7.73 (d, 2H, J=8.1 Hz), 7.29 (d, 2H, J=8.1 Hz), 7.25 (d, 2H, J=8.1 Hz), 7.14 (d, 2H, J=8.1 Hz), 7.05 (dd, 1H, J=2.5, 1.7 Hz), 6.76 (dd, 1H, J=4.0, 1.7 Hz), 6.48 (d, 1H, J=15.9 Hz), 6.40 (dt, 1H, J=15.9, 5.7 Hz), 6.20 (dd, 1H, J=4.0, 2.5 Hz), 5.19 (brd, 2H, J=5.7 Hz), 2.93 (t, 2H, J=7.7 Hz), 2.66 (t, 2H, J=7.7 Hz), 2.43 (s, 3H). |
| 86 | 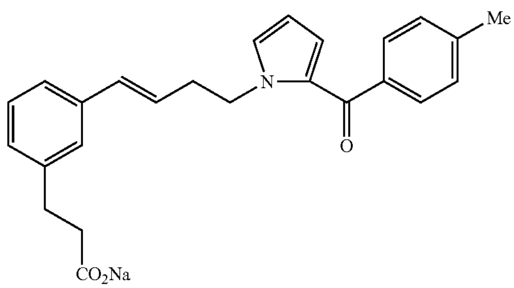 | $^1$H NMR (CDCl$_3$, 400 MHz) δ 7.68 (d, 2H, J=8.1 Hz), 7.23 (d, 2H, J=8.1 Hz), 7.18–7.23 (m, 1H), 7.12–7.16 (m, 2H), 7.05 (brd, 2H, J=7.5 Hz), 6.97 (dd, 1H, J=2.6, 1.7 Hz), 6.72 (dd, 1H, J=4.0, 1.7 Hz), 6.35 (d, 1H, J=15.9 Hz), 6.17 (dt, 1H, J=15.9, 7.2 Hz), 6.15 (dd, 1H, J=4.0, 2.6 Hz), 4.54 (brt, 2H, J=7.0 Hz), 2.91 (t, 2H, J=7.7 Hz), 2.67–2.74 (m, 2H), 2.65 (t, 2H, J=7.7 Hz), 2.42 (s, 3H). |
| 87 | 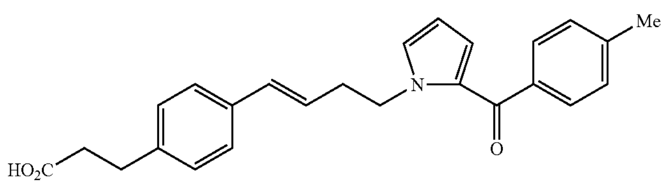 | $^1$H NMR (CDCl$_3$, 400 MHz) δ 7.69 (d, 2H, J=8.1 Hz), 7.23 (d, 2H, J=8.1 Hz), 7.23 (d, 2H, J=8.2 Hz), 7.12 (d, 2H, J=8.2 Hz), 6.96 (dd, 1H, J=2.5, 1.7 Hz), 6.72 (dd, 1H, J=4.0, 1.7 Hz), 6.35 (d, 1H, J=15.8 Hz), 6.15 (dd, 1H, J=4.0, 2.5 Hz), 6.14 (dt, 1H, J=15.8, 7.3 Hz), 4.53 (brt, 2H, J=7.0 Hz), 2.92 (brt, 2H, J=7.7 Hz), 2.66–2.74 (m, 2H), 2.67 (t, 2H, J=7.7 Hz), 2.42 (s, 3H). |
| 88 | 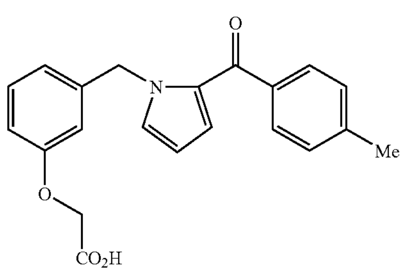 | $^1$H NMR (CDCl$_3$, 400 MHz) δ 7.68 (d, 2H, J=8.1 Hz), 7.24 (t, 1H, J=7.6 Hz), 7.23 (d, 2H, J=8.1 Hz), 7.00 (dd, 1H, J=2.5, 1.7 Hz), 6.83 (brd, 1H, J=7.6 Hz), 6.78–6.81 (m, 1H), 6.78 (dd, 1H, J=4.0, 1.7 Hz), 6.73–6.75 (br, 1H), 6.22 (d, 1H, J=4.0, 2.5 Hz), 5.62 (s, 2H), 4.60 (s, 2H), 2.41 (s, 3H). |
| 89 | 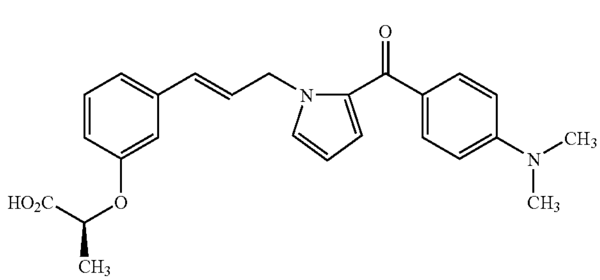 | $^1$H NMR (CDCl$_3$, 400 MHz) δ 7.85 (d, 2H, J=9.0 Hz), 7.21 (dd, 1H, J=7.9, 7.9 Hz), 6.99 (d, 1H, J=7.9 Hz), 6.99–6.98 (m, 1H), 6.89 (s, 1H), 6.76 (d, 1H, J=7.9 Hz), 6.76–6.75 (m, 1H), 6.69 (d, 2H, J=9.0 Hz), 6.45 (d, 1H, J=15.9 Hz), 6.40 (dt, 1H, J=15.9, 4.2 Hz), 6.20–6.19 (m, 1H), 5.14 (d, 2H, J=4.2 Hz), 4.79 (q, 1H, J=6.8 Hz), 3.06 (s, 6H), 1.63 (d, 3H, J=6.8 Hz). |

| Ex. No. | Structure | NMR |
|---|---|---|
| 90 | 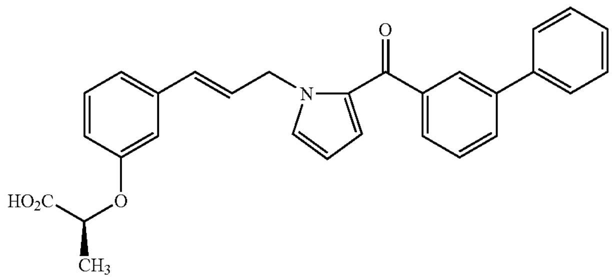 | $^1$H NMR (CDCl$_3$, 400 MHz) δ 8.03 (dd, 1H, J=1.5, 1.5 Hz), 7.78 (ddd, 1H, J=7.7, 1.5, 1.1 Hz), 7.76 (ddd, 1H, J=7.7, 1.5, 1.1 Hz), 7.62 (d, 2H, J=7.1 Hz), 7.52 (dd, 1H, J=7.7, 7.7 Hz), 7.45 (dd, 2H, J=7.3, 7.1 Hz), 7.37 (d, 1H, J=7.3 Hz), 7.21 (dd, 1H, J=8.1, 7.8 Hz), 7.07–7.05 (m, 1H), 7.02 (d, 1H, J=7.8 Hz), 6.93 (s, 1H), 6.83–6.82 (m, 1H), 6.77 (d, 1H, J=8.1 Hz), 6.48 (d, 1H, J=15.9 Hz), 6.42 (dt, 1H, J=15.9, 4.6 Hz), 6.23–6.21 (m, 1H), 5.22 (d, 2H, J=4.6 Hz), 4.80 (q, 1H, J=6.8 Hz), 1.63 (d, 3H, J=6.8 Hz). |
| 91 | 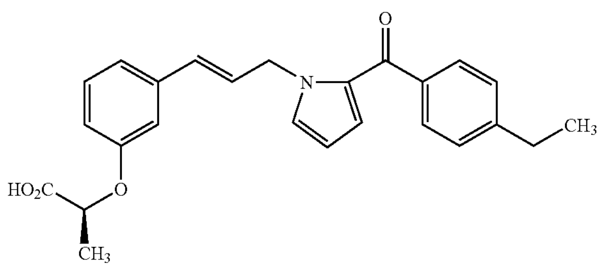 | $^1$H NMR (CDCl$_3$, 400 MHz) δ 7.75 (d, 2H, J=8.2 Hz), 7.26 (d, 2H, J=8.2 Hz), 7.18 (dd, 1H, J=7.8, 7.7 Hz), 7.04–7.03 (m, 1H), 6.99 (d, 1H, J=7.7 Hz), 6.92 (s, 1H), 6.79–6.78 (m, 1H), 6.76 (d, 1H, J=7.8 Hz), 6.45 (d, 1H, J=15.9 Hz), 6.40 (dt, 1H, J=15.9, 4.4 Hz), 6.92–6.91 (m, 1H), 6.79–6.75 (m, 2H), 6.47–6.38 (m, 2H), 6.21–6.20 (m, 1H), 5.18 (d, 2H, J=4.4 Hz), 4.79 (q, 1H, J=6.8 Hz), 2.72 (q, 2H, J=7.6 Hz), 1.63 (d, 3H, J=6.8 Hz), 1.27 (t, 3H, J=7.6 Hz). |
| 92 | 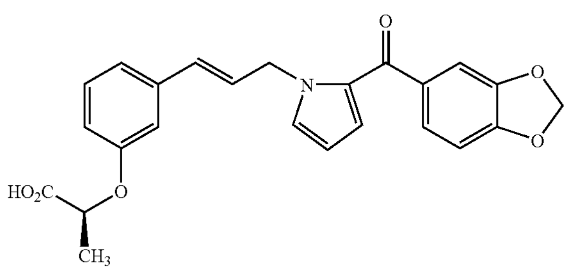 | $^1$H NMR (CDCl$_3$, 400 MHz) δ 7.43 (dd, 1H, J=8.1, 1.7 Hz), 7.33 (d, 1H, J=1.7 Hz), 7.20 (dd, 1H, J=8.2, 7.7 Hz), 7.03–7.02 (m, 1H), 6.99 (d, 1H, J=7.7 Hz), 6.90 (s, 1H), 6.85 (d, 1H, J=8.1 Hz), 6.77 (d, 1H, J=8.2 Hz), 6.76–6.74 (m, 1H), 6.42 (d, 1H, J=15.9 Hz), 6.38 (dt, 1H, J=15.9, 4.6 Hz), 6.21–6.20 (m, 1H), 6.04 (s, 2H), 5.15 (d, 2H, J=4.6 Hz), 4.77 (q, 1H, J=6.8 Hz), 1.64 (d, 3H, J=6.8 Hz). |
| 93 | 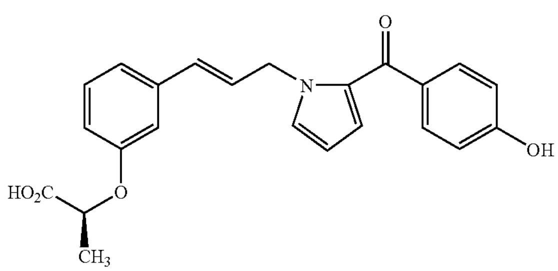 | $^1$H NMR (CDCl$_3$, 400 MHz) δ 7.67 (d, 2H, J=8.7 Hz), 7.11 (dd, 1H, J=8.0, 7.8 Hz), 6.97–6.96 (m, 1H), 6.89 (d, 1H, J=7.8 Hz), 6.80 (s, 1H), 6.79 (d, 2H, J=8.7 Hz), 6.70–6.69 (m, 1H), 6.69 (d, 1H, J=8.0 Hz), 6.37 (dt, 1H, J=15.7, 4.3 Hz), 6.32 (d, 1H, J=15.7 Hz), 6.15–6.13 (m, 1H), 5.08 (d, 2H, J=4.3 Hz), 4.70 (q, 1H, J=6.9 Hz), 1.59 (d, 3H, J=6.9 Hz). |
| 94 | 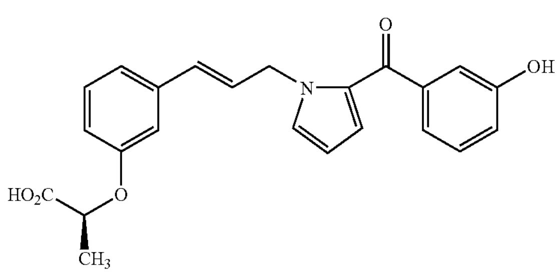 | $^1$H NMR (CDCl$_3$, 400 MHz) δ 7.26 (s, 1H), 7.25 (d, 1H, J=7.9 Hz), 7.22 (dd, 1H, J=8.0, 7.9 Hz), 7.17 (dd, 1H, J=8.1, 7.8 Hz), 7.04–7.03 (m, 1H), 6.98 (d, 1H, J=8.0 Hz), 6.94 (d, 1H, J=7.8 Hz), 6.83 (s, 1H), 6.79–6.77 (m, 1H), 6.74 (d, 1H, J=8.1 Hz), 6.37 (dt, 1H, J=15.7, 4.3 Hz), 6.32 (d, 1H, J=15.7 Hz), 6.18–6.17 (m, 1H), 5.13 (d, 2H, J=4.3 Hz), 4.74 (q, 1H, J=6.8 Hz), 1.59 (d, 3H, J=6.8 Hz). |

| Ex. No. | Structure | NMR |
|---|---|---|
| 95 | 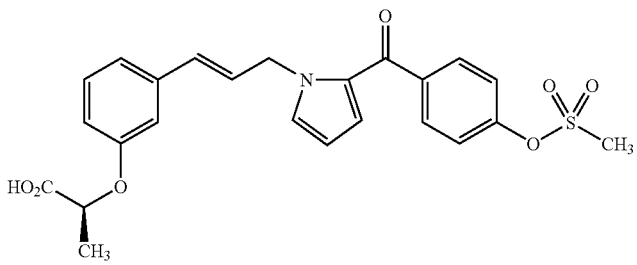 | $^1$H NMR (CDCl$_3$, 400 MHz) δ 7.87 (d, 2H, J=8.7 Hz), 7.37 (d, 2H, J=8.7 Hz), 7.18 (dd, 1H, J=8.1, 7.7 Hz), 7.08–7.07 (m, 1H), 6.99 (d, 1H, J=7.7 Hz), 6.89 (s, 1H), 6.78 (d, 1H, J=8.1 Hz), 6.77–6.76 (m, 1H), 6.44 (dt, 1H, J=15.9, 4.1 Hz), 6.38 (d, 1H, J=15.9 Hz), 6.24–6.22 (m, 1H), 5.18 (d, 2H, J=4.1 Hz), 4.78 (q, 1H, J=6.8 Hz), 3.19 (s, 3H), 1.62 (d, 3H, J=6.8 Hz). |
| 96 | 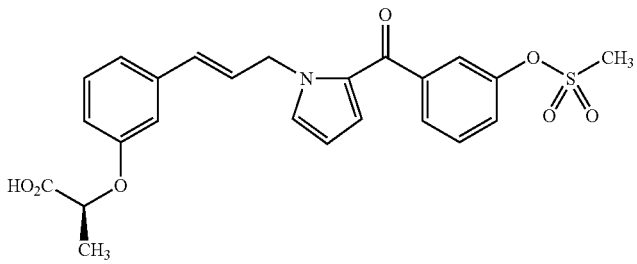 | $^1$H NMR (CDCl$_3$, 400 MHz) δ 7.76 (ddd, 1H, J=7.5, 1.4, 1.4 Hz), 7.70 (dd, 1H, J=1.4, 1.4 Hz), 7.52 (dd, 1H, J=8.2, 7.5 Hz), 7.46 (ddd, 1H, J=8.2, 1.4, 1.4 Hz), 7.21 (dd, 1H, J=8.0, 7.8 Hz), 7.09–7.08 (m, 1H), 7.00 (d, 1H, J=7.8 Hz), 6.90 (s, 1H), 6.81–6.79 (m, 1H), 6.78 (d, 1H, J=8.0 Hz), 6.44 (d, 1H, J=15.9 Hz), 6.38 (dt, 1H, J=15.9, 4.5 Hz), 6.25–6.23 (m, 1H), 5.18 (d, 2H, J=4.5 Hz), 4.79 (q, 1H, J=6.8 Hz), 3.18 (s, 3H), 1.63 (d, 3H, J=6.8 Hz). |
| 97 | 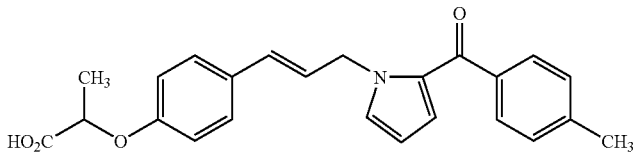 | $^1$H NMR (CDCl$_3$, 400 MHz) δ 7.72 (d, 2H, J=8.0 Hz), 7.28 (d, 2H, J=8.7 Hz), 7.24 (d, 2H, J=8.0 Hz), 7.05–7.04 (m, 1H), 6.81 (d, 2H, J=8.7 Hz), 6.77–6.76 (m, 1H), 6.45 (d, 1H, J=15.8 Hz), 6.30 (dt, 1H, J=15.8, 6.1 Hz), 6.20–6.19 (m, 1H), 5.16 (d, 2H, J=6.1 Hz), 4.76 (q, 1H, J=6.8 Hz), 2.42 (s, 3H), 1.63 (d, 3H, J=6.8 Hz). |
| 98 | 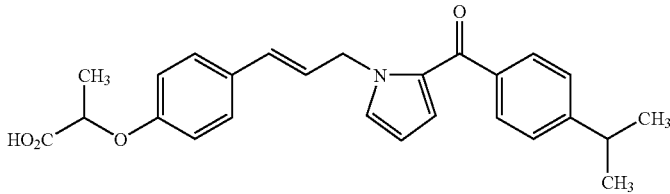 | $^1$H NMR (CDCl$_3$, 400 MHz) δ 7.76 (d, 2H, J=8.3 Hz), 7.30 (d, 2H, J=8.3 Hz), 7.28 (d, 2H, J=8.8 Hz), 7.06–7.05 (m, 1H), 6.81 (d, 2H, J=8.8 Hz), 6.80–6.78 (m, 1H), 6.45 (d, 1H, J=15.8 Hz), 6.30 (dt, 1H, J=15.8, 6.2 Hz), 6.20–6.19 (m, 1H), 5.17 (d, 2H, J=6.2 Hz), 4.76 (q, 1H, J=6.8 Hz), 2.97 (sept, 1H, J=6.9 Hz), 1.63 (d, 3H, J=6.8 Hz), 1.28 (d, 6H, J=6.9 Hz). |
| 99 | 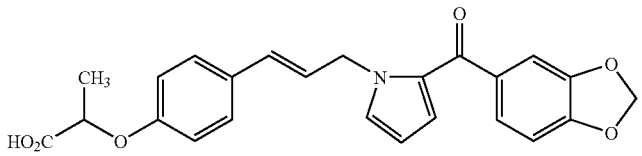 | $^1$H NMR (CDCl$_3$, 400 MHz) δ 7.43 (dd, 1H, J=8.1, 1.6 Hz), 7.33 (d, 1H, J=1.6 Hz), 7.28 (d, 2H, J=8.6 Hz), 7.04–7.03 (m, 1H), 6.85 (d, 1H, J=8.1 Hz), 6.82 (d, 2H, J=8.6 Hz), 6.77–6.75 (m, 1H), 6.44 (d, 1H, J=15.8 Hz), 6.29 (dt, 1H, J=15.8, 6.2 Hz), 6.20–6.19 (m, 1H), 6.04 (s, 2H), 5.13 (d, 2H, J=6.2 Hz), 4.77 (q, 1H, J=6.8 Hz), 1.63 (d, 3H, J=6.8 Hz). |

-continued

| Ex. No. | Structure | NMR |
|---|---|---|
| 100 | 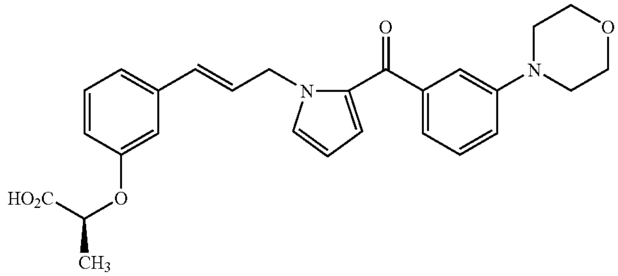 | ¹H NMR (CDCl₃, 400 MHz) δ 7.37–7.31 (m, 3H), 7.18 (d, 1H, J=7.9 Hz), 7.09 (dd, 1H, J=8.0, 7.8 Hz), 7.05–7.04 (m, 1H), 6.98 (d, 1H, J=7.8 Hz), 6.85 (s, 1H), 6.78–6.77 (m, 1H), 6.76 (d, 1H, J=8.0 Hz), 6.41 (d, 1H, J=15.9 Hz), 6.37 (dt, 1H, J=15.9, 4.6 Hz), 6.21–6.19 (m, 1H), 5.17 (d, 2H, J=4.6 Hz), 4.75 (q, 1H, J=6.8 Hz), 3.87 (t, 4H, J=4.7 Hz), 3.20 (t, 4H, J=4.7 Hz), 1.62 (d, 3H, J=6.8 Hz). |
| 101 | 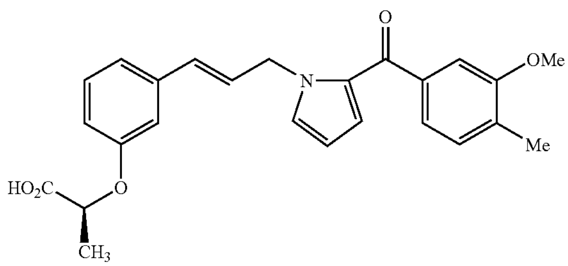 | ¹H NMR (CDCl₃, 400 MHz) δ 7.34 (dd, 1H, J=7.6, 1.5 Hz), 7.30 (d, 1H, 1.5 Hz), 7.20 (dd, 1H, J=7.8, 7.6 Hz), 7.18 (d, 1H, J=7.6 Hz), 7.05 (m, 1H), 7.01 (d, 1H, J=7.8 Hz), 6.91 (s, 1H), 6.81–6.80 (m, 1H), 6.76 (d, 1H, J=7.6 Hz), 6.45 (d, 1H, J=15.8 Hz), 6.43 (dt, 1H, J=15.8, 5.4 Hz), 6.22–6.20 (m, 1H), 5.17 (d, 2H, J=5.4 Hz), 4.80 (q, 1H, J=6.9 Hz), 3.87 (s, 3H), 2.28 (s, 3H), 1.64 (d, 3H, J=6.9 Hz). |
| 102 | 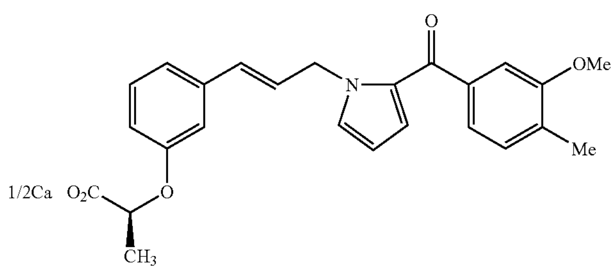 | ¹H NMR (DMSO-d₆, 400 MHz) δ 7.36–7.35 (m, 1H), 7.27–7.26 (m, 3H), 7.11 (dd, 1H, J=8.1, 7.7 Hz), 6.85 (d, 1H, J=7.7 Hz), 6.80 (s, 1H), 6.76–6.74 (m, 1H), 6.67 (d, 1H, J=8.1 Hz), 6.41 (dt, 1H, J=15.9, 5.4 Hz), 6.33 (d, 1H, J=15.9 Hz), 6.24–6.22 (m, 1H), 5.14 (d, 2H, J=5.4 Hz), 4.33 (q, 1H, J=6.7 Hz), 3.83 (s, 3H), 2.21 (s, 3H), 1.36 (d, 3H, J=6.7 Hz). |
| 103 | 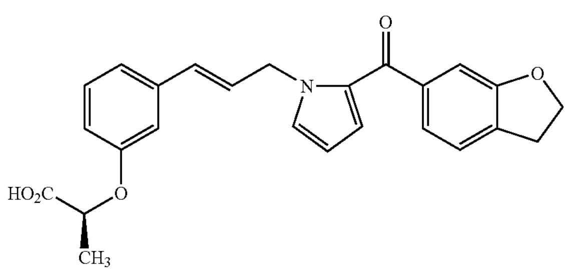 | ¹H NMR (CDCl₃, 400 MHz) δ 7.33 (dd, 1H, J=7.6, 1.4 Hz), 7.25 (d, 1H, J=1.4 Hz), 7.22 (d, 1H, J=7.6 Hz), 7.20 (dd, 1H, J=7.9, 7.8 Hz), 7.04–7.03 (m, 1H), 7.01 (d, 1H, J=7.8 Hz), 6.86 (s, 1H), 6.79–6.78 (m, 1H), 6.77 (d, 1H, J=7.9 Hz), 6.42 (dt, 1H, J=15.9, 5.1 Hz), 6.35 (d, 1H, J=15.9 Hz), 6.21–6.19 (m, 1H), 5.19 (d, 2H, J=5.1 Hz), 4.79 (q, 1H, J=6.8 Hz), 4.64 (t, 2H, J=8.7 Hz), 3.27 (t, 2H, J=8.7 Hz), 1.64 (d, 3H, J=6.8 Hz). |
| 104 | 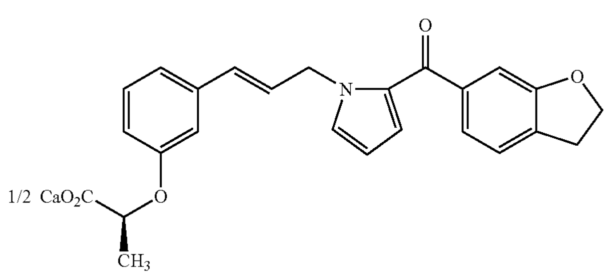 | ¹H NMR (DMSO-d₆, 400 MHz) δ 7.35 (d, 1H, J=1.4 Hz), 7.34 (d, 1H, J=7.6 Hz), 7.23 (dd, 1H, J=7.6, 1.4 Hz), 7.11 (dd, 1H, J=7.9, 7.7 Hz), 7.05–7.04 (m, 1H), 6.84 (d, 1H, J=7.7 Hz), 6.78 (s, 1H), 6.70–6.68 (m, 1H), 6.67 (d, 1H, J=7.9 Hz), 6.39 (dt, 1H, J=15.9, 5.6 Hz), 6.30 (d, 1H, J=15.9 Hz), 6.23–6.21 (m, 1H), 5.13 (d, 2H, J=5.6 Hz), 4.58 (t, 2H, J=8.8 Hz), 4.31 (q, 1H, J=6.7 Hz), 3.25 (t, 2H, J=8.8 Hz), 1.36 (d, 3H, J=6.7 Hz). |

| Ex. No. | Structure | NMR |
|---|---|---|
| 105 | 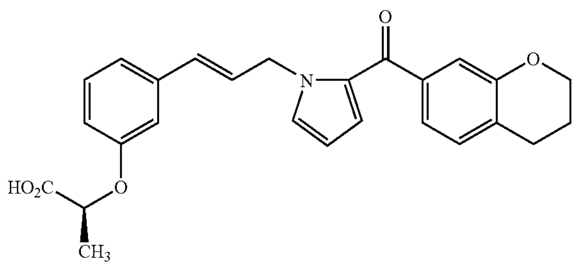 | $^1$H NMR (CDCl$_3$, 400 MHz) δ 7.29 (dd, 1H, J=7.8, 1.7 Hz), 7.23 (d, 1H, J=1.7 Hz), 7.20 (dd, 1H, J=8.2, 7.8 Hz), 7.10 (d, 1H, J=7.8 Hz), 7.03–7.02 (m, 1H), 6.99 (d, 1H, J=7.8 Hz), 6.87 (s, 1H), 6.81–6.78 (m, 1H), 6.74 (d, 1H, J=8.2 Hz), 6.41 (dt, 1H, J=15.9, 4.6 Hz), 6.36 (d, 1H, J=15.9 Hz), 6.20–6.19 (m, 1H), 5.17 (d, 2H, J=4.6 Hz), 4.78 (q, 1H, J=6.8 Hz), 4.22 (t, 2H, J=5.2 Hz), 2.84 (t, 2H, J=6.5 Hz), 2.04 (tt, 2H, J=6.5, 5.2 Hz), 1.63 (d, 3H, J=6.8 Hz). |
| 106 | 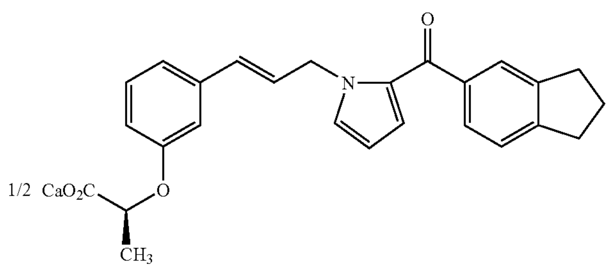 | $^1$H NMR (CDCl$_3$, 400 MHz) δ 7.68 (s, 1H), 7.61 (d, 1H, J=7.7 Hz), 7.27 (d, 1H, J=7.7 Hz), 7.20 (dd, 1H, J=7.9, 7.7 Hz), 7.04–7.02 (m, 1H), 7.00 (d, 1H, J=7.7 Hz), 6.91 (s, 1H), 6.78–6.77 (m, 1H), 6.76 (d, 1H, J=7.9 Hz), 6.45 (d, 1H, J=15.7 Hz), 6.40 (dt, 1H, J=15.7, 4.5 Hz), 6.21–6.19 (m, 1H), 5.18 (d, 2H, J=4.5 Hz), 4.79 (q, 1H, J=6.8 Hz), 2.98–2.94 (m, 4H), 2.16–2.08 (m, 2H), 1.63 (d, 3H, J=6.8 Hz). |
| 107 | 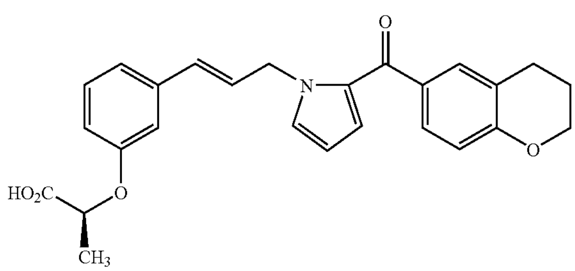 | $^1$H NMR (CDCl$_3$, 400 MHz) δ 7.61 (dd, 1H, J=8.1, 2.2 Hz), 7.60 (d, 1H, J=2.2 Hz), 7.21 (dd, 1H, J=8.0, 7.7 Hz), 7.02–7.01 (m, 1H), 7.00 (d, 1H, J=7.7 Hz), 6.90 (s, 1H), 6.82 (d, 1H, J=8.1 Hz), 6.77 (d, 1H, J=8.1 Hz), 6.77–6.76 (m, 1H), 6.44 (d, 1H, J=15.5 Hz), 6.40 (dt, 1H, J=15.5, 4.5 Hz), 6.21–6.20 (m, 1H), 5.16 (d, 2H, J=4.5 Hz), 4.80 (q, 1H, J=6.8 Hz), 4.25 (t, 2H, J=5.1 Hz), 2.83 (t, 2H, J=6.3 Hz), 2.05 (tt, 2H, J=6.3, 5.1 Hz), 1.63 (d, 3H, J=6.8 Hz). |
| 108 | 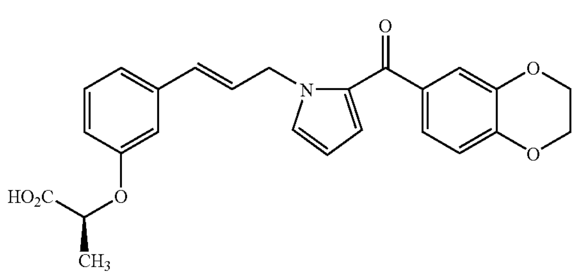 | $^1$H NMR (CDCl$_3$, 400 MHz) δ 7.40 (d, 1H, J=1.9 Hz), 7.37 (dd, 1H, J=8.3, 1.9 Hz), 7.19 (dd, 1H, J=8.2, 7.7 Hz), 7.03–7.02 (m, 1H), 6.99 (d, 1H, J=7.7 Hz), 6.91 (d, 1H, J=8.3 Hz), 6.90 (s, 1H), 6.79–6.78 (m, 1H), 6.75 (d, 1H, J=8.2 Hz), 6.42 (d, 1H, J=15.9 Hz), 6.38 (dt, 1H, J=15.9, 4.5 Hz), 6.20–6.19 (m, 1H), 5.15 (d, 2H, J=4.5 Hz), 4.78 (q, 1H, J=6.8 Hz), 4.33–4.28 (m, 4H), 1.63 (d, 3H, J=6.8 Hz). |
| 109 | 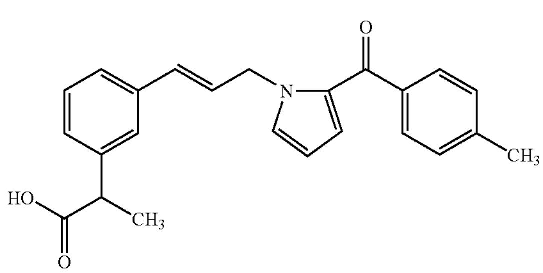 | $^1$H NMR (CDCl$_3$, 400 MHz) δ 7.73 (d, 2H, J=8.1 Hz), 7.29–7.26 (m, 3H), 7.25 (d, 2H, J=8.1 Hz), 7.19–7.17 (m, 1H), 7.05–7.04 (m, 1H), 6.78–6.76 (m, 1H), 6.48 (d, 1H, J=16.0 Hz), 6.43 (dt, 1H, J=16.0, 4.6 Hz), 6.21–6.20 (m, 1H), 5.20 (d, 2H, J=4.6 Hz), 3.71 (q, 1H, J=7.2 Hz), 2.42 (s, 3H), 1.49 (d, 3H, J=7.2 Hz). |

| Ex. No. | Structure | NMR |
|---|---|---|
| 110 | 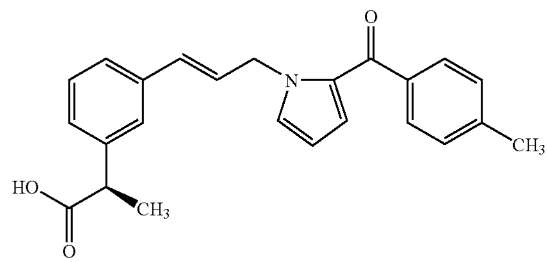 | $^1$H NMR (CDCl$_3$, 400 MHz) δ 7.73 (d, 2H, J=8.1 Hz), 7.31–7.27 (m, 3H), 7.25 (d, 2H, J=8.1 Hz), 7.20–7.17 (m, 1H), 7.05–7.04 (m, 1H), 6.78–6.76 (m, 1H), 6.48 (d, 1H, J=15.9 Hz), 6.43 (dt, 1H, J=15.9, 4.7 Hz), 6.21–6.20 (m, 1H), 5.20 (d, 2H, J=4.7 Hz), 3.71 (q, 1H, J=7.2 Hz), 2.42 (s, 3H), 1.50 (d, 3H, J=7.2 Hz). |
| 111 | 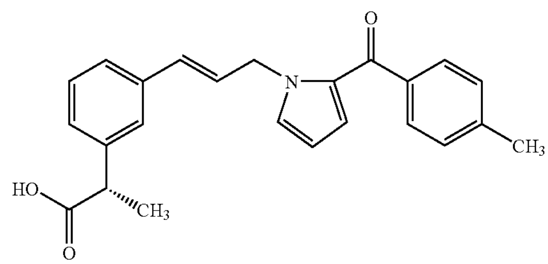 | $^1$H NMR (CDCl$_3$, 400 MHz) δ 7.73 (d, 2H, J=8.1 Hz), 7.29–7.26 (m, 3H), 7.25 (d, 2H, J=8.1 Hz), 7.19–7.16 (m, 1H), 7.05–7.04 (m, 1H), 6.78–6.76 (m, 1H), 6.48 (d, 1H, J=15.9 Hz), 6.43 (dt, 1H, J=15.9, 4.7 Hz), 6.21–6.20 (m, 1H), 5.20 (d, 2H, J=4.7 Hz), 3.71 (q, 1H, J=7.2 Hz), 2.42 (s, 3H), 1.49 (d, 3H, J=7.2 Hz). |
| 112 | 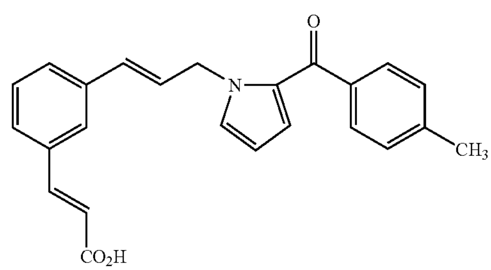 | $^1$H NMR (CDCl$_3$, 400 MHz) δ 7.74 (d, 1H, J=15.9 Hz), 7.74 (d, 2H, J=8.1 Hz), 7.51 (s, 1H), 7.41 (d, 1H, J=7.0 Hz), 7.40 (d, 1H, J=8.4 Hz), 7.33 (dd, 1H, J=8.4, 7.0 Hz), 7.26 (d, 2H, J=8.1 Hz), 7.06–7.05 (m, 1H), 6.79–6.78 (m, 1H), 6.52 (dt, 1H, J=15.9, 4.1 Hz), 6.48 (d, 1H, J=15.9 Hz), 6.23–6.22 (m, 1H), 5.22 (d, 2H, J=4.1 Hz), 2.43 (s, 3H). |
| 113 | 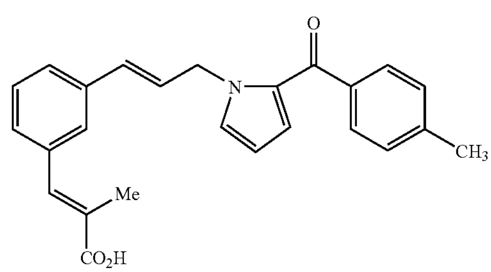 | $^1$H NMR (CDCl$_3$, 400 MHz) δ 7.79 (s, 1H), 7.74 (d, 2H, J=8.1 Hz), 7.38–7.28 (m, 4H), 7.26 (d, 2H, J=8.1 Hz), 7.06–7.05 (m, 1H), 6.79–6.77 (m, 1H), 6.51 (d, 1H, J=15.9 Hz), 6.45 (dt, 1H, J=15.9, 4.6 Hz), 6.23–6.21 (m, 1H), 5.22 (d, 2H, J=4.6 Hz), 2.43 (s, 3H), 2.12 (s, 3H). |
| 114 | 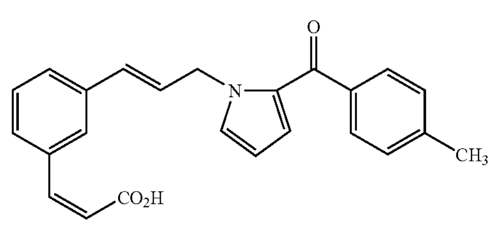 | $^1$H NMR (CDCl$_3$, 400 MHz) δ 7.73 (d, 2H, J=8.1 Hz), 7.56 (s, 1H), 7.48 (d, 1H, J=7.5 Hz), 7.34 (d, 1H, J=7.8 Hz), 7.28 (dd, 1H, J=7.8, 7.5 Hz), 7.25 (d, 2H, J=8.1 Hz), 7.06–7.04 (m, 1H), 7.02 (d, 1H, J=12.7 Hz), 6.78–6.76 (m, 1H), 6.50 (d, 1H, J=15.9 Hz), 6.42 (dt, 1H, J=15.9, 5.1 Hz), 6.20–6.19 (m, 1H), 5.96 (d, 1H, J=12.7 Hz), 5.19 (d, 2H, J=5.1 Hz), 2.43 (s, 3H). |

| Ex. No. | Structure | NMR |
|---|---|---|
| 115 | 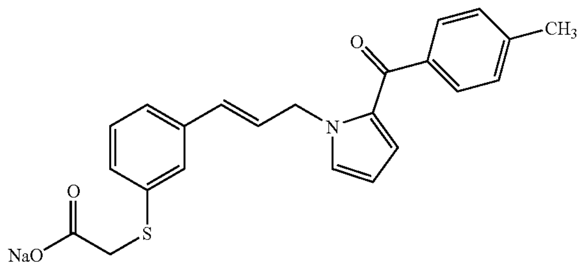 | $^1$H NMR (CDCl$_3$, 400 MHz) δ 7.73 (d, 2H, J=8.1 Hz), 7.41 (s, 1H), 7.27–7.20 (m, 5H), 7.03 (dd, 1H, J=2.5, 1.7 Hz), 6.77 (dd, 1H, J=4.0, 1.7 Hz), 6.48–6.39 (m, 2H), 6.21 (dd, 1H, J=4.0, 2.5 Hz), 5.18 (d, 2H, J=4.7 Hz), 3.66 (s, 2H), 2.42 (s, 3H). |
| 116 | 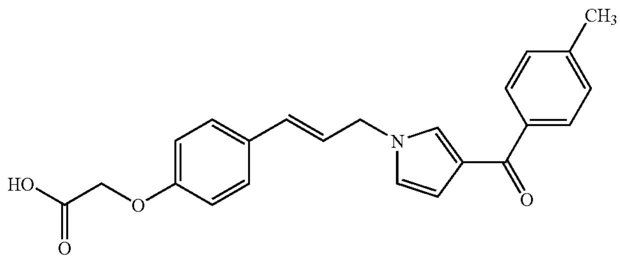 | $^1$H NMR (CDCl$_3$, 400 MHz) δ 7.75 (d, 2H, J=8.1 Hz), 7.32 (d, 2H, J=8.8 Hz), 7.31–7.29 (m, 1H), 7.25 (d, 2H, J=8.1 Hz), 6.88 (d, 2H, J=8.8 Hz), 6.73–6.69 (m, 2H), 6.48 (brd, 1H, J=15.8 Hz), 6.31 (dt, 1H, J=15.8, 6.3 Hz), 4.66 (s, 2H), 4.65 (d, 2H, J=6.3 Hz), 2.42 (s, 3H). |
| 117 | 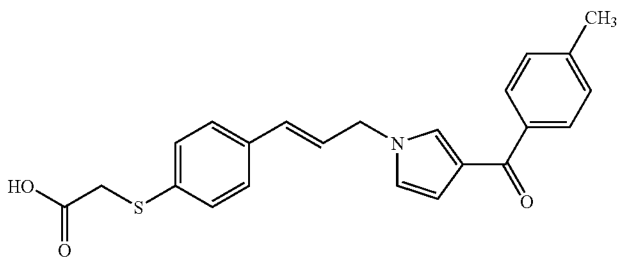 | $^1$H NMR (CDCl$_3$, 400 MHz) δ 7.75 (d, 2H, J=8.1 Hz), 7.37–7.28 (m, 5H), 7.25 (d, 2H, J=8.1 Hz), 6.73–6.70 (m, 2H), 6.47 (brd, 1H, J=15.8 Hz), 6.28 (dt, 1H, J=15.7, 6.1 Hz), 4.66 (d, 2H, J=6.1 Hz), 3.68 (s, 2H), 2.42 (s, 3H). |
| 118 | 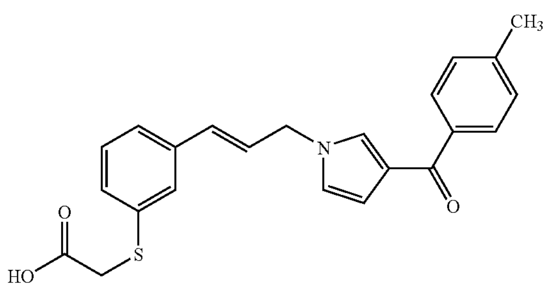 | $^1$H NMR (CDCl$_3$, 400 MHz) δ 7.76 (d, 2H, J=8.1 Hz), 7.43 (s, 1H), 7.33–7.20 (m, 6H), 6.73–6.69 (m, 2H), 6.48 (brd, 1H, J=15.8 Hz), 6.31 (dt, 1H, J=15.7, 6.1 Hz), 4.68 (d, 2H, J=6.1 Hz), 3.68 (s, 2H), 2.42 (s, 3H). |
| 119 | 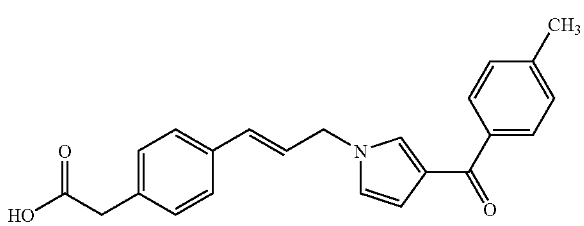 | $^1$H NMR (CDCl$_3$, 400 MHz) δ 7.75 (d, 2H, J=8.1 Hz), 7.34 (d, 2H, J=8.2 Hz), 7.29–7.23 (m, 5H), 6.73–6.70 (m, 2H), 6.52 (brd, 1H, J=15.8 Hz), 6.29 (dt, 1H, J=15.8, 6.2 Hz), 4.68 (d, 2H, J=6.2 Hz), 3.65 (s, 2H), 2.42 (s, 3H). |
| 120 | 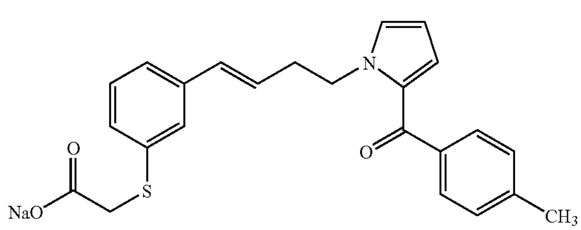 | $^1$H NMR (CDCl$_3$, 400 MHz) δ 7.66 (d, 2H, J=8.1 Hz), 7.35 (s, 1H), 7.25–7.11 (m, 5H), 6.97 (dd, 1H, J=2.4, 1.6 Hz), 6.72 (dd, 1H, J=4.0, 1.6 Hz), 6.31 (brd, 1H, J=15.8 Hz), 6.19 (dt, 1H, J=15.8, 7.1 Hz), 6.15 (dd, 1H, J=4.0, 2.4 Hz), 4.54 (t, 2H, J=7.0 Hz), 3.65 (s, 2H), 2.70 (dt, 2H, J=7.1, 7.0 Hz), 2.41 (s, 3H). |

| Ex. No. | Structure | NMR |
|---|---|---|
| 121 | 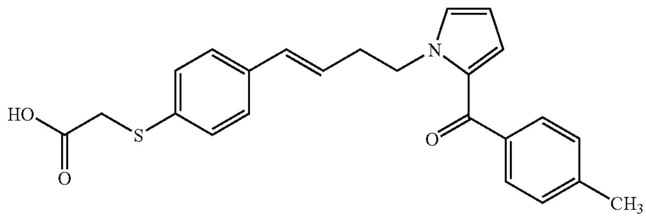 | $^1$H NMR (CDCl$_3$, 400 MHz) δ 7.68 (d, 2H, J=8.1 Hz), 7.30 (d, 2H, J=8.7 Hz), 7.24–7.20 (m, 4H), 6.96 (dd, 1H, J=1.7 and 2.5 Hz), 6.72 (dd, 1H, J=4.0, 1.7 Hz), 6.33 (brd, 1H, J=15.9 Hz), 6.17 (dt, 1H, J=15.9, 7.1 Hz), 6.14 (dd, 1H, J=4.0, 2.5 Hz), 4.53 (t, 2H, J=7.0 Hz), 3.66 (s, 2H), 2.70 (dt, 2H, J=7.1, 7.0 Hz), 2.42 (s, 3H). |
| 122 | 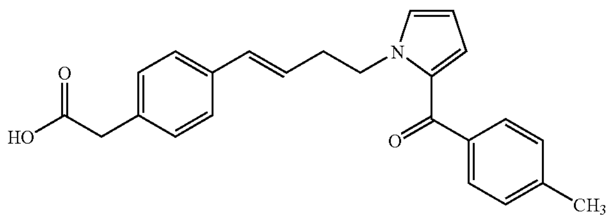 | $^1$H NMR (CDCl$_3$, 400 MHz) δ 7.69 (d, 2H, J=8.1 Hz), 7.26–7.18 (m, 6H), 6.96 (dd, 1H, J=2.5, 1.7 Hz), 6.72 (dd, 1H, J=4.0, 1.7 Hz), 6.36 (brd, 1H, J=15.8 Hz), 6.15 (dt, 1H, J=15.8, 7.1 Hz), 6.13 (dd, 1H, J=4.0, 2.5 Hz), 4.53 (t, 2H, J=7.0 Hz), 3.63 (s, 2H), 2.70 (dt, 2H, J=7.1, 7.0 Hz), 2.42 (s, 3H). |
| 123 | 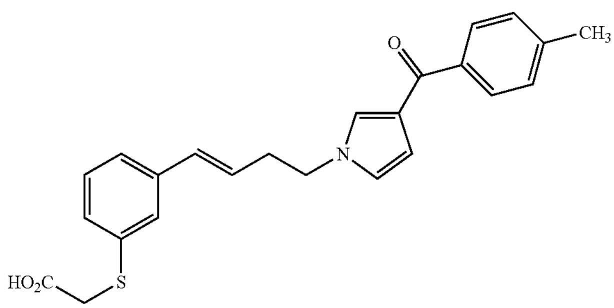 | $^1$H NMR (CDCl$_3$, 400 MHz) δ 7.76 (d, 2H, J=8.1 Hz), 7.40 (dd, 1H, J=1.8, 1.7 Hz), 7.37 (s, 1H), 7.24 (d, 1H, J=7.7 Hz), 7.23 (d, 2H, J=8.1 Hz), 7.18 (dd, 1H, J=7.7, 7.4 Hz), 7.03 (d, 1H, J=7.4 Hz), 6.67 (dd, 1H, J=2.9, 1.8 Hz), 6.62 (dd, 1H, J=2.9, 1.7 Hz), 6.28 (brd, 1H, J=15.8 Hz), 6.02 (dt, 1H, J=15.8, 7.1 Hz), 4.09 (t, 2H, J=6.2 Hz), 3.65 (s, 2H), 2.64 (dt, 2H, J=7.1, 6.2 Hz), 2.42 (s, 3H). |
| 124 | 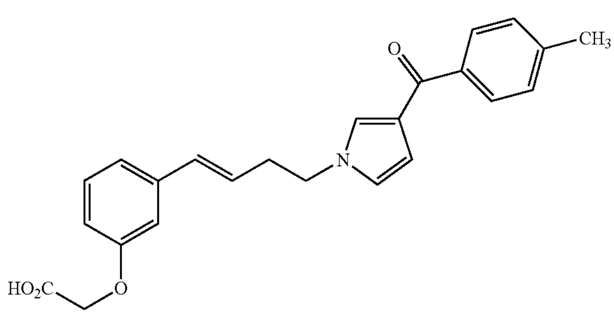 | $^1$H NMR (CDCl$_3$, 400 MHz) δ 7.73 (d, 2H, J=8.1 Hz), 7.28–7.19 (m, 4H), 6.88–6.82 (m, 2H), 6.70–6.67 (m, 2H), 6.35 (brd, 1H, J=15.8 Hz), 5.93 (dt, 1H, J=15.8, 7.1 Hz), 4.65 (s, 2H), 4.06 (t, 2H, J=7.0 Hz), 2.66 (dt, 2H, J=7.1, 7.0 Hz), 2.41 (s, 3H). |
| 125 | 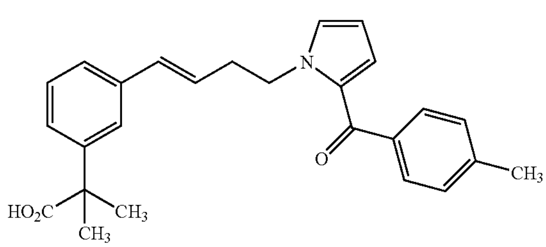 | $^1$H NMR (CDCl$_3$, 400 MHz) δ 7.68 (d, 2H, J=8.1 Hz), 7.29–7.19 (m, 6H), 6.97 (dd, 1H, J=2.4, 1.6 Hz), 6.72 (dd, 1H, J=4.0, 1.6 Hz), 6.39 (brd, 1H, J=15.8 Hz), 6.19 (dt, 1H, J=15.8, 7.1 Hz), 6.15 (dd, 1H, J=4.0, 2.4 Hz), 4.53 (t, 2H, J=7.0 Hz), 2.71 (dt, 2H, J=7.1, 7.0 Hz), 2.42 (s, 3H), 1.59 (s, 6H). |

| Ex. No. | Structure | NMR |
|---|---|---|
| 126 | 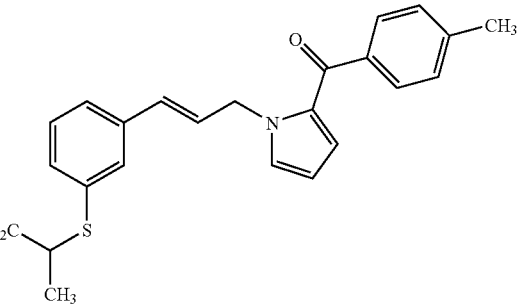 | ¹H NMR (CDCl$_3$, 400 MHz) δ 7.73 (d, 2H, J=8.1 Hz), 7.47 (s, 1H), 7.34–7.23 (m, 5H), 7.04 (dd, 1H, J=2.5, 1.7 Hz), 6.77 (dd, 1H, J=4.0, 1.7 Hz), 6.48–6.41 (m, 2H), 6.21 (dd, 1H, J=4.0, 2.5 Hz), 5.19 (d, 2H, J=4.7 Hz), 3.79 (q, 1H, J=7.1 Hz), 2.43 (s, 3H), 1.50 (d, 3H, J=7.1 Hz). |
| 127 | 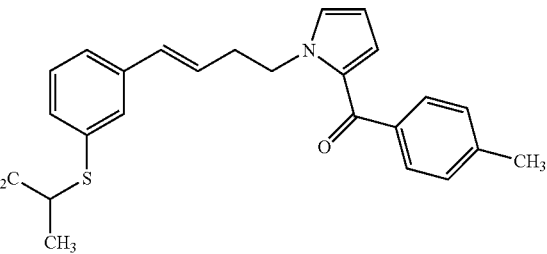 | ¹H NMR (CDCl$_3$, 400 MHz) δ 7.67 (d, 2H, J=8.1 Hz), 7.41 (s, 1H), 7.30–7.18 (m, 5H), 6.97 (dd, 1H, J=2.4, 1.6 Hz), 6.72 (dd, 1H, J=4.0, 1.6 Hz), 6.32 (brd, 1H, J=15.8 Hz), 6.20 (dt, 1H, J=15.8, 7.1 Hz), 6.15 (dd, 1H, J=4.0, 2.4 Hz), 4.54 (t, 2H, J=7.0 Hz), 3.78 (q, 1H, J=7.1 Hz), 2.71 (dt, 2H, J=7.1, 7.0 Hz), 2.42 (s, 3H), 1.50 (d, 3H, J=7.1 Hz). |
| 128 | 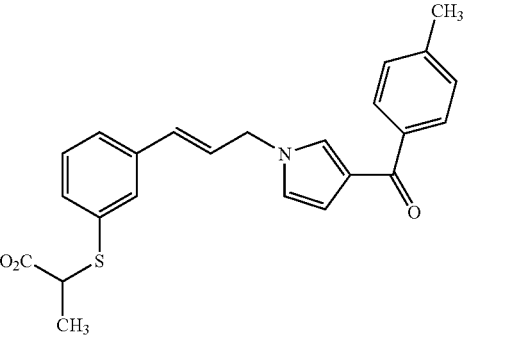 | ¹H NMR (CDCl$_3$, 400 MHz) δ 7.76 (d, 2H, J=8.1 Hz), 7.49 (s, 1H), 7.37–7.35 (m, 1H), 7.31–7.24 (m, 5H), 6.73–6.69 (m, 2H), 6.48 (brd, 1H, J=15.8 Hz), 6.32 (dt, 1H, J=15.7, 6.1 Hz), 4.68 (d, 2H, J=6.1 Hz), 3.81 (q, 1H, J=7.1 Hz), 2.42 (s, 3H), 1.51 (d, 3H, J=7.1 Hz). |
| 129 | 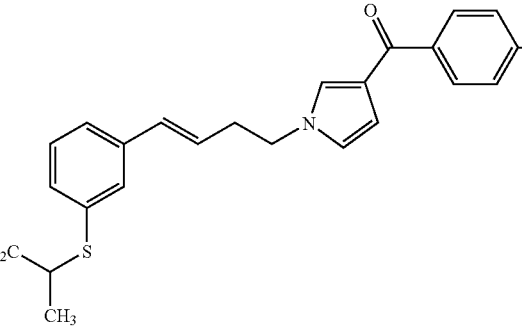 | ¹H NMR (CDCl$_3$, 400 MHz) δ 7.77 (d, 2H, J=8.1 Hz), 7.47 (s, 1H), 7.44–7.43 (m, 1H), 7.30–7.28 (m, 1H), 7.24–7.18 (m, 3H), 7.10 (brd, 2H, J=7.6 Hz), 6.67–6.61 (m, 2H), 6.27 (brd, 1H, J=15.8 Hz), 6.05 (dt, 1H, J=15.8, 7.1 Hz), 4.09 (t, 2H, J=7.0 Hz), 3.80 (q, 1H, J=7.1 Hz), 2.64 (dt, 2H, J=7.1, 7.0 Hz), 2.42 (s, 3H), 1.52 (d, 3H, J=7.1 Hz). |
| 130 | 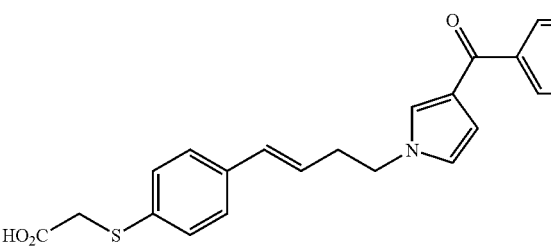 | ¹H NMR (CDCl$_3$, 400 MHz) δ 7.70 (d, 2H, J=8.1 Hz), 7.35 (d, 2H, J=8.4 Hz), 7.25 (d, 2H, J=8.4 Hz), 7.23–7.21 (m, 1H), 7.19 (d, 2H, J=8.1 Hz), 6.69–6.68 (m, 2H), 6.36 (brd, 1H, J=15.8 Hz), 6.09 (dt, 1H, J=15.8, 7.1 Hz), 4.03 (t, 2H, J=7.0 Hz), 3.67 (s, 2H), 2.69 (dt, 2H, J=7.1, 7.0 Hz), 2.41 (s, 3H). |

| Ex. No. | Structure | NMR |
|---|---|---|
| 131 | 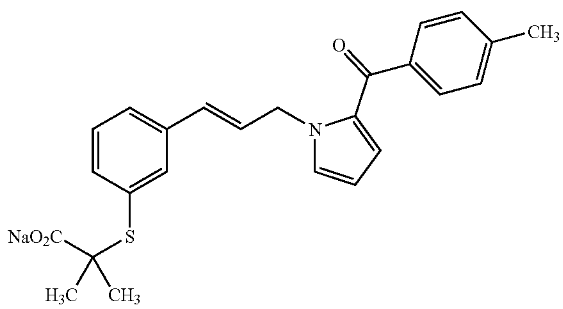 | $^1$H NMR (CDCl$_3$, 400 MHz) δ 7.73 (d, 2H, J=8.1 Hz), 7.50 (s, 1H), 7.37–7.35 (m, 2H), 7.26–7.23 (m, 3H), 7.04 (dd, 1H, J=2.5, 1.7 Hz), 6.77 (dd, 1H, J=4.0, 1.7 Hz), 6.48–6.39 (m, 2H), 6.20 (dd, 1H, J=4.0, 2.5 Hz), 5.18 (d, 2H, J=4.7 Hz), 2.42 (s, 3H), 1.47 (s, 6H). |
| 132 | 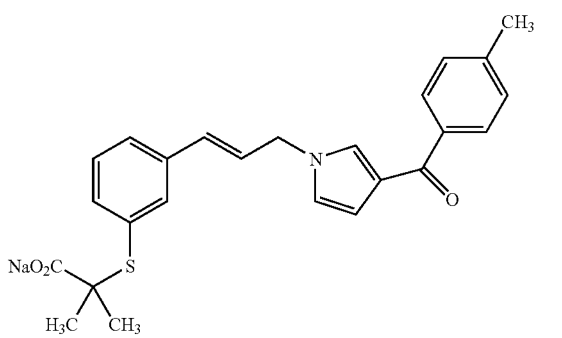 | $^1$H NMR (CDCl$_3$, 400 MHz) δ 7.76 (d, 2H, J=8.1 Hz), 7.52 (s, 1H), 7.42–7.35 (m, 2H), 7.31–7.24 (m, 4H), 6.73–6.69 (m, 2H), 6.49 (brd, 1H, J=15.8 Hz), 6.31 (dt, 1H, J=15.7, 6.1 Hz), 4.67 (d, 2H, J=6.1 Hz), 2.42 (s, 3H), 1.51 (s, 6H). |
| 133 | 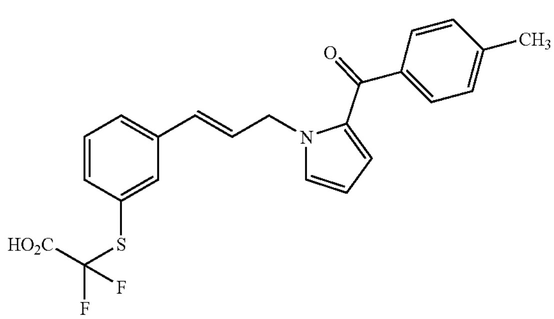 | $^1$H NMR (CDCl$_3$, 400 MHz) δ 7.70 (d, 2H, J=8.1 Hz), 7.64 (s, 1H), 7.48 (d, 1H, J=8.0 Hz), 7.38 (d, 1H, J=7.9 Hz), 7.29 (dd, 1H, J=8.0, 7.9 Hz), 7.25 (d, 2H, J=8.1 Hz), 7.07 (dd, 1H, J=2.5, 1.7 Hz), 6.82 (dd, 1H, J=4.0, 1.7 Hz), 6.51–6.40 (m, 2H), 6.24 (dd, 1H, J=4.0, 2.5 Hz), 5.16 (d, 2H, J=4.8 Hz), 2.43 (s, 3H). |
| 134 | 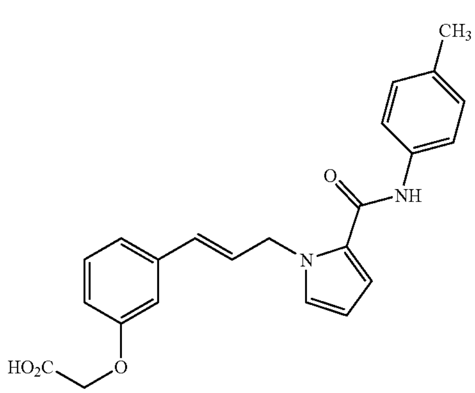 | $^1$H NMR (CDCl$_3$, 400 MHz) δ 7.44 (d, 2H, J=8.1 Hz), 7.20 (dd, 1H, J=7.9, 7.8 Hz), 7.14 (d, 2H, J=8.1 Hz), 6.99 (d, 1H, J=7.8 Hz), 6.93–6.90 (m, 2H), 6.81–6.78 (m, 2H), 6.40–6.39 (m, 2H), 6.19 (dd, 1H, J=4.0, 2.5 Hz), 5.16 (d, 2H, J=4.8 Hz), 4.59 (s, 2H), 2.33 (s, 3H). |

| Ex. No. | Structure | NMR |
|---|---|---|
| 135 | (structure with tolyl amide, pyrrole, styryl, and HO₂C-CH₂-S- on phenyl) | ¹H NMR (CDCl₃, 400 MHz) δ 7.57 (br, 1H), 7.42 (d, 2H, J=8.1 Hz), 7.39 (s, 1H), 7.26–7.20 (m, 3H), 7.14 (d, 2H, J=8.1 Hz), 6.89 (dd, 1H, J=2.5, 1.7 Hz), 6.72 (dd, 1H, J=4.0, 1.7 Hz), 6.46–6.35 (m, H), 6.20 (dd, 1H, J=4.0, 2.5 Hz), 5.16 (d, 2H, J=5.1 Hz), 3.65 (s, 2H), 2.32 (s, 3H). |
| 136 | (structure with 4-pyridyl ketone, pyrrole, styryl, and HOCH₂CO-O- on phenyl) | ¹H NMR (CDCl₃, 400 MHz) δ 8.75 (d, 2H, J=5.9 Hz), 7.64 (d, 2H, J=5.9 Hz), 7.23 (dd, 1H, J=7.9, 7.8 Hz), 7.12 (dd, 1H, J=2.5, 1.7 Hz), 7.01 (d, 1H, J=7.8 Hz), 6.93 (s, 1H), 6.83 (d, 1H, J=7.9 Hz), 6.75 (dd, 1H, J=4.0, 1.7 Hz), 6.44 (brd, 1H, J=15.7 Hz), 6.37 (dt, 1H, J=15.7, 5.5 Hz), 6.24 (dd, 1H, J=4.0, 2.5 Hz), 5.21 (d, 2H, J=5.5 Hz), 4.67 (s, 2H). |
| 137 | (structure with 4-pyridyl ketone, pyrrole, styryl, and HO₂C-CH₂-S- on phenyl) | ¹H NMR (CDCl₃, 400 MHz) δ 8.73–8.71 (m, 2H), 7.62–7.60 (m, 2H), 7.45 (s, 1H), 7.31–7.19 (m, 3H), 7.12 (dd, 1H, J=2.5, 1.7 Hz), 6.74 (dd, 1H, J=4.0, 1.7 Hz), 6.45–6.40 (m, 2H), 6.24 (dd, 1H, J=4.0, 2.5 Hz), 5.20 (d, 2H, J=4.6 Hz), 3.69 (s, 2H). |
| 138 | (structure with p-tolyl ketone, pyrrole, styryl, and NaO₂C-CH(CH₃)-S- on phenyl) | ¹H NMR (CDCl₃, 400 MHz) δ 7.73 (d, 2H, J=8.1 Hz), 7.47 (s, 1H), 7.33–7.31 (m, 1H), 7.29–7.22 (m, 3H), 7.03 (dd, 1H, J=2.5, 1.7 Hz), 6.77 (dd, 1H, J=4.0, 1.7 Hz), 6.50–6.40 (m, 2H), 6.21 (dd, 1H, J=4.0, 2.5 Hz), 5.18 (d, 2H, J=4.4 Hz), 3.78 (q, 1H, J=6.8 Hz), 2.42 (s, 3H), 1.48 (d, 3H, J=6.8 Hz). |
| 139 | (structure with p-tolyl ketone, pyrrole, styryl, and NaO₂C-CH(CH₃)-O- on phenyl) | ¹H NMR (CDCl₃, 400 MHz) δ 7.73 (d, 2H, J=8.1 Hz), 7.25 (d, 2H, J=8.1 Hz), 7.21 (dd, 1H, J=8.1, 7.8 Hz), 7.04 (dd, 1H, J=2.5, 1.7 Hz), 7.02 (d, 1H, J=7.8 Hz), 6.91 (s, 1H), 6.79–6.76 (m, 1H), 6.46–6.37 (m, 2H), 6.20 (dd, 1H, J=4.0, 2.5 Hz), 5.19 (d, 2H, J=4.4 Hz), 4.80 (q, 1H, J=6.8 Hz), 2.43 (s, 3H), 1.63 (d, 3H, J=6.8 Hz). |

| Ex. No. | Structure | NMR |
|---|---|---|
| 140 | 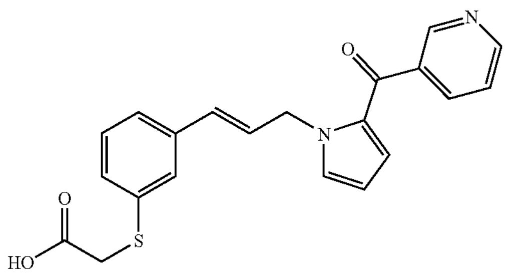 | $^1$H NMR (CDCl$_3$, 400 MHz) δ 8.90 (s, 1H), 8.71–8.70 (m, 1H), 8.17–8.14 (m, 1H), 7.49–7.41 (m, 2H), 7.33–7.30 (m, 1H), 7.26–7.09 (m, 4H), 6.75 (dd, 1H, J=4.0, 1.7 Hz), 6.36 (dt, 1H, J=15.7, 5.0 Hz), 6.28 (dd, 1H, J=4.0, 2.5 Hz), 6.00 (brd, 1H, J=15.7 Hz), 5.19 (d, 2H, J=5.0 Hz), 3.62 (s, 2H). |
| 141 | 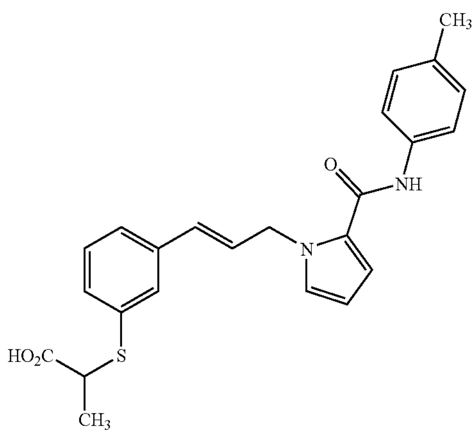 | $^1$H NMR (CDCl$_3$, 400 MHz) δ 7.57 (br, 1H), 7.46 (s, 1H), 7.42 (d, 2H, J=8.1 Hz), 7.33–7.22 (m, 3H), 7.15 (d, 2H, J=8.1 Hz), 6.89 (dd, 1H, J=2.5, 1.7 Hz), 6.71 (dd, 1H, J=4.0, 1.7 Hz), 6.48–6.36 (m, 2H), 6.19 (dd, 1H, J=4.0, 2.5 Hz), 5.16 (d, 2H, J=5.1 Hz), 3.77 (q, 1H, J=7.1 Hz), 2.32 (s, 3H), 1.48 (d, 3H, J=7.1 Hz). |
| 142 | 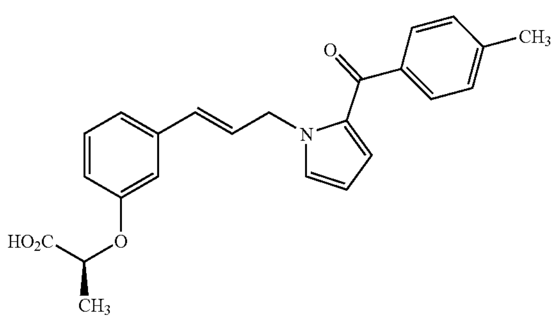 | $^1$H NMR (CDCl$_3$, 400 MHz) δ 7.72 (d, 2H, J=8.1 Hz), 7.25 (d, 2H, J=8.1 Hz), 7.21 (dd, 1H, J=8.1, 7.8 Hz), 7.04 (dd, 1H, J=2.5, 1.7 Hz), 7.02 (d, 1H, J=7.8 Hz), 6.91 (s, 1H), 6.79–6.76 (m, 2H), 6.46–6.37 (m, 2H), 6.20 (dd, 1H, J=4.0, 2.5 Hz), 5.19 (d, 2H, J=4.4 Hz), 4.80 (q, 1H, J=6.8 Hz), 2.42 (s, 3H), 1.63 (d, 3H, J=6.8 Hz). |
| 143 | 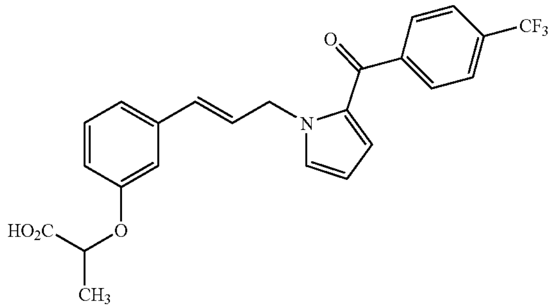 | $^1$H NMR (CDCl$_3$, 400 MHz) δ 7.88 (d, 2H, J=8.0 Hz), 7.71 (d, 2H, J=8.0 Hz), 7.22 (dd, 2H, J=8.0, 7.8 Hz), 7.10 (dd, 1H, J=2.4, 1.6 Hz), 7.01 (d, 1H, J=7.8 Hz), 6.92 (d, 1H, J=2.1 Hz), 6.78 (dd, 1H, J=8.0, 2.1 Hz), 6.74 (dd, 1H, J=4.0, 1.6 Hz), 6.48–6.37 (m, 2H), 6.23 (dd, 1H, J=4.0, 2.4 Hz), 5.21 (d, 2H, J=4.9 Hz), 4.80 (q, 1H, J=6.8 Hz), 1.63 (d, 3H, J=6.8 Hz). |

| Ex. No. | Structure | NMR |
|---|---|---|
| 144 | 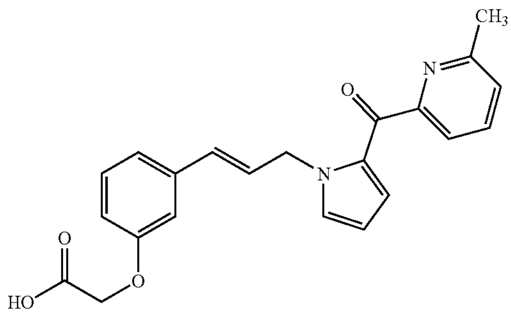 | $^1$H NMR (CDCl$_3$, 400 MHz) δ 7.75–7.68 (m, 2H), 7.31–7.20 (m, 2H), 7.22 (dd, 1H, J=8.0, 7.8 Hz), 7.06 (dd, 1H, J=2.5, 1.6 Hz), 7.00 (d, 1H, J=7.8 Hz), 6.93 (s, 1H), 6.79 (d, 1H, J=8.0 Hz), 6.52–6.42 (m, 2H), 6.24 (dd, 1H, J=4.0, 2.5 Hz), 5.21 (d, 2H, J=4.8 Hz), 4.62 (s, 2H), 2.65 (s, 3H). |
| 145 | 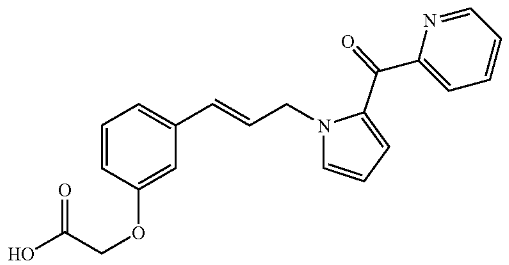 | $^1$H NMR (CDCl$_3$, 400 MHz) δ 8.71–8.70 (m, 1H), 7.93–7.91 (m, 1H), 7.88–7.84 (m, 1H), 7.47–7.43 (m, 1H), 7.27 (dd, 1H, J=4.0, 1.7 Hz), 7.22 (dd, 1H, J=8.0, 7.8 Hz), 7.08 (dd, 1H, J=2.5, 1.7 Hz), 7.00 (d, 1H, J=7.8 Hz), 6.92 (d, 1H, J=2.2 Hz), 6.78 (dd, 1H, J=8.0, 2.2 Hz), 6.51–6.42 (m, 2H), 6.26 (dd, 1H, J=4.0, 2.5 Hz), 5.23 (d, 2H, J=4.6 Hz), 4.63 (s, 2H). |
| 146 | 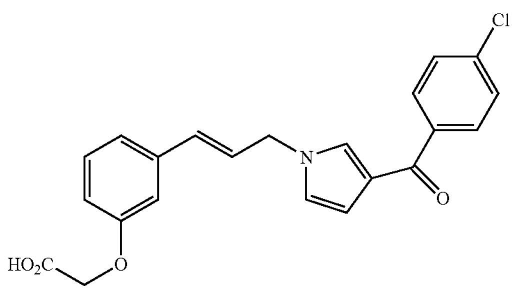 | $^1$H NMR (CDCl$_3$, 400 MHz) δ 7.78 (d, 2H, J=8.6 Hz), 7.43 (d, 2H, J=8.6 Hz), 7.29–7.28 (m, 1H), 7.27 (dd, 1H, J=8.0, 7.8 Hz), 7.03 (d, 1H, J=7.8 Hz), 6.93 (d, 1H, J=2.4 Hz), 6.84 (dd, 1H, J=8.0, 2.4 Hz), 6.75–6.73 (m, 1H), 6.70–6.68 (m, 1H), 6.49 (brd, 1H, J=15.7 Hz), 6.30 (dt, 1H, J=15.7, 6.2 Hz), 4.69 (d, 2H, J=6.2 Hz), 4.68 (s, 2H). |
| 147 | 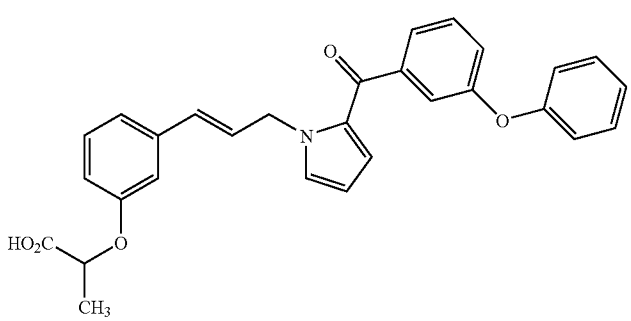 | $^1$H NMR (CDCl$_3$, 400 MHz) δ 7.54–7.52 (m, 1H), 7.43–7.33 (m, 4H), 7.23–7.16 (m, 3H), 7.14–7.10 (m, 1H), 7.06–7.03 (m, 3H), 7.00 (d, 1H, J=7.8 Hz), 6.91 (s, 1H), 6.79–6.76 (m, 2H), 6.45–6.38 (m, 2H), 6.20 (dd, 1H, J=4.0, 2.4 Hz), 5.18 (d, 2H, J=4.4 Hz), 4.80 (q, 1H, J=6.8 Hz), 1.63 (d, 3H, J=6.8 Hz). |
| 148 | 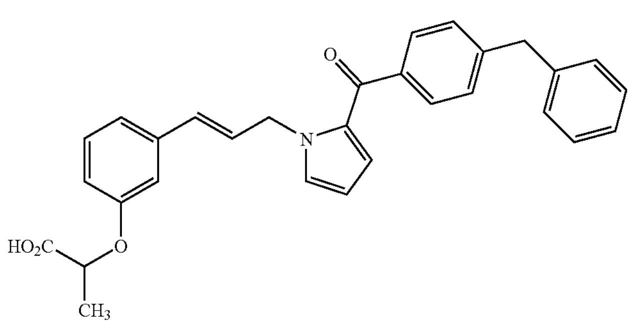 | $^1$H NMR (CDCl$_3$, 400 MHz) δ 7.74 (d, 1H, J=8.1 Hz), 7.33–7.18 (m, 8H), 7.04 (dd, 1H, J=2.4, 1.6 Hz), 7.00 (d, 1H, J=7.8 Hz), 6.90 (s, 1H), 6.78–6.75 (m, 2H), 6.45–6.38 (m, 2H), 6.20 (dd, 1H, J=4.0, 2.4 Hz), 5.18 (d, 2H, J=4.5 Hz), 4.80 (q, 1H, J=6.8 Hz), 4.05 (s, 2H), 1.63 (d, 3H, J=6.8 Hz). |

| Ex. No. | Structure | NMR |
|---|---|---|
| 149 | 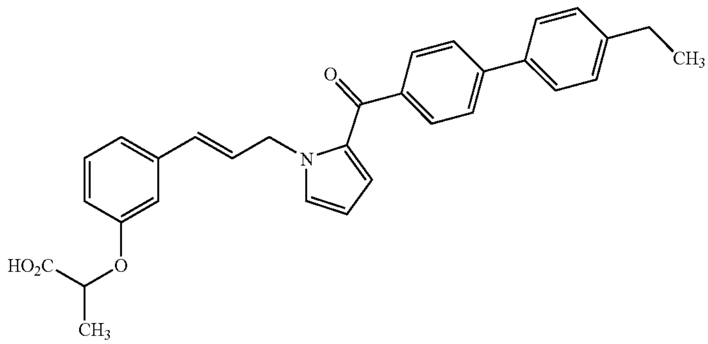 | $^1$H NMR (CDCl$_3$, 400 MHz) δ 7.89 (d, 1H, J=8.4 Hz), 7.66 (d, 1H, J=8.4 Hz), 7.57 (d, 1H, J=8.1 Hz), 7.31 (d, 1H, J=8.1 Hz), 7.22 (dd, 1H, J=8.0, 7.8 Hz), 7.06 (dd, 1H, J=2.4, 1.6 Hz), 7.02 (d, 1H, J=7.8 Hz), 6.92 (d, 1H, J=1.9 Hz), 6.84 (dd, 1H, J=4.0, 1.6 Hz), 6.78 (dd, 1H, J=8.0, 1.9 Hz), 6.45–6.37 (m, 2H), 6.23 (dd, 1H, J=4.0, 2.4 Hz), 5.21 (d, 2H, J=4.4 Hz), 4.81 (q, 1H, J=6.8 Hz), 2.71 (q, 2H, J=7.6 Hz), 1.64 (d, 2H, J=6.8 Hz), 1.29 (t, 3H, J=7.6 Hz). |
| 150 | 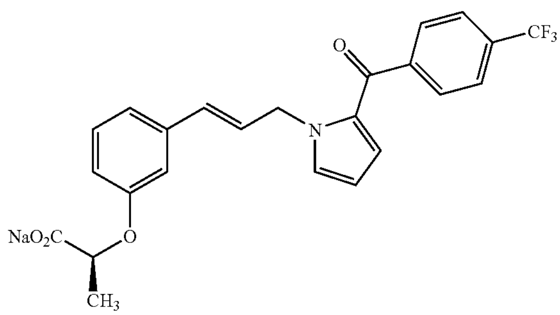 | $^1$H NMR (CDCl$_3$, 400 MHz) δ 7.88 (d, 2H, J=8.0 Hz), 7.71 (d, 2H, J=8.0 Hz), 7.22 (dd, 1H, J=8.0, 7.8 Hz), 7.10 (dd, 1H, J=2.4, 1.6 Hz), 7.01 (d, 1H, J=7.8 Hz), 6.92 (d, 1H, J=2.1 Hz), 6.78 (dd, 1H, J=8.0, 2.1 Hz), 6.74 (dd, 1H, J=4.0, 1.6 Hz), 6.48–6.37 (m, 2H), 6.23 (dd, 1H, J=4.0, 2.4 Hz), 5.21 (d, 2H, J=4.9 Hz), 4.80 (q, 1H, J=6.8 Hz), 1.63 (d, 3H, J=6.8 Hz). |
| 151 | 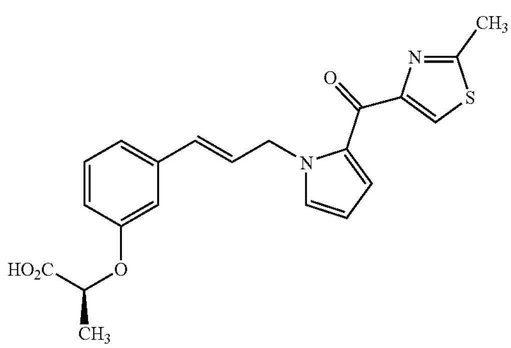 | $^1$H NMR (CDCl$_3$, 400 MHz) δ 7.16–7.12 (m, 1H), 6.99–6.87 (m, 4H), 6.74–6.71 (m, 1H), 6.45–6.36 (m, 2H), 6.16 (dd, 1H, J=4.0, 2.5 Hz), 5.07 (d, 2H, J=4.4 Hz), 4.71 (q, 1H, J=6.6 Hz), 2.40 (s, 3H), 1.55 (d, 3H, J=6.6 Hz). |
| 152 | 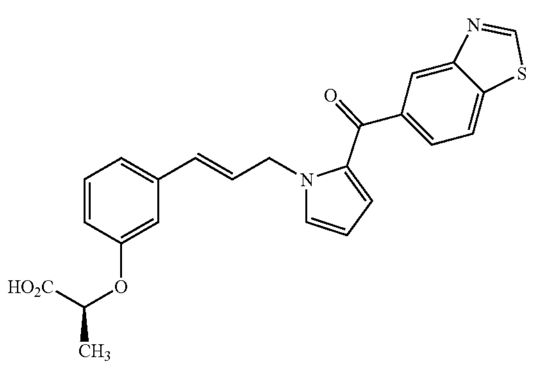 | $^1$H NMR (CD$_3$OD, 400 MHz) δ 7.86 (s, 1H), 7.82 (d, 1H, J=1.7 Hz), 7.65–7.57 (m, 2H), 7.18–7.10 (m, 2H), 6.93 (d, 1H, J=7.8 Hz), 6.87–6.70 (m, 3H), 6.50–6.41 (m, 2H), 6.24–6.20 (m, 1H), 5.12 (d, 2H, J=4.3 Hz), 4.74 (q, 1H, J=6.7 Hz), 1.55 (d, 3H, J=6.7 Hz). |

| Ex. No. | Structure | NMR |
|---|---|---|
| 153 | 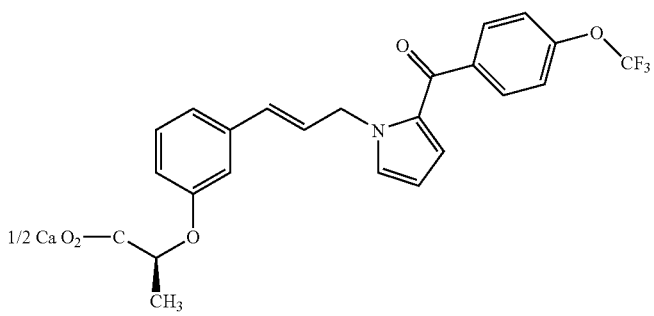 | ¹H NMR (DMSO-d₆, 400 MHz) δ 7.87 (d, 2H, J=8.3 Hz), 7.49 (d, 2H, J=8.3 Hz), 7.41 (dd, 1H, J=2.5, 1.6 Hz), 7.11 (dd, 1H, J=8.0, 7.8 Hz), 6.85 (d, 1H, J=7.8 Hz), 6.80 (d, 1H, J=1.9 Hz), 6.73 (dd, 1H, J=4.0, 1.6 Hz), 6.68 (dd, 1H, J=8.0, 1.9 Hz), 6.41 (dt, 1H, J=15.9, 5.4 Hz), 6.32 (brd, 1H, J=15.9 Hz), 6.25 (dd, 1H, J=4.0, 2.5 Hz), 5.16 (d, 2H, J=5.4 Hz), 4.32 (q, 1H, J=6.7 Hz), 1.37 (d, 3H, J=6.7 Hz). |
| 154 | 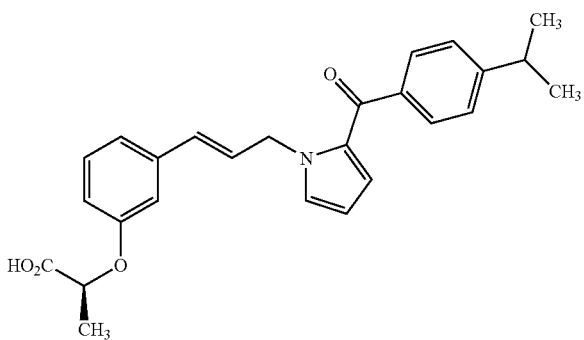 | ¹H NMR (CDCl₃, 400 MHz) δ 7.76 (brd, 2H, J=8.2 Hz), 7.30 (brd, 2H, J=8.2 Hz), 7.20 (brt, 1H, J=7.8 Hz), 7.04 (dd, 1H, J=2.5, 1.7 Hz), 7.01 (brd, 1H, J=7.8 Hz), 6.91 (brt, 1H, J=2.3 Hz), 6.79 (dd, 1H, J=4.0, 1.7 Hz), 6.77 (brdd, 1H, J=7.8, 2.3 Hz), 6.37–6.47 (m, 2H), 6.21 (dd, 1H, J=4.0, 2.5 Hz), 5.17–5.20 (m, 2H), 4.79 (q, 1H, J=6.8 Hz), 2.98 (7th, 1H, J=6.9 Hz), 1.63 (d, 3H, J=6.8 Hz), 1.29 (d, 6H, J=6.9 Hz). |
| 155 | 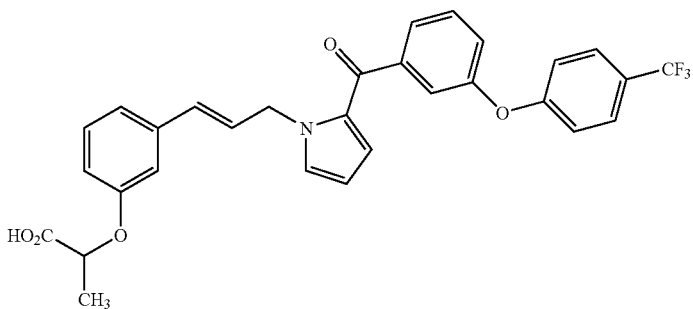 | ¹H NMR (CDCl₃, 400 MHz) δ 7.61–7.59 (m, 1H), 7.48–7.44 (m, 3H), 7.37 (d, 1H, J=7.7 Hz), 7.29 (s, 1H), 7.23–7.18 (m, 3H), 7.05 (dd, 1H, J=2.5, 1.6 Hz), 7.00 (dd, 1H, J=7.8, 1.5 Hz), 6.91 (dd, 1H, J=2.1, 1.5 Hz), 6.78 (dd, 1H, J=4.0, 1.6 Hz), 6.77 (dd, 1H, J=7.9, 2.1 Hz), 6.46–6.37 (m, 2H), 6.21 (dd, 1H, J=4.0, 2.4 Hz), 5.18 (d, 2H, J=4.9 Hz), 4.80 (q, 1H, J=6.8 Hz), 1.63 (d, 3H, J=6.8 Hz). |
| 156 | 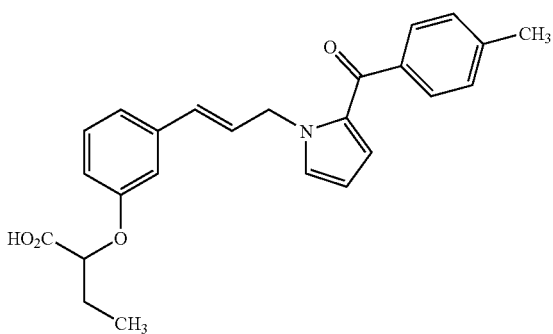 | ¹H NMR (CDCl₃, 400 MHz) δ 7.73 (d, 2H, J=8.1 Hz), 7.25 (d, 2H, J=8.1 Hz), 7.21 (dd, 1H, J=8.0, 7.8 Hz), 7.04 (dd, 1H, J=2.5, 1.6 Hz), 7.00 (d, 2H, J=7.8 Hz), 6.92 (d, 1H, J=1.9 Hz), 6.78 (dd, 1H, J=8.0, 1.9 Hz), 6.77 (dd, 1H, J=4.0, 1.6 Hz), 6.47–6.37 (m, 2H), 6.20 (dd, 1H, J=4.0, 2.5 Hz), 5.19 (d, 2H, J=4.8 Hz), 4.63 (t, 1H, J=6.2 Hz), 2.42 (s, 3H), 2.01 (dq, 2H, J=7.4, 6.2 Hz), 1.08 (t, 3H, J=7.4 Hz). |

-continued

| Ex. No. | Structure | NMR |
|---|---|---|
| 157 | 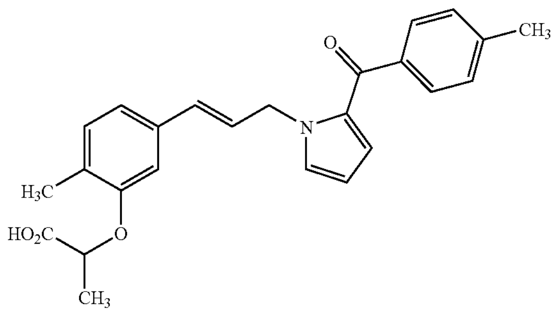 | $^1$H NMR (CDCl$_3$, 400 MHz) δ 7.72 (d, 2H, J=8.1 Hz), 7.25 (d, 2H, J=8.1 Hz), 7.07 (d, .1H, J=7.8 Hz), 7.04 (dd, 1H, J=2.5, 1.6 Hz), 6.91 (dd, 1H, J=7.8, 1.3 Hz), 6.76 (dd, 1H, J=4.0, 1.6 Hz), 6.75 (d, 1H, J=1.3 Hz), 6.43 (brd, 1H, J=15.8 Hz), 6.34 (dt, 1H, J=15.8, 6.2 Hz), 6.20 (dd, 1H, J=4.0, 2.5 Hz), 5.16 (d, 2H, J=6.2 Hz), 4.79 (q, 1H, J=6.8 Hz), 2.42 (s, 3H), 2.24 (s, 3H), 1.64 (d, 3H, J=6.8 Hz). |
| 158 | 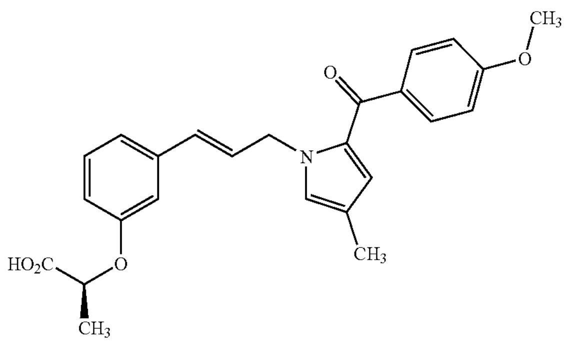 | $^1$H NMR (CDCl$_3$, 400 MHz) δ 7.82 (d, 1H, J=8.8 Hz), 7.21 (dd, 1H, J=7.9, 7.7 Hz), 7.00 (d, 1H, J=7.7 Hz), 6.94 (d, 1H, J=8.8 Hz), 6.91 (d, 1H, J=1.9 Hz), 6.81 (d, 1H, J=1.0 Hz), 6.77 (dd, 1H, J=7.9, 1.9 Hz), 6.56 (d, 1H, J=1.0 Hz), 6.47–6.38 (m, 2H), 5.10 (d, 2H, J=4.6 Hz), 4.79 (q, 1H, J=6.8 Hz), 3.87 (s, 3H), 2.09 (s, 3H), 1.63 (d, 3H, J=6.8 Hz). |
| 159 | 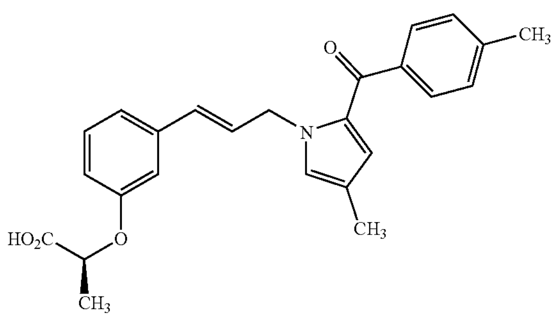 | $^1$H NMR (CDCl$_3$, 400 MHz) δ 7.70 (d, 1H, J=8.1 Hz), 7.24 (d, 1H, J=8.1 Hz), 7.20 (dd, 1H, J=8.0, 7.9 Hz), 7.00 (d, 1H, J=7.9 Hz), 6.91 (d, 1H, J=1.9 Hz), 6.82 (d, 1H, J=1.0 Hz), 6.76 (dd, 1H, J=8.0, 1.9 Hz), 6.56 (d, 1H, J=1.0 Hz), 6.47–6.37 (m, 2H), 5.11 (d, 2H, J=4.7 Hz), 4.79 (q, 1H, J=6.8 Hz), 2.42 (s, 3H), 2.08 (s, 3H), 1.63 (d, 3H, J=6.8 Hz). |
| 160 | 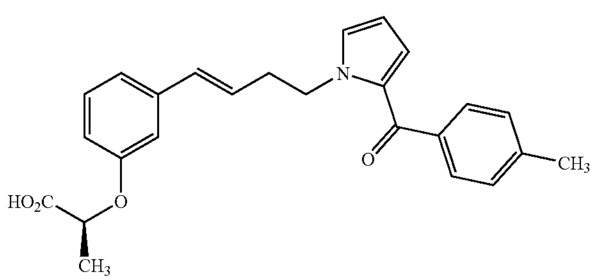 | $^1$H NMR (CDCl$_3$, 400 MHz) δ 7.67 (d, 2H, J=8.0 Hz), 7.21 (d, 1H, J=8.0 Hz), 7.18 (dd, 1H, J=8.0, 7.9 Hz), 6.96 (dd, 1H, J=2.4, 1.6 Hz), 6.91 (d, 1H, J=7.9 Hz), 6.83 (d, 1H, J=1.9 Hz), 6.74 (dd, 1H, J=8.0, 1.9 Hz), 6.72 (dd, 1H, J=4.0, 1.6 Hz), 6.31 (brd, 1H, J=15.8 Hz), 6.15 (dt, 1H, J=15.8, 7.1 Hz), 6.14 (dd, 1H, J=4.0, 2.4 Hz), 4.76 (q, 1H, J=6.8 Hz), 4.53 (t, 2H, J=7.0 Hz), 2.70 (dt, 2H, J=7.1, 7.0 Hz), 2.42 (s, 3H), 1.63 (d, 3H, J=6.8 Hz). |
| 161 | 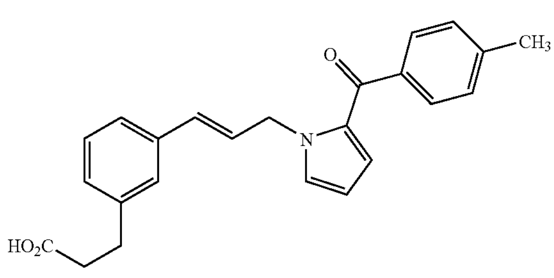 | $^1$H NMR (CDCl$_3$, 400 MHz) δ 7.73 (d, 2H, J=8.4 Hz), 7.25 (d, 2H, J=8.1 Hz), 7.20–7.23 (m, 3H), 7.06–7.10 (m, 1H), 7.05 (dd, 1H, J=2.5, 1.7 Hz), 6.77 (dd, 1H, J=4.0, 1.7 Hz), 6.48 (d, 1H, J=15.8 Hz), 6.43 (dt, 1H, J=15.8, 5.0 Hz), 6.20 (dd, 1H, J=4.0, 2.5 Hz), 5.20 (d, 2H, J=5.0 Hz), 2.93 (t, 2H, J=7.8 Hz), 2.66 (t, 2H, J=7.8 Hz), 2.42 (s, 3H). |

| Ex. No. | Structure | NMR |
|---|---|---|
| 162 | 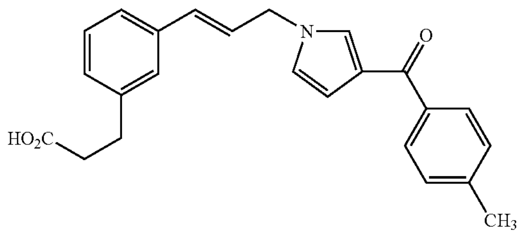 | ¹H NMR (CDCl₃, 400 MHz) δ 7.76 (d, 2H, J=8.1 Hz), 7.30 (brt, 1H, J=1.8 Hz), 7.21–7.28 (m, 5H), 7.13 (brd, 1H, J=7.0 Hz), 6.70–6.75 (m, 2H), 6.51 (d, 1H, J=15.8 Hz), 6.31 (dt, 1H, J=15.8, 6.2 Hz), 4.68 (brd, 2H, J=6.2 Hz), 2.95 (brt, 2H, J=7.7 Hz), 2.68 (brt, 2H, J=7.7 Hz), 2.42 (s, 3H). |
| 163 | 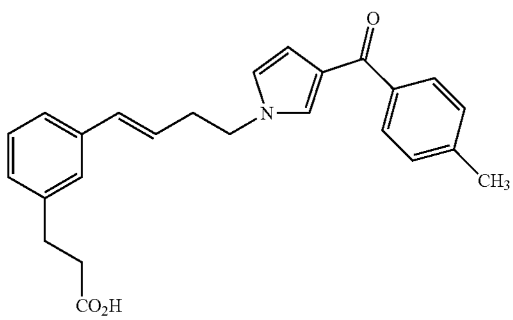 | ¹H NMR (CDCl₃, 400 MHz) δ 7.72 (d, 2H, J=8.1 Hz), 7.28 (brt, 1H, J=1.9 Hz), 7.23 (brt, 1H, J=7.7 Hz), 7.19 (brd, 1H, J=8.1 Hz), 7.17–7.21 (m, 1H), 7.13 (brt, 1H, J=7.7 Hz), 7.08 (brt, 1H, J=7.7 Hz), 6.60–6.70 (m, 2H), 6.34 (d, 1H, J=15.8 Hz), 6.06 (dt, 1H, J=15.8, 6.8 Hz), 4.05 (brt, 2H, J=6.8 Hz), 2.95 (brt, 2H, J=7.4 Hz), 2.66 (brt, 2H, J=7.4 Hz), 2.63–2.69 (m, 2H), 2.40 (s, 3H). |
| 164 | 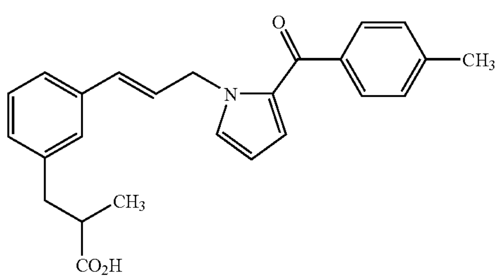 | ¹H NMR (CDCl₃, 400 MHz) δ 7.74 (d, 2H, J=8.1 Hz), 7.25 (d, 2H, J=8.1 Hz), 7.14–7.25 (m, 3H), 7.05 (dd, 1H, J=2.5, 1.7 Hz), 7.04–7.08 (m, 1H), 6.77 (dd, 1H, J=4.0, 1.7 Hz), 6.48 (d, 1H, J=15.9 Hz), 6.43 (dt, 1H, J=15.9, 5.0 Hz), 6.21 (dd, 1H, J=4.0, 2.5 Hz), 5.19 (brd, 2H, J=5.0 Hz), 3.04 (dd, 1H, J=13.4, 6.5 Hz), 2.71–2.81 (m, 1H), 2.64 (dd, 1H, J=13.4, 7.9 Hz), 2.43 (s, 3H), 1.17 (d, 3H, J=6.9 Hz). |
| 165 | 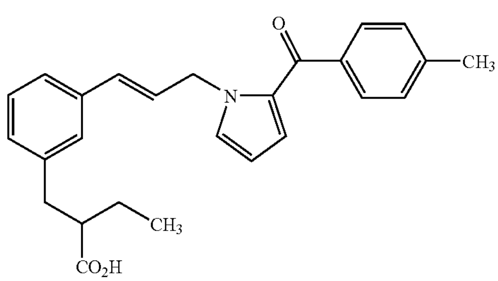 | ¹H NMR (CDCl₃, 400 MHz) δ 7.73 (d, 2H, J=8.1 Hz), 7.25 (d, 2H, J=8.1 Hz), 7.13–7.22 (m, 3H), 7.05 (dd, 1H, J=2.5, 1.6 Hz), 7.04–7.08 (m, 1H), 6.77 (dd, 1H, J=4.0, 1.6 Hz), 6.47 (d, 1H, J=15.9 Hz), 6.43 (dt, 1H, J=15.9, 5.0 Hz), 6.21 (dd, 1H, J=4.0, 2.5 Hz), 5.19 (brd, 2H, J=5.0 Hz), 2.94 (dd, 1H, J=13.6, 8.1 Hz), 2.73 (dd, 1H, J=13.6, 6.8 Hz), 2.58–2.66 (m, 1H), 2.43 (s, 3H), 1.55–1.70 (m, 2H), 0.95 (t, 3H, J=7.4 Hz). |
| 166 | 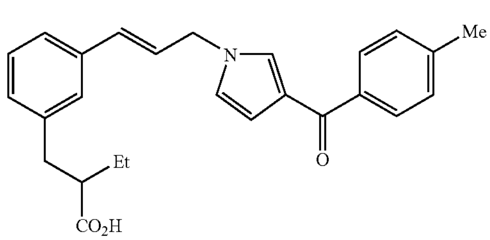 | ¹H NMR (CDCl₃, 400 MHz) δ 7.76 (d, 2H, J=8.1 Hz), 7.30 (t, 1H, J=1.8 Hz), 7.24 (d, 2H, J=8.1 Hz), 7.16–7.23 (m, 3H), 7.11 (brd, 1H, J=6.8 Hz), 6.70–6.75 (m, 2H), 6.50 (d, 1H, J=15.8 Hz), 6.30 (dt, 1H, J=15.8, 6.2 Hz), 4.67 (brd, 2H, J=6.2 Hz), 2.96 (dd, 1H, J=13.6, 8.3 Hz), 2.75 (dd, 1H, J=13.6, 6.7 Hz), 2.59–2.67 (m, 1H), 2.42 (s, 3H), 1.56–1.72 (m, 2H), 0.97 (t, 3H, J=7.4 Hz). |

| Ex. No. | Structure | NMR |
|---|---|---|
| 167 | 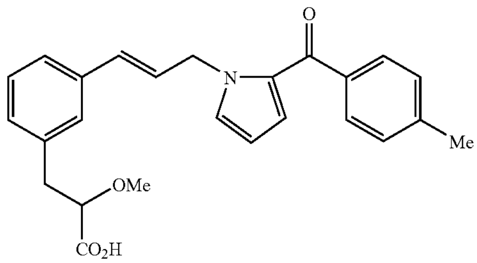 | $^1$H NMR (CDCl$_3$, 400 MHz) δ 7.73 (d, 2H, J=8.1 Hz), 7.16–7.28 (m, 5H), 7.09–7.13 (m, 1H), 7.05 (dd, 1H, J=2.5, 1.7 Hz), 6.77 (dd, 1H, J=4.0, 1.7 Hz), 6.48 (d, 1H, J=15.8 Hz), 6.43 (dt, 1H, J=15.8, 4.8 Hz), 6.21 (dd, 1H, J=4.0, 2.5 Hz), 5.19 (brd, 2H, J=4.8 Hz), 4.01 (dd, 1H, J=7.3, 4.3 Hz), 3.38 (s, 3H), 3.14 (dd, 1H, J=14.1, 4.3 Hz), 2.98 (dd, 1H, J=14.1, 7.3 Hz), 2.43 (s, 3H). |
| 168 | 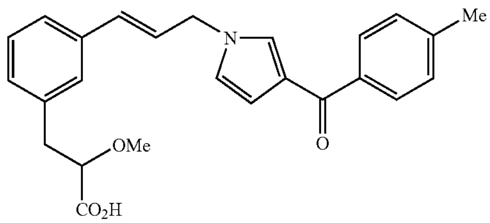 | $^1$H NMR (CDCl$_3$, 400 MHz) δ 7.76 (d, 2H, J=8.1 Hz), 7.31 (t, 1H, J=1.9 Hz), 7.14–7.29 (m, 6H), 6.70–6.75 (m, 2H), 6.51 (d, 1H, J=15.7 Hz), 6.31 (dt, 1H, J=15.7, 6.2 Hz), 4.68 (brd, 2H, J=6.2 Hz), 4.04 (dd, 1H, J=7.1, 4.4 Hz), 3.41 (3H, s), 3.15 (dd, 1H, J=14.1, 4.4 Hz), 3.03 (dd, 1H, J=14.1, 7.1 Hz), 2.42 (s, 3H). |
| 169 | 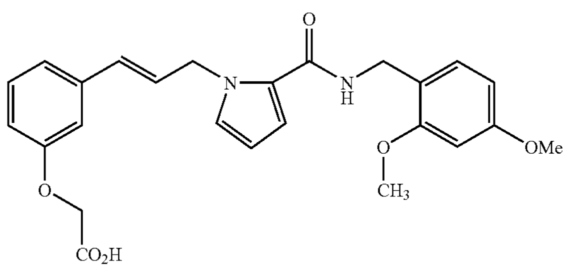 | $^1$H NMR (CDCl$_3$, 400 MHz) δ 7.22 (t, 1H, J=7.7 Hz), 7.20 (dd, 1H, J=7.8 Hz), 6.99 (brd, 1H, J=7.7 Hz), 6.88 (brt, 1H, J=2.3 Hz), 6.80–6.82 (m, 1H), 6.79 (brdd, 1H, J=7.7, 2.3 Hz), 6.52 (dd, 1H, J=3.9, 1.6 Hz), 6.45 (d, 1H, J=2.3 Hz), 6.38 (dd, 1H, J=7.8, 2.3 Hz), 6.30–6.40 (m, 3H), 6.11 (dd, 1H, J=3.9, 2.7 Hz), 5.14 (brd, 2H, J=4.5 Hz), 4.64 (s, 2H), 4.47 (brd, 2H, J=5.9 Hz), 3.83 (s, 3H), 3.79 (s, 3H). |
| 170 | 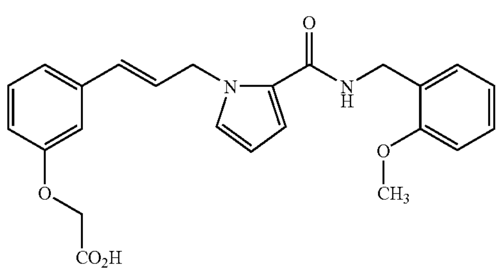 | $^1$H NMR (CDCl$_3$, 400 MHz) δ 7.23–7.32 (m, 2H), 7.22 (t, 1H, J=7.7 Hz), 7.00 (brd, 1H, J=7.7 Hz), 6.85–6.92 (m, 3H), 6.82 (dd, 1H, J=7.7, 2.3 Hz), 6.80 (brdd, 1H, J=7.7, 2.3 Hz), 6.54 (dd, 1H, J=3.9, 1.6 Hz), 6.43 (brs, 1H), 6.40 (dt, 1H, J=15.6, 4.8 Hz), 6.36 (d, 1H, J=15.6 Hz), 6.12 (dd, 1H, J=3.9, 2.7 Hz), 5.14 (brd, 2H, J=4.8 Hz), 4.64 (s, 2H), 4.56 (brd, 2H, J=6.0 Hz), 3.86 (s, 3H). |
| 171 | 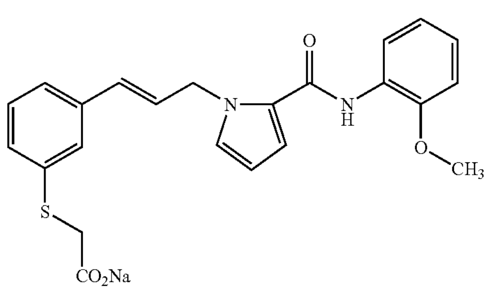 | $^1$H NMR (DMSO-d$_6$, 400 MHz) δ 8.91 (brs, 1H), 7.78 (dd, 1H, J=7.7, 1.5 Hz), 7.19 (brs, 1H), 7.15 (t, 1H, J=7.7 Hz), 7.04–7.14 (m, 5H), 6.99 (dd, 1H, J=3.9, 1.6 Hz), 6.93 (dt, 1H, J=1.5, 7.7 Hz), 6.43 (dt, H, J=15.9, 5.8 Hz), 6.31 (d, 1H, J=15.9 Hz), 6.15 (dd, 1H, J=3.9, 2.6 Hz), 5.12 (brd, 2H, J=5.8 Hz), 3.82 (s, 3H), 3.36 (s, 2H). |

| Ex. No. | Structure | NMR |
|---|---|---|
| 172 | 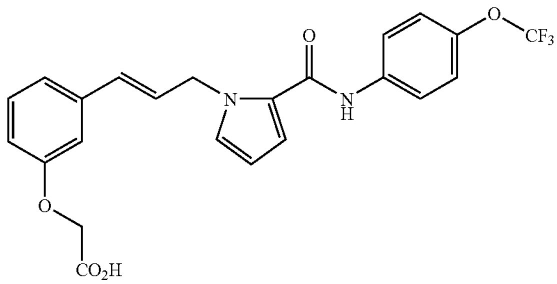 | $^1$H NMR (DMSO-d$_6$, 400 MHz) δ 13.0 (brs, 1H), 10.0 (brs, 1H), 7.82 (brd, 2H, J=8.7 Hz), 7.32 (brd, 2H, J=8.7 Hz), 7.20 (t, 1H, J=7.8 Hz), 7.14 (dd, 1H, J=2.6, 1.7 Hz), 7.08 (dd, 1H, J=4.0, 1.7 Hz), 6.95 (brd, 1H, J=7.8 Hz), 6.90 (brs, 1H), 6.77 (brdd, 1H, J=7.8, 2.5), 6.47 (dt, 1H, J=15.9, 5.8 Hz), 6.33 (d, 1H, J=15.9 Hz), 6.18 (dd, 1H, J=4.0, 2.6 Hz), 5.14 (brd, 2H, J=5.8 Hz), 4.64 (s, 2H). |
| 173 | 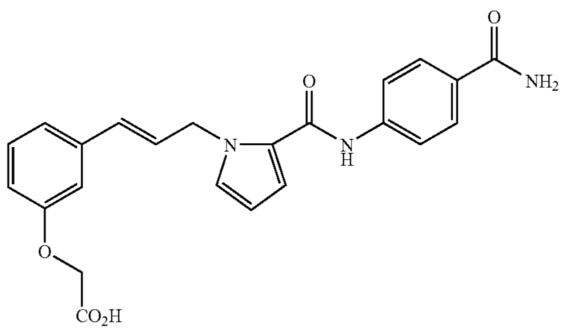 | $^1$H NMR (DMSO-d$_6$, 400 MHz) δ 13.0 (brs, 1H), 9.99 (brs, 1H), 7.83 (brd, 2H, J=8.9 Hz), 7.81–7.88 (br, 2H), 7.78 (brd, 2H, J=8.9 Hz), 7.22 (brt, 1H, J=7.9 Hz), 7.15 (dd, 1H, J=2.6, 1.6 Hz), 7.11 (dd, 1H, J=3.9, 1.6 Hz), 6.96 (brd, 1H, J=7.9 Hz), 6.92 (brt, 1H, J=2.3 Hz), 6.77 (brdd, 1H, J=7.9, 2.3), 6.48 (dt, 1H, J=15.9, 5.7 Hz), 6.34 (d, 1H, J=15.9 Hz), 6.19 (dd, 1H, J=3.9, 2.6 Hz), 5.15 (brd, 2H, J=5.7 Hz), 4.66 (s, 2H). |
| 174 | 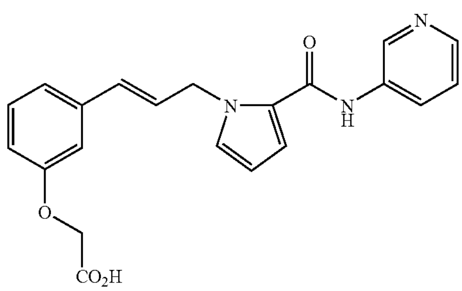 | $^1$H NMR (DMSO-d$_6$, 400 MHz) δ 12.9 (brs, 1H), 10.2 (brs, 1H), 8.95–8.99 (m, 1H), 8.32–8.36 (m, 1H), 8.23–8.36 (m, 1H), 7.49–7.54 (m, 1H), 7.16–7.25 (m, 2H), 7.14 (dd, 1H, J=3.9, 1.6 Hz), 6.96 (brd, 1H, J=7.9 Hz), 6.92 (brs, 1H), 6.78 (brdd, 1H, J=7.9, 2.3 Hz), 6.48 (dt, 1H, J=15.8, 5.9 Hz), 6.34 (d, 1H, J=15.8 Hz), 6.21 (dd, 1H, J=3.9, 2.6 Hz), 5.15 (brd, 2H, J=5.9 Hz), 4.67 (s, 2H). |
| 175 | 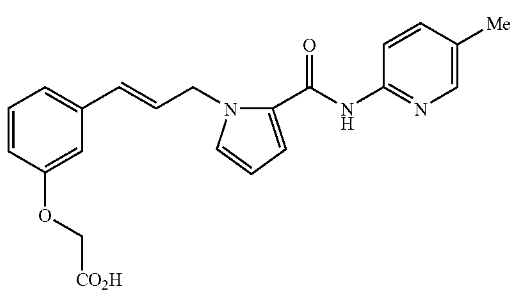 | $^1$H NMR (DMSO-d$_6$, 400 MHz) δ 13.1 (brs, 1H), 10.4 (brs, 1H), 8.37–8.40 (m, 1H), 8.21 (d, 1H, J=8.6 Hz), 7.80–7.84 (m, 1H), 7.49 (dd, 1H, J=4.0, 1.7 Hz), 7.41 (t, 1H, J=7.9 Hz), 7.35 (dd, 1H, J=2.6, 1.7 Hz), 7.17 (brd, 1H, J=7.9 Hz), 7.12–7.14 (m, 1H), 6.99 (brdd, 1H, J=7.9, 2.3 Hz), 6.69 (dt, 1H, J=15.9, 5.4 Hz), 6.55 (d, 1H, J=15.9 Hz), 6.36 (dd, 1H, J=4.0, 2.6 Hz), 5.37 (brd, 2H, J=5.4 Hz), 4.88 (s, 2H), 2.47 (s, 3H). |
| 176 | 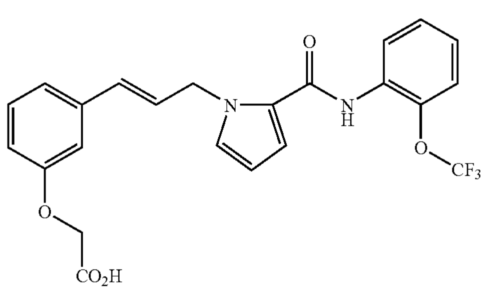 | $^1$H NMR (DMSO-d$_6$, 400 MHz) δ 13.0 (brs, 1H), 9.69 (brs, 1H), 7.63 (dd, 1H, J=7.8, 1.7 Hz), 7.37–7.44 (m, 2H), 7.32 (dt, 1H, J=1.7, 7.8), 7.21 (t, 1H, J=7.9 Hz), 7.13 (dd, 1H, J=2.6, 1.7 Hz), 7.05 (dd, 1H, J=3.9, 1.7 Hz), 6.94 (d, 1H, J=7.9 Hz), 6.90 (brt, 1H, J=2.1 Hz), 6.78 (brdd, 1H, J=7.9, 2.1 Hz), 6.44 (dt, 1H, J=15.9, 5.7 Hz), 6.34 (d, 1H, J=15.9 Hz), 6.17 (dd, 1H, J=3.9, 2.6 Hz), 5.12 (brd, 2H, J=5.7 Hz), 4.66 (s, 2H). |

-continued

| Ex. No. | Structure | NMR |
|---|---|---|
| 177 | 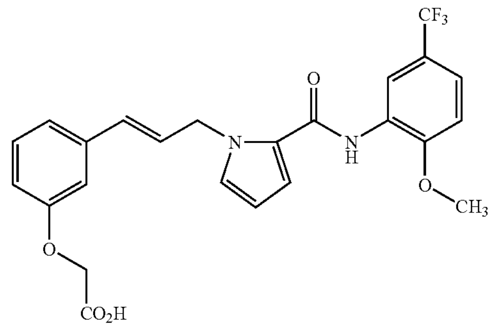 | $^1$H NMR (CDCl$_3$, 400 MHz) δ 8.74 (d, 1H, J=2.1 Hz), 8.35 (brs, 1H), 7.31 (dd, 1H, J=8.5, 1.5 Hz), 7.23 (t, 1H, J=7.9 Hz), 7.03 (d, 1H, J=7.9 Hz), 6.91–6.96 (m, 3H), 6.78 (dd, 1H, J=3.9, 1.7 Hz), 6.77–6.81 (m, 1H), 6.42 (dt, 1H, J=15.8, 4.6 Hz), 6.38 (d, 1H, J=15.8 Hz), 6.22 (dd, 1H, J=3.9, 2.6 Hz), 5.20 (brd, 2H, J=4.6 Hz), 4.65 (s, 2H), 3.92 (s, 3H). |
| 178 | 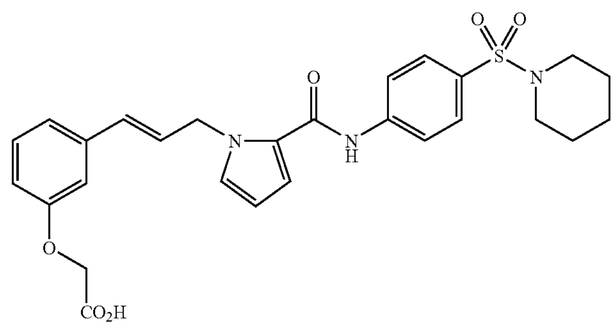 | $^1$H NMR (CDCl$_3$, 400 MHz) δ 7.82 (brs, 1H), 7.72 (brs, 4H), 7.24 (t, 1H, J=7.9 Hz), 7.02 (brd, 1H, J=7.9 Hz), 6.96 (dd, 1H, J=2.6, 1.7 Hz), 6.90 (brt, 1H, J=2.3 Hz), 6.80 (dd, 1H, J=4.0, 1.7 Hz), 6.79 (brdd, 1H, J=7.9, 2.3 Hz), 6.35–6.46 (m, 2H), 6.24 (dd, 1H, J=4.0, 2.6 Hz), 5.16–5.19 (m, 2H), 4.66 (s, 2H), 2.95–3.00 (m, 4H), 1.60–1.68 (m, 4H), 1.37–1.45 (m, 2H). |
| 179 | 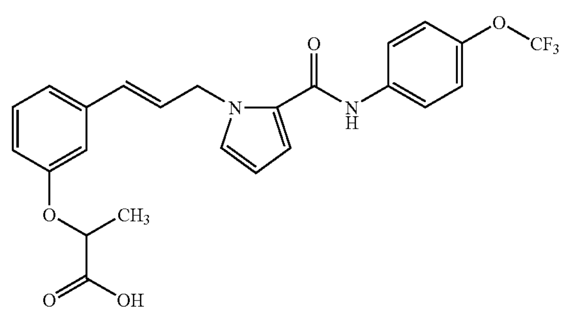 | $^1$H NMR (CDCl$_3$, 400 MHz) δ 7.64 (brs, 1H), 7.58 (brd, 2H, J=8.1 Hz), 7.22 (t, 1H, J=8.0 Hz), 7.20 (brd, 2H, J=8.1 Hz), 6.99 (brd, 1H, J=8.0 Hz), 6.93 (dd, 1H, J=2.7, 1.6 Hz), 6.88–6.91 (m, 1H), 6.77 (brdd, 1H, J=8.0, 2.6 Hz), 6.74 (dd, 1H, J=4.0, 1.6 Hz), 6.34–6.44 (m, 2H), 6.21 (dd, 1H, J=4.0, 2.7 Hz), 5.13–5.19 (m, 2H), 4.79 (q, 1H, J=6.8 Hz), 1.63 (d, 3H, J=6.8 Hz). |
| 180 | 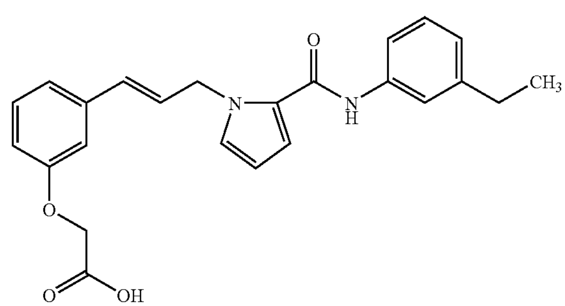 | $^1$H NMR (CDCl$_3$, 400 MHz) δ 7.59 (brs, 1H), 7.41 (brs, 1H), 7.36 (brd, 1H, J=7.6 Hz), 7.26 (brt, 1H, J=7.6 Hz), 7.20 (brt, 1H, J=7.9 Hz), 7.02 (brd, 1H, J=7.9 Hz), 6.96 (brd, 1H, J=7.6 Hz), 6.89–6.92 (m, 2H), 6.79 (brdd, 1H, J=7.9, 2.3 Hz), 6.73 (dd, 1H, J=3.9, 1.6 Hz), 6.36–6.47 (m, 2H), 6.20 (dd, 1H, J=3.9, 2.7 Hz), 5.18 (brd, 2H, J=4.4 Hz), 4.64 (s, 2H), 2.65 (q, 2H, J=7.6 Hz), 1.24 (t, 3H, J=7.6 Hz). |
| 181 | 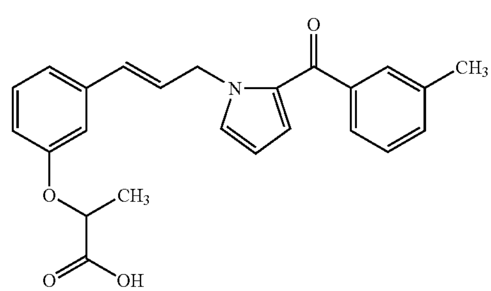 | $^1$H NMR (CDCl$_3$, 400 MHz) δ 7.57–7.63 (m, 2H), 7.30–7.36 (m, 2H), 7.21 (brt, 1H, J=7.9 Hz), 7.04 (dd, 1H, J=2.5, 1.7 Hz), 7.01 (brd, 1H, J=7.9 Hz), 6.91–6.93 (m, 1H), 6.77 (dd, 1H, J=4.0, 1.7 Hz), 6.76–6.79 (m, 1H), 6.46 (d, 1H, J=15.7 Hz), 6.41 (dt, 1H, J=15.7, 4.8 Hz), 6.21 (dd, 1H, J=4.0, 2.5 Hz), 5.19 (brd, 2H, J=4.8 Hz), 4.79 (q, 1H, J=6.8 Hz), 2.41 (s, 3H), 1.63 (d, 3H, J=6.8 Hz). |

| Ex. No. | Structure | NMR |
|---|---|---|
| 182 | 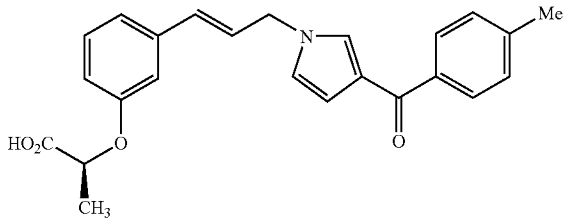 | $^1$H NMR (CDCl$_3$, 400 MHz) δ 7.76 (d, 2H, J=8.1 Hz), 7.29 (t, 1H, J=1.8 Hz), 7.26 (brd, 2H, J=8.1 Hz), 7.25 (brt, 1H, J=8.0 Hz), 7.01 (brt, 1H, J=8.0 Hz), 6.93 (brt, 1H, J=2.3 Hz), 6.82 (brdd, 1H, J=8.0, 2.3 Hz), 6.70–6.74 (m, 2H), 6.48 (d, 1H, J=15.8 Hz), 6.29 (dt, 1H, J=15.8, 6.1 Hz), 4.82 (q, 1H, J=6.8 Hz), 4.67 (brd, 2H, J=6.1 Hz), 2.42 (s, 3H), 1.66 (d, 3H, J=6.8 Hz). |
| 183 | 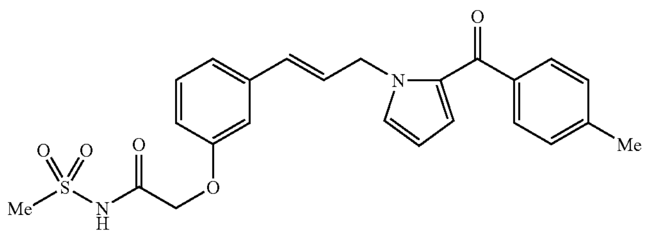 | $^1$H NMR (CDCl$_3$, 400 MHz) δ 8.8 (brs, 1H), 7.73 (brd, 2H, J=8.1 Hz), 7.25 (brd, 2H, J=8.1 Hz), 7.24–7.28 (m, 1H), 7.07 (brd, 1H, J=7.8 Hz), 7.04 (dd, 1H, J=2.6, 1.7 Hz), 6.90 (brs, 1H), 6.78 (dd, 1H, J=4.0, 1.7 Hz), 6.76–6.80 (m, 1H), 6.48 (dt, 1H, J=15.8, 4.5 Hz), 6.43 (d, 1H, J=15.8 Hz), 6.22 (dd, 1H, J=4.0, 2.6 Hz), 5.21 (brd, 2H, J=4.5 Hz), 4.58 (s, 2H), 3.35 (s, 3H), 2.43 (s, 3H). |
| 184 | 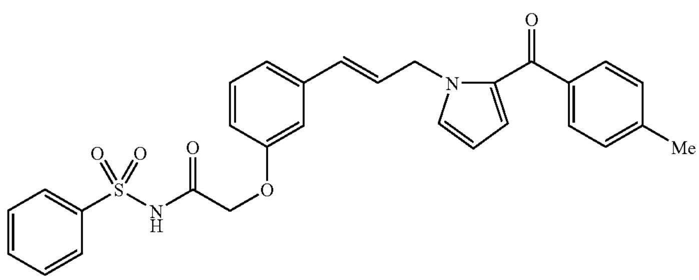 | $^1$H NMR (CDCl$_3$, 400 MHz) δ 8.9 (br, 1H), 8.06–8.10 (m, 2H), 7.73 (brd, 2H, J=8.1 Hz), 7.51–7.69 (m, 3H), 7.25 (brd, 2H, J=8.1 Hz), 7.24–7.26 (m, 1H), 7.02–7.07 (m, 2H), 6.84–6.87 (m, 1H), 6.76–6.79 (m, 1H), 6.70–6.74 (m, 1H), 6.36–6.45 (m, 2H), 6.21–6.24 (m, 1H), 5.17–5.22 (m, 2H), 4.44 (s, 2H), 2.42 (s, 3H). |
| 185 | 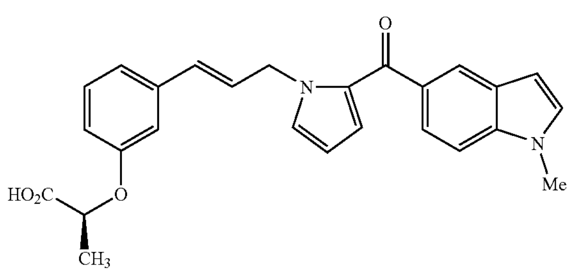 | $^1$H NMR (CDCl$_3$, 400 MHz) δ 8.19 (brd, 1H, J=1.4 Hz), 7.79 (dd, 1H, J=8.6, 1.4 Hz), 7.37 (d, 1H, J=8.6 Hz), 7.20 (brt, 1H, J=7.9 Hz), 7.12 (d, 1H, J=3.1 Hz), 7.03 (dd, 1H, J=2.5, 1.7 Hz), 7.01 (brd, 1H, J=7.9 Hz), 6.91 (brt, 1H, J=2.5 Hz), 6.80 (dd, 1H, J=4.0, 1.7 Hz), 6.77 (brdd, 1H, J=7.9, 2.5 Hz), 6.59 (dd, 1H, J=3.1, 0.70 Hz), 6.40–6.50 (m, 2H), 6.22 (dd, 1H, J=4.0, 2.5 Hz), 5.18–5.22 (m, 2H), 4.79 (q, 1H, J=6.8 Hz), 3.84 (s, 3H), 1.63 (d, 3H, J=6.8 Hz). |
| 186 | 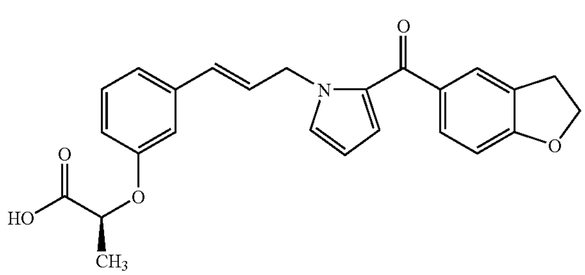 | $^1$H NMR (CDCl$_3$, 400 MHz) δ 7.73 (d, 1H, J=1.5 Hz), 7.69 (dd, 1H, J=8.3, 1.5 Hz), 7.20 (t, 1H, J=7.9 Hz), 7.02 (dd, 1H, J=2.5, 1.7 Hz), 6.90 (brd, 1H, J=7.9 Hz), 6.89–6.91 (m, 1H), 6.81 (d, 1H, J=8.3 Hz), 6.75–6.78 (m, 1H), 6.75 (dd, 1H, J=4.0, 1.7 Hz), 6.43 (d, 1H, J=16.0 Hz), 6.39 (dt, 1H, J=16.0, 4.0 Hz), 6.20 (dd, 1H, J=4.0, 2.5 Hz), 5.14–5.17 (m, 2H), 4.79 (q, 1H, J=6.8 Hz), 4.66 (t, 2H, J=8.7 Hz), 3.26 (t, 2H, J=8.7 Hz), 1.63 (d, 3H, J=6.8 Hz). |

-continued

| Ex. No. | Structure | NMR |
|---|---|---|
| 187 | 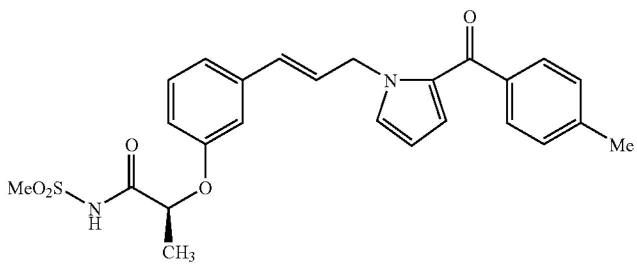 | ¹H NMR (CDCl₃, 400 MHz) δ 8.75 (brs, 1H), 7.73 (brd, 2H, J=8.1 Hz), 7.25 (brd, 2H, J=8.1 Hz), 7.22–7.26 (m, 1H), 7.07 (brd, 1H, J=7.7 Hz), 7.04 (dd, 1H, J=2.6, 1.6 Hz), 6.90 (brs, 1H), 6.78 (dd, 1H, J=4.0, 1.6 Hz), 6.76 (brdd, 1H, J=7.7, 2.3 Hz), 6.46 (dt, 1H, J=15.7, 4.5 Hz), 6.42 (d, 1H, J=15.7 Hz), 6.22 (dd, 1H, J=4.0, 2.6 Hz), 5.20 (brd, 2H, J=4.5 Hz), 4.77 (q, 1H, J=6.8 Hz), 3.28 (s, 3H), 2.43 (s, 3H), 1.59 (d, 3H, J=6.8 Hz). |
| 188 | 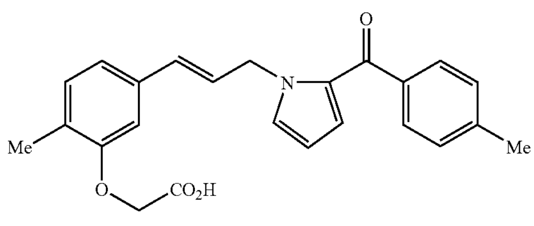 | ¹H NMR (CDCl₃, 400 MHz) δ 7.72 (d, 2H, J=8.1 Hz), 7.25 (d, 2H, J=8.1 Hz), 7.08 (d, 1H, J=7.7 Hz), 7.05 (dd, 1H, J=2.5, 1.7 Hz), 6.93 (dd, 1H, J=7.7, 1.3 Hz), 6.77 (dd, 1H, J=4.0, 1.7 Hz), 6.74 (d, 1H, J=1.3 Hz), 6.45 (d, 1H, J=15.8 Hz), 6.37 (dt, 1H, J=15.8, 5.6 Hz), 6.21 (dd, 1H, J=4.0, 2.5 Hz), 5.17 (d, 2H, J=5.6 Hz), 4.66 (s, 2H), 2.42 (s, 3H), 2.26 (s, 3H). |
| 189 | 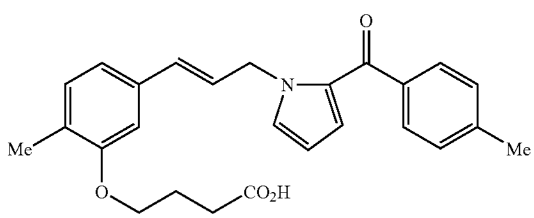 | ¹H NMR (CDCl₃, 400 MHz) δ 7.74 (d, 2H, J=8.1 Hz), 7.25 (d, 2H, J=8.1 Hz), 7.05 (dd, 1H, J=2.5, 1.7 Hz), 7.04 (d, 1H, J=7.6 Hz), 6.87 (d, 1H, J=1.3 Hz), 6.83 (dd, 1H, J=7.6, 1.3 Hz), 6.77 (dd, 1H, J=4.0, 1.7 Hz), 6.48 (d, 1H, J=15.9 Hz), 6.41 (dt, 1H, J=15.9, 5.7 Hz), 6.20 (dd, 1H, J=4.0, 2.5 Hz), 5.16 (d, 2H, J=5.7 Hz), 4.04 (q, 2H, J=6.2 Hz), 2.58 (t, 2H, J=7.1 Hz), 2.42 (s, 3H), 2.18 (s, 3H), 2.10–2.17 (m, 2H). |
| 190 | 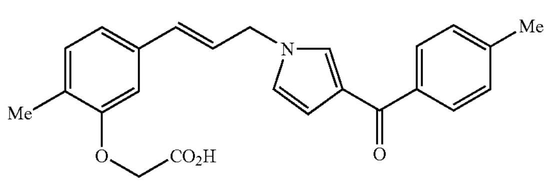 | ¹H NMR (CDCl₃, 400 MHz) δ 7.76 (d, 2H, J=8.1 Hz), 7.30 (t, 1H, J=1.9 Hz), 7.25 (d, 2H, J=8.1 Hz), 7.13 (d, 1H, J=7.7 Hz), 6.95 (dd, 1H, J=7.7, 1.3 Hz), 6.74 (d, 1H, J=1.3 Hz), 6.70–6.74 (m, 2H), 6.47 (d, 1H, J=15.7 Hz), 6.24 (dt, 1H, J=15.7, 6.2 Hz), 4.70 (s, 2H), 4.67 (dd, 2H, J=6.2, 1.2 Hz), 2.42 (s, 3H), 2.28 (s, 3H). |
| 191 | 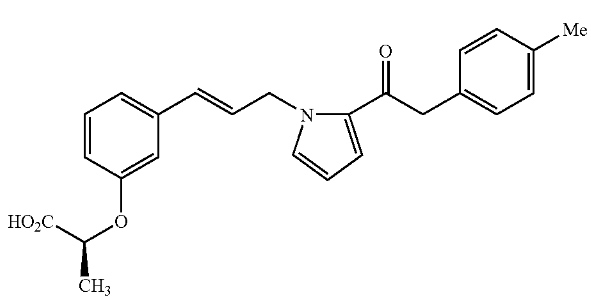 | ¹H NMR (CDCl₃, 400 MHz) δ 7.19 (brt, 1H, J=8.0 Hz), 7.16 (d, 2H, J=8.0 Hz), 7.12 (dd, 1H, J=4.1, 1.6 Hz), 7.09 (d, 2H, J=8.0 Hz), 6.94 (dd, 1H, J=2.5, 1.6 Hz), 6.92–6.95 (m, 1H), 6.86 (dd, 1H, J=2.3, 1.6 Hz), 6.75–6.79 (m, 1H), 6.25–6.35 (m, 2H), 6.19 (dd, 1H, J=4.1, 2.5 Hz), 5.07–5.09 (m, 2H), 4.79 (q, 1H, J=6.8 Hz), 4.04 (s, 2H), 2.30 (s, 3H), 1.64 (d, 3H, J=6.8 Hz). |

| Ex. No. | Structure | NMR |
|---|---|---|
| 192 | 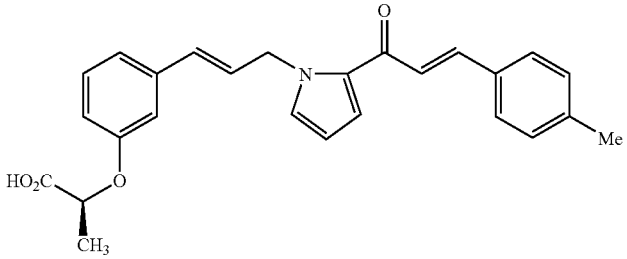 | $^1$H NMR (CDCl$_3$, 400 MHz) δ 7.72 (d, 1H, J=15.6 Hz), 7.51 (d, 2H, J=8.1 Hz), 7.38 (d, 1H, J=15.6 Hz), 7.21 (d, 2H, J=8.1 Hz), 7.18–7.22 (m, 1H), 7.17 (dd, 1H, J=4.0, 1.6 Hz), 6.99–7.03 (m, 2H), 6.91 (dd, 1H, J=2.2, 1.7 Hz), 6.77 (ddd, 1H, J=7.9, 2.5, 2.2 Hz), 6.43 (dt, 1H, J=15.8, 4.9 Hz), 6.37 (d, 1H, J=15.8 Hz), 6.26 (dd, 1H, J=4.0, 2.5 Hz), 5.23 (d, 2H, J=4.9 Hz), 4.81 (q, 1H, J=6.8 Hz), 2.39 (s, 3H), 1.64 (d, 3H, J=6.8 Hz). |
| 193 | 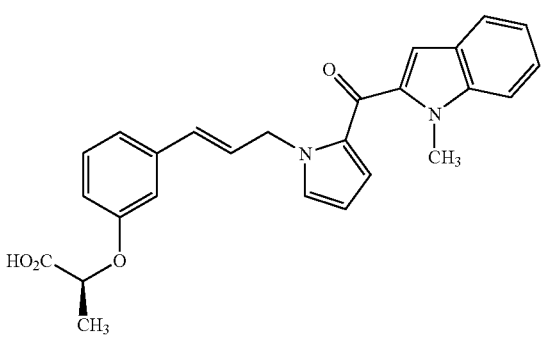 | $^1$H NMR (CDCl$_3$, 400 MHz) δ 7.69 (d, 1H, J=8.0 Hz), 7.43–7.37 (m, 2H), 7.21 (dd, 1H, J=8.0, 7.9 Hz), 7.18–7.14 (m, 1H), 7.09 (s, 1H), 7.06 (dd, 1H, J=2.5, 1.7 Hz), 7.02–7.00 (m, 2H), 6.90 (dd, 1H, J=2.1, 1.4 Hz), 6.76 (dd, 1H, J=8.0, 2.1 Hz), 6.45–6.38 (m, 2H), 6.24 (dd, 1H, J=4.0, 2.5 Hz), 5.20–5.18 (m, 2H), 4.79 (q, 1H, J=6.8 Hz), 4.02 (s, 3H), 1.62 (d, 3H, J=6.8 Hz). |
| 194 | 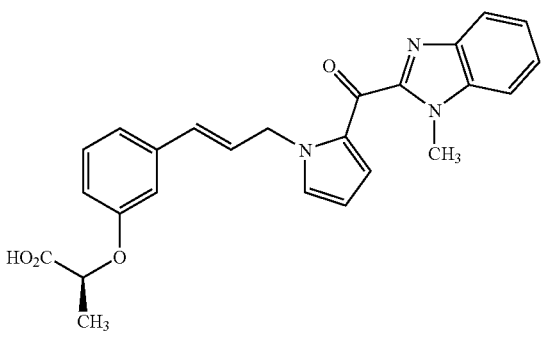 | $^1$H NMR (CDCl$_3$, 400 MHz) δ 7.85 (d, 1H, J=8.0 Hz), 7.52–7.34 (m, 5H), 7.19 (dd, 1H, J=8.0, 7.9 Hz), 7.11 (dd, 1H, J=2.5, 1.7 Hz), 6.97 (d, 1H, J=7.9 Hz), 6.90 (d, 1H, J=2.1 Hz), 6.78 (dd, 1H, J=8.0 2.1 Hz), 6.42 (brd, 1H, J=15.9 Hz), 6.31 (dt, 1H, J=15.9, 5.9 Hz), 6.31 (dd, 1H, J=4.0, 2.5 Hz), 5.34 (dd, 1H, J=16.0, 5.9 Hz), 5.15 (dd, 1H, J=16.0, 5.9 Hz), 4.76 (q, 1H, J=6.8 Hz), 4.03 (s, 3H), 1.58 (d, 3H, J=6.8 Hz). |
| 195 | 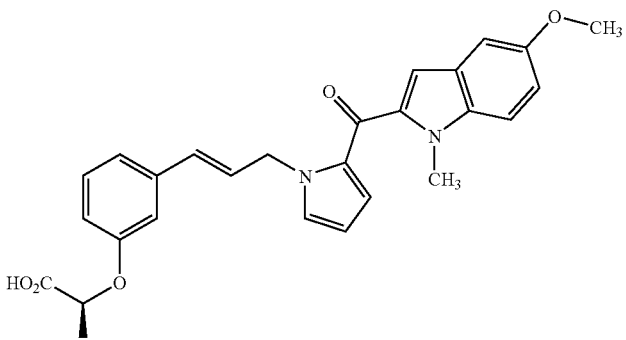 | $^1$H NMR (CDCl$_3$, 400 MHz) δ 7.31 (d, 1H, J=9.0 Hz), 7.21 (dd, 1H, J=8.0, 7.9 Hz), 7.08 (d, 1H, J=2.4 Hz), 7.06–6.98 (m, 5H), 6.90 (d, 1H, J=2.1 Hz), 6.76 (dd, 1H, J=8.0, 2.1 Hz), 6.48–6.38 (m, 2H), 6.23 (dd, 1H, J=4.0, 2.5 Hz), 5.19–5.18 (m, 2H), 4.80 (q, 1H, J=6.8 Hz), 4.00 (s, 3H), 3.86 (s, 3H), 1.62 (d, 3H, J=6.8 Hz). |

| Ex. No. | Structure | NMR |
|---|---|---|
| 196 | 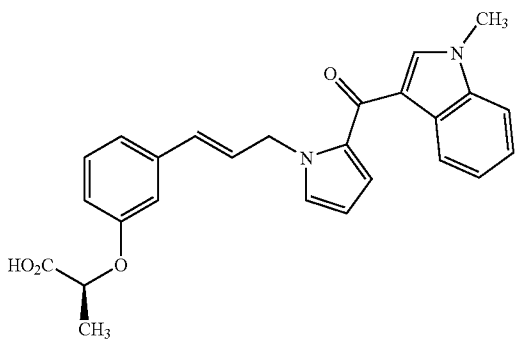 | ¹H NMR (CDCl₃, 400 MHz) δ 8.38–8.36 (m, 1H), 7.70 (s, 1H), 7.38–7.28 (m, 3H), 7.18 (dd, 1H, J=8.0, 7.9 Hz), 6.99–6.97 (m, 2H), 6.88 (d, 1H, J=2.1 Hz), 6.84 (dd, 1H, J=4.0, 1.7 Hz), 6.74 (dd, 1H, J=8.0, 2.1 Hz), 6.48–6.38 (m, 2H), 6.20 (dd, 1H, J=4.0, 2.5 Hz), 5.17 (d, 2H, J=3.0 Hz), 4.76 (q, 1H, J=6.8 Hz), 3.85 (s, 3H), 1.61 (d, 3H, J=6.8 Hz). |
| 197 | 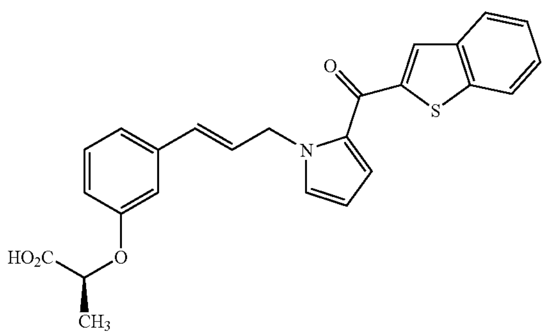 | ¹H NMR (CDCl₃, 400 MHz) δ 7.98 (s, 1H), 7.98–7.88 (m, 2H), 7.47–7.39 (m, 2H), 7.20 (dd, 1H, J=8.0, 7.9 Hz), 7.16 (dd, 1H, J=4.0, 1.7 Hz), 7.09 (dd, 1H, J=2.5, 1.7 Hz), 7.00 (d, 1H, J=7.9 Hz), 6.90 (d, 1H, J=2.1 Hz), 6.76 (dd, 1H, J=8.0, 2.1 Hz), 6.47–6.37 (m, 2H), 6.28 (dd, 1H, J=4.0, 2.5 Hz), 5.16 (d, 1H, J=4.7 Hz), 4.79 (q, 1H, J=6.8 Hz), 1.62 (d, 3H, J=6.8 Hz). |
| 198 | 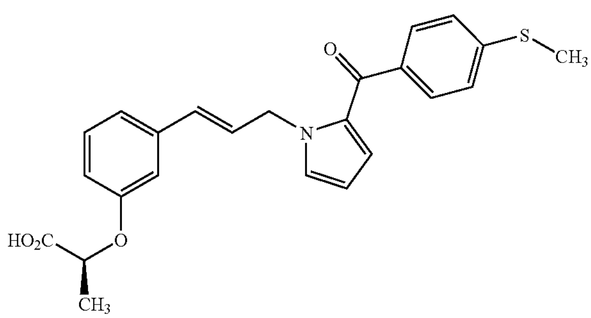 | ¹H NMR (CDCl₃, 400 MHz) δ 7.76 (d, 2H, J=8.5 Hz), 7.28 (d, 2H, J=8.5 Hz), 7.21 (dd, 1H, J=8.1, 7.8 Hz), 7.04 (dd, 1H, J=2.5, 1.7 Hz), 6.99 (d, 1H, J=7.8 Hz), 6.91 (d, 1H, J=2.4 Hz), 6.77 (dd, 1H, J=4.0, 1.7 Hz), 6.77 (dd, 1H, J=8.1, 2.4 Hz), 6.47–6.38 (m, 2H), 6.21 (dd, 1H, J=4.0, 2.5 Hz), 5.18 (d, 2H, J=4.4 Hz), 4.81 (q, 1H, J=6.8 Hz), 2.53 (s, 3H), 1.62 (d, 3H, J=6.8 Hz). |
| 199 | 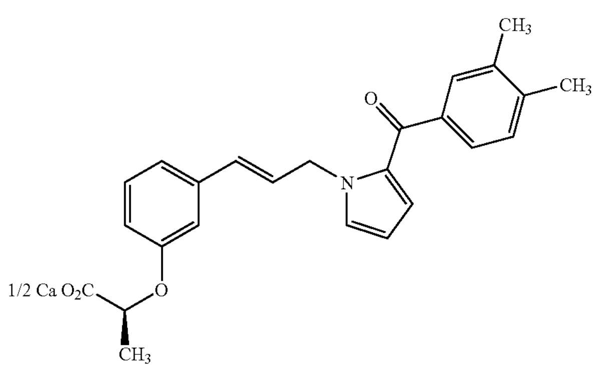 | ¹H NMR (DMSO-d₆, 400 MHz) δ 7.52 (s, 1H), 7.47 (d, 1H, J=7.8 Hz), 7.34 (dd, 1H, J=2.4, 1.6 Hz), 7.26 (d, 1H, J=7.8 Hz), 7.10 (dd, 1H, J=8.0, 7.8 Hz), 6.84 (d, 1H, J=7.8 Hz), 6.79 (s, 1H), 6.69–6.67 (m, 2H), 6.40 (dt, 1H, J=16.0, 5.4 Hz), 6.35 (brd, 1H, J=16.0 Hz), 6.22 (dd, 1H, J=4.0, 2.5 Hz), 5.14 (d, 2H, J=5.4 Hz), 4.34 (q, 1H, J=6.7 Hz), 2.29 (s, 3H), 2.28 (s, 3H), 1.37 (d, 3H, J=6.7 Hz). |

-continued

| Ex. No. | Structure | NMR |
|---|---|---|
| 200 | 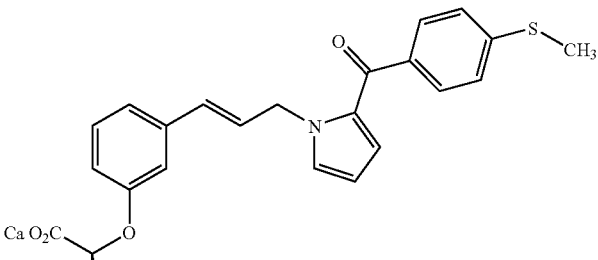 | $^1$H NMR (DMSO-$d_6$, 400 MHz) δ 7.70 (d, 2H, J=8.3 Hz), 7.12–7.08 (m, 3H), 7.10 (dd, 1H, J=8.0, 7.8 Hz), 6.84 (d, 1H, J=7.8 Hz), 6.79 (s, 1H), 6.71–6.67 (m, 2H), 6.40 (dt, 1H, J=16.0, 5.4 Hz), 6.35 (brd, 1H, J=16.0 Hz), 6.23 (dd, 1H, J=4.0, 2.5 Hz), 5.14 (d, 2H, J=5.4 Hz), 4.34 (q, 1H, J=6.7 Hz), 2.53 (s, 3H), 1.38 (d, 3H, J=6.7 Hz). |
| 201 | 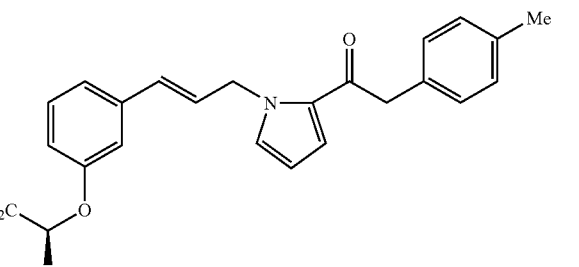 | $^1$H NMR (CDCl$_3$, 400 MHz) δ 7.73 (d, 1H, J=8.1 Hz), 7.25 (d, 1H, J=8.1 Hz), 7.21 (dd, 1H, J=8.1, 7.9 Hz), 7.10 (d, 1H, J=7.8 Hz), 7.04 (dd, 1H, J=2.5, 1.7 Hz), 6.95 (d, 1H, J=2.4 Hz), 6.81 (dd, 1H, J=8.1, 2.4 Hz), 6.78 (dd, 1H, J=4.0, 1.7 Hz), 6.46–6.36 (m, 2H), 6.21 (dd, 1H, J=4.0, 2.5 Hz), 5.18 (d, 2H, J=4.7 Hz), 2.43 (s, 3H), 1.57 (s, 6H). |

Example 202

The compound of Example 1 or the compound of Example 7 was mixed with powdered feed (CE-2, Japan Crea) as to contain the compound 0.1% and the mixture was administered to male db/db mice (7 weeks old) for 2 weeks. On last day blood was taken from tail vein and blood sugar was measured by antosence II (Sankyo-Bayern).

The value of blood sugar was degreased by 70% in case of administering 0.1% of the compound of Example 1, and by 34% in case of the compound of Example 7, respectively. The total amount of administration of the compound of Example 1, and the compound of Example 7 was 141 mg/kg, and 151 mg/kg, respectively.

Example 203

The test compounds described in Examples (these compound were made into a free form from a salt form, a sodium salt or calcium salt, if necessary) were dissolved or suspended in 0.5% carboxymethyl cellulose solution. Mice were forced to orally administer the test compound as to administer the total amount of 30 mg/kg or 100 mg/kg to male db/db mice (7 to 8 weeks old) once a day for 2 weeks. On last day, to the blood just taken from tail vein was added perchloric acid to remove proteins and then the blood sugar was measure by glucose CII Test Waco (Wako Pure Chemical Ind.).

Hypoglycemic activity was calculated as following formula:

$$\text{Hypoglycemic activity (\%)} = \frac{A - B}{A} \times 100$$

A: Blood sugar level of Vehicle (on last day)
B: Blood sugar level of test compound-administered group (on last day)

| Test compound (Ex. No.) | Salt form | Dosage (mg/kg) | Hypoglycemic activity(%) |
|---|---|---|---|
| 35 | Ca salt | 100 | 53 |
| 39 | Na salt | 100 | 65 |
| 53 | Free | 100 | 23 |
| 63 | Na salt | 30 | 19 |
| 91 | Ca salt | 30 | 55 |
| 92 | Ca salt | 30 | 46 |
| 104 | Ca salt | 30 | 58 |
| 110 | Na salt | 30 | 17 |
| 111 | Na salt | 30 | 61 |
| 126 | Na salt | 30 | 56 |
| 128 | Na salt | 100 | 27 |
| 135 | Free | 100 | 16 |
| 139 | Na salt | 100 | 55 |
| 142 | Na salt | 100 | 55 |
| 143 | Free | 30 | 21 |
| 155 | Ca salt | 30 | 57 |
| 158 | Ca salt | 30 | 24 |
| 165 | Na salt | 100 | 68 |
| 171 | Na salt | 100 | 20 |
| 179 | Free | 30 | 22 |
| 186 | Ca salt | 30 | 44 |
| 191 | Ca salt | 30 | 15 |
| 199 | Ca salt | 30 | 22 |
| 201 | Ca salt | 30 | 18 |

THE INDUSTRIAL APPLICABILITY

The pyrrole derivative (1), (1a) or a pharmaceutically acceptable salt thereof of the present invention can be used for an antdiabetic agent, an arrest of diabetes mellitus or a controlling agent for blood sugar.

The invention claimed is:

1. A pyrrole derivative of a generic formula (1):

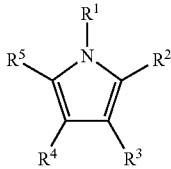

(1)

wherein
$R^1$ is a formula (2):

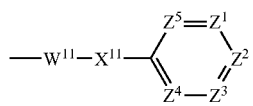

(2)

wherein
$X^{11}$ is a single bond;
$W^{11}$ is $C_{2-5}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl, $C_{1-4}$ alkoxy, hydroxy, $C_{1-4}$ alkanoyloxy or a halogen; or
$C_{2-5}$ alkynylene optionally substituted by $C_{1-4}$ alkyl, $C_{1-4}$ alkoxy, hydroxy, $C_{1-4}$ alkanoyloxy or a halogen;
either of $Z^1$ and $Z^2$ a carbon atom substituted by a formula: $-X^1-Y^1-COR^6$
(wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen,
$C_{1-4}$ alkoxy optionally substituted by $C_{1-4}$ alkyl or a halogen, or a halogen); and
the other is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen); and
$Z^3$, $Z^4$ and $Z^5$ are independently from each other, a carbon atom substituted by hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen; wherein
either of $R^2$ and $R^3$ is a formula: $-W^{21}-A^{21}$
(wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl;
$-CONH-$; or $-CONHCH_2-$; wherein a methylene moiety in said alkylene may form a carbonyl, and wherein a methylene moiety in said alkenylene may form a carbonyl, and
$A^{21}$ is unsubstituted $C_{6-12}$ aryl; $C_{6-12}$ aryl substituted by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by $C_{7-8}$ aralkyl optionally substituted by $C_{1-4}$ alkoxy, $C_{1-4}$ alkyl, halogeno $C_{1-4}$ alkyl or a halogen,
by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano,
by phenoxy optionally substituted by $C_{1-4}$ alkoxy, $C_{1-4}$ alkyl, halogeno $C_{1-4}$ alkyl or a halogen, or
by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl, $C_{2-12}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl
$C_{2-5}$ alkenyl,
$C_{1-4}$ alkylsulfonyloxy,
$C_{1-4}$ alkylsulfonyl,
$C_{1-4}$ alkylthio or
cyano; and
the other is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen;
$R^4$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen; and
$R^5$ is hydrogen; $C_{1-4}$ alkyl optionally, substituted by $C_{1-4}$ alkyl, $C_{1-4}$ alkoxy, hydroxy, $C_{1-4}$ alkanoyloxy or a halogen; or a halogen,
or its salt.

2. The pyrrole derivative or its salt according to claim 1 wherein $Z^1$ is a carbon atom substituted by a formula: —$X^1$—$Y^1$—$COR^6$
(wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
$Z^2$ is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen.

3. The pyrrole derivative or its salt according to claim 1 wherein $Z^2$ is a carbon atom substituted by a formula: —$X^1$—$Y^1$—$COR^6$
(wherein $X^1$ is a single bond, an oxygen atom or a sulfur atom;
$Y^1$ is $C_{1-4}$ alkylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano;
$C_{2-5}$ alkenylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; or
$C_{2-5}$ alkynylene optionally substituted by $C_{1-4}$ alkyl optionally substituted by a halogen, $C_{1-4}$ alkoxy optionally substituted by a halogen, hydroxy, $C_{1-4}$ alkanoyloxy, a halogen or cyano; and
$R^6$ is hydroxy;
$C_{1-4}$ alkoxy optionally substituted by $C_{1-4}$ alkyl;
$C_{1-4}$ alkylsulfonylamino optionally substituted by $C_{1-4}$ alkyl or a halogen;
unsubstituted phenylsulfonylamino; or
phenylsulfonylamino substituted by $C_{1-4}$ alkyl optionally substituted by $C_{1-4}$ alkyl or a halogen, $C_{1-4}$ alkoxy optionally substituted by $C_{1-4}$ alkyl or a halogen, or a halogen); and
$Z^1$ is a carbon atom substituted by
hydrogen;
hydroxy;
a halogen;
cyano;
carbamoyl;
$C_{2-5}$ alkylaminocarbonyl;
$C_{3-9}$ dialkylaminocarbonyl;
$C_{1-4}$ alkyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkenyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino;
$C_{2-5}$ alkynyl optionally substituted by $C_{1-4}$ alkyl, hydroxy, $C_{1-4}$ alkoxy, $C_{2-5}$ alkoxycarbonyl, $C_{2-5}$ alkylcarbonyl, $C_{1-4}$ acyloxy, a halogen, cyano, carbamoyl, amino, $C_{1-4}$ alkylamino or $C_{2-8}$ dialkylamino; or
$C_{1-4}$ alkoxy optionally substituted by $C_{1-4}$ alkyl, $C_{1-4}$ alkoxy or a halogen.

4. The pyrrole derivative or its salt according to claim 2 wherein $R^2$ is a formula: -$W^{21}$-$A^{21}$
(wherein $W^{21}$ is $C_{1-6}$ alkylene optionally substituted by $C_{1-4}$ alkyl, $C_{1-4}$ alkoxy, hydroxy,
$C_{1-4}$ alkanoyloxy or a halogen;

$C_{2-5}$ alkenylene optionally substituted by $C_{1-4}$ alkyl;
—CONH—; or —CONHCH$_2$—; wherein a methylene moiety in said alkylene may form a carbonyl, and wherein a methylene moiety in said alkenylene may form a carbonyl, and $A^{21}$ is unsubstituted $C_{6-12}$ aryl; $C_{6-12}$ aryl substituted by $C_{1-6}$ alkyl optionally substitutd by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by $C_{7-8}$ aralkyl optionally substituted by $C_{1-4}$ alkoxy, $C_{1-4}$ alkyl, halogeno $C_{1-4}$ alkyl or a halogen, by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by phenoxy optionally substituted by $C_{1-4}$ alkoxy, $C_{1-4}$ alkyl, halogeno $C_{1-4}$ alkyl or a halogen, or by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl
$C_{2-5}$ alkenyl,
$C_{1-4}$ alkylsulfonyloxy,
$C_{1-4}$ alkylsulfonyl,
$C_{1-4}$ alkylthio or
cyano; and $R^3$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen.

5. The pyrrole derivative or its salt according to claim 2 wherein $R^3$ is a formula -$W^{21}$-$A^{21}$
wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl;
—CONH—; or —CONHCH$_2$—; wherein a methylene moiety in said alkylene may form a carbonyl, and wherein a methylene moiety in said alkenylene may form a carbonyl, and $A^{21}$ is unsubstituted $C_{6-12}$ aryl; $C_{6-12}$ aryl substituted by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by $C_{7-8}$ aralkyl optionally substituted by $C_{1-4}$ alkoxy, $C_{1-4}$ alkyl, halogeno $C_{1-4}$ alkyl or a halogen, by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-5}$ dialkylsulfamoyl or cyano, by phenoxy optionally substituted by $C_{1-4}$ alkoxy, $C_{1-4}$ alkyl, halogeno $C_{1-4}$ alkyl or a halogen, or by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl,
$C_{2-5}$ alkenyl,
$C_{1-4}$ alkylsulfonyloxy,
$C_{1-4}$ alkylsulfonyl,
$C_{1-4}$ alkylthio or
cyano; and $R^2$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen.

6. The pyrrole derivative or its salt according to claim 3 wherein $R^2$ is a formula: -$W^{21}$-$A^{21}$
(wherein $W^{21}$ is $C_{1-6}$ alkylene optionally substituted by $C_{1-4}$ alkyl, $C_{1-4}$ alkoxy, hydroxy, $C_{1-4}$ alkanoyloxy or a halogen;
$C_{2-5}$ alkenylene optionally substituted by $C_{1-4}$ alkyl;
—CONH—; or —CONHCH$_2$—; wherein a methylene moiety in said alkylene may form a carbonyl, and wherein a methylene moiety in said alkenylene may form a carbonyl, and $A^{21}$ is unsubstituted $C_{6-12}$ aryl; $C_{6-12}$ aryl substituted by $C_{1-6}$ alkyl optionally substituted by hydroxy, $C_{1-4}$ alkoxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-8}$ dialkylsulfamoyl or cyano, by $C_{7-8}$ aralkyl optionally substituted by $C_{1-4}$ alkoxy, $C_{1-4}$ alkyl, halogeno $C_{1-4}$ alkyl or a halogen, by $C_{1-4}$ alkoxy optionally substituted by hydroxy, $C_{1-4}$ alkanoyloxy, a halogen, amino, $C_{1-4}$ alkylamino, $C_{2-8}$ dialkylamino, carbamoyl, $C_{2-5}$ alkylaminocarbonyl, $C_{3-9}$ dialkylaminocarbonyl, sulfamoyl, $C_{1-4}$ alkylsulfamoyl, $C_{2-5}$ dialkylsulfamoyl or cyano, by phenoxy optionally substituted by $C_{1-4}$ alkoxy, $C_{1-4}$ alkyl, halogeno $C_{1-4}$ alkyl or a halogen, or by $C_{3-4}$ alkenyloxy,
hydroxy,
$C_{1-4}$ alkanoyloxy,
a halogen,
amino,
$C_{1-6}$ alkylamino,
$C_{2-12}$ dialkylamino,
carbamoyl,
$C_{2-7}$ alkylaminocarbonyl,
$C_{3-14}$ dialkylaminocarbonyl,
sulfamoyl,
$C_{1-6}$ alkylsulfamoyl,
$C_{2-12}$ dialkylsulfamoyl
$C_{2-5}$ alkenyl,
$C_{1-4}$ alkylsulfonyloxy,
$C_{1-4}$ alkylsulfonyl,
$C_{1-4}$ alkylthio or
cyano; and $R^3$ is hydrogen; $C_{1-4}$ alkyl optionally substituted by $C_{1-4}$ alkyl, $C_{1-4}$ alkoxy, hydroxy, $C_{1-4}$ alkanoyloxy or a halogen; or a halogen.

7. A pyrrole derivative of a generic formula (1a):

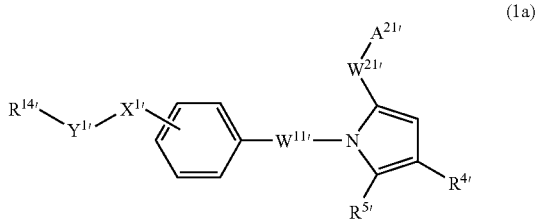

(1a)

wherein
- $R^{4'}$ is hydrogen, $C_{1-4}$ alkyl optionally substituted by $C_{1-4}$ alkyl or a halogen, or a halogen;
- $R^{5'}$ is hydrogen, $C_{1-4}$ alkyl optionally substituted by $C_{1-4}$ alkyl or a halogen, or a halogen;
- $R^{14'}$ is a carboxyl or a group which is convertible to a carboxyl by hydrolysis in vivo;
- $X^{1'}$ is a single bond, an oxygen atom or a sulfur atom;
- $Y^{1'}$ is $C_{1-4}$ alkylene optionally substituted by $C_{1-4}$ alkyl, $C_{1-4}$ alkoxy, hydroxy or a halogen;
- $C_{2-5}$ alkenylene optionally substituted by $C_{1-4}$ alkyl, $C_{1-4}$ alkoxy, hydroxy or a halogen; or
- $C_{2-5}$ alkynylene optionally substituted by $C_{1-4}$ alkyl, $C_{1-4}$ alkoxy, hydroxy or a halogen;
- $W^{11'}$ is $C_{2-5}$ alkylene optionally substituted by $C_{1-4}$ alkyl or a halogen;
- $C_{2-5}$ alkenylene optionally substituted by $C_{1-4}$ alkyl or a halogen; or
- $C_{2-5}$ alkynylene optionally substituted by $C_{1-4}$ alkyl or a a halogen;
- $W^{21'}$ is $C_{1-4}$ alkylene in which methylene may form carbonyl, and said alkylene is optionally substituted by $C_{1-4}$ alkyl;
- $C_{2-5}$ alkenylene in which methylene may form carbonyl, and said alkenylene is optionally substituted by $C_{1-4}$ alkyl;
- —CONH—; or —CONHCH$_2$—; and
- $A^{21'}$ is unsubstituted $C_{6-12}$ aryl; $C_{6-12}$ aryl substituted by $C_{1-4}$ alkyl optionally substituted by hydroxy, a halogen, $C_{1-4}$ alkoxy or $C_{2-8}$ dialkylamino,
- by $C_{1-4}$ alkoxy optionally substituted by a halogen, $C_{1-4}$ alkyl or $C_{2-8}$ dialkylamino,
- by a halogen or $C_{2-12}$ dialkylamino.

8. The pyrrole derivative or its salt according to claim 7 wherein $R^{4'}$ is hydrogen or $C_{1-4}$ alkyl, and $R^{5'}$ is hydrogen.

9. The pyrrole derivative or its salt according to claim 7 wherein $R^{4'}$ and $R^{5'}$ are hydrogen.

10. The pyrrole derivative or its salt according to claim 7 wherein $R^{14'}$ is carboxyl.

11. The pyrrole derivative or its salt according to claim 7 wherein $X^{1'}$ is a single bond.

12. The pyrrole derivative or its salt according to claim 7 wherein $X^{1'}$ is an oxygen atom.

13. The pyrrole derivative or its salt according to claim 7 wherein $X^{1'}$ is a sulfur atom.

14. The pyrrole derivative or its salt according to claim 7 wherein $Y^{1'}$ is $C_{1-4}$ alkylene optionally substituted by $C_{1-4}$ alkyl, $C_{1-4}$ alkoxy, hydroxy or a halogen.

15. The pyrrole derivative or its salt according to claim 7 wherein $Y^{1'}$ is methylene optionally substituted by $C_{1-4}$ alkyl.

16. The pyrrole derivative or its salt according to claim 7 wherein $W^{11'}$ is unsubstituted $C_{2-5}$ alkylene, unsubstituted $C_{2-5}$ alkenylene or unsubstituted $C_{2-5}$ alkynylene.

17. The pyrrole derivative or its salt according to claim 7 wherein $W^{11'}$ is propenylene.

18. The pyrrole derivative or its salt according to claim 7 wherein $W^{11'}$ is propenylene and $X^{1'}$ is an oxygen atom.

19. The pyrrole derivative or its salt according to claim 7 wherein $W^{21'}$ is carbonyl, —CONH—, —CONHCH$_2$— or —C(=O)CH$_2$—.

20. The pyrrole derivative or its salt according to claim 7 wherein $W^{21'}$ is carbonyl.

21. The pyrrole derivative or its salt according to claim 7 wherein $W^{21'}$ is carbonyl and $X^{1'}$ is an oxygen atom.

22. The pyrrole derivative or its salt according to claim 7 wherein $A^{21'}$ is unsubstituted phenyl or phenyl substituted by $C_{1-4}$ alkyl optionally substituted by a halogen, $C_{1-4}$ alkoxy or $C_{2-8}$ dialkylamino, by $C_{1-4}$ alkoxy optionally substituted by a halogen, $C_{1-4}$ alkoxy or $C_{2-8}$ dialkylamino, or by a halogen or $C_{2-12}$ dialkylamino.

23. The pyrrole derivative or its salt according to claim 7 wherein $A^{21'}$ is unsubstituted phenyl or phenyl substituted by $C_{1-4}$ alkyl optionally substituted by a halogen, or by $C_{1-4}$ alkoxy optionally substituted by a halogen.

24. The pyrrole derivative or its salt according to claim 7 wherein $A^{21'}$ is unsubstituted phenyl or phenyl substituted by $C_{1-4}$ alkyl.

25. The pyrrole derivative or its salt according to claim 7 wherein $X^{1'}$ is an oxygen atom, and $A^{21'}$ is unsubstituted phenyl or phenyl substituted by $C_{1-4}$ alkyl.

26. The pyrrole derivative or its salt according to claim 7 wherein $R^{4'}$ and $R^{5'}$ are hydrogen, and $R^{14'}$ is carboxyl.

27. The pyrrole derivative or its salt according to claim 7 wherein $R^{4'}$ and $R^{5'}$ are hydrogen, $R^{14'}$ is carboxyl, and $Y^{1'}$ is $C_{1-4}$ alkylene optionally substituted by $C_{1-4}$ alkyl, $C_{1-4}$ alkoxy, hydroxy or a halogen.

28. The pyrrole derivative or its salt according to claim 7 wherein $R^{4'}$ and $R^{5'}$ are hydrogen, $R^{14'}$ is carboxyl, $X^{1'}$ is an oxygen atom, and $Y^{1'}$ is $C_{1-4}$ alkylene optionally substituted by $C_{1-4}$ alkyl, $C_{1-4}$ alkoxy, hydroxy or a halogen.

29. The pyrrole derivative or its salt according to claim 7 wherein $R^{4'}$ and $R^{5'}$ are hydrogen, $R^{14'}$ is carboxyl, and $W^{11'}$ is unsubstituted $C_{2-5}$ alkylene, unsubstituted $C_{2-5}$ alkenylene or unsubstituted $C_{2-5}$ alkynylene.

30. The pyrrole derivative or its salt according to claim 7 wherein $R^{4'}$ and $R^{5'}$ are hydrogen, $R^{14'}$ is carboxyl, $X^{1'}$ is an oxygen and $W^{11'}$ is unsubstituted $C_{2-5}$ alkylene, unsubstituted $C_{2-5}$ alkenylene or unsubstituted $C_{2-5}$ alkynylene.

31. The pyrrole derivative or its salt according to claim 7 wherein $R^{4'}$ and $R^{5'}$ are hydrogen, $R^{14'}$ is carboxyl, and $W^{11'}$ is propenylene.

32. The pyrrole derivative or its salt according to claim 7 wherein $R^{4'}$ and $R^{5'}$ are hydrogen, $R^{14'}$ is carboxyl, $W^{11'}$ is propenylene, and X is an oxygen.

33. The pyrrole derivative or its salt according to claim 7 wherein $R^{4'}$ and $R^{5'}$ are hydrogen, $R^{14'}$ is carboxyl, and W is carbonyl, —CONH—, —CONHCH$_2$— or —C(=O)CH$_2$—.

34. The pyrrole derivative or its salt according to claim 7 wherein $R^{4'}$ and $R^{5'}$ are hydrogen, $R^{14'}$ is carboxyl, $X^{1'}$ is an oxygen, and $W^{21'}$ is carbonyl, —CONH—, —CONHCH$_2$— or —C(=O)CH$_2$—.

35. The pyrrole derivative or its salt according to claim 7 wherein $R^{4'}$ and $R^{5'}$ are hydrogen, $R^{14'}$ is carboxyl, and $W^{21'}$ is carbonyl.

36. The pyrrole derivative or its salt according to claim 7 wherein $R^{4'}$ and $R^{5'}$ are hydrogen, $R^{14'}$ is carboxyl, $W^{21'}$ is carbonyl, and $X^{1'}$ is an oxygen.

37. The pyrrole derivative or its salt according to claim 7 wherein $R^{4'}$ and $R^{5'}$ are hydrogen, $R^{14'}$ is carboxyl, and $A^{21'}$

38. The pyrrole derivative or its salt according to claim 7 wherein $R^{4'}$ and $R^{5'}$ are hydrogen, $R^{14'}$ is carboxyl, $X^{1'}$ is an oxygen, and $A^{21'}$ is unsubstituted phenyl or phenyl substituted by $C_{1-4}$ alkyl optionally substituted by a halogen, or by $C_{1-4}$ alkoxy optionally substituted by a halogen.

39. The pyrrole derivative or its salt according to claim 7 wherein $R^{4'}$ and $R^{5'}$ are hydrogen, $R^{14'}$ is carboxyl, $W^{11'}$ is propenylene, and $Y^{1'}$ is $C_{1-4}$ alkylene optionally substituted by $C_{1-4}$ alkyl, $C_{1-4}$ alkoxy, hydroxy or a halogen.

40. The pyrrole derivative or its salt according to claim 7 wherein $R^{4'}$ and $R^{5'}$ are hydrogen, $R^{14'}$ is carboxyl, $W^{11'}$ is propenylene, $X^{1'}$ is an oxygen, and $Y^{1'}$ is $C_{1-4}$ alkylene optionally substituted by $C_{1-4}$ alkyl, $C_{1-4}$ alkoxy, hydroxy or a halogen.

41. The pyrrole derivative or its salt according to claim 7 wherein $R^{4'}$ and $R^{5'}$ are hydrogen, $R^{14'}$ is carboxyl, and $W^{21'}$ is carbonyl, —CONH—, —CONHCH$_2$— or —C(=O)CH$_2$—, and $Y^{1'}$ is $C_{1-4}$ alkylene optionally substituted by $C_{1-4}$ alkyl, $C_{1-4}$ alkoxy, hydroxy or a halogen.

42. The pyrrole derivative or its salt according to claim 7 wherein $R^{4'}$ and $R^{5'}$ are hydrogen, $R^{14'}$ is carboxyl, $X^{1'}$ is an oxygen, $W^{21'}$ carbonyl, —CONH—, —CONHCH$_2$— or —C(=O)CH$_2$—, and $Y^{1'}$ is $C_{1-4}$ alkylene optionally substituted by $C_{1-4}$ alkyl, $C_{1-4}$ alkoxy, hydroxy or a halogen.

43. The pyrrole derivative or its salt according to claim 7 wherein $R^{4'}$ and $R^{5'}$ are hydrogen, $R^{14'}$ is carboxyl, $W^{21'}$ is carbonyl, and $Y^{1'}$ is methylene optionally substituted by $C_{1-4}$ alkyl.

44. The pyrrole derivative or its salt according to claim 7 wherein $R^{4'}$ and $R^{5'}$ are hydrogen, $R^{4'}$ is carboxyl, $W^{21'}$ is carbonyl, $X^{1'}$ is an oxygen, and $Y^{1'}$ is methylene optionally substituted by $C_{1-4}$ alkyl.

45. The pyrrole derivative or its salt according to claim 7 wherein $R^{4'}$ and $R^{5'}$ are hydrogen, $R^{14'}$ is carboxyl, $A^{21'}$ is unsubstituted phenyl or phenyl substituted by $C_{1-4}$ alkyl, and $Y^{1'}$ is $C_{1-4}$ alkylene optionally substituted by $C_{1-4}$ alkyl, $C_{1-4}$ alkoxy, hydroxy or a halogen.

46. The pyrrole derivative or its salt according to claim 7 wherein $R^{4'}$ and $R^{5'}$ are hydrogen, $R^{14'}$ is carboxyl, $A^{21'}$ is unsubstituted phenyl or phenyl substituted by $C_{1-4}$ alkyl, $X^{1'}$ is an oxygen, and $Y^{1'}$ is $C_{1-4}$ alkylene optionally substituted by $C_{1-4}$ alkyl, $C_{1-4}$ alkoxy, hydroxy or a halogen.

47. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ is carbonyl, —CONH—, —CONHCH$_2$— or —C(=O)CH$_2$, and $Y^{1'}$ is $C_{1-4}$ alkylene optionally substituted by $C_{1-4}$ alkyl, $C_{1-4}$ alkoxy, hydroxy or a halogen.

48. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ is carbonyl, —CONH—, —CONHCH$_2$— or —C(=O)CH$_2$—, $X^{1'}$ is an oxygen, and $Y^{1'}$ is $C_{1-4}$ alkylene optionally substituted by $C_{1-4}$ alkyl, $C_{1-4}$ alkoxy, hydroxy or a halogen.

49. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ is carbonyl, and $Y^{1'}$ is methylene optionally substituted by $C_{1-4}$ alkyl.

50. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ is carbonyl, $X^{1'}$ is an oxygen, and $Y^{1'}$ is methylene optionally substituted by $C_{1-4}$ alkyl.

51. The pyrrole derivative or its salt according to claim 7 wherein $R^{4'}$ and $R^{5'}$ are hydrogen, $R^{14'}$ is carboxyl, $W^{11'}$ is propenylene, $Y^{1'}$ is methylene optionally substituted by $C_{1-4}$ alkyl, and $A^{21'}$ is unsubstituted phenyl or phenyl substituted by $C_{1-4}$ alkyl.

52. The pyrrole derivative or its salt according to claim 7 wherein $R^{4'}$ and $R^{5'}$ are hydrogen, $R^{4'}$ is carboxyl, $W^{11'}$ is propenylene, $X^{1'}$ is an oxygen, $Y^{1'}$ is methylene optionally substituted by $C_{1-4}$ alkyl, and $A^{21'}$ is unsubstituted phenyl or phenyl substituted by $C_{1-4}$ alkyl.

53. The pyrrole derivative or its salt according to claim 7 wherein $R^{4'}$ and $R^{5'}$ are hydrogen, $R^{14'}$ is carboxyl, $W^{21'}$ is carbonyl, $Y^{1'}$ is methylene optionally substituted by $C_{1-4}$ alkyl, and $A^{21'}$ is unsubstituted phenyl or phenyl substituted by $C_{1-4}$ alkyl.

54. The pyrrole derivative or its salt according to claim 7 wherein $R^{4'}$ and $R^{5'}$ are hydrogen, $R^{14'}$ is carboxyl, $W^{21'}$ is carbonyl, $X^{1'}$ is an oxygen, $Y^{1'}$ is methylene optionally substituted by $C_{1-4}$ alkyl, and $A^{21'}$ is unsubstituted phenyl or phenyl substituted by $C_{1-4}$ alkyl.

55. The pyrrole derivative or its salt according to claim 7 wherein $R^{4'}$ and $R^{5'}$ are hydrogen, $R^{14'}$ is carboxyl, $W^{21'}$ is propenylene, $W^{21'}$ is carbonyl, and $A^{21'}$ is unsubstituted phenyl or phenyl substituted by $C_{1-4}$ alkyl.

56. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ carbonyl, $X^{1'}$ is an oxygen, and $A^{21'}$ is unsubstituted phenyl or phenyl substituted by $C_{1-4}$ alkyl.

57. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ carbonyl, $Y^{1'}$ is methylene optionally substituted by $C_{1-4}$ alkyl, and $A^{21'}$ is unsubstituted phenyl or phenyl substituted by $C_{1-4}$ alkyl.

58. The pyrrole derivative or its salt according to claim 7 wherein $R^{4'}$ and $R^{5'}$ are hydrogen, $R^{14'}$ is carboxyl, $W^{11'}$ is propenylene, $W^{21'}$ is carbonyl, $X^{1'}$ is an oxygen atom, $Y^{1'}$ is methylene optionally substituted by $C_{1-4}$ alkyl, and $A^{21'}$ is unsubstituted phenyl or phenyl substituted by $C_{1-4}$ alkyl.

59. A pharmaceutical composition comprising the pyrrole derivative or its salt as defined in claim 1 or 7.

60. An antidiabetic comprising the pyrrole derivative or its salt as defined in claim 1 or 7.

61. A type II antidiabetic comprising the pyrrole derivative or its salt as defined in claim 1 or 7.

62. A blood sugar-controlling agent comprising the pyrrole derivative or its salt as defined in claim 1 or 7.

63. A method for treating a patient with diabetes mellitus comprising administering an effective amount of the pyrrole derivative or its salt as defined in claim 1 or 7 as an active ingredient to said patient.

64. A method for controlling the blood sugar of a patient with the diabetes mellitus comprising administering an effective amount of the pyrrole derivative or its salt as defined in claim 1 or 7 as an active ingredient to said patient.

* * * * *